United States Patent
Froidevaux et al.

(10) Patent No.: US 11,739,070 B2
(45) Date of Patent: Aug. 29, 2023

(54) C5A RECEPTOR MODULATORS

(71) Applicant: IDORSIA PHARMACEUTICALS LTD, Allschwil (CH)

(72) Inventors: Sylvie Froidevaux, Allschwil (CH); Francis Hubler, Allschwil (CH); Mark Murphy, Allschwil (CH); Dorte Renneberg, Allschwil (CH); Simon Stamm, Allschwil (CH)

(73) Assignee: IDORSIA PHARMACEUTICALS LTD., Allschwil (CH)

( * ) Notice: Subject to any disclaimer, the term of this patent is extended or adjusted under 35 U.S.C. 154(b) by 0 days.

(21) Appl. No.: 16/963,101

(22) PCT Filed: Jan. 18, 2019

(86) PCT No.: PCT/EP2019/051230
§ 371 (c)(1),
(2) Date: Jul. 17, 2020

(87) PCT Pub. No.: WO2019/141803
PCT Pub. Date: Jul. 25, 2019

(65) Prior Publication Data
US 2020/0347029 A1 Nov. 5, 2020

(30) Foreign Application Priority Data
Jan. 19, 2018 (WO) ................. PCT/EP2018/051278

(51) Int. Cl.
C07D 401/04 (2006.01)
C07D 401/14 (2006.01)
C07D 403/04 (2006.01)
C07D 405/14 (2006.01)
C07D 413/14 (2006.01)
C07D 471/04 (2006.01)

(52) U.S. Cl.
CPC ......... *C07D 401/04* (2013.01); *C07D 401/14* (2013.01); *C07D 403/04* (2013.01); *C07D 405/14* (2013.01); *C07D 413/14* (2013.01); *C07D 471/04* (2013.01)

(58) Field of Classification Search
CPC .. C07D 403/04; C07D 401/04; C07D 401/14; C07D 405/14; C07D 413/14; C07D 471/04; C07D 487/04; A61P 25/00; A61P 35/00; A61P 37/00
USPC .................................................. 514/224.2
See application file for complete search history.

(56) References Cited

U.S. PATENT DOCUMENTS

| | | | |
|---|---|---|---|
| 5,661,169 A | 8/1997 | Di Malta et al. | |
| 2012/0143725 A1 | 6/2012 | Hutchinson et al. | |
| 2013/0079327 A1 | 3/2013 | Yamamoto et al. | |
| 2020/0347029 A1 | 11/2020 | Froidevaux et al. | |
| 2021/0122736 A1 | 4/2021 | Froidevaux et al. | |

FOREIGN PATENT DOCUMENTS

| | | |
|---|---|---|
| EP | 1122253 A1 | 8/2001 |
| EP | 1122253 A4 | 5/2003 |
| WO | 9936421 A1 | 7/1999 |
| WO | 0024744 A1 | 5/2000 |
| WO | 0105770 A1 | 1/2001 |
| WO | 0168604 A2 | 9/2001 |
| WO | 03037890 A2 | 5/2003 |
| WO | 03103669 A1 | 12/2003 |
| WO | 2005063209 A1 | 7/2005 |
| WO | 2008147697 A1 | 12/2008 |
| WO | 2011152351 A1 | 12/2011 |
| WO | 2012143725 A1 | 10/2012 |
| WO | 2015033299 A1 | 3/2015 |
| WO | 2015034820 A1 | 3/2015 |
| WO | 2015044900 A1 | 4/2015 |
| WO | 2019137927 A1 | 7/2019 |

(Continued)

OTHER PUBLICATIONS

CAPLUS 1977:405966.*
Owen, D. et al., Bioorg. Med. Chem Lett 2009, vol. 19, pp. 1702-1706.*
Web page Innate Pharma—IPH5401, 2018; https://www.innate-pharma.com/en/pipeline/iph5401-first-class-anti-c5ar-mab.
Remington, The Science and Practice of Pharmacy, 21st Edition (2005), Part 5, "Pharmaceutical Manufacturing" [published by Lippincott Williams & Wilkins]).
Ager, R. R., et al. (2010) J Neurochem 113(2): 389-401.
Amsterdam, E. A., et al. (1995) Am J Physiol 268(1 Pt 2): H448-457.

(Continued)

*Primary Examiner* — Ana Z Muresan
(74) *Attorney, Agent, or Firm* — Culhane Meadows PLLC; Jeff B. Vockrodt

(57) ABSTRACT

The present invention relates to derivatives of formula (I)

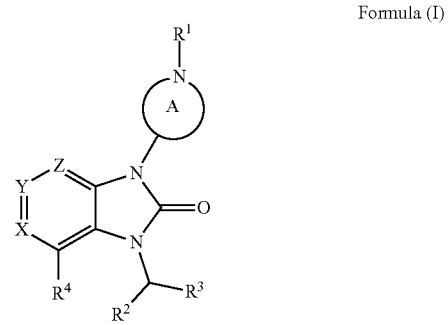

Formula (I)

wherein ring A, X, Y, Z, $R^1$, $R^2$, $R^3$ and $R^4$ are as described in the description, to their preparation, to pharmaceutically acceptable salts thereof, and to their use as pharmaceuticals, to pharmaceutical compositions containing one or more compounds of formula (I), and especially to their use as C5a receptor modulators.

16 Claims, No Drawings

(56) References Cited

FOREIGN PATENT DOCUMENTS

| | | |
|---|---|---|
| WO | 2019141803 A1 | 7/2019 |
| WO | 2019141808 A1 | 7/2019 |

OTHER PUBLICATIONS

Volanikis, J.; Vasculitis, 2nd Edition (2008), Edited by Ball and Bridges, Oxford University Press, pp. 47-53.
Bao, L., et al. (2005) Eur J Immunol 35(8): 2496-2506.
Basta, M. and D. R. Branch (2014) Clin Exp Immunol 178 Suppl 1: 87-88.
Baumann, U., et al. (2000) J Immunol 164(2): 1065-1070.
Bless, N. M., et al. (1999) Am J Physiol 276(1 Pt 1): L57-63.
Bozic, C. R., et al. (1996) Science 273(5282): 1722-1725.
Cao, Q., et al. (2012) Am J Physiol Cell Physiol 302(12): C1731-1740.
Cheng, L., et al. (2013). Invest Ophthalmol Vis Sci 54(13): 8191-8198.
Janeway's Immunobiology, 8th edition (2012), Kenneth Murphy, Garland Science, p. 48-72.
Craddock, P. R., et al. (1977) N Engl J Med 296(14): 769-774.
Craddock, P. R., et al. (1977) J Clin Invest 60(1): 260-264.
Czermak, B. J., et al. (1999) Nat Med 5(7): 788-792.
Czermak, B. J., et al. (1998) J Leukoc Biol 64(1): 40-18.
Dang, L., et al. (2015) Mol Med Rep 11(6): 4183-4189.
Davin, J. C., N. C. van de Kar (2015) Ther Adv Hematol 6(4): 171-185.
De Hoog, V. C., et al. (2014) Cardiovasc Res 103(4): 521-529.
Diani, M., G. Altomare and E. Reali (2015) Autoimmun Rev 14(4): 286-292.
Distelmaier, K., et al. (2009) Thromb Haemost 102(3): 564-572.
Farrar, C. A. and S. H. Sacks (2014) Curr Opin Organ Transplant 19(1): 8-13.
Fiebiger, E., et al. (1998) J Clin Invest 101(1): 243-251.
Fonseca, M. I., et al. (2013) J Neuroinflammation 10:25.
Gammon, W. R. (1989) Immunol Ser 46: 509-525.
Gasque, P., et al. (1997) Am J Pathol 150(1): 31-41.
Grant, E. P., et al. (2002) J Exp Med 196(11): 1461-1471.
"Protective Groups in Organic Synthesis", T.W. Greene, P.G.M. Wuts, Wiley-Interscience, 1999.
Guo, R. F., et al. (2000) J Clin Invest 106(10): 1271-1280.
Guo, R. F. and P. A. Ward (2005) Annu Rev Immunol 23: 821-852.
Halstead, S. K., et al. (2008) Brain 131 (Pt 5): 1197-1208.
Hammerschmidt, D. E., et al. (1980) Lancet 1(8175): 947-949.
Hartung, H. P., et al. (1987) Neurology 37(6): 1006-1009.
Heideman, M. and T. E. Hugli (1984) J Trauma 24(12): 1038-1043.
Heimbach, L., et al. (2011) J Biol Chem 286(17): 15003-15009.
Hoesel, L. M., et al. (2007) J Immunol 178(12): 7902-7910.
Hopken, U., et al. (1996) Eur J Immunol 26(5): 1103-1109.
Howard, R. J., et al. (1988) Arch Surg 123(12): 1496-1501.
Howell et al. (2011), J. Clin. Invest. 121(4): 1429-1444.
Huang, Y. M., et al. (2015) Arthritis Rheumatol 67(10): 2780-2790.
Huber-Lang, M., et al. (2001) J Immunol 166(2): 1193-1199.
Humayun, S., et al. (2009) J Neuroimmunol 210(1-2): 52-62.
Jacob, A., B. Hack, et al. (2010) J Neuroimmunol 221(1-2): 46-52.
Jain, U., et al. (2013) Br J Pharmacol 168(2): 488-501.
Charles J., et al. (2013) Semin Nephrol 33(6): 557-564.
Johswich, K., et al. (2009) Inflamm Bowel Dis 15(12): 1812-1823.
Jose, P. J., et al. (1990) Ann Rheum Dis 49(10): 747-752.
Kallenberg, C. G. and P. Heeringa (2015) Mol Immunol 68(1): 53-56).
Kaplan, A. P. (2004) J Allergy Clin Immunol 114(3): 465-474.
Karsten, C. M. and J. Kohl (2012) Immunobiology 217(11): 1067-1079.
Kirklin, J. K., et al. (1983) J Thorac Cardiovasc Surg 86(6): 845-857.
Kohl, J. and J. E. Gessner (1999) Mol Immunol 36(13-14): 893-903.
Lawley, T. J., et al. (1979) J Immunol 123(3): 1382-1387.
Li, L., et al. (2015) Metabolism 64(5): 597-610.
Liu, L., et al. (2014) J Clin Immunol 34(2): 224-232.
Ma, R., et al. (2013) J Clin Immunol 33(1): 172-178.
Mantovani, S., et al. (2014) J Neuroimmunol 276(1-2): 213-218.
Marc, M. M., et al. (2004) Am J Respir Cell Mol Biol 31(2): 216-219.
Mavroidis, M., et al. (2015) Basic Res Cardiol 110(3): 27.
Mrowietz, U., et al. (2001) Exp Dermatol 10(4): 238-245.
Mueller, M., et al. (2013) Immunobiology 218(9): 1131-1138.
Mulligan, M. S., et al. (1996) J Clin Invest 98(2): 503-512.
Nataf, S., et al. (1999) J Immunol 162(7): 4018-4023.
Neuber, K., R. et al. (1991) Immunology 73(1): 83-87.
O'Barr, S. A., et al. (2001) J Immunol 166(6): 4154-4162.
Pandey, M. K. (2013) Curr Allergy Asthma Rep 13(6): 596-606.
Pandey et al. (2017) Nature 543: 108-112.
Pawaria, S., et al. (2014) J Immunol 193(7): 3288-3295.
Porcel, J. M., et al. (1995) Clin Immunol Immunopathol 74(3): 283-288.
Ricklin, D., et al. (2010), Nat Immunol 11(9): 785-797.
Riley, R. D., et al. (2000) J Thorac Cardiovasc Surg 120(2): 350-358.
Sarma, J. V. and P. A. Ward (2012) Cell Health Cytoskelet 4: 73-82.
Singhrao et al. (1999) Experimental Neurology 159, 362-376.
Smedegard, G., et al. (1989) Am J Pathol 135(3): 489-197.
Song, D., et al. (2015) Am J Reprod Immunol 74(4): 345-356.
Sprott, H., et al. (2000) J Rheumatol 27(2): 402-404.
Staab, E. B., et al. (2014) Int Immunopharmacol 21(2): 293-300.
"Handbook of Pharmaceutical Salts. Properties, Selection and Use.", P. Heinrich Stahl, Camille G. Wermuth (Eds.), Wiley-VCH, 2008.
Stevens, J. H., et al. (1986) J Clin Invest 77(6): 1812-1816.
Strachan, A. J., et al. (2000) J Immunol 164(12): 6560-6565.
Tofukuji, M., et al. (1998) J Thorac Cardiovasc Surg 116(6): 1060-1068.
Tsuji, R. F., et al. (2000) J Immunol 165(3): 1588-1598.
Unnewehr, H., et al. (2013) J Immunol 190(8): 4215-4225.
Wakerley, B. R. and N. Yuki (2015) Expert Rev Neurother 15(8): 847-849.
Wang, X. J., et al. (2007) Neurochem Int 50(1): 39-50.
Wang Y., et al., (2016) Cancer Discovery 6(9) 1022-1035.
Weisman, H. F., T. et al. (1990) Science 249(4965): 146-151.
Werfel, T., et al. (1997) Arch Dermatol Res 289(2): 83-86.
Woodruff, T. M., et al. (2003) J Immunol 171(10): 5514-5520.
Woodruff, T. M., et al. (2008) J Immunol 181(12): 8727-8734.
Wong EK, Kavanagh D, Transl Res. (2015) 165(2):306-20.
Zecher, D., et al. (2014) Arterioscler Thromb Vasc Biol 34(2): 313-320.
Yuan, G., et al. (2003) Chin Med J (Engl) 116(9): 1408-1412.
"Pharmaceutical Salts and Co-crystals", Johan Wouters and Luc Quéré (Eds.), RSC Publishing, 2012.
Xiao, H et al. (2014) J Am Soc Nephrol 25(2): 225-231.
Yan, S., et al. (2014) J Dermatol Sci 76(3): 240-245.
C.W. Pouton, Eur. J. Pharm. Sci. 11 (2000) S93-S98.
Cuiné J. et al. 2008.. J. Pharm. Sci. 97 (2), 995-1012.
E.T. Cole, "Liquid Filled Hard Gelatin Capsules", Pharm. Technol. Int.,Sep./Oct. 1989.
European Pharmacopeia Technical Guide (1999, p. 86).
Feeney et al.; Advanced Drug Delivery Reviews 101 (2016) 167-194.
H. Seager, Soft Gelatin Capsules, Pharm. Tech. 1985, 9(9), 84-104.
International Search Report received in Application No. PCT/EP2019/051245 dated Apr. 4, 2019, 2 pages.
Perry's Chemical Engineers' Handbook, 7th edition, Perry, R.H.; Green, D.W. McGraw-Hill 1997.
Polymorphism in the Pharmaceutical Industry (Ed. R. Hilfiker, VCH, 2006), Chapter 8: U.J. Griesser: The Importance of Solvates.
R.C. Rowe, P.J. Seskey, S.C. Owen, Handbook of Pharmaceutical Excipients, 5th edition, Pharmaceutical Press 2006.
Search Report received in Application No. PCT/EP2020/069230 dated Sep. 21, 2020, 2 pages.
The United States Pharmacopeia (USP) 23, General Information,Pharmaceutical Dosage Forms 1151: 1942-1943 (1995).
Umesh S. Kestur, Lynne S. Taylor; CrystEngComm, 2010, 12, 2390-2397.

(56) References Cited

OTHER PUBLICATIONS

Written Opinion received in Application No. PCT/EP2020/069230 dated Sep. 21, 2020, 5 pages.
Written Opinion received in International Application No. PCT/EP2019/051245, dated Apr. 4, 2019, 5 pages.
Zha H., et al. (2017) Oncoimmunology 6(10): e1349587.
Zhang et al., Clin J Am Soc Nephrol (2014) 9: 1876-1882.
Zwimer, J., et al. (1999) Mol Immunol 36(13-14): 877-884.
N.S. Merle et al. (2015), Front Immunol 6: 257.
NCT02222155.
D. R. Owen et al., Bioorg. Med. Chem. Lett. 19 (2009) 1702-1706.

\* cited by examiner

C5A RECEPTOR MODULATORS

CROSS REFERENCE TO REPLATED APPLICATIONS

This application is filing under 35 U.S.C. § 371 of international application number PCT/EP2019/051230, filed Jan. 18, 2019, which claims priority to application number PCT/EP2018/051278 filed on Jan. 19, 2018, the entire disclosures of each of which are hereby incorporated by reference.

The present invention relates to novel C5a receptor modulators of formula (I) and their use as pharmaceuticals. The invention also concerns related aspects including processes for the preparation of the compounds, pharmaceutical compositions containing one or more compounds of formula (I), and their use as C5a receptor modulators, especially in the treatment of vasculitic diseases or disorders, inflammatory diseases or disorders involving intravascular microvesicle release, immune complex (IC) diseases or disorders, neurodegenerative diseases or disorders, complement related inflammatory diseases or disorders, bullous diseases or disorders, diseases or disorders related to ischemia and/or ischemic reperfusion injury, inflammatory bowel diseases or disorders, and autoimmune diseases or disorders; as well as in contact sensitivity or an inflammation caused by contact with artificial surfaces; increased leukocyte and platelet activation (and infiltration to tissues thereof); pathologic sequelae associated to an intoxication or an injury such as a trauma, an hemorrhage, a shock, or surgery including transplantation, such sequeale including multiple organ failure (MOF), septic shock, shock due to intoxication, or acute lung inflammatory injury; pathologic sequelae associated with insulin-dependent diabetes mellitus; myocardial infarction or thrombosis; edema or an increased capillary permeability; reduction of coronary endothelial dysfunction induced by cardiopulmonary bypass and/or cardioplegia; or cancer.

C5aR1 (CD88) is a seven transmembrane bound G protein coupled receptor (GPCR) belonging to the rhodopsin like family, the gene of which is located on chromosome 19. It couples to pertussis toxin sensitive Gialpha2, Gialpha3 or pertussis toxin insensitive Galpha16 and initiates several downstream signaling pathways. C5aR1 is expressed on a number of immune cell types including monocytes, neutrophils, mast cells, basophils and eosinophils. In addition, it is expressed on many other cell types including hepatocytes, pulmonary and endothelial cells, microglia, neurons and renal glomerular cells. There are a number of ligands described which bind to the C5aR. These include C5a, C5adesArg and C5a+1 kDa. C5a is a central effector molecule of the complement system which itself is a complex enzymatic cascade evolved to crucially complement the immune system against invading pathogens, however, a significant body of evidence shows that inadvertent complement activation leads to many acute inflammatory disorders and autoimmune diseases (Ricklin, D., et al. (2010) "Complement: a key system for immune surveillance and homeostasis." Nat Immunol 11(9): 785-797) and specifically C5a has been shown to be elevated in a number of these inflammatory and autoimmune disorders. The complement system is activated through four pathways: The classical pathway, and the mannose binding lectin (MBL) pathway which is similar to the classical pathway except for the initial recognition and activation steps which recognize pathogens or antibody complexes. The alternative pathway is activated by binding of spontaneously activated complement C3 protein (C3b fragment) to pathogen surface. These three pathways all lead to the eventual formation of C3 convertases, which is the point where the 3 pathways converge (Guo, R. F. and P. A. Ward (2005) Annu Rev Immunol 23: 821-852). Subsequently C3 convertases lead to the formation of the anaphalatoxins C3a and C5a, together with other complement proteins required to produce the membrane attack complex. A fourth pathway, the extrinsic pathway involves plasma proteases (eg. elastase, thrombin) which act directly on C3 or C5 leading to the subsequent production of C3a and C5a. The anaphylatoxin C5a leads to the recruitment and activation of inflammatory cells of the innate and adaptive system, partly through the enhancement of cell adhesion molecule expression, the release of granule-based enzymes, delayed or enhanced apoptosis, phagocytosis, oxidative burst, histamine secretion and release and chemotaxis. In addition, it elicits the release of other pro inflammatory mediators, such as TNF-a, IL-1, IL-6, IL-8, prostaglandins, and leukotrienes) (N. S. Merle et al. (2015) "Complement System Part II: Role in Immunity." Front Immunol 6: 257), activation of endothelial cells and vascular permeability which may lead to events in which at the end thrombotic microangiopathy can occur. Therefore, C5a represents one of the most potent inflammatory molecules produced during immune responses and because of its fundamental biology it is potentially implicated in a very wide range of pathologies (Janeway's Immunobiology, $8^{th}$ edition (2012), Kenneth Murphy, Garland Science, p. 48-72).

C5a is central to the immune system and as such is important in key aspects of inflammation and tissue injury. In addition, there is considerable experimental evidence in the literature that implicates increased levels of C5a with a number of diseases and disorders, in particular in autoimmune and inflammatory diseases and disorders (Ricklin, D., et al. (2010) Nat Immunol 11(9): 785-797).

There is a large body of evidence about C5a and its receptor C5aR in contributing to vasculitic diseases, which demonstrate that C5a levels are elevated and give rise to leukocyte migration and subsequent inflammation which then leads to the eventual destruction of vessel walls (Charles J., et al (2013) Semin Nephrol 33(6): 557-564; Vasculitis, $2^{nd}$ Edition (2008), Edited by Ball and Bridges, Oxford University Press, pp 47-53; Huang, Y. M., et al. (2015) Arthritis Rheumatol 67(10): 2780-2790; Kallenberg, C. G. and P. Heeringa (2015) Mol Immunol 68(1): 53-56). Inhibition of the C5aR with a C5aR antagonist was effective at ameliorated anti-myeloperoxidase (MPO)-induced NCGN in mice expressing the human C5a receptor (Xiao, H. et al (2014) J Am Soc Nephrol 25(2): 225-231) and was confirmed to be effective in a phase II trial of patients with anti-neutrophil cytoplasmic antibody (ANCA) associated vasculitis (ClinicalTrials.gov Identifier NCT02222155). Therefore, a C5a antagonist may be useful to treat vasculitic diseases such as ANCA associated vasculitis, leukoclastic vasculitis, Wegener's granulomatosis, microscopic polyangiitis, Churg-Strauss syndrome, Henoch-Schönlein purpura, polyateritis nodosa, rapidly progressive glomerulonephritis (RPGN), cryoglobulinaemia, giant cell arteritis (GCA), Behcet's disease and Takayasu's arteritis (TAK).

C5a is generated when human blood makes contact with artificial surfaces, such as in cardiopulmonary bypass and hemodialysis procedures for instance on the artificial surface of the heart-lung machine in association with vascular surgery such as coronary artery bypass grafting or heart valve replacement or on surfaces of a kidney dialysis machine (Howard, R. J., et al. (1988) Arch Surg 123(12): 1496-1501; Kirklin, J. K., et al. (1983) J Thorac Cardiovasc Surg 86(6): 845-857; Craddock, P. R., et al. (1977) J Clin Invest 60(1): 260-264; Craddock, P. R., et al. (1977) N Engl J Med 296(14): 769-774) or in association with contact with other artificial vessels or container surfaces (e.g. ventricular assist devices, artificial heart machines, transfusion tubing, blood storage bags, plasmapheresis, plateletpheresis, and the like). As such C5aR antagonists could prove useful in preventing deleterious consequences of contact sensitivity and/or inflammation caused by contact with artificial surfaces. In addition, it may be useful in treating inflammatory disorders involving intravascular microvesicle release such as for example thrombotic microangiopathy and sickle cell disease (Zecher, D., et al. (2014) Arterioscler Thromb Vasc Biol 34(2): 313-320). A C5aR antagonist could also prove useful in certain hemotological diseases which are associated with activation of coagulation and fibrinolytic systems, disseminated intravascular coagulation (DIC), pernicious anemia, warm and cold autoimmune hemolytic anemia (AIHA), anti-phospholipid syndrome and its associated complications, arterial and venous thrombosis, pregnancy complications such as recurrent miscarriage and fetal death, preeclampsia, placental insufficiency, fetal growth restriction, cervical remodeling and preterm birth, idiopathic thrombocytopenic purpura (ITP), atypical hemolytic uremic syndrome (aHUS), paroxysmal nocturnal hemoglobinuria (PNH) and allergic transfusion reactions. The C5-specific humanized antibody, eculizumab is approved for paroxysmal nocturnal hemoglobinuria and atypical haemolytic uraemic syndrome (aHUS) (Wong E K, Kavanagh D, Transl Res. (2015) 165(2):306-20) and has been shown to be efficacious in renal transplant such as acute antibody-mediated kidney allograft rejection and cold agglutinin disease further supporting a potential role for C5aR antagonists in these diseases.

In myocardial ischemia-reperfusion injury C5a has been described to have an important function. Complement depletion reduced myocardial infarct size in mice (Weisman, H. F., T. et al. (1990) Science 249(4965): 146-151; De Hoog, V. C., et al. (2014) Cardiovasc Res 103(4): 521-529) and treatment with anti-C5a antibodies reduced injury in a rat model of hindlimb ischemia-reperfusion (Bless, N. M., et al. (1999) Am J Physiol 276(1 Pt 1): L57-63). Reperfusion injury during myocardial infarction was also markedly reduced in pigs that were re-treated with a monoclonal anti-C5a IgG (Amsterdam, E. A., et al. (1995) Am J Physiol 268(1 Pt 2): H448-457). A recombinant human C5aR antagonist reduces infarct size in a porcine model of surgical revascularization (Riley, R. D., et al. (2000) J Thorac Cardiovasc Surg 120(2): 350-358) providing evidence for the utility of a C5aR antagonist in these diseases. In addition, diseases related to ischemia/reperfusion injury, such as those resulting from transplants, including solid organ transplant, where C5a has been shown to play an important role (Farrar, C. A. and S. H. Sacks (2014) Curr Opin Organ Transplant 19(1): 8-13), could benefit from a C5aR antagonist as could related syndromes such as ischemic reperfusion injury, ischemic colitis and cardiac ischemia (Mueller, M., et al. (2013) Immunobiology 218(9): 1131-1138).

Furthermore, diseases where complement plays a role such as coronary thrombosis (Distelmaier, K., et al. (2009) Thromb Haemost 102(3): 564-572), vascular occlusion, post-surgical vascular reocclusion, atherosclerosis, traumatic central nervous system injury, arrhythmogenic cardiomyopathy (Mavroidis, M., et al. (2015) Basic Res Cardiol 110(3): 27) and Gaucher disease (Pandey et al. (2017) Nature 543: 108-112) could also benefit from a C5aR antagonist. Thus, C5aR modulators may be used preventatively in a patient at risk for myocardial infarction or thrombosis (i.e. a patient who has one or more recognized risk factors for myocardial infarction or thrombosis, such as, but not limited to, obesity, smoking, high blood pressure, hypercholesterolemia, previous or genetic history of myocardial infarction or thrombosis) in order reduce the risk of myocardial infarction or thrombosis. C5a causes increased capillary permeability and edema, leukocyte and platelet activation and infiltration to tissues, as well as bronchoconstriction (Sarma, J. V. and P. A. Ward (2012) Cell Health Cytoskelet 4: 73-82; Czermak, B. J., et al. (1998) J Leukoc Biol 64(1): 40-48). Administration of an anti-C5a monoclonal antibody was shown to reduce cardiopulmonary bypass and cardioplegia-induced coronary endothelial dysfunction (Tofukuji, M., et al. (1998) J Thorac Cardiovasc Surg 116(6): 1060-1068).

C5a and its receptor are also involved in the pathogenesis of acute respiratory distress syndrome (ARDS) (Hammerschmidt, D. E., et al. (1980) Lancet 1(8175): 947-949), Chronic Obstructive Pulmonary Disorder (COPD) (Marc, M. M., et al. (2004) Am J Respir Cell Mol Biol 31(2): 216-219), and multiple organ failure (MOF) (Huber-Lang, M., et al. (2001) "Role of C5a in multiorgan failure during sepsis." J Immunol 166(2): 1193-1199; Heideman, M. and T. E. Hugli (1984) J Trauma 24(12): 1038-1043). C5a increases monocyte production of two important proinflammatory cytokines TNF-α and IL-I which contribute to pathology in these diseases. C5a has also been shown to play an important role in the development of tissue injury, and particularly pulmonary injury, in animal models of septic shock (Smedegard, G., et al. (1989) Am J Pathol 135(3): 489-497; Unnewehr, H., et al. (2013) J Immunol 190(8): 4215-4225). In sepsis models using rats, pigs and non-human primates, anti-C5a antibodies administered to the animals before treatment with endotoxin or *E. coli* resulted in decreased tissue injury, as well as decreased production of IL-6 (Hopken, U., et al. (1996) Eur J Immunol 26(5): 1103-1109; Stevens, J. H., et al. (1986) J Clin Invest 77(6): 1812-1816). Inhibition of C5a with anti-C5a polyclonal antibodies has been shown to significantly improve survival rates in a caecal ligation/puncture model of sepsis in rats (Czermak, B. J., et al. (1999) Nat Med 5(7): 788-792). In the same sepsis model, anti-C5a antibodies were shown to inhibit apoptosis of thymocytes (Guo, R. F., et al. (2000) J Clin Invest 106(10): 1271-1280). Anti-C5a antibodies were also protective in a cobra venom factor model of lung injury in rats, and in immune complex-induced lung injury (Mulligan, M. S., et al. (1996) J Clin Invest 98(2): 503-512). The importance of C5a in immune complex-mediated lung injury was also shown in mouse (Bozic, C. R., et al. (1996) Science 273(5282): 1722-1725). Therefore, a C5aR antagonist could be of benefit in many inflammatory disorders and related conditions including neutropenia, sepsis, septic shock, stroke, inflammation associated with severe burns (Hoesel, L. M., et al. (2007) J Immunol 178(12): 7902-7910), osteoarthritis (Yuan, G., et al. (2003) Chin Med J (Engl) 116(9): 1408-1412), as well as acute (adult) respiratory distress syndrome (ARDS), chronic pulmonary obstructive disorder (COPD), bronchial asthma (Pandey, M. K. (2013) Curr Allergy Asthma Rep 13(6): 596-606), systemic inflammatory response syndrome (SIRS), tissue graft rejection, hyperacute rejection of transplanted organs, and the like, and multiple organ dysfunction syndrome (MODS). In addition, C5aR antagonists may be beneficial in treating pathologic sequelae associated with insulin-dependent diabetes mellitus such as diabetic kidney disease (Li, L., et al. (2015) Metabolism 64(5): 597-610), diabetic retinopathy (Cheng, L., et al. (2013). Invest Ophthalmol Vis Sci 54(13): 8191-8198), lupus nephropathy (Bao, L., et al. (2005) Eur J Immunol 35(8): 2496-2506), Heyman nephritis, membranous nephritis, and other forms of glomerulonephritis such as C3 glomerulopathy including dense deposit disease (DDD) (Zhang et al., Clin J Am Soc Nephrol (2014) 9: 1876-1882). Furthermore, the compound eculizumab has been shown to have potential utility for the treatment of neuromyelitis optica.

C5aR antagonists substantially reduced ovalbumin (OVA)-induced total cell (60%), neutrophil (66%) and eosinophil (65%) influxes in lavage fluid sampling suggesting that C5aR blockage might represent a novel therapeutic agent for reducing asthmatic outcomes (Staab, E. B., et al. (2014) Int Immunopharmacol 21(2): 293-300).

The complement system and in particular C5a contribute to the development of many bullous diseases among other things through activation of innate cells including mast cells and neutrophils (e.g. bullous pemphigoid, bullous acquisita, pemphigus foliaceus and pemphigus vulgaris). The detachment of epidermal basal keratinocytes from the underlying basement membrane is thought to be caused by autoantibodies to keratinocytes at the cutaneous basement membrane leading to blisters and a high influx of neutrophils in both the upper dermal layers and within the blister cavities. In experimental models a reduction of neutrophils or absence of complement (total or C5-selective) can inhibit formation of sub-epidermal blisters (Heimbach, L, et al. (2011) J Biol Chem 286(17): 15003-15009; Gammon, W. R. (1989) Immunol Ser 46: 509-525). Recent evidence has emerged to suggest that inhibition of C5a may prove beneficial in the treatment of the skin disorder hidradenitis suppurativa where an antibody against human C5a was shown to improve patient outcome in an open label phase II clinical trial. A C5a receptor antagonist may therefore be useful in bullous diseases.

Complement is believed to be important in inflammatory bowel disease (IBD) pathology and the C5aR is found to be expressed in the epithelial cells of the colon. (Cao, Q., et al. (2012) Am J Physiol Cell Physiol 302(12): C1731-1740). In addition, pharmacological inhibition of C5a activity by PMX205 a peptidic C5aR antagonist is efficacious in preventing DSS-induced colitis, providing further evidence that targeting CD88 in patients with IBD irritable bowel syndrome, ulcerative colitis, Crohn's disease, inflammatory bowel disease (IBD) (Johswich, K., et al. (2009) Inflamm Bowel Dis 15(12): 1812-1823) could be of therapeutic benefit (Woodruff, T. M., et al. (2003) J Immunol 171(10): 5514-5520; Jain, U., et al. (2013) Br J Pharmacol 168(2): 488-501).

There is a body of evidence suggesting a role for C5a and its receptor in pathologies of the CNS. C5aR expression is upregulated on reactive astrocytes, microglia, and endothelial cells in an inflamed human central nervous system (O'Barr, S. A., et al. (2001) J Immunol 166(6): 4154-4162; Gasque, P., et al. (1997) Am J Pathol 150(1): 31-41) and C5a has been reported to be involved in the pathogenesis of many neurodegenerative diseases, such as amyotrophic lateral sclerosis (ALS) (Mantovani, S., et al. (2014) J Neuroimmunol 276(1-2): 213-218; Humayun, S., et al. (2009) J Neuroimmunol 210(1-2): 52-62; Woodruff, T. M., et al. (2008) J Immunol 181(12): 8727-8734), Alzheimer disease (Fonseca, M. I., et al. (2013) J Neuroinflammation 10: 25; Ager, R. R., et al. (2010) J Neurochem 113(2): 389-401), Parkinson's disease (Wang, X. J., et al. (2007) Neurochem Int 50(1): 39-50) and Huntington's disease (Singhrao et al. (1999) Experimental Neurology 159, 362-376). Furthermore C5a is found to be elevated in the CSF of Guillain-Barre syndrome patients (Hartung, H. P., et al. (1987) Neurology 37(6): 1006-1009; Wakerley, B. R. and N. Yuki (2015) Expert Rev Neurother 15(8): 847-849) and an anti C5 antibody was found to be effective in reducing neuropathy in the mouse (Halstead, S. K., et al. (2008) Brain 131 (Pt 5): 1197-1208; Basta, M. and D. R. Branch (2014) Clin Exp Immunol 178 Suppl 1: 87-88). Also, inhibition of the C5a receptor alleviates experimental CNS lupus (Zwirner, J., et al. (1999) Mol Immunol 36(13-14): 877-884; Jacob, A., B. Hack, et al. (2010) J Neuroimmunol 221(1-2): 46-52). Therefore, C5aR antagonists provided herein may be to treat ALS, Alzheimer's disease, multiple sclerosis, Guillain-Barre syndrome, Parkinson's disease, Huntington's disease and also cognitive function decline associated with cardiopulmonary bypass surgery and related procedures in addition to central nervous system involvement in diseases such as SLE, Sjögren's syndrome and associated immunological profiles.

In many autoimmune diseases Immunoglobulin G-containing immune complex (IC) depositions are found. These contribute to the pathophysiology of the diseases which frequently manifest in different organs of the body including the kidneys, heart, lungs, liver, blood vessels, the nervous system and the skin. There are numerous such IC diseases and examples are systemic lupus erthyematosus (SLE), cryoglobulinemia, rheumatoid arthritis, Sjögren's syndrome (Lawley, T. J., et al. (1979) J Immunol 123(3): 1382-1387), Goodpasture syndrome (antiglomerular basement antibody disease), and hypersensitivity. Immune complexes are known to induce C5 convertases leading to C5a production which subsequently contributes to these diseases (Karsten, C. M. and J. Kohl (2012) Immunobiology 217(11): 1067-1079). In animal models reproducing the mechanisms of IC activation of complement, C5aR has been shown to play an important role. Studies show that C5aR deficient mice and the use of a peptidic C5aR antagonist result in protection from tissue injury induced by ICs. (Strachan, A. J., et al. (2000) J Immunol 164(12): 6560-6565; Kohl, J. and J. E. Gessner (1999) Mol Immunol 36(13-14): 893-903; Baumann, U., et al. (2000) J Immunol 164(2): 1065-1070). Therefore, inhibitors of C5aR could be useful to treat IC diseases including the autoimmune diseases rheumatoid arthritis (Jose, P. J., et al. (1990) Ann Rheum Dis 49(10): 747-752; Grant, E. P., et al. (2002) J Exp Med 196(11): 1461-1471; Yuan, G., et al. (2003) Chin Med J (Engl) 116(9): 1408-1412)), osteoarthritis, systemic lupus erythematosus (Porcel, J. M., et al. (1995) Clin Immunol Immunopathol 74(3): 283-288; Pawaria, S., et al. (2014) J Immunol 193(7): 3288-3295), lupus nephritis (Bao, L, et al. (2005) Eur J Immunol 35(8): 2496-2506), lupus glomerulonephritis and IgA nephropathy (Liu, L, et al. (2014) J Clin Immunol 34(2): 224-232), Heyman nephritis, membranous nephritis and other forms of glomerulonephritis, vasculitis, dermatomyositis (Fiebiger, E., et al. (1998) J Clin Invest 101(1): 243-251), pemphigus, systemic sclerosis (scleroderma) (Sprott, H., et al. (2000) J Rheumatol 27(2): 402-404), bronchial asthma, autoimmune hemolytic and thrombocytopenic states, Goodpasture's syndrome (and associated glomerulonephritis and pulmonary hemorrhage) (Ma, R., et al. (2013) J Clin Immunol 33(1): 172-178), immunovasculitis, and complement mediated thrombotic microangiopathies including atypical haemolytic uremic syndrome (Song, D., et al. (2015) Am J Reprod Immunol 74(4): 345-356; Davin, J. C., N. C. van de Kar (2015) Ther Adv Hematol 6(4): 171-185), mixed cryoglobulinemia, atopic dermatitis (Neuber, K., R. et al. (1991) Immunology 73(1): 83-87; Dang, L., et al. (2015) Mol Med Rep 11(6):

4183-4189), and chronic urticaria (Kaplan, A. P. (2004) J Allergy Clin Immunol 114(3): 465-474; Yan, S., et al. (2014) J Dermatol Sci 76(3): 240-245). Furthermore, the compound eculizumab has been shown to have potential utility for the treatment of myasthenia gravis, and anti-phospholipid syndrome.

C5a is present in psoriatic plaques and C5aR expression has also been reported in psoriasis where T cells, neutrophils mast cells and dendritic cells are involved in pathogenesis of the disease and are chemotactic to C5a (Diani, M., G. Altomare and E. Reali (2015) Autoimmun Rev 14(4): 286-292). Neutrophil accumulation under the stratum corneum is observed in the highly inflamed areas of psoriatic plaques, and psoriatic lesion (scale) extracts contain highly elevated levels of C5a and exhibit potent chemotactic activity towards neutrophils, an effect that can be inhibited by addition of a C5a antibody. Furthermore, T cells and neutrophils are chemo-attracted by C5a under certain conditions (Nataf, S., et al. (1999) J Immunol 162(7): 4018-4023; Tsuji, R. F., et al. (2000) J Immunol 165(3): 1588-1598; Werfel, T., et al. (1997) Arch Dermatol Res 289(2): 83-86; Mrowietz, U., et al. (2001) Exp Dermatol 10(4): 238-245) meaning C5aR antagonists may be of benefit in treating psoriasis. Furthermore, complement has been implicated in the pathogenesis of glaucoma (Howell et al. (2011), J. Clin. Invest. 121(4): 1429-1444). In addition, there is experimental evidence to suggest a beneficial role of C5aR antagonists in treating cancer with checkpoint blockers. For example, an antibody against the C5aR receptor (IPH5401) has been reported to be efficacious in muring models of cancer (web page Innate Pharma— IPH5401, 2018; www.innate-pharma.com/en/pipeline/iph5401-first-class-anti-c5ar-mab; Zah H., et al. (2017) Oncoimmunology 6(10): e1349587; Wang Y., et al., (2016) Cancer Discovery 6(9) 1022-1035).

Thus, C5a and C5aR are believed to be clinically implicated in vasculitic diseases or disorders, inflammatory diseases or disorders involving intravascular microvesicle release, immune complex (IC) diseases or disorders, neurodegenerative diseases or disorders, complement related inflammatory diseases or disorders, bullous diseases or disorders, diseases or disorders related to ischemia and/or ischemic reperfusion injury, inflammatory bowel diseases or disorders, and autoimmune diseases or disorders; as well as in contact sensitivity or an inflammation caused by contact with artificial surfaces; increased leukocyte and platelet activation (and infiltration to tissues thereof); pathologic sequelae associated to an intoxication or an injury such as a trauma, an hemorrhage, a shock, or surgery including transplantation, including multiple organ failure (MOF), septic shock, shock due to intoxication, or acute lung inflammatory injury; pathologic sequelae associated with insulin-dependent diabetes mellitus; myocardial infarction or thrombosis; edema or an increased capillary permeability; reduction of coronary endothelial dysfunction induced by cardiopulmonary bypass and/or cardioplegia, or cancer.

There is therefore a requirement for new small organic molecule modulators of the C5a receptor (C5aR), especially antagonists of the C5aR, that could be useful for inhibiting pathogenic events associated with elevated levels of C5a and/or with C5aR activation.

Certain benzimidazolone derivatives as chymase inhibitors are disclosed in WO2008/147697. 4-(Benzimidazol-1-yl)-piperidines as sodium channel inhibitors are disclosed in WO2003/037890. Certain 3-substituted piperidines comprising urea functionality are disclosed as analgesics in WO2001/068604. Benzimidazolone derivatives as phosphodiesterase inhibitors are disclosed in WO2001/005770.

1-Benzyl-1,3-dihydro-2H-benzimidazol-2-one derivatives as vasopressin and/or oxytocin receptor ligands are disclosed in U.S. Pat. No. 5,661,169. D. R. Owen et al., Bioorg. Med. Chem. Lett. 19 (2009) 1702-1706 discloses the compound 3-(1-(4-aminopyridin-2-yl)piperidin-4-yl)-1-benzyl-1,3-dihydro-2H-imidazo[4,5-b]pyridin-2-one in a series of 2,4-diaminopyridine S-opioid receptor agonists, which however had pronounced activity in the hERG binding assay.

The present invention provides cyclic urea derivatives of formula (I) which are modulators of the C5a receptor, and are useful for the prevention or treatment of diseases which respond to the C5a receptor.

1) A first aspect of the invention relates to compounds of the formula (I)

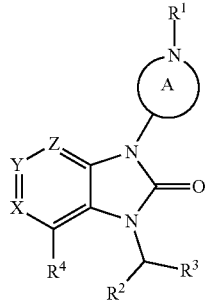

Formula (I)

wherein
ring A represents a saturated 4- to 7-membered monocyclic carbocyclic ring containing the ring nitrogen atom to which $R^1$ is attached, wherein said ring independently is unsubstituted, or mono-, or di-substituted wherein the substituents are independently selected from $(C_{1-3})$alkyl (especially methyl), fluoro, or $(C_{1-4})$alkoxy-carbonyl (especially ethoxy-carbonyl) [especially such ring A is azetidin-1,3-diyl, pyrrolidin-1,3-diyl, 4-methyl-pyrrolidin-1,3-diyl, piperidin-1,3-diyl, piperidin-1,4-diyl, 3-fluoro-piperidin-1,4-diyl, 2-methyl-piperidin-1,4-diyl, 3-methyl-piperidin-1,4-diyl, 3-(ethoxycarbonyl)-piperidin-1,4-diyl, 3,3-dimethyl-piperidin-1,4-diyl, azepan-1,4-diyl]; or
ring A represents a saturated 7- or 8-membered bridged bi-cyclic carbocyclic ring containing the ring nitrogen atom to which $R^1$ is attached, wherein said ring is unsubstituted [especially such ring is 2-aza-bicyclo[2.2.1]heptane-2,5-diyl, 3-aza-bicyclo[3.1.1]heptane-3,6-diyl];
X and Z independently represent $CR^5$ or N; and Y represents $CR^5$; or, in case both X and Z represent CH, Y may in addition represent N; wherein each $R^5$ independently represents hydrogen, or $(C_{1-3})$alkyl (especially methyl) [notably one of X and Z represents CH or N; the other represents CH; and Y represents $CR^5$, wherein especially $R^5$ represents hydrogen];
$R^1$ represents
 $(C_{1-4})$alkyl (especially methyl, isopropyl);
 —CO—$R^{11}$ wherein $R^{11}$ represents $(C_{1-4})$alkyl; $(C_{1-4})$alkoxy; phenyl, phenoxy; $(C_{3-6})$cycloalkyl; or $(C_{3-6})$cycloalkoxy optionally containing one ring oxygen and optionally mono-substituted with methyl or trifluoromethyl [especially such group —CO—$R^{11}$ is tert.-butyl-carbonyl, methoxycarbonyl, ethoxycarbonyl, iso-propoxycarbonyl, n-butoxycarbonyl, tert.-butoxycarbonyl, oxetan-3-yl-oxy-carbonyl, (3-methyloxetan-3-yl)-oxy-carbonyl, (3-trifluoromethyl-oxetan-3-yl)-oxy-carbonyl, phenylcarbonyl, phenoxycarbonyl, cyclopropylcarbonyl];

benzyl wherein the phenyl ring of said benzyl is optionally mono- or di-substituted with halogen [especially 2,4-dichlorobenzyl]; or phenyl, or 5- or 6-membered heteroaryl (especially pyrazolyl, oxadiazolyl, pyridinyl, pyridazinyl, pyrimidinyl); wherein said phenyl or 5- or 6-membered heteroaryl independently is unsubstituted, mono-, di- or tri-substituted, wherein the substituents are independently selected from $(C_{1-4})$alkyl (especially methyl, isopropyl);
$(C_{1-4})$alkoxy (especially methoxy, n-butyloxy);
$(C_{1-3})$fluoroalkyl (especially trifluoromethyl);
$(C_{1-3})$fluoroalkoxy (especially trifluoromethoxy);
halogen (especially fluoro, chloro, bromo);
cyano;
nitro;
hydroxy;
hydroxy-$(C_{1-3})$alkyl (especially 1-hydroxyethyl, hydroxymethyl, 1-hydroxy-1-methyl-ethyl);
$(C_{1-4})$alkoxy-$(C_{1-3})$alkyl (especially 1-methoxyethyl);
hydroxy-$(C_{2-3})$alkoxy (especially 2-hydroxy-ethoxy);
$(C_{1-4})$alkoxy-$(C_{2-3})$alkoxy (especially 2-methoxy-ethoxy);
$(C_{3-6})$cycloalkyl-$X^{12}$—, wherein $X^{12}$ represents a direct bond, —O—, or —$(C_{1-3})$alkylene-O—, and wherein the $(C_{3-6})$cycloalkyl independently contains one optional ring oxygen [especially such group $(C_{3-6})$cycloalkyl-$X^{12}$— is cyclopropyl, cyclopropyl-oxy, cyclobutyl-oxy, oxetan-3-yl-oxy, cyclopropyl-methoxy, or tetrahydropyran-4-yl-oxy];
$R^{13}$—CO—$X^{13}$—, wherein $X^{13}$ represents a direct bond or $(C_{1-3})$alkylene, and $R^{13}$ represents hydrogen or $(C_{1-4})$alkyl (especially such group $R^{13}$—CO—$X^{13}$ is formyl, acetyl, 2-oxo-ethyl);
3-(morpholin-4-yl)-prop-1-ynyl;
$R^{14a}R^{14b}N$—$X^{14}$—, wherein $X^{14}$ represents a direct bond or $(C_{1-3})$alkylene; and wherein $R^{14a}$ and $R^{14b}$ independently represent hydrogen, $(C_{1-4})$alkyl, hydroxy-$(C_{2-4})$alkyl, $(C_{1-3})$alkoxy-$(C_{2-4})$alkyl; or $R^{14a}$ and $R^{14b}$ together with the nitrogen to which they are attached to form a 4- to 6-membered saturated ring optionally containing one additional ring heteroatom selected from oxygen and nitrogen; and wherein said ring is optionally mono-substituted with $(C_{1-4})$alkyl (especially methyl), hydroxy, $(C_{1-4})$alkoxy (especially methoxy), or dimethyl-amino,

[especially such group $R^{14a}R^{14b}N$—$X^{14}$— is amino, methylamino-methyl, dimethylamino-methyl, [(2-hydroxyethyl)-methylamino]-methyl, [(2-hydroxyethyl)-ethylamino]-methyl, [(2-methoxy-1-methyl-ethyl)-amino]-methyl, [(2-methoxyethyl)-methylamino]-methyl, [di-(2-hydroxyethyl)-amino]-methyl, (azetidin-1-yl)-methyl, (pyrrolidin-1-yl)-methyl, (piperidin-1-yl)-methyl, morpholin-4-yl, piperazin-1-ylmethyl, (morpholin-4-yl)-methyl, 2-(morpholin-4-yl)-ethyl, 3-(morpholin-4-yl)-propyl, (3-methoxy-azetidin-1-yl)-methyl, 1-(3-methoxy-azetidin-1-yl)-ethyl, (1-methyl-piperazin-4-yl)-methyl, (4-hydroxypiperidin-1-yl)-methyl, (4-methoxypiperidin-1-yl)-methyl, (3-methoxy-pyrrolidin-1-yl)-methyl, (4-dimethylamino-piperidin-1-yl)-methyl]; or benzyloxy, wherein the phenylring of benzyloxy is optionally mono- or di-substituted with halogen or methyl;

$R^2$ represents phenyl, or 5- or 6-membered heteroaryl (notably 6-membered heteroaryl; in particular thiazolyl, pyridinyl, pyrimidinyl, pyrazinyl, pyridazinyl); wherein said phenyl or 5- or 6-membered heteroaryl independently is mono-, di- or tri-substituted (especially mono-substituted, in particular in ortho position with regard to the point of attachment of the rest of the molecule), wherein the substituents are independently selected from $(C_{1-4})$alkyl (especially methyl, isopropyl);
$(C_{1-4})$alkoxy (especially methoxy, isopropoxy);
$(C_{1-3})$fluoroalkyl (especially trifluoromethyl);
$(C_{1-3})$fluoroalkoxy (especially trifluoromethoxy);
halogen (especially chloro, fluoro); or
$(C_{3-6})$cycloalkyl-$X^{21}$—, wherein $X^{21}$ represents a direct bond, —O—, or —$(C_{1-3})$alkylene-O—, and wherein the $(C_{3-6})$cycloalkyl independently contains one optional ring oxygen [especially such group $(C_{3-6})$cycloalkyl-$X^{21}$— is cyclopropyl, cyclopropyl-oxy, cyclobutyl-oxy, oxetan-3-yl-oxy, cyclopropyl-methoxy;

$R^3$ represents hydrogen, or $(C_{1-3})$alkyl (especially methyl); and $R^4$ represents
$(C_{1-4})$alkyl (especially methyl);
hydroxy-$(C_{1-3})$alkyl (especially hydroxymethyl);
—O—$R^{41}$, wherein $R^{41}$ represents
hydrogen;
$(C_{1-4})$alkyl (especially methyl);
$(C_{2-4})$alkyl which is substituted with one or two hydroxy (especially 2-hydroxyethyl, 2,3-dihydroxypropyl);
$R^{41a}R^{41b}N$—$(C_{2-3})$alkylene-, wherein $R^{41a}$ and $R^{41b}$ independently represent hydrogen or $(C_{1-4})$alkyl (especially such group is 2-dimethylamino-ethyl); or
$(C_{4-7})$heterocyclyl-$X^{41}$—, wherein $X^{41}$ represents a direct bond or $(C_{1-3})$alkylene, and wherein the $(C_{4-7})$heterocyclyl independently contains one or two ring heteroatoms independently selected from nitrogen and oxygen; wherein said $(C_{4-7})$heterocyclyl independently is unsubstituted, or mono-, or di-substituted, wherein the substituents are independently selected from:
$(C_{1-4})$alkyl (especially methyl); and/or
$(C_{1-4})$alkoxy-carbonyl attached to a ring nitrogen atom having a free valency; [especially such $(C_{4-7})$heterocyclyl-$X^{41}$— group is oxetan-3-yl, 1-methyl-pyrrolidin-3-yl, 2,2-dimethyl-dioxolan-4-yl-methyl, 2-morpholin-4-yl-ethyl, 1-tert-butoxy-carbonyl-piperidin-4-yl, piperidin-4-yl];
—$NR^{42a}R^{42b}$ wherein $R^{42a}$ and $R^{42b}$ independently represent hydrogen, $(C_{1-4})$alkyl, $(C_{1-3})$alkoxy-$(C_{2-3})$alkyl, hydroxy-$(C_{2-3})$alkyl, or $R^{42a}$ and $R^{42b}$ together with the nitrogen to which they are attached form a 4- to 7-membered saturated ring optionally containing one further ring heteroatom selected from oxygen and nitrogen, wherein said ring is unsubstituted or mono-substituted with $(C_{1-3})$alkyl (especially methyl), or $(C_{1-3})$alkoxy (especially methoxy) [especially such group —$NR^{42a}R^{42b}$ is (2-hydroxyethyl)-amino, (2-hydroxyethyl)-methyl-amino, (2-methoxyethyl)-amino, morpholin-4-yl, 3-methoxy-azetidinyl, or 4-methyl-piperazin-1-yl]; or —CO—$R^{43}$ wherein $R^{43}$ represents $(C_{1-4})$alkoxy (especially methoxy); or —$NR^{43a}R^{43b}$ wherein $R^{43a}$ and $R^{43b}$ independently represent hydrogen, $(C_{1-4})$alkyl (especially methyl), $(C_{1-3})$alkoxy-$(C_{2-3})$alkyl (especially 2-methoxy-ethyl), or hydroxy-$(C_{2-3})$alkyl (especially 2-hydroxy-ethyl); [especially such group —CO—$R^{43}$ is methoxycarbonyl, carbamoyl, methylcarbamoyl, dimethylcarbamoyl, hydroxyethylcarbamoyl, methoxyethylcarbamoyl].

The compounds of formula (I) may contain one or more further stereogenic or asymmetric centers, such as one or more additional asymmetric carbon atoms. The compounds of formula (I) may thus be present as mixtures of stereoisomers or preferably as pure stereoisomers. Mixtures of stereoisomers may be separated in a manner known to a person skilled in the art.

In case a particular compound (or generic structure) is designated as (R)- or (S)-enantiomer/as having an absolute (R)- or (S)-configuration, such designation is to be understood as referring to the respective compound (or generic structure) in enriched, especially essentially pure, enantiomeric form. Likewise, in case a specific asymmetric center in a compound is designated as being in (R)- or (S)-configuration or as being in a certain relative configuration, such designation is to be understood as referring to the compound that is in enriched, especially essentially pure, form with regard to the respective configuration of said asymmetric center. In analogy, cis- or trans-designations (or (R*,R*) designations) are to be understood as referring to the respective stereoisomer of the respective relative configuration in enriched form, especially in essentially pure form.

The term "enriched", when used in the context of stereoisomers, is to be understood in the context of the present invention to mean that the respective stereoisomer is present in a ratio of at least 70:30, especially of at least 90:10 (i.e., in a purity of at least 70% by weight, especially of at least 90% by weight), with regard to the respective other stereoisomer/the entirety of the respective other stereoisomers.

The term "essentially pure", when used in the context of stereoisomers, is to be understood in the context of the present invention to mean that the respective stereoisomer is present in a purity of at least 95% by weight, especially of at least 99% by weight, with regard to the respective other stereoisomer/the entirety of the respective other stereoisomers.

In some instances, the compounds of formula (I) may contain tautomeric forms. Such tautomeric forms are encompassed in the scope of the present invention. For example, in case the present compounds may contain heteroaromatic aromatic rings containing unsubstituted ring nitrogen atoms having a free valency such as pyrazolyl, such rings may be present in tautomeric forms. For example, the group pyrazol-3-yl represents the tautomeric forms 1H-pyrazol-3-yl and 2H-pyrazol-3-yl.

The present invention also includes isotopically labelled, especially $^2$H (deuterium) labelled compounds of formula (I), which compounds are identical to the compounds of formula (I) except that one or more atoms have each been replaced by an atom having the same atomic number but an atomic mass different from the atomic mass usually found in nature. Isotopically labelled, especially $^2$H (deuterium) labelled compounds of formula (I) and salts thereof are within the scope of the present invention. Substitution of hydrogen with the heavier isotope $^2$H (deuterium) may lead to greater metabolic stability, resulting e.g. in increased in-vivo half-life and/or reduced dosage requirements, and/or may lead to a modified metabolism pathway, resulting e.g. in an improved safety profile. In one embodiment of the invention, the compounds of formula (I) are not isotopically labelled, or they are labelled only with one or more deuterium atoms. In a sub-embodiment, the compounds of formula (I) are not isotopically labelled at all. Isotopically labelled compounds of formula (I) may be prepared in analogy to the methods described hereinafter, but using the appropriate isotopic variation of suitable reagents or starting materials.

In this patent application, a bond drawn as a dotted line shows the point of attachment of the radical drawn. For example, the radical drawn below

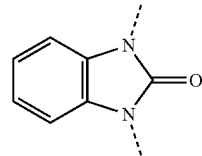

is the 2-oxo-2,3-dihydro-1H-benzo[d]imidazol-1,3-diyl group.

In addition, it is well understood that in certain instances the drawn structure of the present compounds may represent several tautomers and such tautomers are comprised in the scope of the present invention:

For example compounds of formula (I) wherein Z and Y are CH, X is N, and R4 is hydroxy: i.e. compounds wherein the fragment:

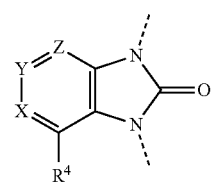

represents

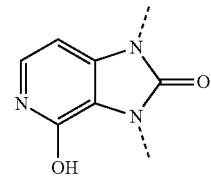

are understood as being one of two possible tautomeric forms. Such compounds, thus, also comprise the compounds wherein said fragment represents the corresponding tautomer:

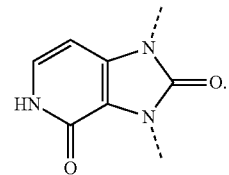

Where the plural form is used for compounds, salts, pharmaceutical compositions, diseases and the like, this is intended to mean also a single compound, salt, or the like.

Any reference to compounds of formula (I) according to embodiments 1) to 25) is to be understood as referring also to the salts (and especially the pharmaceutically acceptable salts) of such compounds, as appropriate and expedient.

The term "pharmaceutically acceptable salts" refers to salts that retain the desired biological activity of the subject compound and exhibit minimal undesired toxicological effects. Such salts include inorganic or organic acid and/or base addition salts depending on the presence of basic and/or acidic groups in the subject compound. For reference see for example "Handbook of Pharmaceutical Salts. Properties, Selection and Use.", P. Heinrich Stahl, Camille G. Wermuth (Eds.), Wiley-VCH, 2008; and "Pharmaceutical Salts and Co-crystals", Johan Wouters and Luc Quéré (Eds.), RSC Publishing, 2012.

Definitions provided herein are intended to apply uniformly to the compounds of formula (I), as defined in any one of embodiments 1) to 25), and, mutatis mutandis, throughout the description and the claims unless an otherwise expressly set out definition provides a broader or narrower definition. It is well understood that a definition or preferred definition of a term defines and may replace the respective term independently of (and in combination with) any definition or preferred definition of any or all other terms as defined herein.

The term "halogen" means fluorine, chlorine, or bromine, preferably fluorine or chlorine.

The term "alkyl", used alone or in combination, refers to a saturated straight or branched chain hydrocarbon group containing one to six carbon atoms. The term "$(C_{x-y})$alkyl" (x and y each being an integer), refers to an alkyl group as defined before, containing x to y carbon atoms. For example a $(C_{1-6})$alkyl group contains from one to six carbon atoms. Examples of alkyl groups are methyl, ethyl, propyl, isopropyl, butyl, isobutyl, tert.-butyl, 3-methyl-butyl, 2,2-dimethyl-propyl and 3,3-dimethyl-butyl. For example a $(C_{1-4})$alkyl group contains from one to four carbon atoms. Examples of alkyl groups are methyl, ethyl, propyl, isopropyl, butyl, isobutyl, sec-butyl and tert.-butyl. For avoidance of any doubt, in case a group is referred to as e.g. propyl or butyl, it is meant to be n-propyl, respectively n-butyl. Preferred are methyl, ethyl and isopropyl. Most preferred is methyl. Examples of $(C_{1-3})$alkyl groups as used for the substituents at ring A (without $R^1$) is methyl. Examples of $(C_{1-4})$alkyl groups as used for $R^1$ are methyl and isopropyl. An example of $R^{11}$ in —CO—$R^{11}$ is tert-butyl, an example of a $(C_{1-4})$alkyl substituent at phenyl in $R^1$ is methyl, an example of $(C_{1-4})$alkyl of $R^{14a}$ or $R^{14b}$ is methyl and ethyl. Examples of $(C_{1-4})$alkyl groups as used for $R^2$ are methyl and isopropyl. Examples of $(C_{1-3})$alkyl groups as used for $R^3$ is methyl. An example of $(C_{1-4})$alkyl groups as used for $R^4$, $R^{41}$, $R^{41a}$, $R^{41b}$, $R^{43a}$ and $R^{43b}$ is methyl.

The term "—$(C_{x-y})$alkylene-", used alone or in combination, refers to bivalently bound alkyl group as defined before containing x to y carbon atoms. Preferably, the points of attachment of a —$(C_{1-y})$alkylene group are in 1,1-diyl, in 1,2-diyl, or in 1,3-diyl arrangement. Preferably, the points of attachment of a —$(C_{2-y})$alkylene group are in 1,2-diyl or in 1,3-diyl arrangement. Preferred alkylene groups are methylene, ethylene and propylene. A —$(C_0)$alkylene-group is absent and refers to a direct bond.

Alkylene-oxy linker groups —$(C_{1-3})$alkylene-O— as used for example in the substituents $(C_{3-6})$cycloalkyl-$X^{12}$— or $(C_{3-6})$cycloalkyl-$X^{21}$— are to be read from left to right, i.e. they refer to the respective $(C_{3-6})$cycloalkyl-$(C_{1-3})$alkylene-O— groups. An example for $(C_{3-6})$cycloalkyl-$(C_{1-3})$alkylene-O— is cyclopropyl-methoxy.

Alkylene-amino linker groups $R^{14a}R^{14b}N$—$X^{14}$—, wherein $X^{14}$ represents $(C_{1-3})$alkylene, are used for example in the substituents methylamino-methyl, dimethylamino-methyl, (2-hydroxy-ethyl)-methyl-amino]-methyl, (2-methoxy-1-methyl-ethylamino)-methyl, (2-methoxy-ethyl)-methyl-amino]-methyl, [ethyl-(2-hydroxy-ethyl)-amino]-methyl, and [bis-(2-hydroxy-ethyl)-amino]-methyl. Further, alkylene-amino linker groups $R^{14a}R^{14b}N$—$X^{14}$—, wherein $X^{14}$ represents $(C_{1-3})$alkylene and $R^{14a}$ and $R^{14b}$ together with the nitrogen to which they are attached to form a 4- to 6-membered saturated ring optionally containing one additional ring heteroatom selected from oxygen and nitrogen, are used for example in the substituents azetidin-1-ylmethyl, pyrrolidin-1-ylmethyl, piperidin-1-ylmethyl, piperazin-1-ylmethyl, morpholin-4-ylmethyl, morpholin-4-yl-ethyl, morpholin-4-yl-propyl, 1-methyl-piperazin-4-yl)-methyl, 3-methoxy-azetidin-1-ylmethyl, 4-hydroxy-piperidin-1-ylmethyl, 3-methoxy-pyrrolidin-1-ylmethyl, 4-methoxy-piperidin-1-ylmethyl, and 4-dimethylamino-piperidin-1-ylmethyl.

The term "alkoxy", used alone or in combination, refers to an alkyl-O— group wherein the alkyl group is as defined before. The term "$(C_{x-y})$alkoxy" (x and y each being an integer) refers to an alkoxy group as defined before containing x to y carbon atoms. For example a $(C_{1-4})$alkoxy group means a group of the formula $(C_{1-4})$alkyl-O— in which the term "$(C_{1-4})$alkyl" has the previously given significance. Examples of alkoxy groups are methoxy, ethoxy, n-propoxy, isopropoxy, n-butoxy, isobutoxy, sec.-butoxy and tert.-butoxy. Preferred are ethoxy and especially methoxy. Examples of $(C_{1-4})$alkoxy groups as used for $R^{11}$ in —CO—$R^{11}$ are methoxy, ethoxy, isopropoxy, n-butyloxy and tert-butoxy. An example of a $(C_{1-4})$alkoxy substituent at phenyl in $R^1$ is methoxy and n-butyloxy. Examples of $(C_{1-4})$alkoxy groups as used for $R^2$ are methoxy and isopropoxy. An example of a $(C_{1-4})$alkoxy group as used for $R^{43}$ is methoxy.

The term "hydroxy-$(C_{1-3})$alkyl" relates to an alkyl group wherein a hydroxyl group can be attached to any of the carbon atoms of the alkyl group, for instance 1-hydroxyethyl, 2-hydroxyethyl, hydroxymethyl, 1-hydroxy-1-methyl-ethyl. An example for "hydroxy-$(C_{2-4})$alkyl" is 2-hydroxyethyl.

The term "$(C_{1-4})$alkoxy-$(C_{1-3})$alkyl" relates to an alkyl group wherein an alkoxy group can be attached to any of the carbon atoms of the alkyl group, for instance 1-methoxyethyl, 2-methoxy-1-methyl-ethyl and 2-methoxyethyl.

The term "hydroxyl-$(C_{2-3})$alkoxy" relates to an alkoxy group wherein a hydroxyl group can be attached to any of the carbon atoms of the alkoxy group, for instance 2-hydroxy-ethoxy.

The term "$(C_{1-4})$alkoxy-$(C_{2-3})$alkoxy" relates to a first alkoxy group wherein a second alkoxy group can be attached to any of the carbon atoms of the first alkoxy group, for instance 2-methoxy-ethoxy.

The term "alkynyl", used alone or in combination, refers to a straight or branched hydrocarbon chain containing two to five carbon atoms and one carbon-carbon triple bond. The term "$(C_{x-y})$alkynyl" (x and y each being an integer), refers to an alkynyl group as defined before containing x to y carbon atoms. For example a $(C_2-C_5)$alkynyl group contains from two to five carbon atoms. An example of an alkynyl group is prop-2-yn-1-yl. An example for an alkynyl group as used for the phenyl substituent in $R^1$ is 3-morpholin-4-yl-prop-1-ynyl.

The term "fluoroalkyl", used alone or in combination, refers to an alkyl group as defined before containing one to three carbon atoms in which one or more (and possibly all) hydrogen atoms have been replaced with fluorine. The term "$(C_{x-y})$fluoroalkyl" (x and y each being an integer) refers to a fluoroalkyl group as defined before containing x to y carbon atoms. For example a $(C_{1-3})$fluoroalkyl group contains from one to three carbon atoms in which one to seven hydrogen atoms have been replaced with fluorine. Representative examples of fluoroalkyl groups include trifluoromethyl, 2-fluoroethyl, 2,2-difluoroethyl and 2,2,2-trifluoroethyl. Preferred are $(C_1)$fluoroalkyl groups, especially trifluoromethyl.

The term "fluoroalkoxy", used alone or in combination, refers to an alkoxy group as defined before containing one to three carbon atoms in which one or more (and possibly all) hydrogen atoms have been replaced with fluorine. The term "$(C_{x-y})$fluoroalkoxy" (x and y each being an integer) refers to a fluoroalkoxy group as defined before containing x to y carbon atoms. For example a $(C_{1-3})$fluoroalkoxy group contains from one to three carbon atoms in which one to seven hydrogen atoms have been replaced with fluorine. Representative examples of fluoroalkoxy groups include trifluoromethoxy, difluoromethoxy, 2-fluoroethoxy, 2,2-difluoroethoxy and 2,2,2-trifluoroethoxy. Preferred are $(C_1)$fluoroalkoxy groups, especially trifluoromethoxy.

The term "cyano" refers to a group —CN.

The term "cycloalkyl", used alone or in combination, refers to a saturated monocyclic hydrocarbon ring containing three to six carbon atoms. The term "$(C_{x-y})$cycloalkyl" (x and y each being an integer), refers to a cycloalkyl group as defined before containing x to y carbon atoms. For example a $(C_{3-6})$cycloalkyl group contains from three to six carbon atoms. Examples of cycloalkyl groups are cyclopropyl, cyclobutyl, cyclopentyl, cyclohexyl, and cycloheptyl. Preferred are cyclopropyl, cyclopentyl and cyclohexyl; especially cyclopropyl. An example of $(C_{3-6})$cycloalkyl groups as used for the group $R^{11}$ is cyclopropyl. An example for a $(C_{3-6})$cycloalkyl group as used for the phenyl substituent in $(C_{3-6})$cycloalkyl-$X^{12}$— is cyclopropyl, examples for a $(C_{3-6})$cycloalkyl group as used for the phenyl or heteroaryl substituent in $(C_{3-6})$cycloalkyl-$X^{21}$— are cyclopropyl and cyclobutyl.

The term "$(C_{x-y})$cycloalkyl-$(C_{x-y})$alkyl-O—" refers to a $(C_{x-y})$cycloalkyl group as defined before, which is linked through a $(C_{x-y})$alkylene-O— group as defined before to the rest of the molecule. A particular example of such groups is cyclopropyl-methoxy.

The term "$(C_{3-6})$cycloalkyl optionally containing one ring oxygen atom", used alone or in combination, refers to a cycloalkyl group as defined before. In addition, one ring carbon atom of said cycloalkyl may be replaced by an oxygen atom. Examples of such groups are especially cycloalkyl groups such as cyclopropyl, cyclobutyl, cyclopentyl, and cyclohexyl; as well as oxygen containing groups such as oxetanyl, tetrahydrofuranyl, and tetrahydro-2H-pyranyl.

The term "heterocyclyl", used alone or in combination, and if not explicitly defined in a more narrow way, refers to a saturated monocyclic hydrocarbon ring containing one or two ring heteroatoms independently selected from nitrogen and oxygen (especially one nitrogen atom, two nitrogen atoms, one nitrogen atom and one oxygen atom, one oxygen atom, or two oxygen atoms; preferably such heterocyclyl contains one or two oxygen atoms, or one nitrogen atom). The term "$(C_{x-y})$heterocyclyl" refers to such a heterocyclyl group containing x to y ring atoms. Heterocyclyl groups are unsubstituted or substituted as explicitly defined. Examples of heterocyclyl groups as used for the group $R^{41}$ wherein $R^{41}$ represents $(C_4)$heterocyclyl-$X^{41}$— are oxetan-3-yl, 1-methyl-pyrrolidin-3-yl, piperidin-4-yl, 2,2-dimethyl-dioxolan-4-yl (notably 2,2-dimethyl-dioxolan-4-yl-methyl), morpholin-4-yl (notably morpholin-4-yl-ethyl) and 1-tert-butoxy-carbonyl-piperidin-4-yl.

The term "$(C_{x-y})$ heterocyclyl-$(C_{x-y})$alkyl" refers to a $(C_{x-y})$heterocyclyl group as defined before, which is linked through a $(C_{x-y})$alkylene group as defined before to the rest of the molecule. For the $(C_{4-7})$heterocyclyl-$(C_{1-3})$alkyl groups as used for $R^{41}$ examples of —$(C_{1-3})$alkylene-groups are methylene, and ethylene. Examples of heterocyclyl groups part of such $(C_{4-7})$heterocyclyl-$(C_{1-3})$alkylene groups as used for the group $R^{41}$ wherein $R^{41}$ represents $(C_{4-7})$heterocyclyl-$X^{41}$— are 2,2-dimethyl-dioxolan-4-yl-methylene and morpholin-4-yl-ethylene.

The substituent phenyl of $R^1$ independently is unsubstituted, mono-, di or trisubstituted. Examples for mono-, di or trisubstituted phenyl as $R^1$ are 2,6-di-methyl-phenyl, 2-methoxy-phenyl, 2-n-butyloxy-phenyl, 2,6-di-methoxy-phenyl, 2-methoxy-ethoxy-phenyl, 2-methoxy-6-methyl-phenyl, 2-bromo-6-fluoro-phenyl, 2,6-di-fluoro-phenyl, 2-fluoro-phenyl, 2-fluoro-6-methoxy-phenyl, 2-fluoro-6-(1-methoxy-ethyl)-phenyl, 2-fluoro-6-methyl-phenyl, 2-Fluoro-6-(3-morpholin-4-yl-prop-1-ynyl)-phenyl, 2-fluoro-6-formyl-phenyl, 2-fluoro-6-cyano-phenyl, 2-fluoro-6-hydroxymethyl-phenyl, 2-fluoro-6-(1-hydroxy-ethyl)-phenyl, 2-fluoro-6-(1-hydroxy-1-methyl-ethyl)-phenyl, 2-fluoro-6-nitro-phenyl, 2-fluoro-6-acetyl-phenyl, 2-amino-6-fluoro-phenyl, 2-fluoro-6-methylaminomethyl-phenyl, 2-dimethylaminomethyl-6-fluoro-phenyl, 2-fluoro-6-{[(2-hydroxy-ethyl)-methyl-amino]-methyl}-phenyl, 2-fluoro-6-[(2-methoxy-1-methyl-ethylamino)-methyl]-phenyl, 2-Fluoro-6-{[(2-methoxy-ethyl)-methyl-amino]-methyl}-phenyl, 2-{[Ethyl-(2-hydroxy-ethyl)-amino]-methyl}-6-fluoro-phenyl, 2-{[bis-(2-hydroxy-ethyl)-amino]-methyl}-6-fluoro-phenyl, 2-azetidin-1-ylmethyl-5-fluoro-phenyl, 2-fluoro-6-pyrrolidin-1-ylmethyl-phenyl, 2-Fluoro-6-piperidin-1-ylmethyl-phenyl, 2-fluoro-6-morpholin-4-yl-phenyl, 2-Fluoro-6-piperazin-1-ylmethyl-phenyl, 2-Fluoro-6-morpholin-4-ylmethyl-phenyl, 2-Fluoro-6-(2-morpholin-4-yl-ethyl)-phenyl, 2-Fluoro-6-(3-morpholin-4-yl-propyl)-phenyl, 2-Fluoro-6-(1-methyl-piperazin-4-yl)-methyl-phenyl, 2-Fluoro-6-(3-methoxy-azetidin-1-ylmethyl)-phenyl, 2-Fluoro-6-(4-hydroxy-piperidin-1-ylmethyl)-phenyl, 2-Fluoro-6-(3-methoxy-pyrrolidin-1-ylmethyl)-phenyl, 2-Fluoro-6-[1-(3-methoxy-azetidin-1-yl)-ethyl]-phenyl, 2-Fluoro-6-(4-methoxy-piperidin-1-ylmethyl)-phenyl, 2-(4-Dimethylamino-piperidin-1-ylmethyl)-6-fluoro-phenyl, 1-hydroxy-phenyl, 2-hydroxy-ethoxy-phenyl, oxetan-3-yl-oxy-phenyl, cyclopropyl-methoxy-phenyl, cyclobutyl-oxy,-phenyl, 2-(tetrahydro-pyran-4-yloxy)-phenyl, 1-benzyloxy-phenyl or 1-trifluoromethoxy-phenyl.

The substituent phenyl of $R^2$ independently is unsubstituted, mono-, di or trisubstituted, especially mono- or tri-substituted. Examples for mono or trisubstituted phenyl as $R^2$ are 2-trifluoromethoxy-phenyl, 2-trifluoromethyl-phenyl, 2-methoxy-phenyl, 2-isopropoxy-phenyl, 2-cyclopropyl-phenyl, 2-cyclopropyl-oxy-phenyl, 2-oxetan-3-yl-oxy-phenyl, 2-cyclopropylmethoxy-phenyl, 2-cyclobutyl-oxy-phenyl or 2,4-difluoro-6-isopropoxy-phenyl.

The term "heteroaryl", used alone or in combination, means a 5- or 6-membered monocyclic aromatic ring containing one to a maximum of three heteroatoms, each independently selected from oxygen, nitrogen and sulfur. Examples of such heteroaryl groups are furanyl, oxazolyl, isoxazolyl, oxadiazolyl, thiophenyl, thiazolyl, isothiazolyl, thiadiazolyl, pyrrolyl, imidazolyl, pyrazolyl, triazolyl, pyridinyl, pyrimidinyl, pyridazinyl, and pyrazinyl. Preferred 5- or 6-membered heteroaryl groups are pyrazolyl, oxodiazolyl, thiazolyl, pyridinyl, pyridazinyl, pyrimidinyl and pyrazinyl. The above-mentioned heteroaryl groups are unsubstituted or substituted as explicitly defined. In case 5- or 6-membered heteroaryl group is substituted in ortho-position with regard to the point of attachment of the rest of the molecule, it is understood that such substituent is attached in direct neighbourhood with regard to the point of attachment of the rest of the molecule, i.e. in a relative 1,2-arrangement. In case $R^1$ represents "5- or 6-membered heteroaryl", the term means the above-mentioned 5- or 6-membered groups, especially pyrazolyl, oxodiazolyl, pyridinyl, pyrimidinyl or pyridazinyl. For the substituent $R^1$, such 5- or 6-membered heteroaryl group is unsubstituted or mono-, di- or tri-substituted (especially mono-, or di-substituted, in particular di-substituted) wherein the substituents are independently selected from $(C_{1-4})$alkyl, $(C_1)$alkoxy, cyano, or halogen (especially fluoro or chloro, in particular fluoro). Examples for the 5-membered heteroaryl containing at least one nitrogen atom and optionally one or two further heteroatoms selected from nitrogen or oxygen are 2,5-dimethyl-2H-pyrazol-3-yl, 4-chloro-2,5-dimethyl-2H-pyrazol-3-yl, 2,4,5-trimethyl-2H-pyrazol-3-yl, 5-cyclopropyl-2-methyl-2H-pyrazol-3-yl, 4-formyl-2,5-dimethyl-2H-pyrazol-3-yl, 4-cyano-2,5-dimethyl-2H-pyrazol-3-yl, 4-chloro-5-cyclopropyl-2-methyl-2H-pyrazol-3-yl, 5-cyclopropyl-2,4-dimethyl-2H-pyrazol-3-yl, 5-cyclopropyl-4-formyl-2-methyl-2H-pyrazol-3-yl, 5-isopropyl-[1,3,4]oxodiazol-2-yl, 5-trifluoromethyl-[1,3,4]oxodiazol-2-yl. Examples for the 6-membered heteroaryl group containing one or two nitrogen atoms are 3-methoxy-pyridin-2-yl, 3,5-dimethoxy-pyridin-4-yl, 2,4-dimethoxy-pyridin-3-yl, 3-methyl-pyridin-2-yl, 4-methyl-2-methoxy-pyridin-3-yl, 2-methyl-4-methoxy-pyridin-3-yl, 2-cyano-4-methyl-pyridin-3-yl, 2,4-dimethyl-pyridin-3-yl, 3,5-dimethyl-pyridin-4-yl, 3-fluoro-pyridin-2-yl, 2-fluoro-pyridin-3-yl, 4-fluoro-pyridin-3-yl, 3,5-difluoro-pyridin-4-yl, 3,5-dichloro-pyridazin-4-yl, 3,4-dichloro-pyridazin-2-yl, 4,6-dimethoxy-pyrimidin-5-yl or 4-methyl-6-methoxy-pyrimidin-5-yl.

For the substituent $R^2$, such 5- or 6-membered heteroaryl group is unsubstituted or mono-, di- or tri-substituted (especially mono-substituted) pyridinyl, pyridazinyl, pyrimidinyl, or pyrazinyl, wherein the substituents are independently selected from $(C_{1-3})$fluoroalkyl (especially trifluoromethyl), $(C_{1-3})$fluoroalkoxy (especially trifluoromethoxy), $(C_{1-4})$alkyl (especially methyl and isopropyl), $(C_{1-4})$alkoxy (especially methoxy and isopropoxy), halogen (especially chloro). Examples for the 5-membered heteroaryl containing at least one nitrogen atom and optionally one or two further heteroatoms selected from nitrogen or oxygen are 2-trifluoromethyl-thiazol-4-yl and 2-methyl-4-trifluoromethyl-thiazol-5-yl. Examples for the 6-membered heteroaryl group containing one or two nitrogen atoms are 3-methoxy-pyridin-2-yl, 3-isopropoxy-pyridin-2-yl, 4-trifluoromethyl-pyridin-3-yl, 2-trifluoro-pyridin-3-yl, 4-isopropyl-pyridin-3-yl, 3-trifluoromethyl-pyridin-4-yl, 4-methoxy-pyridazin-3-yl, 4-isopropoxy-pyridazin-3-yl, 4-methyl-pyridazin-3-yl, 6-chloro-4-methoxy-pyridazin-3-yl, 6-chloro-4-isopropoxy-pyridazin-3-yl, 4-methoxy-pyrimidin-5-yl, 4-trifluoromethyl-pyrimidin-5-yl, 3-trifluoromethyl-pyrazin-2-yl, 3-methoxy-pyrazin-2-yl, 3-isopropoxy-pyrazin-2-yl or 3-isopropyl-pyrazin-2-yl.

Further embodiments of the invention are presented hereinafter:

2) A second embodiment relates to compounds according to embodiment 1), wherein
ring A represents a saturated 4- to 7-membered mono-cyclic carbocyclic ring containing the ring nitrogen atom to which $R^1$ is attached, wherein said ring independently is unsubstituted, or mono-substituted with $(C_{1-3})$alkyl (especially methyl), fluoro, or $(C_{1-4})$alkoxy-carbonyl (especially ethoxy-carbonyl), or di-substituted wherein the substituents are two $(C_{1-3})$alkyl (especially methyl) substituents, or two fluoro substituents [especially such ring A is azetidin-1,3-diyl, pyrrolidin-1,3-diyl, 4-methyl-pyrolidin-1,3-diyl, piperidin-1,3-diyl, piperidin-1,4-diyl, 3-fluoro-piperidin-1,4-diyl, 2-methyl-piperidin-1,4-diyl, 3-methyl-piperidin-1,4-diyl, 3-(ethoxycarbonyl)-piperidin-1,4-diyl, 3,3-dimethyl-piperidin-1,4-diyl, azepan-1,4-diyl]; or
ring A represents a saturated 7- or 8-membered bridged bi-cyclic carbocyclic ring containing the ring nitrogen atom to which $R^1$ is attached, wherein said ring is unsubstituted [especially such ring is 2-aza-bicyclo[2.2.1]heptane-2,5-diyl, 3-aza-bicyclo[3.1.1]heptane-3,6-diyl].

3) Another embodiment relates to compounds according to embodiment 1), wherein ring A represents a saturated 4- to 7-membered mono-cyclic carbocyclic ring containing the ring nitrogen atom to which $R^1$ is attached, wherein said ring independently is unsubstituted, or mono-substituted with $(C_{1-3})$alkyl (especially methyl), fluoro, or $(C_{1-4})$alkoxy-carbonyl (especially ethoxy-carbonyl), or di-substituted wherein the substituents are two $(C_{1-3})$alkyl (especially methyl) substituents, or two fluoro substituents [especially such ring A is azetidin-1,3-diyl, pyrrolidin-1,3-diyl, 4-methyl-pyrolidin-1,3-diyl, piperidin-1,3-diyl, piperidin-1,4-diyl, 3-fluoro-piperidin-1,4-diyl, 2-methyl-piperidin-1,4-diyl, 3-methyl-piperidin-1,4-diyl, 3-(ethoxycarbonyl)-piperidin-1,4-diyl, 3,3-dimethyl-piperidin-1,4-diyl, azepan-1,4-diyl].

4) Another embodiment relates to compounds according to embodiment 1), wherein ring A represents unsubstituted, mono- or di-substituted azetidin-1,3-diyl, pyrrolidin-1,3-diyl, piperidin-1,3-diyl, piperidin-1,4-diyl, azepan-1,4-diyl, 2-aza-bicyclo[2.2.1]heptane-2,5-diyl, 3-aza-bicyclo[3.1.1]heptane-3,6-diyl, wherein the substituents are selected from the group of $(C_{1-3})$alkyl (especially methyl), fluoro, or $(C_{1-4})$alkoxy-carbonyl (especially ethoxy-carbonyl) [especially such ring A is azetidin-1,3-diyl, pyrrolidin-1,3-diyl, 4-methyl-pyrolidin-1,3-diyl, piperidin-1,3-diyl, piperidin-1,4-diyl, 3-fluoro-piperidin-1,4-diyl, 2-methyl-piperidin-1,4-diyl, 3-methyl-piperidin-1,4-diyl, 3-(ethoxycarbonyl)-piperidin-1,4-diyl, 3,3-dimethyl-piperidin-1,4-diyl, azepan-1,4-diyl, 2-aza-bicyclo[2.2.1]heptane-2,5-diyl, 3-aza-bicyclo[3.1.1]heptane-3,6-diyl].

5) Another embodiment relates to compounds according to embodiment 1), wherein ring A represents
azetidin-1,3-diyl, pyrrolidin-1,3-diyl, 4-methyl-pyrolidin-1,3-diyl, piperidin-1,3-diyl, piperidin-1,4-diyl, 3-fluoro-piperidin-1,4-diyl, 2-methyl-piperidin-1,4-diyl, 3-methyl-piperidin-1,4-diyl, 3-(ethoxycarbonyl)-piperidin-1,4-diyl, 3,3-dimethyl-piperidin-1,4-diyl, or azepan-1,4-diyl; or
2-aza-bicyclo[2.2.1]heptane-2,5-diyl, 3-aza-bicyclo[3.1.1]heptane-3,6-diyl; wherein in a sub-embodiment ring A represents pyrrolidin-1,3-diyl, or piperidin-1,4-diyl (especially piperidin-1,4-diyl).

6) Another embodiment relates to compounds according to any one of embodiments 1) to 5), wherein X represents CR$^5$; Z represents CR$^5$; and Y represents CR$^5$; wherein each R$^5$ independently represents hydrogen, or (C$_{1-3}$)alkyl (especially methyl); wherein preferably at maximum one R$^5$ is different from hydrogen [especially all R$^5$ represent hydrogen];

X represents CH; Z represents N; and Y represents CR$^5$; wherein each R$^5$ independently represents hydrogen, or (C$_{1-3}$)alkyl (especially methyl); [especially R$^5$ represents hydrogen];

X represents N; Z represents CR$^5$; and Y represents CR$^5$; wherein each R$^5$ independently represents hydrogen, or (C$_{1-3}$)alkyl (especially methyl); wherein preferably at maximum one R$^5$ is different from hydrogen; [especially all R$^5$ represent hydrogen];

X represents N; Z represents N; and Y represents CR$^5$; wherein R$^5$ represents hydrogen, or (C$_{1-3}$)alkyl (especially methyl); [especially R$^5$ represents hydrogen].

7) Another embodiment relates to compounds according to any one of embodiments 1) to 5), wherein one of X and Z represents CH or N; the other represents CH; and Y represents CR$^5$, wherein R$^5$ represents hydrogen or (C$_{1-3}$)alkyl (especially R$^5$ represents hydrogen).

8) Another embodiment relates to compounds according to any one of embodiments 1) to 7), wherein R$^1$ represents (C$_{1-4}$)alkyl (especially methyl, isopropyl);

—CO—R$^{11}$ wherein R$^{11}$ represents (C$_{1-4}$)alkyl (especially tert-butyl); (C$_{1-4}$)alkoxy (especially methoxy, ethoxy, isopropoxy, n-butoxy, tert-butoxy); phenyl, phenoxy; (C$_{3-6}$)cycloalkyl (especially cyclopropyl); or (C$_{3-6}$)cycloalkoxy optionally containing one ring oxygen (especially oxetan-3-yloxy) and optionally mono-substituted with methyl or trifluoromethyl (especially 3-methyl-oxetan-3-yloxy, 3-trifluoromethyl-oxetan-3-yloxy); [especially such group —CO—R$^{11}$ is tert.-butyl-carbonyl, methoxycarbonyl, ethoxycarbonyl, isopropoxycarbonyl, n-butoxycarbonyl, tert.-butoxycarbonyl, oxetan-3-yl-oxy-carbonyl, (3-methyl-oxetan-3-yl)-oxy-carbonyl, (3-trifluoromethyl-oxetan-3-yl)-oxy-carbonyl, phenylcarbonyl, phenoxycarbonyl, cyclopropylcarbonyl];

benzyl wherein the phenyl ring of said benzyl is optionally mono- or di-substituted with halogen [especially 2,4-dichlorobenzyl];

phenyl which is unsubstituted, mono-, di- or tri-substituted (notably mono- or di-substituted, wherein at least one substituent is attached in ortho position with regard to the point of attachment of the rest of the molecule; especially di-substituted in ortho position), wherein the substituents are independently selected from (C$_{1-4}$)alkyl (especially methyl, isopropyl);
(C$_{1-4}$)alkoxy (especially methoxy, n-butyloxy);
(C$_{1-3}$)fluoroalkyl (especially trifluoromethyl);
(C$_{1-3}$)fluoroalkoxy (especially trifluoromethoxy);
halogen (especially fluoro, bromo);
cyano;
nitro;
hydroxy;
hydroxy-(C$_{1-3}$)alkyl (especially 1-hydroxyethyl, hydroxymethyl, 1-hydroxy-1-methyl-ethyl);
(C$_{1-4}$)alkoxy-(C$_{1-3}$)alkyl (especially 1-methoxyethyl);
hydroxy-(C$_{2-3}$)alkoxy(especially 2-hydroxy-ethoxy);
(C$_{1-4}$)alkoxy-(C$_{2-3}$)alkoxy (especially 2-methoxy-ethoxy);
(C$_{3-6}$)cycloalkyl-X$^{12}$—, wherein X$^{12}$ represents a direct bond, —O—, or —(C$_{1-3}$)alkylene-O—, and wherein the (C$_{3-6}$)cycloalkyl independently contains one optional ring oxygen [especially such group (C$_{3-6}$)cycloalkyl-X$^{12}$— is cyclopropyl, cyclopropyl-oxy, cyclobutyl-oxy, oxetan-3-yl-oxy, cyclopropyl-methoxy or tetrahydropyran-4-yl-oxy];

R$^{13}$—CO—X$^{13}$—, wherein X$^{13}$ represents a direct bond or (C$_{1-3}$)alkylene, and R$^{13}$ represents hydrogen or (C$_{1-4}$)alkyl (especially such group R$^{13}$—CO—X$^{13}$ is formyl, acetyl, 2-oxo-ethyl);

3-(morpholin-4-yl)-prop-1-ynyl;

R$^{14a}$R$^{14b}$N—X$^{14}$—, wherein X$^{14}$ represents a direct bond or (C$_{1-3}$)alkylene; and wherein R$^{14a}$ and R$^{14b}$ independently represent hydrogen, (C$_{1-4}$)alkyl, hydroxy-(C$_{2-4}$)alkyl, (C$_{1-3}$)alkoxy-(C$_{2-4}$)alkyl; or R$^{14a}$ and R$^{14b}$ together with the nitrogen to which they are attached to form a 4- to 6-membered saturated ring optionally containing one additional ring heteroatom selected from oxygen and nitrogen; and wherein said ring is optionally mono-substituted with (C$_{1-4}$)alkyl (especially methyl), hydroxy, (C$_{1-4}$)alkoxy (especially methoxy), or dimethylamino;

[especially such group R$^{14a}$R$^{14b}$N—X$^{14}$— is amino, methylamino-methyl, dimethylamino-methyl, [(2-hydroxyethyl)-methylamino]-methyl, [(2-hydroxyethyl)-ethylamino]-methyl, [(2-methoxy-1-methyl-ethyl)-amino]-methyl, [(2-methoxyethyl)-methylamino]-methyl, [di-(2-hydroxyethyl)-amino]-methyl, (azetidin-1-yl)-methyl, (pyrrolidin-1-yl)-methyl, (piperidin-1-yl)-methyl, morpholin-4-yl, piperazin-1-ylmethyl (morpholin-4-yl)-methyl, 2-(morpholin-4-yl)-ethyl, 3-(morpholin-4-yl)-propyl, (3-methoxy-azetidin-1-yl)-methyl, 1-(3-methoxy-azetidin-1-yl)-ethyl, (1-methyl-piperazin-4-yl)-methyl, (4-hydroxypiperidin-1-yl)-methyl, (4-methoxypiperidin-1-yl)-methyl, (3-methoxy-pyrrolidin-1-yl)-methyl, (4-dimethylamino-piperidin-1-yl)-methyl]; or benzyloxy; or 5- or 6-membered heteroaryl (especially pyrazolyl, oxadiazolyl, pyridinyl, pyridazinyl, pyrimidinyl); wherein said 5- or 6-membered heteroaryl independently is mono-, di- or tri-substituted (notably mono-, di-, or tri-substituted wherein at least one substituent is attached in ortho position with regard to the point of attachment of the rest of the molecule; especially di-substituted in ortho position), wherein the substituents are independently selected from (C$_{1-4}$)alkyl (especially methyl, isopropyl);
(C$_{1-4}$)alkoxy (especially methoxy);
(C$_{1-3}$)fluoroalkyl (especially trifluoromethyl);
(C$_{1-3}$)fluoroalkoxy (especially trifluoromethoxy);
halogen (especially fluoro, chloro);
cyano;
(C$_{3-6}$)cycloalkyl-X$^{12}$—, wherein X$^{12}$ represents a direct bond, —O—, or —(C$_{1-3}$)alkylene-O—; [especially such group (C$_{3-6}$)cycloalkyl-X$^{12}$— is cyclopropyl]; or
R$^{13}$—CO—X$^{13}$—, wherein X$^{13}$ represents a direct bond or (C$_{1-3}$)alkylene, and R$^{13}$ represents hydrogen or (C$_{1-4}$)alkyl (especially such group R$^{13}$—CO—X$^{13}$ is formyl).

wherein in a sub-embodiment R$^1$ represents phenyl, or 5- or 6-membered heteroaryl (especially pyrazolyl, oxadiazolyl, pyridinyl, pyridazinyl, pyrimidinyl); wherein said phenyl or 5- or 6-membered heteroaryl are substituted as defined herein before.

9) Another embodiment relates to compounds according to any one of embodiments 1) to 7), wherein R$^1$ represents —CO—$R^{11}$ wherein $R^{11}$ represents ($C_{1-4}$)alkyl (especially tert-butyl); or ($C_{1-4}$)alkoxy (especially methoxy, ethoxy, isopropoxy, n-butoxy, tert-butoxy); [especially such group —CO—$R^{11}$ is tert.-butyl-carbonyl, methoxycarbonyl, ethoxycarbonyl, isopropoxycarbonyl, n-butoxycarbonyl, tert.-butoxycarbonyl];

phenyl which is mono-, or di- or tri-substituted (notably mono- or di-substituted wherein at least one substituent is attached in ortho position with regard to the point of attachment of the rest of the molecule; especially di-substituted in ortho position), wherein the substituents are independently selected from ($C_{1-4}$)alkyl (especially methyl, isopropyl);
($C_{1-4}$)alkoxy (especially methoxy);
($C_{1-3}$)fluoroalkyl (especially trifluoromethyl);
($C_{1-3}$)fluoroalkoxy (especially trifluoromethoxy);
halogen (especially fluoro, bromo);
cyano;
nitro;
hydroxy-($C_{1-3}$)alkyl (especially 1-hydroxyethyl, hydroxymethyl, 1-hydroxy-1-methyl-ethyl);
($C_{1-4}$)alkoxy-($C_{1-3}$)alkyl (especially 1-methoxyethyl);
hydroxy-($C_{2-3}$)alkoxy (especially 2-hydroxy-ethoxy);
($C_{1-4}$)alkoxy-($C_{2-3}$)alkoxy (especially 2-methoxy-ethoxy);
($C_{3-6}$)cycloalkyl-$X^{12}$—, wherein $X^{12}$ represents a direct bond, —O—, or —($C_{1-3}$)alkylene-O—; [especially such group ($C_{3-6}$)cycloalkyl-$X^{12}$— is cyclobutyl-oxy, or cyclopropyl-methoxy]; or
$R^{14a}R^{14b}$N—$X^{14}$—, wherein $X^{14}$ represents a direct bond or ($C_{1-3}$)alkylene; and wherein $R^{14a}$ and $R^{14b}$ independently represent hydrogen, ($C_{1-4}$)alkyl, hydroxy-($C_{2-4}$)alkyl, ($C_{1-3}$)alkoxy-($C_{2-4}$)alkyl; or $R^{14a}$ and $R^{14b}$ together with the nitrogen to which they are attached to form a 4- to 6-membered saturated ring optionally containing one additional ring heteroatom selected from oxygen and nitrogen; and wherein said ring is optionally mono-substituted with ($C_{1-4}$)alkyl (especially methyl), hydroxy, ($C_{1-4}$)alkoxy (especially methoxy), or dimethylamino;
[especially such group $R^{14a}R^{14b}$N—$X^{14}$— is amino, methylamino-methyl, dimethylamino-methyl, [(2-hydroxyethyl)-methylamino]-methyl, [(2-hydroxyethyl)-ethylamino]-methyl, [(2-methoxy-1-methylethyl)-amino]-methyl, [(2-methoxyethyl)-methylamino]-methyl, [di-(2-hydroxyethyl)-amino]-methyl, (azetidin-1-yl)-methyl, (pyrrolidin-1-yl)-methyl, (piperidin-1-yl)-methyl, morpholin-4-yl, (morpholin-4-yl)-methyl, piperazin-1-ylmethyl, 2-(morpholin-4-yl)-ethyl, 3-(morpholin-4-yl)-propyl, (3-methoxy-azetidin-1-yl)-methyl, 1-(3-methoxy-azetidin-1-yl)-ethyl, (1-methyl-piperazin-4-yl)-methyl, (4-hydroxypiperidin-1-yl)-methyl, (4-methoxypiperidin-1-yl)-methyl, (3-methoxy-pyrrolidin-1-yl)-methyl, (4-dimethylamino-piperidin-1-yl)-methyl.]; or 5- or 6-membered heteroaryl (especially pyrazolyl, oxadiazolyl, pyridinyl, pyridazinyl, pyrimidinyl); wherein said 5- or 6-membered heteroaryl independently is mono-, di- or tri-substituted (notably mono-, di-, or tri-substituted wherein at least one substituent is attached in ortho position with regard to the point of attachment of the rest of the molecule; especially di-substituted in ortho position), wherein the substituents are independently selected from
($C_{1-4}$)alkyl (especially methyl, isopropyl);
($C_{1-4}$)alkoxy (especially methoxy);
($C_{1-3}$)fluoroalkyl (especially trifluoromethyl);
halogen (especially fluoro, chloro);
cyano; or
($C_{3-6}$)cycloalkyl-$X^{12}$—, wherein $X^{12}$ represents a direct bond, [especially such group ($C_{3-6}$)cycloalkyl-$X^{12}$— is cyclopropyl].

wherein in a sub-embodiment $R^1$ represents phenyl, or 5- or 6-membered heteroaryl (especially pyrazolyl, oxadiazolyl, pyridinyl, pyridazinyl, pyrimidinyl); wherein said phenyl or 5- or 6-membered heteroaryl are substituted as defined herein before.

10) Another embodiment relates to compounds according to any one of embodiments 1) to 7), wherein $R^1$ represents
—CO—$R^{11}$ wherein $R^{11}$ represents ($C_{1-4}$)alkyl (especially tert-butyl); or ($C_{1-4}$)alkoxy (especially methoxy, ethoxy, isopropoxy, n-butoxy, tert-butoxy); [especially such group —CO—$R^{11}$ is tert.-butyl-carbonyl, methoxycarbonyl, ethoxycarbonyl, isopropoxycarbonyl, n-butoxycarbonyl, tert.-butoxycarbonyl];

phenyl which is mono-, or di- or tri-substituted (notably mono- or di-substituted); wherein one substituent is ($C_{1-4}$)alkyl (especially methyl), ($C_{1-4}$)alkoxy (especially methoxy), or halogen (especially fluoro) [especially such substituent is methyl, methoxy or fluoro; in particular methyl]; wherein said substituent is attached in ortho position with regard to the point of attachment of the rest of the molecule; and, if present, the remaining substituent(s) are independently selected from:
($C_{1-4}$)alkyl (especially methyl, isopropyl);
($C_{1-4}$)alkoxy (especially methoxy);
($C_{1-3}$)fluoroalkyl (especially trifluoromethyl);
($C_{1-3}$)fluoroalkoxy (especially trifluoromethoxy);
halogen (especially fluoro, bromo);
cyano;
hydroxy-($C_{1-3}$)alkyl (especially 1-hydroxyethyl, hydroxymethyl, 1-hydroxy-1-methyl-ethyl);
($C_{1-4}$)alkoxy-($C_{1-3}$)alkyl (especially 1-methoxyethyl);
($C_{1-4}$)alkoxy-($C_{2-3}$)alkoxy (especially 2-methoxy-ethoxy);
($C_{3-6}$)cycloalkyl-$X^{12}$—, wherein $X^{12}$ represents a direct bond, —O—, or —($C_{1-3}$)alkylene-O—; [especially such group ($C_{3-6}$)cycloalkyl-$X^{12}$— is, cyclobutyl-oxy or cyclopropyl-methoxy]; or
$R^{14a}R^{14b}$N—$X^{14}$—, wherein $X^{14}$ represents a direct bond or ($C_{1-3}$)alkylene; and wherein $R^{14a}$ and $R^{14b}$ independently represent hydrogen, ($C_{1-4}$)alkyl, hydroxy-($C_{2-4}$)alkyl, ($C_{1-3}$)alkoxy-($C_{2-4}$)alkyl; or $R^{14a}$ and $R^{14b}$ together with the nitrogen to which they are attached to form a 4- to 6-membered saturated ring optionally containing one additional ring heteroatom selected from oxygen and nitrogen; and wherein said ring is optionally mono-substituted with ($C_{1-4}$)alkyl (especially methyl), hydroxy, ($C_{1-4}$)alkoxy (especially methoxy), or dimethylamino;
[especially such group $R^{14a}R^{14b}$N—$X^{14}$— is amino, methylamino-methyl, dimethylamino-methyl, [(2-hydroxyethyl)-methylamino]-methyl, [(2-hydroxyethyl)-ethylamino]-methyl, [(2-methoxy-1-methylethyl)-amino]-methyl, [(2-methoxyethyl)-methylamino]-methyl, [di-(2-hydroxyethyl)-amino]-methyl, (azetidin-1-yl)-methyl, (pyrrolidin-1-yl)-methyl, (piperidin-1-yl)-methyl, morpholin-4-yl, (morpholin-4-yl)-methyl, piperazin-1-ylmethyl, 2-(morpholin-4-yl)-ethyl, 3-(morpholin-4-yl)-propyl, (3-methoxy-azetidin-1-yl)-methyl, 1-(3-methoxy-azetidin-1-yl)-ethyl, (1-methyl-piperazin-4-yl)-methyl, (4-hydroxypiperidin-1-yl)-methyl, (4-methoxypiperidin-1-yl)-methyl, (3-methoxy-pyrrolidin-1-yl)-methyl, (4-dimethylamino-piperidin-1-yl)-methyl.]; or 5- or 6-membered heteroaryl (especially pyrazolyl, oxadiazolyl, pyridinyl, pyridazinyl, pyrimidinyl); wherein said 5- or 6-membered heteroaryl independently is mono-, di- or tri-substituted; wherein one substituent is $(C_{1-4})$alkyl (especially methyl), $(C_{1-4})$alkoxy (especially methoxy), or halogen (especially fluoro); wherein said substituent is attached in ortho position with regard to the point of attachment of the rest of the molecule; and, if present, the remaining substituent(s) are independently selected from $(C_{1-4})$alkyl (especially methyl, isopropyl);
$(C_{1-4})$alkoxy (especially methoxy);
$(C_{1-3})$fluoroalkyl (especially trifluoromethyl);
halogen (especially fluoro, chloro);
cyano; or
$(C_{3-6})$cycloalkyl-$X^{12}$—, wherein $X^{12}$ represents a direct bond; [especially such group $(C_{3-6})$cycloalkyl-$X^{12}$— is cyclopropyl].

wherein in a sub-embodiment $R^1$ represents phenyl, or 5- or 6-membered heteroaryl selected from pyrazolyl, oxadiazolyl, pyridinyl, pyridazinyl, and pyrimidinyl; wherein said phenyl or 5- or 6-membered heteroaryl are substituted as defined herein before.

11) Another embodiment relates to compounds according to any one of embodiments 1) to 7), wherein $R^1$ represents —CO—$R^{11}$ wherein $R^{11}$ represents $(C_{1-4})$alkoxy (especially isopropoxy, tert-butoxy);

phenyl which is mono-, or di- or tri-substituted (notably mono- or di-substituted); wherein one substituent is $(C_{1-4})$alkyl (especially methyl), $(C_{1-4})$alkoxy (especially methoxy), or halogen (especially fluoro) [especially such substituent is methyl, methoxy or fluoro; in particular methyl]; wherein said substituent is attached in ortho position with regard to the point of attachment of the rest of the molecule; and, if present, the remaining substituent(s) are independently selected from:

$(C_{1-4})$alkyl (especially methyl, isopropyl);
$(C_{1-4})$alkoxy (especially methoxy);
$(C_{1-3})$fluoroalkyl (especially trifluoromethyl);
$(C_{1-3})$fluoroalkoxy (especially trifluoromethoxy);
halogen (especially fluoro, bromo);
cyano;
hydroxy-$(C_{1-3})$alkyl (especially 1-hydroxyethyl, hydroxymethyl, 1-hydroxy-1-methyl-ethyl);
$(C_{1-4})$alkoxy-$(C_{1-3})$alkyl (especially 1-methoxyethyl);
$(C_{1-4})$alkoxy-$(C_{2-3})$alkoxy (especially 2-methoxyethoxy);
$(C_{3-6})$cycloalkyl-$X^{12}$—, wherein $X^{12}$ represents a direct bond, —O—, or —$(C_{1-3})$alkylene-O—; [especially such group $(C_{3-6})$cycloalkyl-$X^{12}$— is cyclobutyl-oxy, or cyclopropyl-methoxy]; or
$R^{14a}R^{14b}$N—$X^{14}$—, wherein $X^{14}$ represents a direct bond or $(C_{1-3})$alkylene; and wherein $R^{14a}$ represents hydrogen or $(C_{1-4})$alkyl, and $R^{14b}$ independently represents hydrogen, $(C_{1-4})$alkyl, hydroxy-$(C_{2-4})$alkyl, or $(C_{1-3})$alkoxy-$(C_{2-4})$alkyl; or $R^{14a}$ and $R^{14b}$ together with the nitrogen to which they are attached to form a 4- to 6-membered saturated ring optionally containing one additional ring heteroatom selected from oxygen and nitrogen; and wherein said ring is optionally mono-substituted with $(C_{1-4})$alkyl (especially methyl), hydroxy, $(C_{1-4})$alkoxy (especially methoxy), or dimethylamino;

[especially such group $R^{14a}R^{14b}$N—$X^{14}$— is amino, methylamino-methyl, dimethylamino-methyl, [(2-hydroxyethyl)-methylamino]-methyl, [(2-hydroxyethyl)-ethylamino]-methyl, [(2-methoxy-1-methylethyl)-amino]-methyl, [(2-methoxyethyl)-methylamino]-methyl, [di-(2-hydroxyethyl)-amino]-methyl, (azetidin-1-yl)-methyl, (pyrrolidin-1-yl)-methyl, (piperidin-1-yl)-methyl, morpholin-4-yl, piperazin-1-ylmethyl, (morpholin-4-yl)-methyl, 2-(morpholin-4-yl)-ethyl, 3-(morpholin-4-yl)-propyl, (3-methoxy-azetidin-1-yl)-methyl, 1-(3-methoxy-azetidin-1-yl)-ethyl, (1-methyl-piperazin-4-yl)-methyl, (4-hydroxypiperidin-1-yl)-methyl, (4-methoxypiperidin-1-yl)-methyl, (3-methoxy-pyrrolidin-1-yl)-methyl, (4-dimethylamino-piperidin-1-yl)-methyl.]; or 6-membered heteroaryl (especially pyridinyl, pyridazinyl, pyrimidinyl); wherein said 6-membered heteroaryl independently is mono-, di- or tri-substituted (notably mono-, or di-substituted); wherein one substituent is $(C_{1-4})$alkyl (especially methyl), $(C_{1-4})$alkoxy (especially methoxy), or halogen (especially fluoro); wherein said substituent is attached in ortho position with regard to the point of attachment of the rest of the molecule; and, if present, the remaining substituent(s) are independently selected from $(C_{1-4})$alkyl (especially methyl, isopropyl);
$(C_{1-4})$alkoxy (especially methoxy);
$(C_{1-3})$fluoroalkyl (especially trifluoromethyl);
halogen (especially fluoro);
cyano; or
$(C_{3-6})$cycloalkyl-$X^{12}$—, wherein $X^{12}$ represents a direct bond [especially such group $(C_{3-6})$cycloalkyl-$X^{12}$— is cyclopropyl];

wherein in a sub-embodiment $R^1$ represents phenyl, or 6-membered heteroaryl selected from pyridinyl, pyridazinyl, and pyrimidinyl; wherein said phenyl or 6-membered heteroaryl are substituted as defined herein before.

12) Another embodiment relates to compounds according to any one of embodiments 1) to 7), wherein $R^1$ represents phenyl which is mono-, or di- or tri-substituted (notably mono- or di-substituted); wherein one substituent is
$(C_{1-4})$alkyl (especially methyl);
$(C_{1-4})$alkoxy (especially methoxy); or
halogen (especially fluoro);
wherein said substituent is attached in ortho position with regard to the point of attachment of the rest of the molecule [especially such substituent is methyl, methoxy or fluoro; in particular methyl];
and, if present, the remaining substituent(s) is/are independently selected from:
methyl;
methoxy;
halogen (especially fluoro);
cyano, or
amino.

13) Another embodiment relates to compounds according to any one of embodiments 1) to 12), wherein $R^2$ represents phenyl, or 6-membered heteroaryl (in particular pyridinyl, pyrimidinyl, pyrazinyl, pyridazinyl) [especially $R^2$ represents phenyl]; wherein said phenyl or 6-membered heteroaryl independently is mono-, or di-substituted (especially mono-substituted, in particular mono-substituted in ortho position with regard to the point of attachment of the rest of the molecule), wherein the substituents are independently selected from ($C_{1-4}$)alkyl (especially methyl, isopropyl);
($C_1$-4)alkoxy (especially methoxy, isopropoxy);
($C_{1-3}$)fluoroalkyl (especially trifluoromethyl);
($C_{1-3}$)fluoroalkoxy (especially trifluoromethoxy);
halogen (especially chloro, fluoro); or
($C_{3-6}$)cycloalkyl-$X^{21}$—, wherein $X^{21}$ represents a direct bond, —O—, or —($C_{1-3}$)alkylene-O—, and wherein the ($C_{3-6}$)cycloalkyl independently contains one optional ring oxygen; [especially such group ($C_{3-6}$)cycloalkyl-$X^{21}$— is cyclopropyl, cyclopropyl-oxy, cyclobutyl-oxy, oxetan-3-yl-oxy, cyclopropyl-methoxy].

14) Another embodiment relates to compounds according to any one of embodiments 1) to 12), wherein $R^2$ represents phenyl, or 6-membered heteroaryl (in particular pyridinyl, pyrimidinyl, pyrazinyl, pyridazinyl) [especially $R^2$ represents phenyl]; wherein said phenyl or 6-membered heteroaryl is mono-substituted in ortho position with regard to the point of attachment of the rest of the molecule, wherein the substituent is independently selected from
($C_{1-4}$)alkyl (especially methyl, isopropyl);
($C_{1-4}$)alkoxy (especially methoxy, isopropoxy);
($C_{1-3}$)fluoroalkyl (especially trifluoromethyl);
($C_{1-3}$)fluoroalkoxy (especially trifluoromethoxy); or
($C_{3-6}$)cycloalkyl-$X^{21}$—, wherein $X^{21}$ represents a direct bond, —O—, or —($C_{1-3}$)alkylene-O—, and wherein the ($C_{3-6}$)cycloalkyl independently contains one optional ring oxygen; [especially such group ($C_{3-6}$)cycloalkyl-$X^{21}$— is cyclopropyl, cyclopropyl-oxy, cyclobutyl-oxy, oxetan-3-yl-oxy, cyclopropyl-methoxy].

15) Another embodiment relates to compounds according to any one of embodiments 1) to 12), wherein $R^2$ represents phenyl, which is mono-substituted in ortho position with regard to the point of attachment of the rest of the molecule, wherein the substituent is independently selected from
($C_{1-4}$)alkyl (especially isopropyl);
($C_{1-4}$)alkoxy (especially methoxy, isopropoxy);
($C_{1-3}$)fluoroalkyl (especially trifluoromethyl);
($C_{1-3}$)fluoroalkoxy (especially trifluoromethoxy); or
cyclopropyl-oxy, cyclopropyl-methoxy, cyclobutyl-oxy, oxetan-3-yl-oxy;
or $R^2$ represents 6-membered heteroaryl (in particular pyridinyl, pyrimidinyl, pyrazinyl, pyridazinyl); wherein said 6-membered heteroaryl is mono-substituted in ortho position with regard to the point of attachment of the rest of the molecule, wherein the substituent is independently selected from
($C_{1-4}$)alkyl (especially isopropyl);
($C_{1-4}$)alkoxy (especially methoxy, isopropoxy);
($C_{1-3}$)fluoroalkyl (especially trifluoromethyl); or
($C_{1-3}$)fluoroalkoxy (especially trifluoromethoxy).

16) Another embodiment relates to compounds according to any one of embodiments 1) to 15), wherein $R^3$ represents hydrogen, or methyl (especially hydrogen). In a sub-embodiment $R^3$ represents hydrogen.

17) Another embodiment relates to compounds according to any one of embodiments 1) to 16),
$R^4$ represents
($C_{1-4}$)alkyl (especially methyl);
hydroxy-($C_{1-3}$)alkyl (especially hydroxymethyl);
—O—$R^{41}$, wherein $R^{41}$ represents
hydrogen;
($C_{1-4}$)alkyl (especially methyl);
($C_{2-4}$)alkyl which is substituted with one or two hydroxy (especially 2-hydroxyethyl, 2,3-dihydroxypropyl);
$R^{41a}R^{41b}N$—($C_{2-3}$)alkylene-, wherein $R^{41a}$ and $R^{41b}$ independently represent hydrogen or ($C_{1-4}$)alkyl (especially such group is 2-dimethylamino-ethyl); or
($C_{4-7}$)heterocyclyl-$X^{41}$—, wherein $X^{41}$ represents a direct bond or ($C_{1-3}$)alkylene, and wherein the ($C_{4-7}$)heterocyclyl independently contains one or two ring heteroatoms independently selected from nitrogen and oxygen; wherein the oxygen atom of such group ($C_{4-7}$)heterocyclyl-$X^{41}$—O— is separated by at least two (ring and/or chain) carbon atoms from such ring heteroatom; wherein said ($C_{4-7}$)heterocyclyl independently is unsubstituted, or mono-, or di-substituted, wherein the substituents are independently selected from:
($C_{1-4}$)alkyl (especially methyl); and/or
($C_{1-4}$)alkoxy-carbonyl attached to a ring nitrogen atom having a free valency;
[especially such ($C_{4-7}$)heterocyclyl-$X^{41}$— group is oxetan-3-yl, 1-methyl-pyrrolidin-3-yl, 2,2-dimethyl-dioxolan-4-yl-methyl, 2-morpholin-4-yl-ethyl, 1-tert-butoxy-carbonyl-piperidin-4-yl, piperidin-4-yl];
—$NR^{42a}R^{42b}$ wherein $R^{42a}$ represents hydrogen or ($C_{1-4}$)alkyl, and $R^{42b}$ independently represents hydrogen, ($C_{1-4}$)alkyl, ($C_{1-3}$)alkoxy-($C_{2-3}$)alkyl, hydroxy-($C_{2-3}$)alkyl, or $R^{42a}$ and $R^{42b}$ together with the nitrogen to which they are attached form a 4- to 7-membered saturated ring optionally containing one further ring heteroatom selected from oxygen and nitrogen, wherein said ring is unsubstituted or mono-substituted with ($C_{1-3}$)alkyl (especially methyl), or ($C_{1-3}$)alkoxy (especially methoxy) [especially such group —$NR^{42a}R^{42b}$ is (2-hydroxyethyl)-amino, (2-hydroxyethyl)-methyl-amino, (2-methoxyethyl)-amino, morpholin-4-yl, 3-methoxy-azetidinyl, or 4-methyl-piperazin-1-yl]; or
—CO—$R^{43}$ wherein $R^{43}$ represents ($C_{1-4}$)alkoxy (especially methoxy); or —$NR^{43a}R^{43b}$ wherein $R^{43a}$ represents hydrogen or ($C_{1-4}$)alkyl (especially methyl), and $R^{43b}$ independently represents hydrogen, ($C_{1-4}$)alkyl (especially methyl), ($C_{1-3}$)alkoxy-($C_{2-3}$)alkyl (especially 2-methoxy-ethyl), or hydroxy-($C_{2-3}$)alkyl (especially 2-hydroxy-ethyl); [especially such group —CO—$R^{43}$ is methoxycarbonyl, carbamoyl, methylcarbamoyl, dimethylcarbamoyl, hydroxyethylcarbamoyl, methoxyethylcarbamoyl];
wherein in a sub-embodiment $R^4$ represents —O—$R^{41}$ as defined herein above; especially $R^4$ represents ($C_{1-4}$)alkoxy (in particular methoxy).

18) Another embodiment relates to compounds according to any one of embodiments 1) to 16), wherein $R^4$ represents
($C_{1-4}$)alkyl (especially methyl);
hydroxy-($C_{1-3}$)alkyl (especially hydroxymethyl);
—O—$R^{41}$, wherein $R^{41}$ represents
hydrogen;
($C_{1-4}$)alkyl (especially methyl);
($C_2$)alkyl which is substituted with one or two hydroxy (especially 2-hydroxyethyl, 2,3-dihydroxypropyl);
$R^{41a}R^{41b}N$—($C_{2-3}$)alkylene-, wherein $R^{41a}$ and $R^{41b}$ independently represent hydrogen or ($C_{1-4}$)alkyl (especially such group is 2-dimethylamino-ethyl); or
($C_{4-7}$)heterocyclyl-$X^{41}$—, wherein $X^{41}$ represents a direct bond or —$CH_2$—, and wherein the ($C_{4-7}$)heterocyclyl independently contains one or two ring heteroatoms independently selected from nitrogen and oxygen; wherein the oxygen atom of such group ($C_{4-7}$)heterocyclyl-$X^{41}$—O— is separated by at least two (ring and/or chain) carbon atoms from such ring heteroatom; wherein said $(C_{4-7})$heterocyclyl independently is unsubstituted, or mono-substituted with $(C_{1-4})$alkyl (especially methyl) at a ring nitrogen atom having a free valency, or di-substituted with methyl;

[especially such $(C_{4-7})$heterocyclyl-$X^{41}$— group is oxetan-3-yl, 1-methyl-pyrrolidin-3-yl, 2,2-dimethyl-dioxolan-4-yl-methyl, 2-morpholin-4-yl-ethyl];

—$NR^{42a}R^{42b}$ wherein $R^{42a}$ represents hydrogen or $(C_{1-4})$alkyl (especially methyl), and $R^{42b}$ independently represents $(C_{1-4})$alkyl, $(C_{1-3})$alkoxy-$(C_{2-3})$alkyl, hydroxy-$(C_{2-3})$alkyl; or $R^{42a}$ and $R^{42b}$ together with the nitrogen to which they are attached form a 4- to 7-membered saturated ring optionally containing one further ring heteroatom selected from oxygen and nitrogen, wherein said ring is unsubstituted, or mono-substituted with $(C_{1-3})$alkyl (especially methyl) attached to a ring nitrogen atom having a free valency, or $(C_{1-3})$alkoxy (especially methoxy) attached to a ring carbon atom [especially such group —$NR^{42a}R^{42b}$ is (2-hydroxy-ethyl)-amino, (2-hydroxyethyl)-methyl-amino, (2-methoxyethyl)-amino, morpholin-4-yl, 3-methoxy-azetidinyl, or 4-methyl-piperazin-1-yl]; or —CO—$R^{43}$ wherein $R^{43}$ represents $(C_{1-4})$alkoxy (especially methoxy); or —$NR^{43a}R^{43b}$ wherein $R^{43a}$ represents hydrogen or $(C_{1-4})$alkyl (especially methyl), and $R^{43b}$ independently represents hydrogen, $(C_{1-4})$alkyl (especially methyl), $(C_{1-3})$alkoxy-$(C_{2-3})$alkyl (especially 2-methoxy-ethyl), or hydroxy-$(C_{2-3})$alkyl (especially 2-hydroxy-ethyl); [especially such group —CO—$R^{43}$ is methoxycarbonyl, carbamoyl, methylcarbamoyl, dimethylcarbamoyl, hydroxyethylcarbamoyl, methoxyethylcarbamoyl];

wherein in a sub-embodiment $R^4$ represents —O—$R^{41}$ as defined herein above; especially $R^4$ represents $(C_{1-4})$alkoxy (in particular methoxy).

19) Another embodiment relates to compounds according to any one of embodiments 1) to 16), wherein $R^4$ represents
$(C_{1-4})$alkyl (especially methyl);
hydroxy-$(C_{1-3})$alkyl (especially hydroxymethyl);
—O—$R^{41}$, wherein $R^{41}$ represents
hydrogen;
$(C_{1-4})$alkyl (especially methyl);
$(C_{2-4})$alkyl which is substituted with one or two hydroxy (especially 2-hydroxyethyl, 2,3-dihydroxypropyl);
$R^{41a}R^{41b}N$—$(C_{2-3})$alkylene-, wherein $R^{41a}$ represent hydrogen or $(C_{1-4})$alkyl, and $R^{41b}$ independently represents $(C_{1-4})$alkyl (especially such group is 2-dimethylamino-ethyl); or
$(C_{4-7})$heterocyclyl-$X^{41}$—, wherein $X^{41}$ represents a direct bond, —$CH_2$—, or —$CH_2$—$CH_2$—, and wherein the $(C_{4-7})$heterocyclyl independently contains one or two ring heteroatoms independently selected from nitrogen and oxygen; wherein the oxygen atom of such group $(C_{4-7})$heterocyclyl-$X^{41}$—O— is separated by at least two (ring and/or chain) carbon atoms from such ring heteroatom; wherein said $(C_{4-7})$heterocyclyl independently is unsubstituted, or mono-substituted with $(C_{1-4})$alkyl (especially methyl) at a ring nitrogen atom having a free valency, or di-substituted with methyl;

[especially such $(C_{4-7})$heterocyclyl-$X^{41}$— group is oxetan-3-yl, 1-methyl-pyrrolidin-3-yl, 2,2-dimethyl-dioxolan-4-yl-methyl, 2-morpholin-4-yl-ethyl];

—$NR^{42a}R^{42b}$ wherein $R^{42a}$ represents hydrogen or $(C_{1-4})$alkyl (especially methyl), and $R^{42b}$ independently represents $(C_{1-4})$alkyl, $(C_{1-3})$alkoxy-$(C_{2-3})$alkyl, hydroxy-$(C_{2-3})$alkyl; or $R^{42a}$ and $R^{42b}$ together with the nitrogen to which they are attached form a 4- to 7-membered saturated ring optionally containing one further ring heteroatom selected from oxygen and nitrogen, wherein said ring is unsubstituted, or mono-substituted with $(C_{1-3})$alkyl (especially methyl) attached to a ring nitrogen atom having a free valency, or mono-substituted with $(C_{1-3})$alkoxy (especially methoxy) attached to a ring carbon atom [especially such group —$NR^{42a}R^{42b}$ is (2-hydroxyethyl)-amino, (2-hydroxyethyl)-methyl-amino, (2-methoxyethyl)-amino, morpholin-4-yl, 3-methoxy-azetidinyl, or 4-methyl-piperazin-1-yl]; or —CO—$R^{43}$ wherein $R^{43}$ represents $(C_{1-4})$alkoxy (especially methoxy); or —$NR^{43a}R^{43b}$ wherein $R^{43a}$ represents hydrogen or $(C_{1-4})$alkyl (especially methyl), and $R^{43b}$ independently represents hydrogen, $(C_{1-4})$alkyl (especially methyl), $(C_{1-3})$alkoxy-$(C_{2-3})$alkyl (especially 2-methoxy-ethyl), or hydroxy-$(C_{2-3})$alkyl (especially 2-hydroxy-ethyl); [especially such group —CO—$R^{43}$ is methoxycarbonyl, carbamoyl, methylcarbamoyl, dimethylcarbamoyl, hydroxyethylcarbamoyl, methoxyethylcarbamoyl];

wherein in a sub-embodiment $R^4$ represents —O—$R^{41}$ as defined herein above; especially $R^4$ represents $(C_{1-4})$alkoxy (in particular methoxy).

20) Another embodiment relates to compounds according to any one of embodiments 1) to 16), wherein $R^4$ represents
hydroxy;
$(C_{1-4})$alkoxy (especially methoxy);
2-hydroxy-ethoxy, or 2,3-dihydroxy-propoxy;
(oxetan-3-yl)-oxy-, (2,2-dimethyl-dioxolan-4-yl)-methoxy, or (2-morpholin-4-yl)-ethyl;
(2-hydroxyethyl)-amino, (2-hydroxyethyl)-methyl-amino, or (2-methoxyethyl)-amino; or
morpholin-4-yl, or 3-methoxy-azetidinyl;
wherein in a sub-embodiment $R^4$ represents $(C_{1-4})$alkoxy (especially methoxy) or 2-hydroxy-ethoxy.

21) Another embodiment relates to compounds according to any one of embodiments 1) to 16), wherein $R^4$ represents
hydroxy;
$(C_{1-4})$alkoxy (especially methoxy);
2-hydroxy-ethoxy;
2,3-dihydroxy-propoxy;
(oxetan-3-yl)-oxy-;
(2,2-dimethyl-dioxolan-4-yl)-methoxy;
(2-hydroxyethyl)-methyl-amino; or
morpholin-4-yl; or
3-methoxy-azetidinyl;
wherein in a sub-embodiment $R^4$ represents $(C_{1-4})$alkoxy (especially methoxy).

22) The invention, thus, relates to compounds of the formula (I) as defined in embodiment 1), or to such compounds further limited by the characteristics of any one of embodiments 2) to 21), under consideration of their respective dependencies; to pharmaceutically acceptable salts thereof; and to the use of such compounds as medicaments especially in the treatment of disorders relating to diseases and disorders related to pathogenic events associated with elevated levels of C5a and/or with C5aR activation. For avoidance of any doubt, especially the following embodiments relating to the compounds of formula (I) are thus possible and intended and herewith specifically disclosed in individualized form:

1, 2+1, 3+1, 5+1, 6+1, 6+2+1, 6+3+1, 7+1, 7+5+1, 8+1, 8+2+1, 8+3+1, 8+6+1, 8+6+2+1, 8+6+3+1, 9+1, 9+2+1, 9+3+1, 9+6+1, 9+6+2+1, 9+6+3+1, 11+1, 11+5+1, 11+7+1, 11+7+5+1, 12+1, 12+5+1, 12+7+1, 12+7+5+1, 13+1, 13+2+1, 13+3+1, 13+6+1, 13+6+2+1, 13+6+3+1, 13+8+1, 13+8+2+1, 13+8+3+1, 13+8+6+1, 13+8+6+2+1, 13+8+6+3+1, 13+9+1, 13+9+2+1, 13+9+3+1, 13+9+6+1, 13+9+6+2+1, 13+9+6+3+1, 14+1, 14+5+1, 14+7+1, 14+7+5+1, 14+11+1, 14+11+5+1, 14+11+7+1, 14+11+7+5+1, 14+12+1, 14+12+5+1, 14+12+7+1, 14+12+7+5+1, 15+1, 15+5+1, 15+7+1, 15+7+5+1, 15+11+1, 15+11+5+1, 15+11+7+1, 15+11+7+5+1, 15+12+1, 15+12+5+1, 15+12+7+1, 15+12+7+5+1, 16+1, 16+2+1, 16+3+1, 16+5+1, 16+6+1, 16+6+2+1, 16+6+3+1, 16+7+1, 16+7+5+1, 16+8+1, 16+8+2+1, 16+8+3+1, 16+8+6+1, 16+8+6+2+1, 16+8+6+3+1, 16+9+1, 16+9+2+1, 16+9+3+1, 16+9+6+1, 16+9+6+2+1, 16+9+6+3+1, 16+11+1, 16+11+5+1, 16+11+7+1, 16+11+7+5+1, 16+12+1, 16+12+5+1, 16+12+7+1, 16+12+7+5+1, 16+13+1, 16+13+2+1, 16+13+3+1, 16+13+6+1, 16+13+6+2+1, 16+13+6+3+1, 16+13+8+1, 16+13+8+2+1, 16+13+8+3+1, 16+13+8+6+1, 16+13+8+6+2+1, 16+13+8+6+3+1, 16+13+9+1, 16+13+9+2+1, 16+13+9+3+1, 16+13+9+6+1, 16+13+9+6+2+1, 16+13+9+6+3+1, 16+14+1, 16+14+5+1, 16+14+7+1, 16+14+7+5+1, 16+14+11+1, 16+14+11+5+1, 16+14+11+7+1, 16+14+11+7+5+1, 16+14+12+1, 16+14+12+5+1, 16+14+12+7+1, 16+14+12+7+5+1, 16+15+1, 16+15+5+1, 16+15+7+1, 16+15+7+5+1, 16+15+11+1, 16+15+11+5+1, 16+15+11+7+1, 16+15+11+7+5+1, 16+15+12+1, 16+15+12+5+1, 16+15+12+7+1, 16+15+12+7+5+1, 17+1, 17+2+1, 17+3+1, 17+6+1, 17+6+2+1, 17+6+3+1, 17+8+1, 17+8+2+1, 17+8+3+1, 17+8+6+1, 17+8+6+2+1, 17+8+6+3+1, 17+9+1, 17+9+2+1, 17+9+3+1, 17+9+6+1, 17+9+6+2+1, 17+9+6+3+1, 17+13+1, 17+13+2+1, 17+13+3+1, 17+13+6+1, 17+13+6+2+1, 17+13+6+3+1, 17+13+8+1, 17+13+8+2+1, 17+13+8+3+1, 17+13+8+6+1, 17+13+8+6+2+1, 17+13+8+6+3+1, 17+13+9+1, 17+13+9+2+1, 17+13+9+3+1, 17+13+9+6+1, 17+13+9+6+2+1, 17+13+9+6+3+1, 17+16+1, 17+16+2+1, 17+16+3+1, 17+16+5+1, 17+16+6+1, 17+16+6+2+1, 17+16+6+3+1, 17+16+7+1, 17+16+7+5+1, 17+16+8+1, 17+16+8+2+1, 17+16+8+3+1, 17+16+8+6+1, 17+16+8+6+2+1, 17+16+8+6+3+1, 17+16+9+1, 17+16+9+2+1, 17+16+9+3+1, 17+16+9+6+1, 17+16+9+6+2+1, 17+16+9+6+3+1, 17+16+11+1, 17+16+11+5+1, 17+16+11+7+1, 17+16+11+7+5+1, 17+16+12+1, 17+16+12+5+1, 17+16+12+7+1, 17+16+12+7+5+1, 17+16+13+1, 17+16+13+2+1, 17+16+13+3+1, 17+16+13+6+1, 17+16+13+6+2+1, 17+16+13+6+3+1, 17+16+13+8+1, 17+16+13+8+2+1, 17+16+13+8+3+1, 17+16+13+8+6+1, 17+16+13+8+6+2+1, 17+16+13+8+6+3+1, 17+16+13+9+1, 17+16+13+9+2+1, 17+16+13+9+3+1, 17+16+13+9+6+1, 17+16+13+9+6+2+1, 17+16+13+9+6+3+1, 17+16+14+1, 17+16+14+5+1, 17+16+14+7+1, 17+16+14+7+5+1, 17+16+14+11+1, 17+16+14+11+5+1, 17+16+14+11+7+1, 17+16+14+11+7+5+1, 17+16+14+12+1, 17+16+14+12+5+1, 17+16+14+12+7+1, 17+16+14+12+7+5+1, 17+16+15+1, 17+16+15+5+1, 17+16+15+7+1, 17+16+15+7+5+1, 17+16+15+11+1, 17+16+15+11+5+1, 17+16+15+11+7+1, 17+16+15+11+7+5+1, 17+16+15+12+1, 17+16+15+12+5+1, 17+16+15+12+7+1, 17+16+15+12+7+5+1, 19+1, 19+5+1, 19+7+1, 19+7+5+1, 19+11+1, 19+11+5+1, 19+11+7+1, 19+11+7+5+1, 19+12+1, 19+12+5+1, 19+12+7+1, 19+12+7+5+1, 19+14+1, 19+14+5+1, 19+14+7+1, 19+14+7+5+1, 19+14+11+1, 19+14+11+5+1, 19+14+11+7+1, 19+14+11+7+5+1, 19+14+12+1, 19+14+12+5+1, 19+14+12+7+1, 19+14+12+7+5+1, 19+15+1, 19+15+5+1, 19+15+7+1, 19+15+7+5+1, 19+15+11+1, 19+15+11+5+1, 19+15+11+7+1, 19+15+11+7+5+1, 19+15+12+1, 19+15+12+5+1, 19+15+12+7+1, 19+15+12+7+5+1, 19+16+1, 19+16+2+1, 19+16+3+1, 19+16+5+1, 19+16+6+1, 19+16+6+2+1, 19+16+6+3+1, 19+16+7+1, 19+16+7+5+1, 19+16+8+1, 19+16+8+2+1, 19+16+8+3+1, 19+16+8+6+1, 19+16+8+6+2+1, 19+16+8+6+3+1, 19+16+9+1, 19+16+9+2+1, 19+16+9+3+1, 19+16+9+6+1, 19+16+9+6+2+1, 19+16+9+6+3+1, 19+16+11+1, 19+16+11+5+1, 19+16+11+7+1, 19+16+11+7+5+1, 19+16+12+1, 19+16+12+5+1, 19+16+12+7+1, 19+16+12+7+5+1, 19+16+13+1, 19+16+13+2+1, 19+16+13+3+1, 19+16+13+6+1, 19+16+13+6+2+1, 19+16+13+6+3+1, 19+16+13+8+1, 19+16+13+8+2+1, 19+16+13+8+3+1, 19+16+13+8+6+1, 19+16+13+8+6+2+1, 19+16+13+8+6+3+1, 19+16+13+9+1, 19+16+13+9+2+1, 19+16+13+9+3+1, 19+16+13+9+6+1, 19+16+13+9+6+2+1, 19+16+13+9+6+3+1, 19+16+14+1, 19+16+14+5+1, 19+16+14+7+1, 19+16+14+7+5+1, 19+16+14+11+1, 19+16+14+11+5+1, 19+16+14+11+7+1, 19+16+14+11+7+5+1, 19+16+14+12+1, 19+16+14+12+5+1, 19+16+14+12+7+1, 19+16+14+12+7+5+1, 19+16+15+1, 19+16+15+5+1, 19+16+15+7+1, 19+16+15+7+5+1, 19+16+15+11+1, 19+16+15+11+5+1, 19+16+15+11+7+1, 19+16+15+11+7+5+1, 19+16+15+12+1, 19+16+15+12+5+1, 19+16+15+12+7+1, 19+16+15+12+7+5+1, 20+1, 20+5+1, 20+7+1, 20+7+5+1, 20+11+1, 20+11+5+1, 20+11+7+1, 20+11+7+5+1, 20+12+1, 20+12+5+1, 20+12+7+1, 20+12+7+5+1, 20+14+1, 20+14+5+1, 20+14+7+1, 20+14+7+5+1, 20+14+11+1, 20+14+11+5+1, 20+14+11+7+1, 20+14+11+7+5+1, 20+14+12+1, 20+14+12+5+1, 20+14+12+7+1, 20+14+12+7+5+1, 20+15+1, 20+15+5+1, 20+15+7+1, 20+15+7+5+1, 20+15+11+1, 20+15+11+5+1, 20+15+11+7+1, 20+15+11+7+5+1, 20+15+12+1, 20+15+12+5+1, 20+15+12+7+1, 20+15+12+7+5+1, 20+16+1, 20+16+2+1, 20+16+3+1, 20+16+5+1, 20+16+6+1, 20+16+6+2+1, 20+16+6+3+1, 20+16+7+1, 20+16+7+5+1, 20+16+8+1, 20+16+8+2+1, 20+16+8+3+1, 20+16+8+6+1, 20+16+8+6+2+1, 20+16+8+6+3+1, 20+16+9+1, 20+16+9+2+1, 20+16+9+3+1, 20+16+9+6+1, 20+16+9+6+2+1, 20+16+9+6+3+1, 20+16+11+1, 20+16+11+5+1, 20+16+11+7+1, 20+16+11+7+5+1, 20+16+12+1, 20+16+12+5+1, 20+16+12+7+1, 20+16+12+7+5+1, 20+16+13+1, 20+16+13+2+1, 20+16+13+3+1, 20+16+13+6+1, 20+16+13+6+2+1, 20+16+13+6+3+1, 20+16+13+8+1, 20+16+13+8+2+1, 20+16+13+8+3+1, 20+16+13+8+6+1, 20+16+13+8+6+2+1, 20+16+13+8+6+3+1, 20+16+13+9+1, 20+16+13+9+2+1, 20+16+13+9+3+1, 20+16+13+9+6+1, 20+16+13+9+6+2+1, 20+16+13+9+6+3+1, 20+16+14+1, 20+16+14+5+1, 20+16+14+7+1, 20+16+14+7+5+1, 20+16+14+11+1, 20+16+14+11+5+1, 20+16+14+11+7+1, 20+16+14+11+7+5+1, 20+16+14+12+1, 20+16+14+12+5+1, 20+16+14+12+7+1, 20+16+14+12+7+5+1, 20+16+15+1, 20+16+15+5+1, 20+16+15+7+1, 20+16+15+7+5+1, 20+16+15+11+1, 20+16+15+11+5+1, 20+16+15+11+7+1, 20+16+15+11+7+5+1, 20+16+15+12+1, 20+16+15+12+5+1, 20+16+15+12+7+1, 20+16+15+12+7+5+1, 21+1, 21+5+1, 21+7+1, 21+7+5+1, 21+11+1, 21+11+5+1, 21+11+7+1, 21+11+7+5+1, 21+12+1, 21+12+5+1, 21+12+7+1, 21+12+7+5+1, 21+14+1, 21+14+5+1, 21+14+7+1, 21+14+7+5+1, 21+14+11+1, 21+14+11+5+1, 21+14+11+7+1, 21+14+11+7+5+1, 21+14+12+1, 21+14+12+5+1, 21+14+12+7+1, 21+14+12+7+5+1, 21+15+1, 21+15+5+1, 21+15+7+1, 21+15+7+5+1, 21+15+11+1, 21+15+11+5+1, 21+15+11+7+1, 21+15+11+7+5+1, 21+15+12+1, 21+15+12+5+1, 21+15+12+7+1, 21+15+12+7+5+1, 21+16+1, 21+16+2+1, 21+16+3+1, 21+16+5+1, 21+16+6+1, 21+16+6+2+1, 21+16+6+3+1, 21+16+7+1, 21+16+7+5+1, 21+16+8+1, 21+16+8+2+1, 21+16+8+3+1, 21+16+8+6+1, 21+16+8+6+2+1, 21+16+8+6+3+1, 21+16+9+1, 21+16+9+2+1, 21+16+9+3+1, 21+16+9+6+1, 21+16+9+6+2+1, 21+16+9+6+3+1, 21+16+11+1, 21+16+11+5+1, 21+16+11+7+1, 21+16+11+7+5+1, 21+16+

12+1, 21+16+12+5+1, 21+16+12+7+1, 21+16+12+7+5+1, 21+16+13+1, 21+16+13+2+1, 21+16+13+3+1, 21+16+13+6+1, 21+16+13+6+2+1, 21+16+13+6+3+1, 21+16+13+8+1, 21+16+13+8+2+1, 21+16+13+8+3+1, 21+16+13+8+6+1, 21+16+13+8+6+2+1, 21+16+13+8+6+3+1, 21+16+13+9+1, 21+16+13+9+2+1, 21+16+13+9+3+1, 21+16+13+9+6+1, 21+16+13+9+6+2+1, 21+16+13+9+6+3+1, 21+16+14+1, 21+16+14+5+1, 21+16+14+7+1, 21+16+14+7+5+1, 21+16+14+11+1, 21+16+14+11+5+1, 21+16+14+11+7+1, 21+16+14+11+7+5+1, 21+16+14+12+1, 21+16+14+12+5+1, 21+16+14+12+7+1, 21+16+14+12+7+5+1, 21+16+15+1, 21+16+15+5+1, 21+16+15+7+1, 21+16+15+7+5+1, 21+16+15+11+1, 21+16+15+11+5+1, 21+16+15+11+7+1, 21+16+15+11+7+5+1, 21+16+15+12+1, 21+16+15+12+5+1, 21+16+15+12+7+1, 21+16+15+12+7+5+1.

In the list above the numbers refer to the embodiments according to their numbering provided hereinabove whereas "+" indicates the dependency from another embodiment. The different individualized embodiments are separated by commas. In other words, "20+15+12+1" for example refers to embodiment 20) depending on embodiment 15), depending on embodiment 12), depending on embodiment 1), i.e. embodiment "20+15+12+1" corresponds to the compounds of formula (I) according to embodiment 1) further limited by all the features of the embodiments 12), 15), and 20).

23) A second aspect of the invention relates to compounds of the formula (I) according to embodiment 1) which are also compounds of the formula (II)

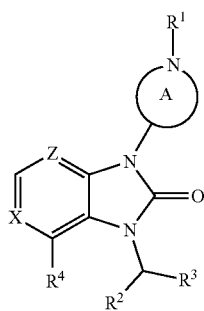

Formula (II)

wherein X is CH and Z is CH, X is N and Z is CH, or X is CH and Z is N;

ring A represents a saturated 4- to 7-membered monocyclic carbocyclic ring containing the ring nitrogen atom to which $R^1$ is attached, wherein said ring independently is unsubstituted, or mono-, or di-substituted wherein the substituents are independently selected from $(C_{1-3})$alkyl (especially methyl), fluoro, or $(C_{1-4})$alkoxy-carbonyl (especially ethoxy-carbonyl) [especially such ring A is azetidin-1,3-diyl, pyrrolidin-1,3-diyl, 4-methyl-pyrrolidin-1,3-diyl, piperidin-1,3-diyl, piperidin-1,4-diyl, 3-fluoro-piperidin-1,4-diyl, 2-methyl-piperidin-1,4-diyl, 3-methyl-piperidin-1,4-diyl, 3-(ethoxycarbonyl)-piperidin-1,4-diyl, 3,3-dimethyl-piperidin-1,4-diyl, azepan-1,4-diyl]; or ring A represents a saturated bridged bi-cyclic 7- or 8-membered carbocyclic ring containing the ring nitrogen atom to which $R^1$ is attached, wherein said ring is unsubstituted [especially such ring is 2-aza-bicyclo[2.2.1]heptane-2,5-diyl, 3-aza-bicyclo[3.1.1]heptane-3,6-diyl];

$R^1$ represents $(C_{1-4})$alkyl (especially methyl, isopropyl);

—CO—$R^{11}$ wherein $R^{11}$ represents $(C_{1-4})$alkyl; $(C_{1-4})$alkoxy; phenyl, phenoxy; $(C_{3-6})$cycloalkyl; or $(C_{3-6})$cycloalkoxy optionally containing one ring oxygen and optionally mono-substituted with methyl or trifluoromethyl [especially such group —CO—$R^{11}$ is tert.-butyl-carbonyl, methoxycarbonyl, ethoxycarbonyl, isopropoxycarbonyl, n-butoxycarbonyl, tert.-butoxycarbonyl, oxetan-3-yl-oxy-carbonyl, (3-methyl-oxetan-3-yl)-oxy-carbonyl, (3-trifluoromethyl-oxetan-3-yl)-oxy-carbonyl, phenylcarbonyl, phenoxycarbonyl, cyclopropylcarbonyl];

benzyl wherein the phenyl ring of said benzyl is optionally mono- or di-substituted with halogen [especially 2,4-dichlorobenzyl]; or phenyl, or 5- or 6-membered heteroaryl (especially pyrazolyl, oxadiazolyl, pyridinyl, pyridazinyl, pyrimidinyl); wherein said phenyl or 5- or 6-membered heteroaryl independently is unsubstituted, mono-, di- or tri-substituted, wherein the substituents are independently selected from $(C_{1-4})$alkyl (especially methyl, isopropyl);
$(C_{1-4})$alkoxy (especially methoxy, n-butyloxy);
$(C_{1-3})$fluoroalkyl (especially trifluoromethyl);
$(C_{1-3})$fluoroalkoxy (especially trifluoromethoxy);
halogen (especially fluoro, chloro, bromo);
cyano;
nitro;
hydroxy;
hydroxy-$(C_{1-3})$alkyl (especially 1-hydroxyethyl, hydroxymethyl, 1-hydroxy-1-methyl-ethyl);
$(C_{1-4})$alkoxy-$(C_{1-3})$alkyl (especially 1-methoxyethyl);
hydroxy-$(C_{2-3})$alkoxy (especially 2-hydroxy-ethoxy);
$(C_{1-4})$alkoxy-$(C_{2-3})$alkoxy (especially 2-methoxy-ethoxy);
$(C_{3-6})$cycloalkyl-$X^{12}$—, wherein $X^{12}$ represents a direct bond, —O—, or —$(C_{1-3})$alkylene-O—, and wherein the $(C_{3-6})$cycloalkyl independently contains one optional ring oxygen [especially such group $(C_{3-6})$cycloalkyl-$X^{12}$— is cyclopropyl, cyclopropyloxy, cyclobutyl-oxy, oxetan-3-yl-oxy, cyclopropyl-methoxy, or tetrahydropyran-4-yl-oxy];
$R^{13}$—CO—$X^{13}$—, wherein $X^{13}$ represents a direct bond or $(C_{1-3})$alkylene, and $R^{13}$ represents hydrogen or $(C_{1-4})$alkyl (especially such group $R^{13}$—CO—$X^{13}$ is formyl, acetyl, 2-oxo-ethyl);
3-(morpholin-4-yl)-prop-1-ynyl;
$R^{14a}R^{14b}N$—$X^{14}$—, wherein $X^{14}$ represents a direct bond or $(C_{1-3})$alkylene; and wherein $R^{14a}$ and $R^{14b}$ independently represent hydrogen, $(C_{1-4})$alkyl, hydroxy-$(C_{2-4})$alkyl, $(C_{1-3})$alkoxy-$(C_{2-4})$alkyl; or $R^{14a}$ and $R^{14b}$ together with the nitrogen to which they are attached to form a 4- to 6-membered saturated ring optionally containing one additional ring heteroatom selected from oxygen and nitrogen; and wherein said ring is optionally mono-substituted with $(C_{1-4})$alkyl (especially methyl), hydroxy, $(C_{1-4})$alkoxy (especially methoxy), or dimethylamino,

[especially such group $R^{14a}R^{14b}N$—$X^{14}$— is amino, methylamino-methyl, dimethylamino-methyl, [(2-hydroxyethyl)-methylamino]-methyl, [(2-hydroxyethyl)-ethylamino]-methyl, [(2-methoxy-1-methyl-ethyl)-amino]-methyl, [(2-methoxyethyl)-methylamino]-methyl, [di-(2-hydroxyethyl)-amino]-methyl, (azetidin-1-yl)-methyl, (pyrrolidin-1-yl)-methyl, (piperidin-1-yl)-methyl, morpholin-4-yl, piperazin-1-ylmethyl, (morpholin-4-yl)-methyl, 2-(morpholin-4-yl)-ethyl, 3-(morpholin-4-yl)-propyl, (3-methoxy-azetidin-1-yl)-methyl, 1-(3-methoxy-azetidin-1-yl)-ethyl, (1-methyl-piperazin-4-yl)-methyl, (4-hydroxypiperidin-1-yl)-methyl, (4-methoxypiperidin-1-yl)-methyl, (3-methoxy-pyrrolidin-1-yl)-methyl, (4-dimethylamino-piperidin-1-yl)-methyl]; or benzyloxy, wherein the phenylring of benzyloxy is optionally mono- or di-substituted with halogen or methyl);

wherein in a sub-embodiment $R^1$ represents phenyl, or 5- or 6-membered heteroaryl (especially pyrazolyl, oxadiazolyl, pyridinyl, pyridazinyl, pyrimidinyl); wherein said phenyl or 5- or 6-membered heteroaryl are substituted as defined herein before;

$R^2$ represents phenyl, or 5- or 6-membered heteroaryl (notably 6-membered heteroaryl; in particular thiazolyl, pyridinyl, pyrimidinyl, pyrazinyl, pyridazinyl); wherein said phenyl or 5- or 6-membered heteroaryl independently is mono-, di- or tri-substituted (especially mono-substituted, in particular in ortho position with regard to the point of attachment of the rest of the molecule), wherein the substituents are independently selected from $(C_{1-4})$alkyl (especially methyl, isopropyl);
$(C_{1-4})$alkoxy (especially methoxy, isopropoxy);
$(C_{1-3})$fluoroalkyl (especially trifluoromethyl);
$(C_{1-3})$fluoroalkoxy (especially trifluoromethoxy);
halogen (especially chloro, fluoro); or
$(C_{3-6})$cycloalkyl-$X^{21}$—, wherein $X^{21}$ represents a direct bond, —O—, or —$(C_{1-3})$alkylene-O—, and wherein the $(C_{3-6})$cycloalkyl independently contains one optional ring oxygen [especially such group $(C_{3-6})$cycloalkyl-$X^{21}$— is cyclopropyl, cyclopropyl-oxy, cyclobutyl-oxy, oxetan-3-yl-oxy, cyclopropyl-methoxy];

$R^3$ represents hydrogen, or $(C_{1-3})$alkyl (especially methyl); and $R^4$ represents
$(C_{1-4})$alkyl (especially methyl);
hydroxy-$(C_{1-3})$alkyl (especially hydroxymethyl);
—O—$R^{41}$, wherein $R^{41}$ represents
hydrogen;
$(C_{1-4})$alkyl (especially methyl);
$(C_{2-4})$alkyl which is substituted with one or two hydroxy (especially 2-hydroxyethyl, 2,3-dihydroxypropyl);
$R^{41a}R^{41b}N$—$(C_{2-3})$alkylene-, wherein $R^{41a}$ and $R^{41b}$ independently represent hydrogen or $(C_{1-4})$alkyl (especially such group is 2-dimethylamino-ethyl); or
$(C_{4-7})$heterocyclyl-$X^{41}$—, wherein $X^{41}$ represents a direct bond or $(C_{1-3})$alkylene, and wherein the $(C_{4-7})$heterocyclyl independently contains one or two ring heteroatoms independently selected from nitrogen and oxygen; wherein said $(C_{4-7})$heterocyclyl independently is unsubstituted, or mono-, or di-substituted, wherein the substituents are independently selected from:
$(C_{1-4})$alkyl (especially methyl); and/or
$(C_{1-4})$alkoxy-carbonyl attached to a ring nitrogen atom having a free valency;
[especially such $(C_{4-7})$heterocyclyl-$X^{41}$— group is oxetan-3-yl, 1-methyl-pyrrolidin-3-yl, 2,2-dimethyl-dioxolan-4-yl-methyl, 2-morpholin-4-yl-ethyl, 1-tert-butoxy-carbonyl-piperidin-4-yl, piperidin-4-yl];
—$NR^{42a}R^{42b}$ wherein $R^{42a}$ and $R^{42b}$ independently represent hydrogen, $(C_{1-4})$alkyl, $(C_{1-3})$alkoxy-$(C_{2-3})$alkyl, hydroxy-$(C_{2-3})$alkyl, or $R^{42a}$ and $R^{42b}$ together with the nitrogen to which they are attached form a 4- to 7-membered saturated ring optionally containing one further ring heteroatom selected from oxygen and nitrogen, wherein said ring is unsubstituted or mono-substituted with $(C_{1-3})$alkyl (especially methyl), or $(C_{1-3})$alkoxy (especially methoxy) [especially such group —$NR^{42a}R^{42b}$ is (2-hydroxyethyl)-amino, (2-hydroxyethyl)-methyl-amino, (2-methoxyethyl)-amino, morpholin-4-yl, 3-methoxy-azetidinyl, or 4-methyl-piperazin-1-yl]; or —CO—$R^{43}$ wherein $R^{43}$ represents $(C_{1-4})$alkoxy (especially methoxy); or —$NR^{43a}R^{43b}$ wherein $R^{43a}$ and $R^{43b}$ independently represent hydrogen, $(C_{1-4})$alkyl (especially methyl), $(C_{1-3})$alkoxy-$(C_{2-3})$alkyl (especially 2-methoxy-ethyl), or hydroxy-$(C_{2-3})$alkyl (especially 2-hydroxy-ethyl); [especially such group —CO—$R^{43}$ is methoxycarbonyl, carbamoyl, methylcarbamoyl, dimethylcarbamoyl, hydroxyethylcarbamoyl, methoxyethylcarbamoyl].

wherein the characteristics disclosed in embodiments 2) to 22) are intended to apply mutatis mutandis also to the compounds formula (II) according to embodiment 23); wherein especially the following embodiments are thus possible and intended and herewith specifically disclosed in individualized form:

23+2, 23+3, 23+5, 23+8+2, 23+8+3, 23+8+6, 8, 23+9+2, 23+9+3, 23+9+6, 9, 23+11+5, 23+11, 23+12+5, 23+12, 23+13+2, 23+13+3, 23+13+8+2, 23+13+8+3, 23+13+8+6, 13+8, 23+13+9+2, 23+13+9+3, 23+13+9+6, 13+9, 23+13, 23+14+5, 23+14+11+5, 23+14+11, 23+14+12+5, 23+14+12, 23+14, 23+15+5, 23+15+11+5, 23+15+11, 23+15+12+5, 23+15+12, 23+15, 23+16+2, 23+16+3, 23+16+5, 23+16+8+2, 23+16+8+3, 23+16+8+6, 16+8, 23+16+9+2, 23+16+9+3, 23+16+9+6, 16+9, 23+16+11+5, 23+16+11, 23+16+12+5, 23+16+12, 23+16+13+2, 23+16+13+3, 23+16+13+8+2, 23+16+13+8+3, 23+16+13+8+6, 16+13+8, 23+16+13+9+2, 23+16+13+9+3, 23+16+13+9+6, 16+13+9, 23+16+13, 23+16+14+5, 23+16+14+11+5, 23+16+14+11, 23+16+14+12+5, 23+16+14+12, 23+16+14, 23+16+15+5, 23+16+15+11+5, 23+16+15+11, 23+16+15+12+5, 23+16+15+12, 23+16+15, 23+16, 23+17+2, 23+17+3, 23+17+8+2, 23+17+8+3, 23+17+8+6, 17+8, 23+17+9+2, 23+17+9+3, 23+17+9+6, 17+9, 23+17+13+2, 23+17+13+3, 23+17+13+8+2, 23+17+13+8+3, 23+17+13+8+6, 17+13+8, 23+17+13+9+2, 23+17+13+9+3, 23+17+13+9+6, 17+13+9, 23+17+13, 23+17+16+2, 23+17+16+3, 23+17+16+5, 23+17+16+8+2, 23+17+16+8+3, 23+17+16+8+6, 17+16+8, 23+17+16+9+2, 23+17+16+9+3, 23+17+16+9+6, 17+16+9, 23+17+16+11+5, 23+17+16+11, 23+17+16+12+5, 23+17+16+12, 23+17+16+13+2, 23+17+16+13+3, 23+17+16+13+8+2, 23+17+16+13+8+3, 23+17+16+13+8+6, 17+16+13+8, 23+17+16+13+9+2, 23+17+16+13+9+3, 23+17+16+13+9+6, 17+16+13+9, 23+17+16+13, 23+17+16+14+5, 23+17+16+14+11+5, 23+17+16+14+11, 23+17+16+14+12+5, 23+17+16+14+12, 23+17+16+14, 23+17+16+15+5, 23+17+16+15+11+5, 23+17+16+15+11, 23+17+16+15+12+5, 23+17+16+15+12, 23+17+16+15, 23+17+16, 23+17, 23+19+5, 23+19+11+5, 23+19+11, 23+19+12+5, 23+19+12, 23+19+14+5, 23+19+14+11+5, 23+19+14+11, 23+19+14+12+5, 23+19+14+12, 23+19+14, 23+19+15+5, 23+19+15+11+5, 23+19+15+11, 23+19+15+12+5, 23+19+15+12, 23+19+15, 23+19+16+2, 23+19+16+3, 23+19+16+5, 23+19+16+8+2, 23+19+16+8+3, 23+19+16+8+6, 19+16+8, 23+19+16+9+2, 23+19+16+9+3, 23+19+16+9+6, 19+16+9, 23+19+16+11+5, 23+19+16+11, 23+19+16+12+5, 23+19+16+12, 23+19+16+13+2, 23+19+16+13+3, 23+19+16+13+8+2, 23+19+16+13+8+3, 23+19+16+13+8+6, 19+16+13+8, 23+19+16+13+9+2,

23+19+16+13+9+3, 23+19+16+13+9+6, 19+16+13+9, 23+19+16+13, 23+19+16+14+5, 23+19+16+14+11+5, 23+19+16+14+11, 23+19+16+14+12+5, 23+19+16+14+12, 23+19+16+14, 23+19+16+15+5, 23+19+16+15+11+5, 23+19+16+15+11, 23+19+16+15+12+5, 23+19+16+15+12, 23+19+16+15, 23+19+16, 23+19, 23+20+5, 23+20+11+5, 23+20+11, 23+20+12+5, 23+20+12, 23+20+14+5, 23+20+14+11+5, 23+20+14+11, 23+20+14+12+5, 23+20+14+12, 23+20+14, 23+20+15+5, 23+20+15+11+5, 23+20+15+11, 23+20+15+12+5, 23+20+15+12, 23+20+15, 23+20+16+2, 23+20+16+3, 23+20+16+5, 23+20+16+8+2, 23+20+16+8+3, 23+20+16+8+6, 20+16+8, 23+20+16+9+2, 23+20+16+9+3, 23+20+16+9+6, 20+16+9, 23+20+16+11+5, 23+20+16+11, 23+20+16+12+5, 23+20+16+12, 23+20+16+13+2, 23+20+16+13+3, 23+20+16+13+8+2, 23+20+16+13+8+3, 23+20+16+13+8+6, 20+16+13+8, 23+20+16+13+9+2, 23+20+16+13+9+3, 23+20+16+13+9+6, 20+16+13+9, 23+20+16+13, 23+20+16+14+5, 23+20+16+14+11+5, 23+20+16+14+11, 23+20+16+14+12+5, 23+20+16+14+12, 23+20+16+14, 23+20+16+15+5, 23+20+16+15+11+5, 23+20+16+15+11, 23+20+16+15+12+5, 23+20+16+15+12, 23+20+16+15, 23+20+16, 23+20, 23+21+5, 23+21+11+5, 23+21+11, 23+21+12+5, 23+21+12, 23+21+14+5, 23+21+14+11+5, 23+21+14+11, 23+21+14+12+5, 23+21+14+12, 23+21+14, 23+21+15+5, 23+21+15+11+5, 23+21+15+11, 23+21+15+12+5, 23+21+15+12, 23+21+15, 23+21+16+2, 23+21+16+3, 23+21+16+5, 23+21+16+8+2, 23+21+16+8+3, 23+21+16+8+6, 21+16+8, 23+21+16+9+2, 23+21+16+9+3, 23+21+16+9+6, 21+16+9, 23+21+16+11+5, 23+21+16+11, 23+21+16+12+5, 23+21+16+12, 23+21+16+13+2, 23+21+16+13+3, 23+21+16+13+8+2, 23+21+16+13+8+3, 23+21+16+13+8+6, 21+16+13+8, 23+21+16+13+9+2, 23+21+16+13+9+3, 23+21+16+13+9+6, 21+16+13+9, 23+21+16+13, 23+21+16+14+5, 23+21+16+14+11+5, 23+21+16+14+11, 23+21+16+14+12+5, 23+21+16+14+12, 23+21+16+14, 23+21+16+15+5, 23+21+16+15+11+5, 23+21+16+15+11, 23+21+16+15+12+5, 23+21+16+15+12, 23+21+16+15, 23+21+16, 23+21.

In the list above the numbers refer to the embodiments according to their numbering provided hereinabove whereas "+" indicates the limitations as outlined above.

24) A third aspect of the invention relates to compounds of the formula (I) according to embodiment 1) which are also compounds of the formula (III)

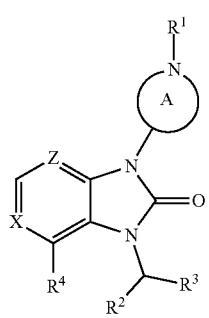

Formula (III)

wherein X is CH and Z is CH, X is N and Z is CH, or X is CH and Z is N;

ring A represents a saturated 4- to 7-membered monocyclic carbocyclic ring containing the ring nitrogen atom to which $R^1$ is attached, wherein said ring independently is unsubstituted, or mono-, or di-substituted wherein the substituents are independently selected from $(C_{1-3})$alkyl (especially methyl), fluoro, or $(C_{1-4})$alkoxy-carbonyl (especially ethoxy-carbonyl) [especially such ring A is azetidin-1,3-diyl, pyrrolidin-1,3-diyl, 4-methyl-pyrrolidin-1,3-diyl, piperidin-1,3-diyl, piperidin-1,4-diyl, 3-fluoro-piperidin-1,4-diyl, 2-methyl-piperidin-1,4-diyl, 3-methyl-piperidin-1,4-diyl, 3-(ethoxycarbonyl)-piperidin-1,4-diyl, 3,3-dimethyl-piperidin-1,4-diyl, azepan-1,4-diyl]; or ring A represents a saturated 7- or 8-membered bridged bi-cyclic carbocyclic ring containing the ring nitrogen atom to which $R^1$ is attached, wherein said ring is unsubstituted [especially such ring is 2-aza-bicyclo[2.2.1]heptane-2,5-diyl, 3-aza-bicyclo[3.1.1]heptane-3,6-diyl];

$R^1$ represents $(C_{1-4})$alkyl (especially methyl, isopropyl);

—CO—$R^{11}$ wherein $R^{11}$ represents $(C_{1-4})$alkyl; $(C_{1-4})$alkoxy; phenyl, phenoxy; $(C_{3-6})$cycloalkyl; or $(C_{3-6})$cycloalkoxy optionally containing one ring oxygen and optionally mono-substituted with methyl or trifluoromethyl [especially such group —CO—$R^{11}$ is tert.-butylcarbonyl, methoxycarbonyl, ethoxycarbonyl, isopropoxycarbonyl, n-butoxycarbonyl, tert.-butoxycarbonyl, oxetan-3-yl-oxy-carbonyl, (3-methyloxetan-3-yl)-oxy-carbonyl, (3-trifluoromethyl-oxetan-3-yl)-oxy-carbonyl, phenylcarbonyl, phenoxycarbonyl, cyclopropylcarbonyl];

benzyl wherein the phenyl ring of said benzyl is optionally mono- or di-substituted with halogen [especially 2,4-dichlorobenzyl]; or phenyl, or 5- or 6-membered heteroaryl (especially pyrazolyl, oxadiazolyl, pyridinyl, pyridazinyl, pyrimidinyl); wherein said phenyl or 5- or 6-membered heteroaryl independently is unsubstituted, mono-, di- or tri-substituted, wherein the substituents are independently selected from $(C_{1-4})$alkyl (especially methyl, isopropyl);
$(C_{1-4})$alkoxy (especially methoxy, n-butyloxy);
$(C_{1-3})$fluoroalkyl (especially trifluoromethyl);
$(C_{1-3})$fluoroalkoxy (especially trifluoromethoxy);
halogen (especially fluoro, chloro, bromo);
cyano;
nitro;
hydroxy;
hydroxy-$(C_{1-3})$alkyl (especially 1-hydroxyethyl, hydroxymethyl, 1-hydroxy-1-methyl-ethyl);
$(C_{1-4})$alkoxy-$(C_{1-3})$alkyl (especially 1-methoxyethyl);
hydroxy-$(C_{2-3})$alkoxy (especially 2-hydroxy-ethoxy);
$(C_{1-4})$alkoxy-$(C_{2-3})$alkoxy (especially 2-methoxy-ethoxy);
$(C_{3-6})$cycloalkyl-$X^{12}$—, wherein $X^{12}$ represents a direct bond, —O—, or —$(C_{1-3})$alkylene-O—, and wherein the $(C_{3-6})$cycloalkyl independently contains one optional ring oxygen [especially such group $(C_{3-6})$cycloalkyl-$X^{12}$— is cyclopropyl, cyclopropyloxy, cyclobutyl-oxy, oxetan-3-yl-oxy, cyclopropylmethoxy, or tetrahydropyran-4-yl-oxy];
$R^{13}$—CO—$X^{13}$—, wherein $X^{13}$ represents a direct bond or $(C_{1-3})$alkylene, and $R^{13}$ represents hydrogen or $(C_{1-4})$alkyl (especially such group $R^{13}$—CO—$X^{13}$ is formyl, acetyl, 2-oxo-ethyl);
3-(morpholin-4-yl)-prop-1-ynyl;
$R^{14a}R^{14b}$N—$X^{14}$—, wherein $X^{14}$ represents a direct bond or $(C_{1-3})$alkylene; and wherein $R^{14a}$ and $R^{14b}$ independently represent hydrogen, $(C_{1-4})$alkyl, hydroxy-$(C_{2-4})$alkyl, $(C_{1-3})$alkoxy-$(C_{2-4})$alkyl; or $R^{14a}$ and $R^{14b}$ together with the nitrogen to which they are attached to form a 4- to 6-membered saturated ring optionally containing one additional ring heteroatom selected from oxygen and nitrogen; and wherein said ring is optionally mono-substituted with $(C_{1-4})$alkyl (especially methyl), hydroxy, $(C_{1-4})$alkoxy (especially methoxy), or dimethylamino,

[especially such group $R^{14a}R^{14b}N—X^{14}—$ is amino, methylamino-methyl, dimethylamino-methyl, [(2-hydroxyethyl)-methylamino]-methyl, [(2-hydroxyethyl)-ethylamino]-methyl, [(2-methoxy-1-methylethyl)-amino]-methyl, [(2-methoxyethyl)-methylamino]-methyl, [di-(2-hydroxyethyl)-amino]-methyl, (azetidin-1-yl)-methyl, (pyrrolidin-1-yl)-methyl, (piperidin-1-yl)-methyl, morpholin-4-yl, piperazin-1-ylmethyl, (morpholin-4-yl)-methyl, 2-(morpholin-4-yl)-ethyl, 3-(morpholin-4-yl)-propyl, (3-methoxy-azetidin-1-yl)-methyl, 1-(3-methoxy-azetidin-1-yl)-ethyl, (1-methyl-piperazin-4-yl)-methyl, (4-hydroxypiperidin-1-yl)-methyl, (4-methoxypiperidin-1-yl)-methyl, (3-methoxy-pyrrolidin-1-yl)-methyl, (4-dimethylamino-piperidin-1-yl)-methyl]; or benzyloxy, wherein the phenylring of benzyloxy is optionally mono- or di-substituted with halogen or methyl);

wherein in a sub-embodiment $R^1$ represents phenyl, or 5- or 6-membered heteroaryl (especially pyrazolyl, oxadiazolyl, pyridinyl, pyridazinyl, pyrimidinyl); wherein said phenyl or 5- or 6-membered heteroaryl are substituted as defined herein before;

$R^2$ represents phenyl, or 6-membered heteroaryl (especially pyridinyl, pyrimidinyl, pyrazinyl, pyridazinyl); wherein said phenyl or 6-membered heteroaryl independently is mono-substituted in ortho position with regard to the point of attachment of the rest of the molecule, wherein the substituents is independently selected from $(C_{1-4})$alkyl (especially methyl, isopropyl);
$(C_{1-4})$alkoxy (especially methoxy, isopropoxy);
$(C_{1-3})$fluoroalkyl (especially trifluoromethyl);
$(C_{1-3})$fluoroalkoxy (especially trifluoromethoxy);
$(C_{3-6})$cycloalkyl-$X^{21}—$, wherein $X^{21}$ represents a direct bond, —O—, or —$(C_{1-3})$alkylene-O—, and wherein the $(C_{3-6})$cycloalkyl independently contains one optional ring oxygen [especially such group $(C_{3-6})$cycloalkyl-$X^{21}—$ is cyclopropyl, cyclopropyl-oxy, cyclobutyl-oxy, oxetan-3-yl-oxy, cyclopropyl-methoxy];

$R^3$ represents hydrogen, or $(C_{1-3})$alkyl (especially methyl) [$R^3$ represents hydrogen]; and $R^4$ represents
  —O—$R^{41}$, wherein $R^{41}$ represents
    hydrogen;
    $(C_{1-4})$alkyl (especially methyl);
    $(C_{2-4})$alkyl which is substituted with one or two hydroxy (especially 2-hydroxyethyl, 2,3-dihydroxypropyl);
    oxetan-3-yl;
    2,2-dimethyl-dioxolan-4-yl-methyl; or
  (2-hydroxyethyl)-methyl-amino, morpholin-4-yl, or 3-methoxy-azetidinyl;

wherein in a sub-embodiment $R^4$ represents —O—$R^{41}$ as defined herein above; especially $R^4$ represents $(C_{1-4})$alkoxy (in particular methoxy).

wherein the characteristics disclosed in embodiments 2) to 22) are intended to apply mutatis mutandis also to the compounds formula (III) according to embodiment 24);

wherein especially the following embodiments are thus possible and intended and herewith specifically disclosed in individualized form:

24, 24+2, 24+3, 24+5, 24+8+2, 24+8+3, 24+8, 24+9+2, 24+9+3, 24+9, 24+11+5, 24+11, 24+12+5, 24+12, 24+15+5, 24+15+11+5, 24+15+11, 24+15+12+5, 24+15+12, 24+15, 24+16+2, 24+16+3, 24+16+5, 24+16+8+2, 24+16+8+3, 24+16+8, 24+16+9+2, 24+16+9+3, 24+16+9, 24+16+11+5, 24+16+11, 24+16+12+5, 24+16+12, 24+16+15+5, 24+16+15+11+5, 24+16+15+11, 24+16+15+12+5, 24+16+15+12, 24+16+15, 24+16, 24+21+5, 24+21+11+5, 24+21+11, 24+21+12+5, 24+21+12, 24+21+15+5, 24+21+15+11+5, 24+21+15+11, 24+21+15+12+5, 24+21+15+12, 24+21+15, 24+21+16+2, 24+21+16+3, 24+21+16+5, 24+21+16+8+2, 24+21+16+8+3, 24+21+16+8, 24+21+16+9+2, 24+21+16+9+3, 24+21+16+9, 24+21+16+11+5, 24+21+16+11, 24+21+16+12+5, 24+21+16+12, 24+21+16+15+5, 24+21+16+15+11+5, 24+21+16+15+11, 24+21+16+15+12+5, 24+21+16+15+12, 24+21+16+15, 24+21+16, 24+21.

In the list above the numbers refer to the embodiments according to their numbering provided hereinabove whereas "+" indicates the limitations as outlined above.

25) Another embodiment relates to compounds according to embodiment 1) which are selected from the following compounds:

4-[4-Methoxy-2-oxo-3-(2-trifluoromethyl-benzyl)-2,3-dihydro-benzoimidazol-1-yl]-piperidine-1-carboxylic acid tert-butyl ester;

1-[1-(2,6-Dimethyl-phenyl)-piperidin-4-yl]-4-methoxy-3-(2-trifluoromethyl-benzyl)-1,3-dihydro-benzoimidazol-2-one;

1-(1-(2,6-dimethylphenyl)piperidin-4-yl)-4-methoxy-3-(2-(trifluoromethyl)benzyl)-1,3-dihydro-benzoimidazol-2-one-7-d;

4-Methoxy-1-(1-phenyl-piperidin-4-yl)-3-(2-trifluoromethyl-benzyl)-1,3-dihydro-benzoimidazol-2-one;

1-[1-(2,4-Dichloro-benzyl)-piperidin-4-yl]-4-methoxy-3-(2-trifluoromethyl-benzyl)-1,3-dihydro-benzoimidazol-2-one; (R)-3-[4-Methoxy-2-oxo-3-(2-trifluoromethyl-benzyl)-2,3-dihydro-benzoimidazol-1-yl]-pyrrolidine-1-carboxylic acid tert-butyl ester;

1-[(R)-1-(2,6-Difluoro-phenyl)-pyrrolidin-3-yl]-4-methoxy-3-(2-trifluoromethyl-benzyl)-1,3-dihydro-benzoimidazol-2-one;

1-[(R)-1-(2,6-Dimethyl-phenyl)-pyrrolidin-3-yl]-4-methoxy-3-(2-trifluoromethyl-benzyl)-1,3-dihydro-benzoimidazol-2-one;

1-[1-(2,6-Difluoro-phenyl)-piperidin-4-yl]-4-methoxy-3-(2-trifluoromethyl-benzyl)-1,3-dihydro-benzoimidazol-2-one;

1-[1-(2,6-Dimethoxy-phenyl)-piperidin-4-yl]-4-methoxy-3-(2-trifluoromethyl-benzyl)-1,3-dihydro-benzoimidazol-2-one;

1-[1-(2-Fluoro-6-methoxy-phenyl)-piperidin-4-yl]-4-methoxy-3-(2-trifluoromethyl-benzyl)-1,3-dihydro-benzoimidazol-2-one;

4-Methoxy-1-[1-(2-methoxy-6-methyl-phenyl)-piperidin-4-yl]-3-(2-trifluoromethyl-benzyl)-1,3-dihydro-benzoimidazol-2-one;

1-[1-(2-Fluoro-6-methyl-phenyl)-piperidin-4-yl]-4-methoxy-3-(2-trifluoromethyl-benzyl)-1,3-dihydro-benzoimidazol-2-one;

3-Cyclopropyl-5-{4-[4-methoxy-2-oxo-3-(2-trifluoromethyl-benzyl)-2,3-dihydro-benzoimidazol-1-yl]-piperidin-1-yl}-1-methyl-1H-pyrazole-4-carbaldehyde;

1-[(R)-1-(2-Fluoro-6-methyl-phenyl)-pyrrolidin-3-yl]-4-methoxy-3-(2-trifluoromethyl-benzyl)-1,3-dihydro-benzoimidazol-2-one;

4-Methoxy-1-[(R)-1-(2-methoxy-phenyl)-pyrrolidin-3-yl]-3-(2-trifluoromethyl-benzyl)-1,3-dihydro-benzoimidazol-2-one;

1-[(R)-1-(2,6-Dimethoxy-phenyl)-pyrrolidin-3-yl]-4-methoxy-3-(2-trifluoromethyl-benzyl)-1,3-dihydro-benzoimidazol-2-one;

4-Methoxy-1-[(R)-1-(2-methoxy-6-methyl-phenyl)-pyrrolidin-3-yl]-3-(2-trifluoromethyl-benzyl)-1,3-dihydro-benzoimidazol-2-one;

1-[(R)-1-(2-Fluoro-6-methoxy-phenyl)-pyrrolidin-3-yl]-4-methoxy-3-(2-trifluoromethyl-benzyl)-1,3-dihydro-benzoimidazol-2-one;

(R)-3-[4-Methoxy-2-oxo-3-(2-trifluoromethoxy-benzyl)-2,3-dihydro-benzoimidazol-1-yl]-pyrrolidine-1-carboxylicacid tert-butyl ester;

1-[1-(5-Cyclopropyl-2-methyl-2H-pyrazol-3-yl)-piperidin-4-yl]-4-methoxy-3-(2-trifluoromethyl-benzyl)-1,3-dihydro-benzoimidazol-2-one;

1-[(R)-1-(2,6-Dimethyl-phenyl)-pyrrolidin-3-yl]-4-methoxy-3-(2-trifluoromethoxy-benzyl)-1,3-dihydro-benzoimidazol-2-one;

1-[(R)-1-(2,6-Difluoro-phenyl)-pyrrolidin-3-yl]-4-methoxy-3-(2-trifluoromethoxy-benzyl)-1,3-dihydro-benzoimidazol-2-one;

1-[1-(4-Chloro-5-cyclopropyl-2-methyl-2H-pyrazol-3-yl)-piperidin-4-yl]-4-methoxy-3-(2-trifluoromethyl-benzyl)-1,3-dihydro-benzoimidazol-2-one;

1-[1-(5-Cyclopropyl-2,4-dimethyl-2H-pyrazol-3-yl)-piperidin-4-yl]-4-methoxy-3-(2-trifluoromethyl-benzyl)-1,3-dihydro-benzoimidazol-2-one;

(R)-3-[4-Methoxy-2-oxo-3-(2-trifluoromethyl-benzyl)-2,3-dihydro-benzoimidazol-1-yl]-pyrrolidine-1-carboxylicacid methyl ester;

1-((R)-1-Benzoyl-pyrrolidin-3-yl)-4-methoxy-3-(2-trifluoromethyl-benzyl)-1,3-dihydro-benzoimidazol-2-one;

1-[1-(2,2-Dimethyl-propionyl)-piperidin-4-yl]-4-methoxy-3-(2-trifluoromethyl-benzyl)-1,3-dihydro-benzoimidazol-2-one;

4-[4-Methoxy-2-oxo-3-(2-trifluoromethyl-benzyl)-2,3-dihydro-benzoimidazol-1-yl]-piperidine-1-carboxylic acid methyl ester;

1-(1-Benzoyl-piperidin-4-yl)-4-methoxy-3-(2-trifluoromethyl-benzyl)-1,3-dihydro-benzoimidazol-2-one;

4-Methoxy-1-((R)-1-methyl-pyrrolidin-3-yl)-3-(2-trifluoromethyl-benzyl)-1,3-dihydro-benzoimidazol-2-one;

1-((R)-1-Isopropyl-pyrrolidin-3-yl)-4-methoxy-3-(2-trifluoromethyl-benzyl)-1,3-dihydro-benzoimidazol-2-one;

4-Methoxy-1-[(R)-1-(2-methoxy-4-methyl-pyridin-3-yl)-pyrrolidin-3-yl]-3-(2-trifluoromethyl-benzyl)-1,3-dihydro-benzoimidazol-2-one;

1-[(R)-1-(3,5-Difluoro-pyridin-4-yl)-pyrrolidin-3-yl]-4-methoxy-3-(2-trifluoromethyl-benzyl)-1,3-dihydro-benzoimidazol-2-one;

1-(1-Isopropyl-piperidin-4-yl)-4-methoxy-3-(2-trifluoromethyl-benzyl)-1,3-dihydro-benzoimidazol-2-one;

1-[(R)-1-(3,5-Dimethyl-pyridin-4-yl)-pyrrolidin-3-yl]-4-methoxy-3-(2-trifluoromethyl-benzyl)-1,3-dihydro-benzoimidazol-2-one;

1-[(R)-1-(2-Fluoro-4-methyl-pyridin-3-yl)-pyrrolidin-3-yl]-4-methoxy-3-(2-trifluoromethyl-benzyl)-1,3-dihydro-benzoimidazol-2-one;

1-[(R)-1-(3,5-Dimethoxy-pyridin-4-yl)-pyrrolidin-3-yl]-4-methoxy-3-(2-trifluoromethyl-benzyl)-1,3-dihydro-benzoimidazol-2-one;

(R)-3-[4-Methoxy-2-oxo-3-(2-trifluoromethyl-benzyl)-2,3-dihydro-imidazo[4,5-c]pyridin-1-yl]-pyrrolidine-1-carboxylic acid tert-butyl ester;

1-[(R)-1-(2-Fluoro-6-methyl-phenyl)-pyrrolidin-3-yl]-4-hydroxy-3-(2-trifluoromethyl-benzyl)-1,3-dihydro-benzoimidazol-2-one;

1-[(R)-1-(2,6-Dimethyl-phenyl)-pyrrolidin-3-yl]-4-methoxy-3-(2-trifluoromethyl-benzyl)-1,3-dihydro-imidazo[4,5-c]pyridin-2-one;

1-[(R)-1-(2,6-Difluoro-phenyl)-pyrrolidin-3-yl]-4-methoxy-3-(2-trifluoromethyl-benzyl)-1,3-dihydro-imidazo[4,5-c]pyridin-2-one;

(R)-3-[7-Methoxy-2-oxo-1-(2-trifluoromethyl-benzyl)-1,2-dihydro-imidazo[4,5-b]pyridin-3-yl]-pyrrolidine-1-carboxylic acid tert-butyl ester;

1-[(R)-1-(2,6-Dimethyl-phenyl)-pyrrolidin-3-yl]-4-hydroxy-3-(2-trifluoromethyl-benzyl)-1,3-dihydro-benzoimidazol-2-one;

3-[(R)-1-(2,6-Dimethyl-phenyl)-pyrrolidin-3-yl]-7-methoxy-1-(2-trifluoromethyl-benzyl)-1,3-dihydro-imidazo[4,5-b]pyridin-2-one;

3-[(R)-1-(2,6-Difluoro-phenyl)-pyrrolidin-3-yl]-7-methoxy-1-(2-trifluoromethyl-benzyl)-1,3-dihydro-imidazo[4,5-b]pyridin-2-one;

4-Methoxy-1-[(R)-1-(2-methoxy-4-methyl-pyridin-3-yl)-pyrrolidin-3-yl]-3-(2-trifluoromethyl-benzyl)-1,3-dihydro-imidazo[4,5-c]pyridin-2-one;

1-[(R)-1-(2-Fluoro-4-methyl-pyridin-3-yl)-pyrrolidin-3-yl]-4-methoxy-3-(2-trifluoromethyl-benzyl)-1,3-dihydro-imidazo[4,5-c]pyridin-2-one;

1-[(R)-1-(2-Fluoro-6-methoxy-phenyl)-pyrrolidin-3-yl]-4-methoxy-3-(2-trifluoromethyl-benzyl)-1,3-dihydro-imidazo[4,5-c]pyridin-2-one;

1-[(R)-1-(2-Fluoro-6-methyl-phenyl)-pyrrolidin-3-yl]-4-methoxy-3-(2-trifluoromethyl-benzyl)-1,3-dihydro-imidazo[4,5-c]pyridin-2-one;

4-Methoxy-1-[(R)-1-(2-methoxy-6-methyl-phenyl)-pyrrolidin-3-yl]-3-(2-trifluoromethyl-benzyl)-1,3-dihydro-imidazo[4,5-c]pyridin-2-one;

1-[(R)-1-(2,6-Dimethyl-phenyl)-pyrrolidin-3-yl]-4-(2-hydroxy-ethoxy)-3-(2-trifluoromethyl-benzyl)-1,3-dihydro-benzoimidazol-2-one;

4-[4-Methoxy-2-oxo-3-(4-trifluoromethyl-pyridin-3-ylmethyl)-2,3-dihydro-benzoimidazol-1-yl]-piperidine-1-carboxylic acid tert-butyl ester;

1-[1-(2,6-Dimethyl-phenyl)-piperidin-4-yl]-4-methoxy-3-(2-trifluoromethyl-pyridin-3-ylmethyl)-1,3-dihydro-benzoimidazol-2-one;

1-[1-(2,6-Difluoro-phenyl)-piperidin-4-yl]-4-methoxy-3-(2-trifluoromethyl-pyridin-3-ylmethyl)-1,3-dihydro-benzoimidazol-2-one;

1-[(R)-1-(2-Fluoro-6-methoxy-phenyl)-pyrrolidin-3-yl]-3-(2-trifluoromethyl-benzyl)-3,5-dihydro-1H-imidazo[4,5-c]pyridine-2,4-dione;

1-[(R)-1-(2-Fluoro-6-methyl-phenyl)-pyrrolidin-3-yl]-3-(2-trifluoromethyl-benzyl)-3,5-dihydro-1H-imidazo[4,5-c]pyridine-2,4-dione;

1-[1-(2,6-Dimethyl-phenyl)-piperidin-4-yl]-4-methoxy-3-(4-trifluoromethyl-pyridin-3-ylmethyl)-1,3-dihydro-benzoimidazol-2-one;

1-[1-(2,6-Difluoro-phenyl)-piperidin-4-yl]-4-methoxy-3-(4-trifluoromethyl-pyridin-3-ylmethyl)-1,3-dihydro-benzoimidazol-2-one;

(R)-3-[4-Methoxy-2-oxo-3-(2-trifluoromethyl-benzyl)-2,3-dihydro-benzoimidazol-1-yl]-pyrrolidine-1-carboxylic acid ethyl ester;
(R)-3-[4-Methoxy-2-oxo-3-(2-trifluoromethyl-benzyl)-2,3-dihydro-benzoimidazol-1-yl]-pyrrolidine-1-carboxylic acid isopropyl ester;
(R)-3-[4-Methoxy-2-oxo-3-(2-trifluoromethyl-benzyl)-2,3-dihydro-benzoimidazol-1-yl]-pyrrolidine-1-carboxylic acid butyl ester;
(R)-3-[4-Methoxy-2-oxo-3-(2-trifluoromethyl-benzyl)-2,3-dihydro-benzoimidazol-1-yl]-pyrrolidine-1-carboxylic acid phenyl ester;
4-[4-Methoxy-2-oxo-3-(3-trifluoromethyl-pyridin-2-ylmethyl)-2,3-dihydro-benzoimidazol-1-yl]-piperidine-1-carboxylic acid tert-butyl ester;
(R)-3-[4-Methoxy-3-(2-methoxy-benzyl)-2-oxo-2,3-dihydro-benzoimidazol-1-yl]-pyrrolidine-1-carboxylic acid tert-butyl ester;
1-[(R)-1-(2,4-Dimethyl-pyridin-3-yl)-pyrrolidin-3-yl]-4-methoxy-3-(2-trifluoromethyl-benzyl)-1,3-dihydro-benzoimidazol-2-one;
1-[(R)-1-(2,6-Dimethyl-phenyl)-pyrrolidin-3-yl]-4-methoxy-3-(2-methoxy-benzyl)-1,3-dihydro-benzoimidazol-2-one;
1-[(R)-1-(2,6-Difluoro-phenyl)-pyrrolidin-3-yl]-4-methoxy-3-(2-methoxy-benzyl)-1,3-dihydro-benzoimidazol-2-one;
1-[(R)-1-(5-Isopropyl-[1,3,4]oxadiazol-2-yl)-pyrrolidin-3-yl]-4-methoxy-3-(2-trifluoromethyl-benzyl)-1,3-dihydro-benzoimidazol-2-one;
(R)-3-[4-Methoxy-2-oxo-3-(2-trifluoromethyl-benzyl)-2,3-dihydro-benzoimidazol-1-yl]-pyrrolidine-1-carboxylic acid 3-methyl-oxetan-3-yl ester;
5-{(R)-3-[4-Methoxy-2-oxo-3-(2-trifluoromethyl-benzyl)-2,3-dihydro-benzoimidazol-1-yl]-pyrrolidin-1-yl}-1,3-dimethyl-1H-pyrazole-4-carbaldehyde;
(R)-3-[4-Methoxy-2-oxo-3-(2-trifluoromethyl-benzyl)-2,3-dihydro-benzoimidazol-1-yl]-pyrrolidine-1-carboxylic acid oxetan-3-yl ester;
1-[1-(2,6-Dimethyl-phenyl)-piperidin-4-yl]-4-methoxy-3-(3-trifluoromethyl-pyridin-4-ylmethyl)-1,3-dihydro-benzoimidazol-2-one;
1-[1-(2,6-Difluoro-phenyl)-piperidin-4-yl]-4-methoxy-3-(3-trifluoromethyl-pyridin-4-ylmethyl)-1,3-dihydro-benzoimidazol-2-one;
1-[1-(2,6-Dimethyl-phenyl)-piperidin-4-yl]-4-methoxy-3-(3-trifluoromethyl-pyridin-2-ylmethyl)-1,3-dihydro-benzoimidazol-2-one;
1-[1-(2,6-Difluoro-phenyl)-piperidin-4-yl]-4-methoxy-3-(3-trifluoromethyl-pyridin-2-ylmethyl)-1,3-dihydro-benzoimidazol-2-one;
1-[(R)-1-(2,6-Dimethyl-phenyl)-pyrrolidin-3-yl]-4-methoxy-3-(2-methoxy-benzyl)-1,3-dihydro-imidazo[4,5-c]pyridin-2-one;
1-[(R)-1-(2-Fluoro-6-methyl-phenyl)-pyrrolidin-3-yl]-4-methoxy-3-(2-methoxy-benzyl)-1,3-dihydro-imidazo[4,5-c]pyridin-2-one;
1-[(R)-1-(2,5-Dimethyl-2H-pyrazol-3-yl)-pyrrolidin-3-yl]-4-methoxy-3-(2-trifluoromethyl-benzyl)-1,3-dihydro-benzoimidazol-2-one;
1-[(R)-1-(4-Chloro-2,5-dimethyl-2H-pyrazol-3-yl)-pyrrolidin-3-yl]-4-methoxy-3-(2-trifluoromethyl-benzyl)-1,3-dihydro-benzoimidazol-2-one;
1-[(R)-1-(2-Fluoro-6-methyl-phenyl)-pyrrolidin-3-yl]-3-(2-methoxy-benzyl)-3,5-dihydro-1H-imidazo[4,5-c]pyridine-2,4-dione;
3-Fluoro-2-{(R)-3-[4-methoxy-2-oxo-3-(2-trifluoromethyl-benzyl)-2,3-dihydro-benzoimidazol-1-yl]-pyrrolidin-1-yl}-benzonitrile;
3-Fluoro-2-{(R)-3-[4-methoxy-2-oxo-3-(2-trifluoromethyl-benzyl)-2,3-dihydro-benzoimidazol-1-yl]-pyrrolidin-1-yl}-benzaldehyde;
4-Methoxy-3-(2-trifluoromethyl-benzyl)-1-[(R)-1-(5-trifluoromethyl-[1,3,4]oxadiazol-2-yl)-pyrrolidin-3-yl]-1,3-dihydro-benzoimidazol-2-one;
4-Methoxy-3-(2-trifluoromethyl-benzyl)-1-[(R)-1-(2,4,5-trimethyl-2H-pyrazol-3-yl)-pyrrolidin-3-yl]-1,3-dihydro-benzoimidazol-2-one;
(R)-3-[4-Methoxy-2-oxo-3-(2-trifluoromethyl-benzyl)-2,3-dihydro-benzoimidazol-1-yl]-pyrrolidine-1-carboxylic acid 3-trifluoromethyl-oxetan-3-yl ester;
5-{(R)-3-[4-Methoxy-2-oxo-3-(2-trifluoromethyl-benzyl)-2,3-dihydro-benzoimidazol-1-yl]-pyrrolidin-1-yl}-1,3-dimethyl-1H-pyrazole-4-carbonitrile;
1-[(R)-1-(2-Fluoro-6-hydroxymethyl-phenyl)-pyrrolidin-3-yl]-4-methoxy-3-(2-trifluoromethyl-benzyl)-1,3-dihydro-benzoimidazol-2-one;
1-{(R)-1-[2-Fluoro-6-(1-hydroxy-ethyl)-phenyl]-pyrrolidin-3-yl}-4-methoxy-3-(2-trifluoromethyl-benzyl)-1,3-dihydro-benzoimidazol-2-one;
1-[(R)-1-(2-Acetyl-6-fluoro-phenyl)-pyrrolidin-3-yl]-4-methoxy-3-(2-trifluoromethyl-benzyl)-1,3-dihydro-benzoimidazol-2-one;
1-{(R)-1-[2-Fluoro-6-(1-hydroxy-1-methyl-ethyl)-phenyl]-pyrrolidin-3-yl}-4-methoxy-3-(2-trifluoromethyl-benzyl)-1,3-dihydro-benzoimidazol-2-one;
3-(6-Chloro-4-methoxy-pyridazin-3-ylmethyl)-1-[(R)-1-(2-fluoro-6-methyl-phenyl)-pyrrolidin-3-yl]-4-methoxy-1,3-dihydro-benzoimidazol-2-one;
1-[(R)-1-(2,6-Dimethyl-phenyl)-pyrrolidin-3-yl]-3-(2-trifluoromethyl-benzyl)-3,5-dihydro-1H-imidazo[4,5-c]pyridine-2,4-dione;
1-[(R)-1-(2-Methoxy-6-methyl-phenyl)-pyrrolidin-3-yl]-3-(2-trifluoromethyl-benzyl)-3,5-dihydro-1H-imidazo[4,5-c]pyridine-2,4-dione;
1-[(R)-1-(2-Fluoro-6-methyl-phenyl)-pyrrolidin-3-yl]-4-methoxy-3-(4-methoxy-pyridazin-3-ylmethyl)-1,3-dihydro-benzoimidazol-2-one;
3-Fluoro-2-{4-[4-methoxy-2-oxo-3-(3-trifluoromethyl-pyrazin-2-ylmethyl)-2,3-dihydro-benzoimidazol-1-yl]-piperidin-1-yl}-benzonitrile;
3-Fluoro-2-{4-[4-methoxy-3-(3-methoxy-pyrazin-2-ylmethyl)-2-oxo-2,3-dihydro-benzoimidazol-1-yl]-piperidin-1-yl}-benzonitrile;
1-[(R)-1-(2-Cyano-6-fluoro-phenyl)-pyrrolidin-3-yl]-2-oxo-3-(2-trifluoromethyl-benzyl)-2,3-dihydro-1H-benzoimidazole-4-carboxylic acid methyl ester;
1-[(R)-1-(2-Cyano-6-fluoro-phenyl)-pyrrolidin-3-yl]-2-oxo-3-(2-trifluoromethyl-benzyl)-2,3-dihydro-1H-benzoimidazole-4-carboxylic acid methylamide;
1-[(R)-1-(2-Cyano-6-fluoro-phenyl)-pyrrolidin-3-yl]-2-oxo-3-(2-trifluoromethyl-benzyl)-2,3-dihydro-1H-benzoimidazole-4-carboxylic acid amide;
1-[(R)-1-(2-Cyano-6-fluoro-phenyl)-pyrrolidin-3-yl]-2-oxo-3-(2-trifluoromethyl-benzyl)-2,3-dihydro-1H-benzoimidazole-4-carboxylic acid dimethylamide;
3-Fluoro-2-{(R)-3-[4-hydroxymethyl-2-oxo-3-(2-trifluoromethyl-benzyl)-2,3-dihydro-benzoimidazol-1-yl]-pyrrolidin-1-yl}-benzonitrile;
1-[(R)-1-(2-Fluoro-6-methylaminomethyl-phenyl)-pyrrolidin-3-yl]-4-methoxy-3-(2-trifluoromethyl-benzyl)-1,3-dihydro-benzoimidazol-2-one;

3-Fluoro-2-{(R)-3-[6-methoxy-8-oxo-7-(2-trifluoromethyl-benzyl)-7,8-dihydro-purin-9-yl]-pyrrolidin-1-yl}-benzonitrile;

3-Fluoro-2-{(R)-3-[6-methoxy-7-(2-methoxy-benzyl)-8-oxo-7,8-dihydro-purin-9-yl]-pyrrolidin-1-yl}-benzonitrile;

1-[(R)-1-(2-Dimethylaminomethyl-6-fluoro-phenyl)-pyrrolidin-3-yl]-4-methoxy-3-(2-trifluoromethyl-benzyl)-1,3-dihydro-benzoimidazol-2-one;

1-[(R)-1-(2-Fluoro-6-{[(2-hydroxy-ethyl)-methyl-amino]-methyl}-phenyl)-pyrrolidin-3-yl]-4-methoxy-3-(2-trifluoromethyl-benzyl)-1,3-dihydro-benzoimidazol-2-one;

1-[(R)-1-(2-Azetidin-1-ylmethyl-6-fluoro-phenyl)-pyrrolidin-3-yl]-4-methoxy-3-(2-trifluoromethyl-benzyl)-1,3-dihydro-benzoimidazol-2-one;

3-Fluoro-2-{(R)-3-[4-methoxy-3-(2-methoxy-benzyl)-2-oxo-2,3-dihydro-benzoimidazol-1-yl]-pyrrolidin-1-yl}-benzonitrile;

1-[(R)-1-(2-Fluoro-6-methyl-phenyl)-pyrrolidin-3-yl]-4-methoxy-3-(2-methoxy-benzyl)-1,3-dihydro-benzoimidazol-2-one;

3-Fluoro-2-{(R)-3-[4-methoxy-2-oxo-3-(3-trifluoromethyl-pyrazin-2-ylmethyl)-2,3-dihydro-benzoimidazol-1-yl]-pyrrolidin-1-yl}-benzonitrile;

3-Fluoro-2-{(R)-3-[4-methoxy-3-(3-methoxy-pyrazin-2-ylmethyl)-2-oxo-2,3-dihydro-benzoimidazol-1-yl]-pyrrolidin-1-yl}-benzonitrile;

3-Fluoro-2-{4-[4-methoxy-3-(4-methoxy-pyrimidin-5-ylmethyl)-2-oxo-2,3-dihydro-benzoimidazol-1-yl]-piperidin-1-yl}-benzonitrile;

3-Fluoro-2-{(R)-3-[4-methoxy-3-(4-methoxy-pyrimidin-5-ylmethyl)-2-oxo-2,3-dihydro-benzoimidazol-1-yl]-pyrrolidin-1-yl}-benzonitrile;

1-[(R)-1-(2-Fluoro-6-morpholin-4-ylmethyl-phenyl)-pyrrolidin-3-yl]-4-methoxy-3-(2-trifluoromethyl-benzyl)-1,3-dihydro-benzoimidazol-2-one;

1-[(R)-1-(2-Fluoro-6-pyrrolidin-1-ylmethyl-phenyl)-pyrrolidin-3-yl]-4-methoxy-3-(2-trifluoromethyl-benzyl)-1,3-dihydro-benzoimidazol-2-one;

3-Fluoro-2-{4-[4-methoxy-2-oxo-3-(4-trifluoromethyl-pyrimidin-5-ylmethyl)-2,3-dihydro-benzoimidazol-1-yl]-piperidin-1-yl}-benzonitrile;

1-[(R)-1-(2,6-Dimethyl-phenyl)-pyrrolidin-3-yl]-4-(2-hydroxy-ethylamino)-3-(2-trifluoromethyl-benzyl)-1,3-dihydro-imidazo[4,5-c]pyridin-2-one;

1-[(R)-1-(2,6-Dimethyl-phenyl)-pyrrolidin-3-yl]-4-(2-hydroxy-ethoxy)-3-(2-trifluoromethyl-benzyl)-1,3-dihydro-imidazo[4,5-c]pyridin-2-one;

4-(2-Dimethylamino-ethoxy)-1-[(R)-1-(2-fluoro-6-methyl-phenyl)-pyrrolidin-3-yl]-3-(2-trifluoromethyl-benzyl)-1,3-dihydro-imidazo[4,5-c]pyridin-2-one;

1-[(R)-1-(2-Fluoro-6-methyl-phenyl)-pyrrolidin-3-yl]-4-(2-morpholin-4-yl-ethoxy)-3-(2-trifluoromethyl-benzyl)-1,3-dihydro-imidazo[4,5-c]pyridin-2-one;

4-[1-[(R)-1-(2-Fluoro-6-methyl-phenyl)-pyrrolidin-3-yl]-2-oxo-3-(2-trifluoromethyl-benzyl)-2,3-dihydro-1H-imidazo[4,5-c]pyridin-4-yloxy]-piperidine-1-carboxylic acid tert-butyl ester;

1-[(R)-1-(2-Fluoro-6-methyl-phenyl)-pyrrolidin-3-yl]-4-[(2-hydroxy-ethyl)-methyl-amino]-3-(2-trifluoromethyl-benzyl)-1,3-dihydro-imidazo[4,5-c]pyridin-2-one;

1-[(R)-1-(2-Fluoro-6-methyl-phenyl)-pyrrolidin-3-yl]-4-(piperidin-4-yloxy)-3-(2-trifluoromethyl-benzyl)-1,3-dihydro-imidazo[4,5-c]pyridin-2-one;

4-(2,2-Dimethyl-[1,3]dioxolan-4-ylmethoxy)-1-[(R)-1-(2-fluoro-6-methyl-phenyl)-pyrrolidin-3-yl]-3-(2-trifluoromethyl-benzyl)-1,3-dihydro-imidazo[4,5-c]pyridin-2-one;

(3-Fluoro-2-{(R)-3-[4-methoxy-2-oxo-3-(2-trifluoromethyl-benzyl)-2,3-dihydro-benzoimidazol-1-yl]-pyrrolidin-1-yl}-phenyl)-acetaldehyde;

1-[(R)-1-(2-Fluoro-6-methyl-phenyl)-pyrrolidin-3-yl]-4-(oxetan-3-yloxy)-3-(2-trifluoromethyl-benzyl)-1,3-dihydro-imidazo[4,5-c]pyridin-2-one;

4-(2,3-Dihydroxy-propoxy)-1-[(R)-1-(2-fluoro-6-methyl-phenyl)-pyrrolidin-3-yl]-3-(2-trifluoromethyl-benzyl)-1,3-dihydro-imidazo[4,5-c]pyridin-2-one;

1-[(R)-1-(2-Fluoro-6-methyl-phenyl)-pyrrolidin-3-yl]-4-morpholin-4-yl-3-(2-trifluoromethyl-benzyl)-1,3-dihydro-imidazo[4,5-c]pyridin-2-one;

1-[(R)-1-(2-Fluoro-6-methyl-phenyl)-pyrrolidin-3-yl]-4-(1-methyl-pyrrolidin-3-yloxy)-3-(2-trifluoromethyl-benzyl)-1,3-dihydro-imidazo[4,5-c]pyridin-2-one;

1-{(R)-1-[2-Fluoro-6-(2-morpholin-4-yl-ethyl)-phenyl]-pyrrolidin-3-yl}-4-methoxy-3-(2-trifluoromethyl-benzyl)-1,3-dihydro-benzoimidazol-2-one;

1-{(R)-1-[2-Fluoro-6-(4-methyl-piperazin-1-ylmethyl)-phenyl]-pyrrolidin-3-yl}-4-methoxy-3-(2-trifluoromethyl-benzyl)-1,3-dihydro-benzoimidazol-2-one;

1-[(R)-1-(2-Fluoro-6-piperidin-1-ylmethyl-phenyl)-pyrrolidin-3-yl]-4-methoxy-3-(2-trifluoromethyl-benzyl)-1,3-dihydro-benzoimidazol-2-one;

1-{(R)-1-[2-Fluoro-6-(4-hydroxy-piperidin-1-ylmethyl)-phenyl]-pyrrolidin-3-yl}-4-methoxy-3-(2-trifluoromethyl-benzyl)-1,3-dihydro-benzoimidazol-2-one;

1-[(R)-1-(2-Fluoro-6-piperazin-1-ylmethyl-phenyl)-pyrrolidin-3-yl]-4-methoxy-3-(2-trifluoromethyl-benzyl)-1,3-dihydro-benzoimidazol-2-one;

1-{(R)-1-[2-(4-Dimethylamino-piperidin-1-ylmethyl)-6-fluoro-phenyl]-pyrrolidin-3-yl}-4-methoxy-3-(2-trifluoromethyl-benzyl)-1,3-dihydro-benzoimidazol-2-one;

1-{(R)-1-[2-Fluoro-6-(4-methoxy-piperidin-1-ylmethyl)-phenyl]-pyrrolidin-3-yl}-4-methoxy-3-(2-trifluoromethyl-benzyl)-1,3-dihydro-benzoimidazol-2-one;

1-{(R)-1-[2-Fluoro-6-(3-methoxy-pyrrolidin-1-ylmethyl)-phenyl]-pyrrolidin-3-yl}-4-methoxy-3-(2-trifluoromethyl-benzyl)-1,3-dihydro-benzoimidazol-2-one;

1-[(R)-1-(2-Fluoro-6-{[(2-methoxy-ethyl)-methyl-amino]-methyl}-phenyl)-pyrrolidin-3-yl]-4-methoxy-3-(2-trifluoromethyl-benzyl)-1,3-dihydro-benzoimidazol-2-one;

1-[(R)-1-(2-{[Ethyl-(2-hydroxy-ethyl)-amino]-methyl}-6-fluoro-phenyl)-pyrrolidin-3-yl]-4-methoxy-3-(2-trifluoromethyl-benzyl)-1,3-dihydro-benzoimidazol-2-one;

1-[(R)-1-(2-{[Bis-(2-hydroxy-ethyl)-amino]-methyl}-6-fluoro-phenyl)-pyrrolidin-3-yl]-4-methoxy-3-(2-trifluoromethyl-benzyl)-1,3-dihydro-benzoimidazol-2-one;

1-((R)-1-{2-Fluoro-6-[(2-methoxy-1-methyl-ethylamino)-methyl]-phenyl}-pyrrolidin-3-yl)-4-methoxy-3-(2-trifluoromethyl-benzyl)-1,3-dihydro-benzoimidazol-2-one;

1-{(R)-1-[2-Fluoro-6-(3-methoxy-azetidin-1-ylmethyl)-phenyl]-pyrrolidin-3-yl}-4-methoxy-3-(2-trifluoromethyl-benzyl)-1,3-dihydro-benzoimidazol-2-one;

4-[4-Methoxy-2-oxo-3-(2-trifluoromethyl-benzyl)-2,3-dihydro-benzoimidazol-1-yl]-2-methyl-piperidine-1-carboxylic acid tert-butyl ester;

3-Fluoro-2-{4-[4-methoxy-2-oxo-3-(2-trifluoromethyl-benzyl)-2,3-dihydro-benzoimidazol-1-yl]-2-methyl-piperidin-1-yl}-benzaldehyde;

4-[4-Methoxy-2-oxo-3-(2-trifluoromethyl-benzyl)-2,3-dihydro-benzoimidazol-1-yl]-3-methyl-piperidine-1-carboxylic acid tert-butyl ester;

1-[1-(2-Fluoro-6-methyl-phenyl)-3-methyl-piperidin-4-yl]-4-methoxy-3-(2-trifluoromethyl-benzyl)-1,3-dihydro-benzoimidazol-2-one;

1-{(R)-1-[2-Fluoro-6-(1-methoxy-ethyl)-phenyl]-pyrrolidin-3-yl}-4-methoxy-3-(2-trifluoromethyl-benzyl)-1,3-dihydro-benzoimidazol-2-one;

1-[(R)-1-(2-Fluoro-6-methyl-phenyl)-pyrrolidin-3-yl]-4-(oxetan-3-yloxy)-3-(2-trifluoromethyl-benzyl)-1,3-dihydro-benzoimidazol-2-one;

1-[(R)-1-(2-Fluoro-6-methyl-phenyl)-pyrrolidin-3-yl]-4-(2-hydroxy-ethoxy)-3-(2-trifluoromethyl-benzyl)-1,3-dihydro-benzoimidazol-2-one;

4-(2,2-Dimethyl-[1,3]dioxolan-4-ylmethoxy)-1-[(R)-1-(2-fluoro-6-methyl-phenyl)-pyrrolidin-3-yl]-3-(2-trifluoromethyl-benzyl)-1,3-dihydro-benzoimidazol-2-one;

4-(2,3-Dihydroxy-propoxy)-1-[(R)-1-(2-fluoro-6-methyl-phenyl)-pyrrolidin-3-yl]-3-(2-trifluoromethyl-benzyl)-1,3-dihydro-benzoimidazol-2-one;

3-Fluoro-2-{(R)-3-[4-methoxy-2-oxo-3-(4-trifluoromethyl-pyrimidin-5-ylmethyl)-2,3-dihydro-benzoimidazol-1-yl]-pyrrolidin-1-yl}-benzonitrile;

1-[(R)-1-(2-Fluoro-6-nitro-phenyl)-pyrrolidin-3-yl]-4-methoxy-3-(2-trifluoromethyl-benzyl)-1,3-dihydro-benzoimidazol-2-one;

1-[(R)-1-(2-Amino-6-fluoro-phenyl)-pyrrolidin-3-yl]-4-methoxy-3-(2-trifluoromethyl-benzyl)-1,3-dihydro-benzoimidazol-2-one;

1-[(R)-1-(2-Bromo-6-fluoro-phenyl)-pyrrolidin-3-yl]-4-methoxy-3-(2-trifluoromethyl-benzyl)-1,3-dihydro-benzoimidazol-2-one;

1-[(R)-1-(4,5-Dichloro-pyridazin-3-yl)-pyrrolidin-3-yl]-4-methoxy-3-(2-trifluoromethyl-benzyl)-1,3-dihydro-benzoimidazol-2-one;

1-[(R)-1-(3,5-Dichloro-pyridazin-4-yl)-pyrrolidin-3-yl]-4-methoxy-3-(2-trifluoromethyl-benzyl)-1,3-dihydro-benzoimidazol-2-one;

1-{(R)-1-[2-Fluoro-6-(3-morpholin-4-yl-prop-1-ynyl)-phenyl]-pyrrolidin-3-yl}-4-methoxy-3-(2-trifluoromethyl-benzyl)-1,3-dihydro-benzoimidazol-2-one;

1-[(R)-1-(2-Fluoro-phenyl)-pyrrolidin-3-yl]-4-methoxy-3-(2-trifluoromethyl-benzyl)-1,3-dihydro-benzoimidazol-2-one;

1-[(R)-1-(2-Fluoro-6-morpholin-4-yl-phenyl)-pyrrolidin-3-yl]-4-methoxy-3-(2-trifluoromethyl-benzyl)-1,3-dihydro-benzoimidazol-2-one;

1-{(R)-1-[2-Fluoro-6-(3-morpholin-4-yl-propyl)-phenyl]-pyrrolidin-3-yl}-4-methoxy-3-(2-trifluoromethyl-benzyl)-1,3-dihydro-benzoimidazol-2-one:

1-((R)-1-{2-Fluoro-6-[1-(3-methoxy-azetidin-1-yl)-ethyl]-phenyl}-pyrrolidin-3-yl)-4-methoxy-3-(2-trifluoromethyl-benzyl)-1,3-dihydro-benzoimidazol-2-one;

4-[4-Methoxy-2-oxo-3-(2-trifluoromethyl-benzyl)-2,3-dihydro-benzoimidazol-1-yl]-piperidine-1,3-dicarboxylic acid 1-tert-butyl ester 3-ethyl ester;

1-[(R)-1-(2-Fluoro-6-methyl-phenyl)-pyrrolidin-3-yl]-3-(2-isopropoxy-benzyl)-4-methoxy-1,3-dihydro-benzoimidazol-2-one;

1-[1-(2-Fluoro-6-methyl-phenyl)-piperidin-4-yl]-3-(2-isopropoxy-benzyl)-4-methoxy-1,3-dihydro-benzoimidazol-2-one;

1-[(R)-1-(2-Fluoro-6-methyl-phenyl)-pyrrolidin-3-yl]-4-methoxy-3-(3-trifluoromethyl-pyrazin-2-ylmethyl)-1,3-dihydro-benzoimidazol-2-one;

1-[1-(2-Fluoro-6-methyl-phenyl)-piperidin-4-yl]-4-methoxy-3-(3-trifluoromethyl-pyrazin-2-ylmethyl)-1,3-dihydro-benzoimidazol-2-one;

1-[(R)-1-(2-Fluoro-6-methyl-phenyl)-pyrrolidin-3-yl]-4-methoxy-3-(3-methoxy-pyrazin-2-ylmethyl)-1,3-dihydro-benzoimidazol-2-one;

1-[1-(2-Fluoro-6-methyl-phenyl)-piperidin-4-yl]-4-methoxy-3-(3-methoxy-pyrazin-2-ylmethyl)-1,3-dihydro-benzoimidazol-2-one;

3-[(R)-1-(2-Fluoro-6-methyl-phenyl)-pyrrolidin-3-yl]-7-methoxy-5-methyl-1-(2-trifluoromethyl-benzyl)-1,3-dihydro-imidazo[4,5-b]pyridin-2-one;

3-(6-Chloro-4-isopropoxy-pyridazin-3-ylmethyl)-1-[(R)-1-(2-fluoro-6-methyl-phenyl)-pyrrolidin-3-yl]-4-methoxy-1,3-dihydro-benzoimidazol-2-one;

1-[(R)-1-(2-Fluoro-6-methyl-phenyl)-pyrrolidin-3-yl]-3-(4-isopropoxy-pyridazin-3-ylmethyl)-4-methoxy-1,3-dihydro-benzoimidazol-2-one;

1-[(R)-1-(2-Fluoro-6-methyl-phenyl)-pyrrolidin-3-yl]-4-methoxy-3-(4-methyl-pyridazin-3-ylmethyl)-1,3-dihydro-benzoimidazol-2-one;

1-[(R)-1-(2-Fluoro-6-methyl-phenyl)-pyrrolidin-3-yl]-4-methoxy-3-(4-methoxy-pyrimidin-5-ylmethyl)-1,3-dihydro-benzoimidazol-2-one;

1-[(R)-1-(2-Fluoro-6-methyl-phenyl)-pyrrolidin-3-yl]-4-methoxy-3-(4-trifluoromethyl-pyrimidin-5-ylmethyl)-1,3-dihydro-benzoimidazol-2-one;

1-[(R)-1-(2-Fluoro-6-methyl-phenyl)-pyrrolidin-3-yl]-3-(3-isopropoxy-pyrazin-2-ylmethyl)-4-methoxy-1,3-dihydro-benzoimidazol-2-one;

1-[1-(2-Fluoro-6-methyl-phenyl)-piperidin-4-yl]-3-(3-isopropoxy-pyrazin-2-ylmethyl)-4-methoxy-1,3-dihydro-benzoimidazol-2-one;

4-[4-Methoxy-2-oxo-3-(2-trifluoromethyl-benzyl)-2,3-dihydro-benzoimidazol-1-yl]-azepane-1-carboxylic acid tert-butyl ester;

1-[(R)-1-(2-Fluoro-6-methyl-phenyl)-pyrrolidin-3-yl]-3-(4-isopropyl-pyridin-3-ylmethyl)-4-methoxy-1,3-dihydro-benzoimidazol-2-one;

1-[1-(2-Fluoro-6-methyl-phenyl)-piperidin-4-yl]-3-(4-isopropyl-pyridin-3-ylmethyl)-4-methoxy-1,3-dihydro-benzoimidazol-2-one;

1-[(R)-1-(2-Fluoro-6-methyl-phenyl)-pyrrolidin-3-yl]-3-(3-isopropoxy-pyridin-2-ylmethyl)-4-methoxy-1,3-dihydro-benzoimidazol-2-one;

1-[1-(2-Fluoro-6-methyl-phenyl)-piperidin-4-yl]-3-(3-isopropoxy-pyridin-2-ylmethyl)-4-methoxy-1,3-dihydro-benzoimidazol-2-one;

1-[1-(2-Fluoro-6-methyl-phenyl)-azepan-4-yl]-4-methoxy-3-(2-trifluoromethyl-benzyl)-1,3-dihydro-benzoimidazol-2-one;

1-[1-(2,6-Dimethyl-phenyl)-azepan-4-yl]-4-methoxy-3-(2-trifluoromethyl-benzyl)-1,3-dihydro-benzoimidazol-2-one;

1-[(R)-1-(2-Fluoro-6-methyl-phenyl)-pyrrolidin-3-yl]-3-(4-isopropyl-pyrimidin-5-ylmethyl)-4-methoxy-1,3-dihydro-benzoimidazol-2-one;

1-[1-(2-Fluoro-6-methyl-phenyl)-piperidin-4-yl]-3-(3-isopropyl-pyrazin-2-ylmethyl)-4-methoxy-1,3-dihydro-benzoimidazol-2-one;

5-[4-Methoxy-2-oxo-3-(2-trifluoromethyl-benzyl)-2,3-dihydro-benzoimidazol-1-yl]-2-aza-bicyclo[2.2.1]heptane-2-carboxylic acid tert-butyl ester;

1-[(R)-1-(2-Fluoro-6-methyl-phenyl)-pyrrolidin-3-yl]-3-(3-isopropyl-pyrazin-2-ylmethyl)-4-methoxy-1,3-dihydro-benzoimidazol-2-one;

1-[2-(2-Fluoro-6-methyl-phenyl)-2-aza-bicyclo[2.2.1]hept-5-yl]-4-methoxy-3-(2-trifluoromethyl-benzyl)-1,3-dihydro-benzoimidazol-2-one;

6-[4-Methoxy-2-oxo-3-(2-trifluoromethyl-benzyl)-2,3-dihydro-benzoimidazol-1-yl]-3-aza-bicyclo[3.1.1]heptane-3-carboxylic acid tert-butyl ester;

1-[1-(2-Fluoro-6-methyl-phenyl)-piperidin-4-yl]-3-(4-isopropyl-pyrimidin-5-ylmethyl)-4-methoxy-1,3-dihydro-benzoimidazol-2-one;

1-[(R)-1-(2-Cyano-6-fluoro-phenyl)-pyrrolidin-3-yl]-2-oxo-3-(2-trifluoromethyl-benzyl)-2,3-dihydro-1H-benzoimidazole-4-carboxylic acid (2-hydroxy-ethyl)-amide;

1-[(R)-1-(2-Cyano-6-fluoro-phenyl)-pyrrolidin-3-yl]-2-oxo-3-(2-trifluoromethyl-benzyl)-2,3-dihydro-1H-benzoimidazole-4-carboxylic acid (2-methoxy-ethyl)-amide;

1-[(R)-1-(2-Fluoro-6-methyl-phenyl)-pyrrolidin-3-yl]-4-methoxy-3-(2-trifluoromethyl-pyridin-3-ylmethyl)-1,3-dihydro-benzoimidazol-2-one;

(3R*,4S*)-3-[4-Methoxy-2-oxo-3-(2-trifluoromethyl-benzyl)-2,3-dihydro-benzoimidazol-1-yl]-4-methyl-pyrrolidine-1-carboxylic acid tert-butyl ester;

1-[3-(2-Fluoro-6-methyl-phenyl)-3-aza-bicyclo[3.1.1]hept-6-yl]-4-methoxy-3-(2-trifluoromethyl-benzyl)-1,3-dihydro-benzoimidazol-2-one;

1-[(3R*,4S*)-1-(2-Fluoro-6-methyl-phenyl)-4-methyl-pyrrolidin-3-yl]-4-methoxy-3-(2-trifluoromethyl-benzyl)-1,3-dihydro-benzoimidazol-2-one;

(3R*,4R*)-3-[4-Methoxy-2-oxo-3-(2-trifluoromethyl-benzyl)-2,3-dihydro-benzoimidazol-1-yl]-4-methyl-pyrrolidine-1-carboxylic acid tert-butyl ester;

1-[(3R*,4R*)-1-(2-Fluoro-6-methyl-phenyl)-4-methyl-pyrrolidin-3-yl]-4-methoxy-3-(2-trifluoromethyl-benzyl)-1,3-dihydro-benzoimidazol-2-one;

4-Methoxy-1-[(R)-1-(2-trifluoromethoxy-phenyl)-pyrrolidin-3-yl]-3-(2-trifluoromethyl-benzyl)-1,3-dihydro-benzoimidazol-2-one;

1-[(R)-1-(2-Fluoro-6-methyl-phenyl)-pyrrolidin-3-yl]-4-methoxy-3-(3-trifluoromethyl-pyridin-2-ylmethyl)-1,3-dihydro-benzoimidazol-2-one;

1-[(R)-1-(2-Fluoro-6-methyl-phenyl)-pyrrolidin-3-yl]-4-methoxy-3-(4-trifluoromethyl-pyridin-3-ylmethyl)-1,3-dihydro-benzoimidazol-2-one;

4-Methoxy-1-{(R)-1-[2-(2-methoxy-ethoxy)-phenyl]-pyrrolidin-3-yl}-3-(2-trifluoromethyl-benzyl)-1,3-dihydro-benzoimidazol-2-one;

1-[(R)-1-(2-Fluoro-6-methyl-phenyl)-pyrrolidin-3-yl]-4-(3-methoxy-azetidin-1-yl)-3-(2-trifluoromethyl-benzyl)-1,3-dihydro-imidazo[4,5-c]pyridin-2-one;

1-[(R)-1-(2-Fluoro-6-methyl-phenyl)-pyrrolidin-3-yl]-4-(4-methyl-piperazin-1-yl)-3-(2-trifluoromethyl-benzyl)-1,3-dihydro-imidazo[4,5-c]pyridin-2-one;

1-[(R)-1-(2-Fluoro-6-methyl-phenyl)-pyrrolidin-3-yl]-4-(2-methoxy-ethylamino)-3-(2-trifluoromethyl-benzyl)-1,3-dihydro-imidazo[4,5-c]pyridin-2-one;

3-(2-Cyclopropoxy-benzyl)-1-[(R)-1-(2-fluoro-6-methyl-phenyl)-pyrrolidin-3-yl]-4-methoxy-1,3-dihydro-benzoimidazol-2-one;

3-(2-Cyclopropoxy-benzyl)-1-[1-(2-fluoro-6-methyl-phenyl)-piperidin-4-yl]-4-methoxy-1,3-dihydro-benzoimidazol-2-one;

3-Fluoro-4-[4-methoxy-2-oxo-3-(2-trifluoromethyl-benzyl)-2,3-dihydro-benzoimidazol-1-yl]-piperidine-1-carboxylic acid tert-butyl ester;

1-[3-Fluoro-1-(2-fluoro-6-methyl-phenyl)-piperidin-4-yl]-4-methoxy-3-(2-trifluoromethyl-benzyl)-1,3-dihydro-benzoimidazol-2-one;

1-[1-(2-Fluoro-6-methyl-phenyl)-piperidin-3-yl]-4-methoxy-3-(2-trifluoromethyl-benzyl)-1,3-dihydro-benzoimidazol-2-one;

3-[4-Methoxy-2-oxo-3-(2-trifluoromethyl-benzyl)-2,3-dihydro-benzoimidazol-1-yl]-azetidine-1-carboxylic acid tert-butyl ester;

3-[4-Methoxy-2-oxo-3-(2-trifluoromethyl-benzyl)-2,3-dihydro-benzoimidazol-1-yl]-piperidine-1-carboxylic acid tert-butyl ester;

1-[1-(2-Fluoro-6-methyl-phenyl)-azetidin-3-yl]-4-methoxy-3-(2-trifluoromethyl-benzyl)-1,3-dihydro-benzoimidazol-2-one;

1-[1-(2-Fluoro-6-methyl-phenyl)-piperidin-4-yl]-4-methoxy-3-(3-trifluoromethyl-pyridin-2-ylmethyl)-1,3-dihydro-benzoimidazol-2-one;

1-[1-(2,6-Dimethyl-phenyl)-piperidin-3-yl]-4-methoxy-3-(2-trifluoromethyl-benzyl)-1,3-dihydro-benzoimidazol-2-one;

1-[(R)-1-(2-Fluoro-6-methyl-phenyl)-pyrrolidin-3-yl]-4-methoxy-3-(2-trifluoromethyl-thiazol-4-ylmethyl)-1,3-dihydro-benzoimidazol-2-one;

1-[1-(2-Fluoro-6-methyl-phenyl)-pyrrolidin-3-yl]-4-methoxy-3-[(S)-1-(2-trifluoromethyl-phenyl)-ethyl]-1,3-dihydro-benzoimidazol-2-one;

3-(2,4-Difluoro-6-isopropoxy-benzyl)-1-[(R)-1-(2-fluoro-6-methyl-phenyl)-pyrrolidin-3-yl]-4-methoxy-1,3-dihydro-benzoimidazol-2-one;

1-[(R)-1-(2-Fluoro-6-methyl-phenyl)-pyrrolidin-3-yl]-4-methoxy-3-(2-methyl-4-trifluoromethyl-thiazol-5-ylmethyl)-1,3-dihydro-benzoimidazol-2-one;

1-(1-Cyclopropanecarbonyl-piperidin-4-yl)-4-methoxy-3-(2-trifluoromethyl-benzyl)-1,3-dihydro-benzoimidazol-2-one;

3-(2-Cyclopropyl-benzyl)-1-[1-(2-fluoro-6-methyl-phenyl)-piperidin-4-yl]-4-methoxy-1,3-dihydro-benzoimidazol-2-one;

3-(2-Cyclopropylmethoxy-benzyl)-1-[1-(2-fluoro-6-methyl-phenyl)-piperidin-4-yl]-4-methoxy-1,3-dihydro-benzoimidazol-2-one;

1-[1-(2-Fluoro-6-methyl-phenyl)-piperidin-4-yl]-4-methoxy-3-[2-(oxetan-3-yloxy)-benzyl]-1,3-dihydro-benzoimidazol-2-one;

3-(2-Cyclobutoxy-benzyl)-1-[1-(2-fluoro-6-methyl-phenyl)-piperidin-4-yl]-4-methoxy-1,3-dihydro-benzoimidazol-2-one;

1-[1-(2-Fluoro-6-methyl-phenyl)-3,3-dimethyl-piperidin-4-yl]-4-methoxy-3-(2-trifluoromethyl-benzyl)-1,3-dihydro-benzoimidazol-2-one;

4-[4-Methoxy-2-oxo-3-(2-trifluoromethyl-benzyl)-2,3-dihydro-benzoimidazol-1-yl]-3,3-dimethyl-piperidine-1-carboxylic acid tert-butyl ester;

3-[1-(2-Fluoro-6-methyl-phenyl)-piperidin-4-yl]-7-methoxy-1-(2-trifluoromethyl-benzyl)-1,3-dihydro-imidazo[4,5-c]pyridin-2-one;

1-[1-(2-Hydroxy-phenyl)-piperidin-4-yl]-4-methoxy-3-(2-trifluoromethyl-benzyl)-1,3-dihydro-benzoimidazol-2-one;

1-[1-(2-Benzyloxy-phenyl)-piperidin-4-yl]-4-methoxy-3-(2-trifluoromethyl-benzyl)-1,3-dihydro-benzoimidazol-2-one;

4-Methoxy-1-(3'-methyl-3,4,5,6-tetrahydro-2H-[1,2']bipyridinyl-4-yl)-3-(2-trifluoromethyl-benzyl)-1,3-dihydro-benzoimidazol-2-one;

4-Methoxy-1-(3'-methoxy-3,4,5,6-tetrahydro-2H-[1,2']bipyridinyl-4-yl)-3-(2-trifluoromethyl-benzyl)-1,3-dihydro-benzoimidazol-2-one;

4-Methoxy-1-(2'-methoxy-4'-methyl-3,4,5,6-tetrahydro-2H-[1,3']bipyridinyl-4-yl)-3-(2-trifluoromethyl-benzyl)-1,3-dihydro-benzoimidazol-2-one;

1-(2'-Fluoro-4'-methyl-3,4,5,6-tetrahydro-2H-[1,3']bipyridi-
nyl-4-yl)-4-methoxy-3-(2-trifluoromethyl-benzyl)-1,3-
dihydro-benzoimidazol-2-one;

1-(3'-Fluoro-3,4,5,6-tetrahydro-2H-[1,2']bipyridinyl-4-yl)-
4-methoxy-3-(2-trifluoromethyl-benzyl)-1,3-dihydro-
benzoimidazol-2-one;

1-(2',4'-Dimethyl-3,4,5,6-tetrahydro-2H-[1,3']bipyridinyl-
4-yl)-4-methoxy-3-(2-trifluoromethyl-benzyl)-1,3-di-
hydro-benzoimidazol-2-one;

1-{1-[2-(2-Hydroxy-ethoxy)-phenyl]-piperidin-4-yl}-4-
methoxy-3-(2-trifluoromethyl-benzyl)-1,3-dihydro-ben-
zoimidazol-2-one;

4-Methoxy-1-{1-[2-(tetrahydro-pyran-4-yloxy)-phenyl]-pi-
peridin-4-yl}-3-(2-trifluoromethyl-benzyl)-1,3-dihydro-
benzoimidazol-2-one;

1-[1-(2-Cyclopropylmethoxy-phenyl)-piperidin-4-yl]-4-
methoxy-3-(2-trifluoromethyl-benzyl)-1,3-dihydro-ben-
zoimidazol-2-one;

1-[1-(2-Cyclobutoxy-phenyl)-piperidin-4-yl]-4-methoxy-3-
(2-trifluoromethyl-benzyl)-1,3-dihydro-benzoimidazol-
2-one;

4-Methoxy-1-{1-[2-(oxetan-3-yloxy)-phenyl]-piperidin-4-
yl}-3-(2-trifluoromethyl-benzyl)-1,3-dihydro-benzoimi-
dazol-2-one;

1-[1-(2-Butoxy-phenyl)-piperidin-4-yl]-4-methoxy-3-(2-tri-
fluoromethyl-benzyl)-1,3-dihydro-benzoimidazol-2-one;

1-(4'-Fluoro-2'-methyl-3,4,5,6-tetrahydro-2H-[1,3']bipyridi-
nyl-4-yl)-4-methoxy-3-(2-trifluoromethyl-benzyl)-1,3-
dihydro-benzoimidazol-2-one;

1-[1-(2-Fluoro-6-methyl-phenyl)-piperidin-4-yl]-4-methyl-
3-(2-trifluoromethyl-benzyl)-1,3-dihydro-benzoimida-
zol-2-one;

4-[4-Methoxy-2-oxo-3-(2-trifluoromethyl-benzyl)-2,3-di-
hydro-benzoimidazol-1-yl]-4'-methyl-3,4,5,6-tetrahydro-
2H-[1,3']bipyridinyl-2'-carbonitrile;

4-Methoxy-1-(4'-methoxy-2'-methyl-3,4,5,6-tetrahydro-2H-
[1,3']bipyridinyl-4-yl)-3-(2-trifluoromethyl-benzyl)-1,3-
dihydro-benzoimidazol-2-one;

1-(2',4'-Dimethoxy-3,4,5,6-tetrahydro-2H-[1,3']bipyridinyl-
4-yl)-4-methoxy-3-(2-trifluoromethyl-benzyl)-1,3-di-
hydro-benzoimidazol-2-one;

4-Methoxy-1-[1-(4-methoxy-6-methyl-pyrimidin-5-yl)-pip-
eridin-4-yl]-3-(2-trifluoromethyl-benzyl)-1,3-dihydro-
benzoimidazol-2-one; or 1-[1-(4,6-Dimethoxy-pyrimidin-5-yl)-piperidin-4-yl]-4-
methoxy-3-(2-trifluoromethyl-benzyl)-1,3-dihydro-ben-
zoimidazol-2-one;

or a pharmaceutically acceptable salt thereof.

The compounds of formula (I), (II) and (III) according to embodiments 1) to 25) and their pharmaceutically acceptable salts can be used as medicaments, e.g. in the form of pharmaceutical compositions for enteral (such especially oral) or parenteral administration (including topical application or inhalation).

The production of the pharmaceutical compositions can be effected in a manner which will be familiar to any person skilled in the art (see for example Remington, *The Science and Practice of Pharmacy*, 21st Edition (2005), Part 5, "Pharmaceutical Manufacturing" [published by Lippincott Williams & Wilkins]) by bringing the described compounds of formula (I), (II) or (III), or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

The present invention also relates to a method for the prevention or treatment of a disease or disorder mentioned herein comprising administering to a subject a pharmaceutically active amount of a compound of formula (I), (II) or (III) as defined in any one of embodiments 1) to 25).

In a preferred embodiment of the invention, the administered amount is comprised between 1 mg and 1000 mg per day, particularly between 5 mg and 500 mg per day, more particularly between 25 mg and 400 mg per day, especially between 50 mg and 200 mg per day.

Whenever the word "between" is used to describe a numerical range, it is to be understood that the end points of the indicated range are explicitly included in the range. For example: if a temperature range is described to be between 40° C. and 80° C., this means that the end points 40° C. and 80° C. are included in the range; or if a variable is defined as being an integer between 1 and 4, this means that the variable is the integer 1, 2, 3, or 4.

Unless used regarding temperatures, the term "about" placed before a numerical value "X" refers in the current application to an interval extending from X minus 10% of X to X plus 10% of X, and preferably to an interval extending from X minus 5% of X to X plus 5% of X. In the particular case of temperatures, the term "about" placed before a temperature "Y" refers in the current application to an interval extending from the temperature Y minus 10° C. to Y plus 10° C., and preferably to an interval extending from Y minus 5° C. to Y plus 5° C.

For avoidance of any doubt, if compounds are described as useful for the prevention or treatment of certain diseases, such compounds are likewise suitable for use in the preparation of a medicament for the prevention or treatment of said diseases.

The compounds of formula (I), (II) and (III) as defined in any one of embodiments 1) to 25) are useful for the prevention/prophylaxis or treatment of diseases and disorders related to pathogenic events associated with elevated levels of C5a and/or with C5aR activation.

Such diseases and disorders related to pathogenic events associated with elevated levels of C5a and/or with C5aR activation are especially:

vasculitic diseases or disorders,
inflammatory diseases or disorders involving intravascular microvesicle release,
immune complex (IC) diseases or disorders,
neurodegenerative diseases or disorders,
complement related inflammatory diseases or disorders,
bullous diseases or disorders,
diseases or disorders related to ischemia and/or ischemic reperfusion injury,
inflammatory bowel diseases or disorders,
autoimmune diseases or disorders, or, in addition to the above listed;
cancer.

In addition to the above-listed diseases and disorders, further diseases and disorders related to pathogenic events associated with elevated levels of C5a and/or with C5aR activation are:

further inflammatory diseases or disorders associated with elevated levels of C5a and/or with C5aR activation such as especially neutropenia, sepsis, septic shock, stroke, inflammation associated with severe burns, osteoarthritis, acute (adult) respiratory distress syndrome (ARDS), chronic pulmonary obstructive disorder (COPD), asthma (especially bronchial asthma), systemic inflammatory response syndrome (SIRS), tissue graft rejection, hyperacute rejection of transplanted organs, multiple organ dysfunction syndrome (MODS), diabetic retinopathy, neuromyelitis optica, and glomerulonephritis including Heyman nephritis/membranous glomerulonephritis, Berger's disease (IgA nephropathy), and other forms of glomerulonephritis including C3 glomerulopathy;

as well as hemotological diseases which are associated with activation of coagulation and fibrinolytic systems, disseminated intravascular coagulation (DIC), pernicious anemia, warm and cold autoimmune hemolytic anemia (AIHA), anti-phospholipid syndrome and its associated complications, arterial or venous thrombosis, pregnancy complications such as recurrent miscarriage and fetal death, preeclampsia, placental insufficiency, fetal growth restriction, cervical remodeling and preterm birth, idiopathic thrombocytopenic purpura (ITP), atypical hemolytic uremic syndrome (aHUS), paroxysmal nocturnal hemoglobinuria (PNH), allergic transfusion reactions, acute antibody-mediated kidney allograft rejection, cold agglutinin disease and glaucoma.

The present compounds may in addition be useful for the prevention or treatment of deleterious consequences of contact sensitivity and inflammation caused by contact with artificial surfaces;

the prevention or treatment of increased leukocyte and platelet activation (and infiltration to tissues thereof);

the prevention or treatment of pathologic sequelae (such as especially prevention or treatment of the development of tissue injury, especially of pulmonary tissue injury) associated to an intoxication or an injury such as a trauma, an hemorrhage, a shock, or surgery including transplantation, including multiple organ failure (MOF), septic shock, shock due to intoxication (such as shock due to snake venom), or acute lung inflammatory injury;

the prevention or treatment of pathologic sequelae associated with insulin-dependent diabetes mellitus;

the prevention of/the reduction of the risk of myocardial infarction or thrombosis; prevention or treatment of edema or increased capillary permeability;

the prevention of/the reduction of coronary endothelial dysfunction induced by cardiopulmonary bypass and/or cardioplegia.

Vasculitic diseases or disorders include especially vasculitis, ANCA associated vasculitis and glomerulonephritis (GN, especially rapidly progressive GN) associated with ANCA associated vasculitis, leukoclastic vasculitis, granulomatosis with polyangiitis (GPA, also referred to as Wegener's granulomatosis), microscopic polyangiitis, Churg-Strauss syndrome, Henoch-Schönlein purpura, polyateritis nodosa, cryoglobulinaemia, giant cell arteritis (GCA), Behcet's disease, and Takayasu's arteritis (TAK).

Inflammatory diseases or disorders involving intravascular microvesicle release include especially thrombotic microangiopathy, and sickle cell disease.

Immune complex (IC) diseases or disorders include especially cryoglobulinemia, Sjögren's syndrome (and associated immunological profiles), Goodpasture syndrome (anti-glomerular basement antibody disease) and glomerulonephritis (GN, especially rapidly progressive GN) or pulmonary hemorrhage associated with Goodpasture syndrome, and hypersensitivity;

Neurodegenerative diseases and disorders include especially amyotrophic lateral sclerosis (ALS), Alzheimer's disease, Parkinson's disease, Guillain-Barre syndrome, neuropathy, and cognitive function decline associated with cardiopulmonary bypass surgery and related procedures.

Complement related inflammatory diseases or disorders include especially coronary thrombosis, vascular occlusion, post-surgical vascular reocclusion, atherosclerosis, traumatic central nervous system injury, arrhythmogenic cardiomyopathy, bronchoconstriction, acute respiratory distress syndrome (ARDS), Chronic Obstructive Pulmonary Disorder (COPD), complement mediated thrombotic microangiopathies including atypical haemolytic uremic syndrome, and Gaucher disease.

Bullous diseases or disorders include especially bullous pemphigoid, bullous acquisita, pemphigus foliaceus, pemphigus vulgaris, and sub-epidermal blisters.

Diseases or disorders related to ischemia and/or ischemic reperfusion injury include especially ischemic reperfusion injury (including myocardial ischemia-reperfusion injury, and ischemic/reperfusion injury resulting from transplantation, including solid organ transplant), ischemic colitis, and cardiac ischemia.

Inflammatory bowel diseases or disorders include especially irritable bowel syndrome, ulcerative colitis, Crohn's disease, and inflammatory bowel disease (IBD).

Autoimmune diseases or disorders include especially rheumatoid arthritis, osteoarthritis, systemic lupus erythematosus (SLE) and glomerulonephritis (GN, especially rapidly progressive GN) associated with lupus erythematosus (lupus nephritis), central nervous system (CNS) lupus, dermatomyositis, pemphigus, systemic sclerosis (scleroderma), autoimmune hemolytic and thrombocytopenic states, immunovasculitis, mixed cryoglobulinemia, atopic dermatitis, chronic urticaria, psoriasis, myasthenia gravis, and anti-phospholipid syndrome.

Further inflammatory diseases or disorders associated with elevated levels of C5a and/or with C5aR activation include especially neutropenia, sepsis, septic shock, stroke, inflammation associated with severe burns, osteoarthritis, acute (adult) respiratory distress syndrome (ARDS), chronic pulmonary obstructive disorder (COPD), asthma, especially bronchial asthma, systemic inflammatory response syndrome (SIRS), tissue graft rejection, hyperacute rejection of transplanted organs, multiple organ dysfunction syndrome (MODS), diabetic retinopathy, neuromyelitis optica, and glomerulonephritis including Heyman nephritis/membranous glomerulonephritis, Berger's disease (IgA nephropathy), and other forms of glomerulonephritis including C3 glomerulopathy.

The term "cancer" notably refers to skin cancer including melanoma including metastatic melanoma; lung cancer including non-small cell lung cancer; bladder cancer including urinary bladder cancer, urothelial cell carcinoma; renal carcinomas including renal cell carcinoma, metastatic renal cell carcinoma, metastatic renal clear cell carcinoma; gastrointestinal cancers including colorectal cancer, metastatic colorectal cancer, familial adenomatous polyposis (FAP), oesophageal cancer, gastric cancer, gallbladder cancer, cholangiocarcinoma, hepatocellular carcinoma, and pancreatic cancer such as pancreatic adenocarcinoma or pancreatic ductal carcinoma; endometrial cancer; ovarian cancer; cervical cancer; neuroblastoma; prostate cancer including castrate-resistant prostate cancer; brain tumors including brain metastases, malignant gliomas, glioblastoma multiforme, medulloblastoma, meningiomas; breast cancer including triple negative breast carcinoma; oral tumors; nasopharyngeal tumors; thoracic cancer; head and neck cancer; leukemias including acute myeloid leukemia, adult T-cell leukemia; carcinomas; adenocarcinomas; thyroid carcinoma including papillary thyroid carcinoma; choriocarcinoma; Ewing's sarcoma; osteosarcoma; rhabdomyosarcoma; Kaposi's sarcoma; lymphoma including Burkitt's lymphoma, Hodgkin's lymphoma, MALT lymphoma; multiple myelomas; or virally induced tumors.

When used for the prevention/prophylaxis or treatment of a cancer, such use includes use of the present compounds as single therapeutic agents and their use in combination with one or more chemotherapy agents and/or radiotherapy and/or targeted therapy (especially in combination with targeted therapy).

The terms "radiotherapy" or "radiation therapy" or "radiation oncology", refer to the medical use of ionizing radiation in the prevention/prophylaxis (adjuvant therapy) and/or treatment of cancer; including external and internal radiotherapy.

The term "targeted therapy" refers to the prevention/prophylaxis (adjuvant therapy) and/or treatment of cancer with one or more anti-neoplastic agents such as small molecules or antibodies which act on specific types of cancer cells or stromal cells. Some targeted therapies block the action of certain enzymes, proteins, or other molecules involved in the growth and spread of cancer cells. Other types of targeted therapies help the immune system kill cancer cells (immunotherapies); or inhibit angiogenesis, the growth and formation of new blood vessels in the tumor; or deliver toxic substances directly to cancer cells and kill them. An example of a targeted therapy which is in particular suitable to be combined with the compounds of the present invention is immunotherapy, especially immunotherapy targeting the programmed cell death receptor 1 (PD-1 receptor) or its ligand PD-L1.

When used in combination with the present compounds, the term "targeted therapy" especially refers to agents such as:

a) Epidermal growth factor receptor (EGFR) inhibitors or blocking antibodies (for example Gefitinib, Erlotinib, Afatinib, Icotinib, Lapatinib, Panitumumab, Zalutumumab, Nimotuzumab, Matuzumab and Cetuximab);

b) RAS/RAF/MEK pathway inhibitors (for example Vemurafenib, Sorafenib, Dabrafenib, GDC-0879, PLX-4720, LGX818, RG7304, Trametinib (GSK1120212), Cobimetinib (GDC-0973/XL518), Binimetinib (MEK162, ARRY-162), Selumetinib (AZD6244));

c) Aromatase inhibitors (for example Exemestane, Letrozole, Anastrozole, Vorozole, Formestane, Fadrozole);

d) Angiogenesis inhibitors, especially VEGF signalling inhibitors such as Bevacuzimab (Avastin), Ramucirumab, Sorafenib or Axitinib;

e) Immune Checkpoint inhibitors (for example: anti-PD1 antibodies such as Pembrolizumab (Lambrolizumab, MK-3475), Nivolumab, Pidilizumab (CT-011), AMP-514/MED10680, PDR001, SHR-1210; REGN2810, BGBA317; fusion proteins targeting PD-1 such as AMP-224; small molecule anti-PD1 agents such as for example compounds disclosed in WO2015/033299, WO2015/044900 and WO2015/034820; anti-PD1L antibodies, such as BMS-936559, atezolizumab (MPDL3280A, RG7446), MEDI4736, avelumab (MSB0010718C), durvalumab (MEDI4736); anti-PDL2 antibodies, such as AMP224; anti-CTLA-4 antibodies, such as ipilimumab, tremilmumab; anti-Lymphocyte-activation gene 3 (LAG-3) antibodies, such as BMS-986016, IMP701, MK-4280, ImmuFact IMP321; anti T cell immunoglobulin mucin-3 (TIM-3) antibodies, such as MBG453; anti-CD137/4-1BB antibodies, such as BMS-663513/urelumab, PF-05082566; anti T cell immunoreceptor with Ig and ITIM domains (TIGIT) antibodies, such as RG6058 (anti-TIGIT, MTIG7192A);

f) Vaccination approaches (for example dendritic cell vaccination, peptide or protein vaccination (for example with gp100 peptide or MAGE-A3 peptide);

g) Re-introduction of patient derived or allogenic (non-self) cancer cells genetically modified to secrete immunomodulatory factors such as granulocyte monocyte colony stimulating factor (GMCSF) gene-transfected tumor cell vaccine (GVAX) or Fms-related tyrosine kinase 3 (Flt-3) ligand gene-transfected tumor cell vaccine (FVAX), or Toll like receptor enhanced GM-CSF tumor based vaccine (TEGVAX);

h) T-cell based adoptive immunotherapies, including chimeric antigen receptor (CAR) engineered T-cells (for example CTL019);

i) Cytokine or immunocytokine based therapy (for example Interferon alpha, interferon beta, interferon gamma, interleukin 2, interleukin 15);

j) Toll-like receptor (TLR) agonists (for example resiquimod, imiquimod, glucopyranosyl lipid A, CpG oligodesoxynucleotides);

k) Thalidomide analogues (for example Lenalidomide, Pomalidomide);

l) Indoleamin-2,3-Dioxgenase (IDO) and/or Tryptophane-2,3-Dioxygenase (TDO) inhibitors (for example RG6078/NLG919/GDC-0919; Indoximod/1MT (1-methyltryptophan), INCB024360/Epacadostat, PF-06840003 (EOS200271), F001287);

m) Activators of T-cell co-stimulatory receptors (for example anti-OX40/CD134 (Tumor necrosis factor receptor superfamily, member 4, such as RG7888 (MOXR0916), 9B12; MED6469, GSK3174998, MED0562), anti OX40-Ligand/CD252; anti-glucocorticoid-induced TNFR family related gene (GITR) (such as TRX518, MEDI1873, MK-4166, BMS-986156), anti-CD40 (TNF receptor superfamily member 5) antibodies (such as Dacetuzumab (SGN-40), HCD122, CP-870,893, RG7876, ADC-1013, APX005M, SEA-CD40); anti-CD40-Ligand antibodies (such as BG9588); anti-CD27 antibodies such as Varlilumab);

n) Molecules binding a tumor specific antigen as well as a T-cell surface marker such as bispecific antibodies (for example RG7802 targeting CEA and CD3) or antibody fragments, antibody mimetic proteins such as designed ankyrin repeat proteins (DARPINS), bispecific T-cell engager (BITE, for example AMG103, AMG330);

o) Antibodies or small molecular weight inhibitors targeting colony-stimulating factor-1 receptor (CSF-1R) (for example Emactuzumab (RG7155), Cabiralizumab (FPA-008), PLX3397);

p) Agents targeting immune cell check points on natural killer cells such as antibodies against Killer-cell immunoglobulin-like receptors (KIR) for example Lirilumab (IPH2102/BMS-986015);

q) Agents targeting the Adenosine receptors or the ectonucleases CD39 and CD73 that convert ATP to Adenosine, such as MEDI9447 (anti-CD73 antibody), PBF-509; CPI-444 (Adenosine A2a receptor antagonist).

When used in combination with the present compounds, immune checkpoint inhibitors, and especially those targeting the PD-1 receptor or its ligand PD-L1, are preferred.

The invention further relates to a method of modulating (especially downregulating) the consequences of the complement activation (especially by activating innate cells) in a subject in need thereof [especially in a subject having a disease or disorder related to pathogenic events associated with elevated levels of C5a and/or with C5aR activation; in particular in a subject having a vasculitic disease or disorder, an inflammatory disease or disorder involving intravascular microvesicle release, an immune complex (IC) disease or disorder, a neurodegenerative disease or disorder, a complement related inflammatory disease or disorder, a bullous disease or disorder, a disease or disorder related to ischemia and/or ischemic reperfusion injury, an inflammatory bowel disease or disorder, or an autoimmune disease or disorder; or in a subject having a contact sensitivity or an inflammation caused by contact with artificial surfaces; an increased leukocyte and platelet activation (and infiltration to tissues thereof); a pathologic sequelae associated to an intoxication or an injury such as a trauma, an hemorrhage, a shock, or surgery including transplantation, including multiple organ failure (MOF), septic shock, shock due to intoxication (such as shock due to snake venom), or acute lung inflammatory injury; a pathologic sequelae associated with insulin-dependent diabetes mellitus; a myocardial infarction or thrombosis; an edema or an increased capillary permeability; or a reduction of coronary endothelial dysfunction induced by cardiopulmonary bypass and/or cardioplegia], comprising administering to said subject a pharmaceutically active amount of a compound of formula (I), (II) and (III) as defined in any one of embodiments 1) to 25). For avoidance of doubt, the term "modulating the complement activation" is to be understood as downregulating/reducing the amplification of the immune response and downregulating/reducing the activation of the cell-killing membrane attack complex, especially by activating innate cells.

Preparation of Compounds of Formula (I):

The compounds of formula (I), (II) and (III) can be prepared by the methods given below, by the methods given in the experimental part below or by analogous methods. Optimum reaction conditions may vary with the particular reactants or solvents used, but such conditions can be determined by a person skilled in the art by routine optimisation procedures. In the schemes below, the generic groups Ring A, $R^1$, $R^{1a}$, $R^{14a}$, $R^{14b}$, $X^{14}$, $R^2$, $R^{2a}$, $X^{21}$, $R^3$, $R^4$, $R^{41}R^{41a}$, $R^{41b}$, $X^{41}$, $R^{42a}$, $R^{42b}$, $R^{43a}$, $R^{43b}$ are as defined for the compounds of formula (I), (II) and (III). In some instances, the generic groups Ring A, $R^1$, $R^{1a}$, $R^{14a}$, $R^{14b}$, $X^{14}$, $R^2$, $R^{2a}$, $X^{21}$, $R^3$, $R^4$, $R^{41}$, $R^{41a}$, $R^{41b}$, $X^{41}$, $R^{42a}$, $R^{42b}$, $R^{43a}$, $R^{43b}$ may be incompatible with the assembly illustrated in the schemes, or will require the use of protecting groups (PG). The use of protecting groups is well known in the art (see for example "Protective Groups in Organic Synthesis", T. W. Greene, P. G. M. Wuts, Wiley-Interscience, 1999). For the purposes of this discussion, it will be assumed that such protecting groups as necessary are in place. In some cases, the final product may be further modified, for example, by manipulation of substituents to give a new final product. These manipulations may include, but are not limited to, reduction, oxidation, alkylation, acylation, and hydrolysis reactions which are commonly known to those skilled in the art. The compounds obtained may also be converted into salts, especially pharmaceutically acceptable salts in a manner known per se.

Compounds of structure Ia can be prepared according to the synthetic route given in scheme A below.

Compounds of structure A-1 can be prepared by aromatic nucleophilic substitution of amine of structure BB-1 on halides of structure BB-2 wherein X represents fluorine or chlorine in the presence of a suitable base such as DIPEA and heating in a suitable solvent such as DMSO at temperatures between 80° C. and 100° C. (Scheme A, step a).

Diamino compounds of structure A-2 can be prepared by reduction of the nitro group in compounds of structure A-1 using standard conditions such as catalytic hydrogenation with a suitable catalyst such as Pd/C and in the presence of a suitable solvent such as EtOAc and under a hydrogen atmosphere. Alternatively, reduction of the nitro group in compounds of structure A-1 may be performed by treatment with zinc dust and ammonium formate in solvents such as MeOH at temperatures around 0° C. (Scheme A, step b).

Cyclic ureas of structure A-3 can be prepared by cyclisation of diamines of structure A-2 by treatment with a suitable carbonyl transfer agent such as CDI in the presence of a suitable non protic solvent such as MeCN at temperatures between RT and 45° C. (Scheme A, step c).

Alkylation of the nitrogen atom having a free valency in compounds of structure A-3 with a suitable halide of structure BB-3 wherein X represents chlorine or bromine, in the presence of a suitable base such as NaH or $K_2CO_3$ and in solvents such as THF, DMF or a mixture of both at temperatures between 0° C. and 50° C. may afford compounds of structure Ia (Scheme A, step d).

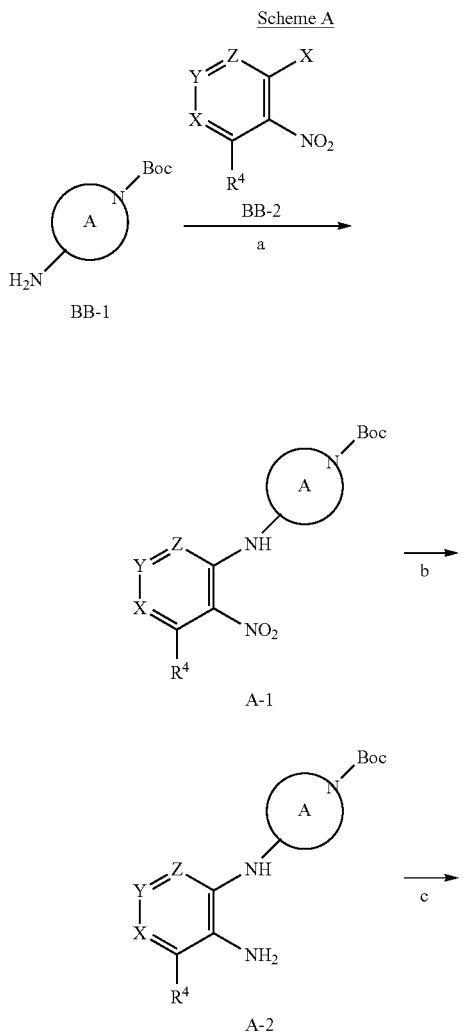

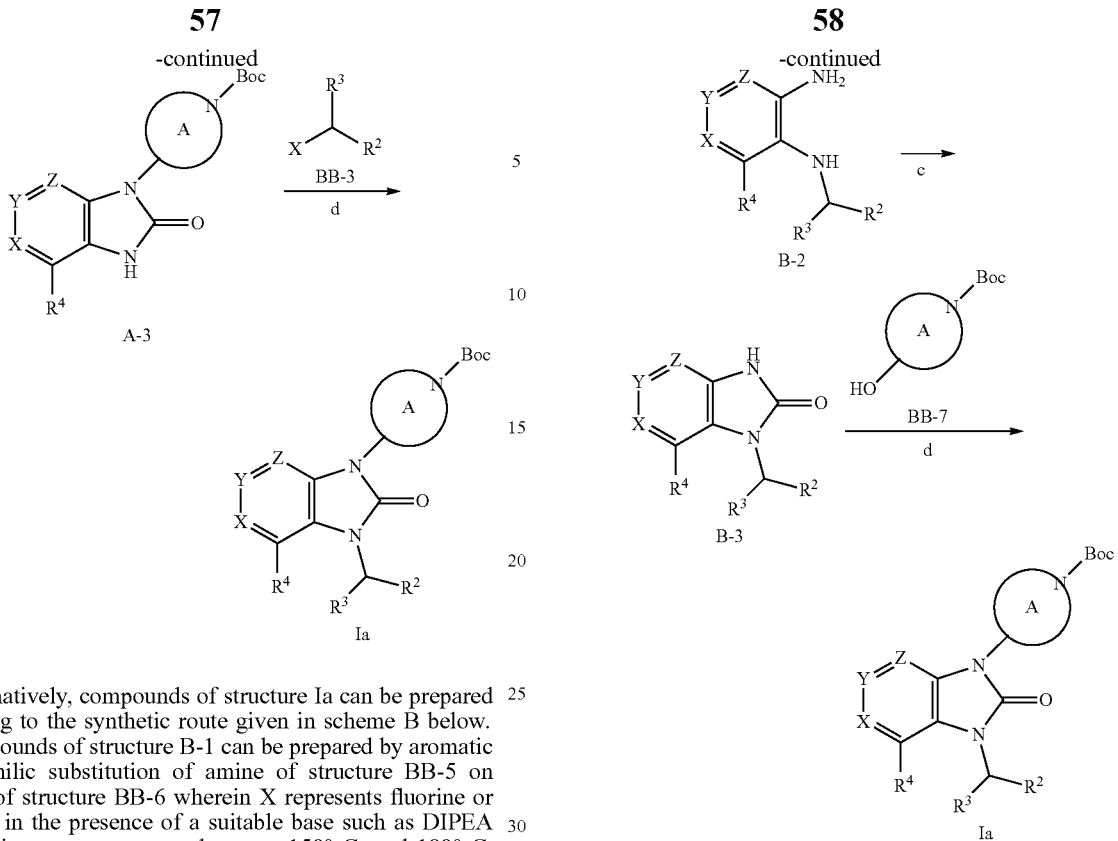

Alternatively, compounds of structure Ia can be prepared according to the synthetic route given in scheme B below.

Compounds of structure B-1 can be prepared by aromatic nucleophilic substitution of amine of structure BB-5 on halides of structure BB-6 wherein X represents fluorine or chlorine in the presence of a suitable base such as DIPEA and heating at temperatures between 150° C. and 180° C. (Scheme B, step a).

Reduction of the nitro group in compounds of structure B-1 using standard conditions such as treatment by zinc dust and ammonium formate in solvents such as MeOH at temperatures around 0° C. may afford diamines of structure B-2. Alternatively, reduction of the nitro group in compounds of structure B-1 may be performed by catalytic hydrogenation with a suitable catalyst such as Pd/C in the presence of a suitable solvent such as EtOAc and under a hydrogen atmosphere (Scheme B, step b).

Cyclisation of diamines of structure B-2 to form cyclic urea of structure B-3 (Scheme B, step c) can be performed following conditions as those previously described for the synthesis of compounds of structure A-3 (Scheme A, step c).

Alkylation of the nitrogen atom having a free valency in compounds of structure B-3 can be achieved using Mitsunobu conditions by treatment with a suitable alcohol of structure BB-7 and for instance a (cyanomethylene)trialkylphosphorane reagent in the presence of a suitable solvent such as toluene at temperatures around 110° C. (Scheme B, step d).

Scheme B

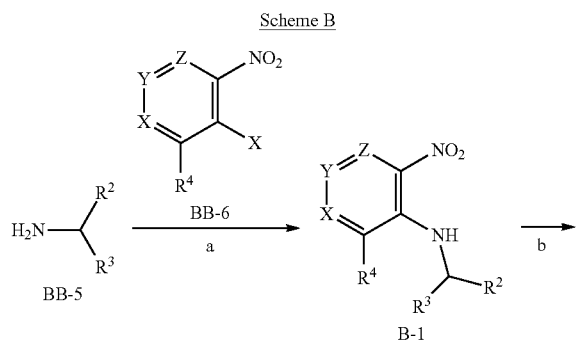

Compounds of structure Ib, Ic, Ig, Ih, Ii, Iq and Iag can be prepared according to the synthetic route given in scheme C below.

Cleavage of the Boc protecting group in compounds of formula Ia can be performed using a suitable acid such as HCl or TFA in the presence of a suitable solvent such as dioxane, MeOH or DCM at temperatures around RT (Scheme C, step a).

Compounds of structure Ib wherein $R^1$ represents an unsubstituted, mono-, di- or tri-substituted phenyl or 5- or 6-membered heteroaryl can be prepared by Buchwald-Hartwig cross coupling of halides of structure $R^1$—X wherein X represents iodine, bromine or chloride and $R^1$ represents an unsubstituted, mono-, di- or tri-substituted phenyl or 5- or 6-membered heteroaryl with an amine of structure C-1 in the presence of a suitable palladium catalyst such as $Pd_2(dba)_3$ and a ligand such as BINAP, in the presence of a suitable base such as sodium tert-butoxide and heating in a suitable solvent such as toluene at temperatures between 100° C. and 110° C. (Scheme C, step b).

Compounds of structure Ib wherein $R^1$ represents an unsubstituted, mono- or di-substituted benzyl can be prepared by reductive amination of benzaldehyde of structure $R^{1a}$—CHO wherein $R^{1a}$ represents a mono- or di-substituted phenyl with an amine of structure C-1 using standard conditions such as treatment with $NaBH(OAc)_3$ in the presence of AcOH and a suitable solvent such as DCM or THF at temperatures around RT (Scheme C, step b).

Compounds of structure Ic wherein $R^1$ represents an unsubstituted, mono-, di- or tri-substituted phenyl or 5- or 6-membered heteroaryl can be prepared by aromatic nucleophilic substitution of amines of structure C-1 on activated halides of structure $R^1$—X wherein X represents fluorine or chlorine and $R^1$ represents a suitable unsubstituted, mono-, di- or tri-substituted phenyl or 5- or 6-membered heteroaryl in the presence of a suitable base such as CsF or K₂CO₃ and heating in a suitable solvent such as DMSO at temperatures between 60° C. and 110° C. (Scheme C, step b).

Alternatively, compounds of structure Ic wherein $R^1$ represents a 5- or 6-membered heteroaryl can be prepared by aromatic nucleophilic substitution of amines of structure C-1 on alcohol of structure $R^1$—X wherein X represents hydroxy and $R^1$ represents a suitable 5- or 6-membered heteroaryl by activation of the corresponding alcohol with PyBOP in the presence of a suitable base such as DIPEA in solvents such as DMF at temperatures around RT (Scheme C, step b).

Compounds of structure Ig wherein $R^1$ represents a $(C_{1-4})$alkoxy-carbonyl, phenoxy-carbonyl or $(C_{3-6})$cycloalkoxy-carbonyl can be prepared by treatment of amines of structure C-1 with chloroformate (or pentafluorophenyl-carbonate, respectively) of structure $R^1$—X wherein $R^1$ represents $(C_{1-4})$alkoxy-carbonyl, phenoxy-carbonyl or $(C_{3-6})$cycloalkoxy-carbonyl and X represents chlorine (or X represents pentafluorophenoxy, respectively) in the presence of a suitable base such as TEA and in a suitable solvent such as DCM or DMF at temperatures between RT and 110° C. (Scheme C, step b).

Compounds of structure Ih wherein $R^1$ represents a $(C_{1-4})$alkyl-carbonyl, phenyl-carbonyl or $(C_{3-6})$cycloalkyl-carbonyl optionally containing one ring oxygen and optionally mono-substituted with methyl or trifluoromethyl can be prepared by treatment of amines of structure C-1 with acid chlorides of structure $R^1$—X wherein $R^1$ represents $(C_{1-4})$alkyl-carbonyl, phenyl-carbonyl or $(C_{3-6})$cycloalkyl-carbonyl optionally containing one ring oxygen and optionally mono-substituted with methyl or trifluoromethyl and X represents chlorine in the presence of a suitable base such as TEA and in a suitable solvent such as DCM at temperatures between 0° C. and RT (Scheme C, step b).

Compounds of structure Ii wherein $R^1$ represents $(C_{1-4})$ alkyl can be prepared by reductive amination of a suitable aldehyde of structure $R^{1a}$—CHO wherein $R^{1a}$ represents hydrogen or $(C_{1-3})$alkyl, acetone or butanone with amines of structure C-1 using standard conditions such as treatment with NaBH(OAc)₃ in the presence of AcOH and a suitable solvent such as DCM, MeOH, THF or mixture thereof at temperatures around RT (Scheme C, step b). Alternatively, triethylsilane in solvents such as MeOH in the presence of catalytic amount of indium chloride (III) at temperatures around RT can be used as reductive conditions. Alternatively, alkylation of amines of structure C-1 with halides of structure $R^1$—X wherein X represents chlorine, bromine or iodine in the presence of a suitable base such as K₂CO₃ and a suitable solvent such as MeCN at temperatures between RT and 65° C. may afford compounds of structure Ii (Scheme C, step b).

Compounds of structure C-2 can be prepared by alkylation of carbamates of structure BB-10 by treatment with an appropriate halide of formula BB-3 wherein X represents chlorine or bromine in the presence of a suitable base such as K₂CO₃ and carrying out the rxn in a suitable solvent such as MeCN at temperatures around 80° C. (Scheme C, step c).

Compounds of formula Iag can be prepared by Buchwald-Hartwig cross coupling of halides of formula C-2 with amines of formula BB-4 by treatment with a suitable palladium catalyst such as BrettPhos precatalyst and a suitable ligand such as BrettPhos, in the presence of a suitable base such as sodium tert-butoxide and heating in a suitable solvent such as dioxane at temperatures around 80° C. Using those conditions, the consecutive cyclisation to form the cyclic urea occurred and afforded the compounds of formula Iag (Scheme C, step d).

Compounds of structure C-3 can be prepared by aromatic nucleophilic substitution of amine of structure BB-4 on halides of structure BB-2 wherein X represents fluorine or chlorine in the presence of a suitable base such as DIPEA and heating in a suitable solvent such as DMSO at temperatures between 50° C. and 105° C. (Scheme C, step e).

Diamino compounds of structure C-4 can be prepared by reduction of the nitro group in compounds of structure C-3 using standard conditions such as catalytic hydrogenation with a suitable catalyst such as Pd/C and in the presence of a suitable solvent such as EtOAc and under a hydrogen atmosphere. Alternatively, the reduction of the nitro group can be performed by treatment with ammonium formate and zinc dust in the presence of a suitable solvent such as MeOH at temperatures around RT (Scheme C, step f).

Cyclic urea of structure C-6 can be prepared by cyclisation of diamines of structure C-4 by treatment with a suitable carbonyl transfer agent such as CDI in the presence of a suitable non protic solvent such as MeCN at temperatures between RT and 45° C. (Scheme C, step g).

Alternatively, compounds of structure C-6 can be prepared by aromatic nucleophilic substitution of amines of structure C-5 on halides of structure BB-8 wherein X represents fluorine or chlorine in the presence of a suitable base such as K₂CO₃ and heating in a suitable solvent such as DMSO at temperatures around 100° C. (Scheme C, step i). Compounds of structure C-5 can be prepared by cleavage of the Boc protecting group in compounds of formula A-3 using a suitable acid such as HCl or TFA in the presence of a suitable solvent such as dioxane, MeOH or DCM at temperatures around RT (Scheme C, step h).

Scheme C

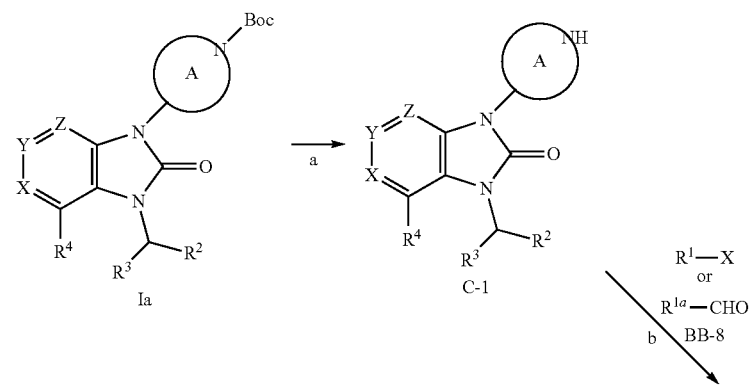

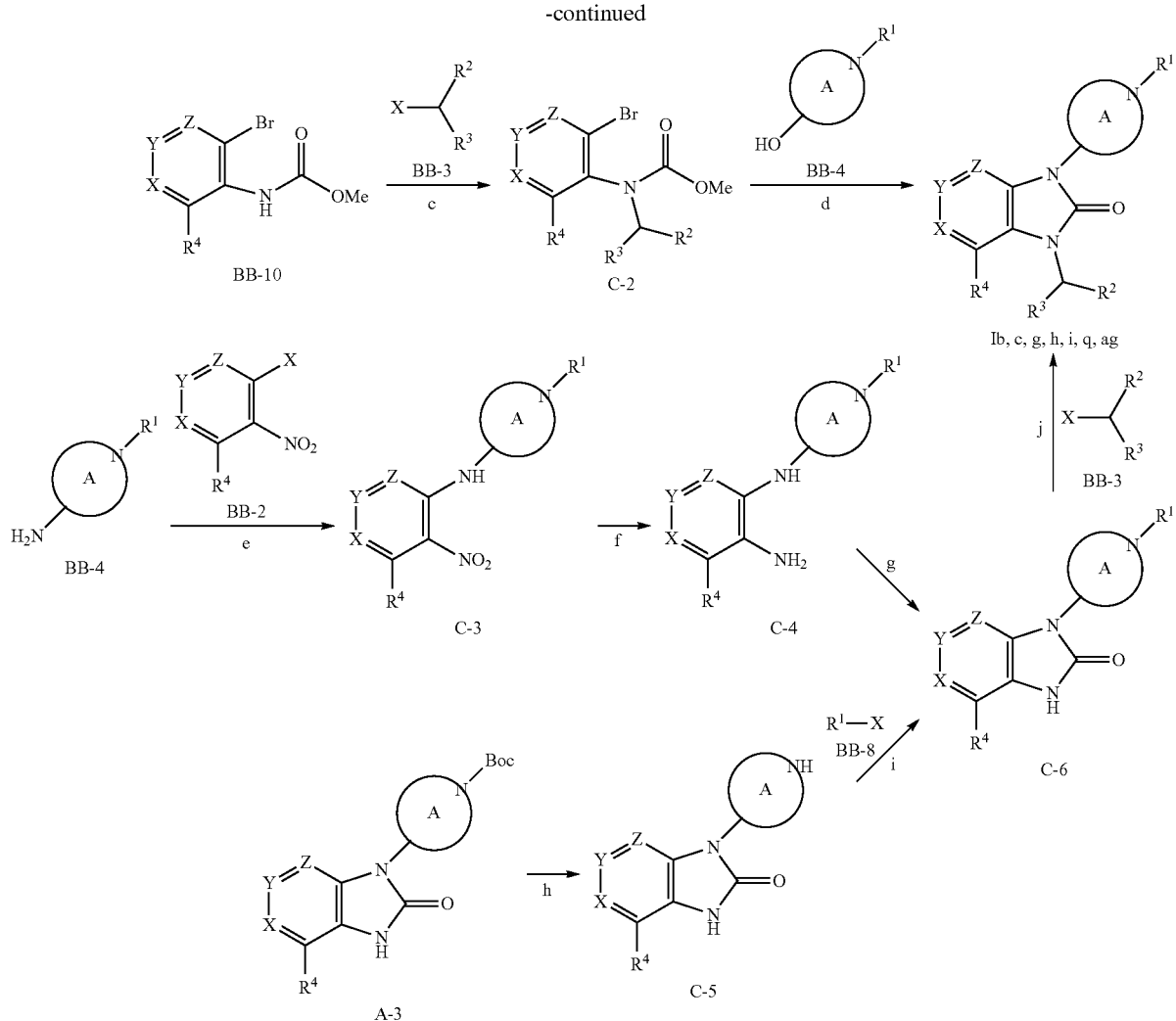

Compounds of structure Id to If, Ij to Ip, Iu to Iz and Iae can be prepared according to the synthetic route given in scheme D below.

Alkylation of the nitrogen atom having a free valency in compounds of structure C-6 with a suitable halide of structure BB-3 wherein X represents chlorine or bromine, in the presence of a suitable base such as NaH or $K_2CO_3$ and in solvents such as THF, DMF or a mixture of both at temperatures between 0° C. and 50° C. may afford compounds of structure Iq (Scheme C, step j). Alternatively, alkylation of the nitrogen atom having a free valency in compounds of structure C-6 can be achieved using Mitsunobu conditions by treatment with a suitable alcohol of structure BB-3 wherein X represents hydroxy and for instance a (cyanomethylene)trialkylphosphorane reagent in the presence of a suitable solvent such as toluene at temperatures around 110° C. (Scheme C, step j).

Compounds of structure Id wherein $R^1$ represents a 5- or 6-membered heteroaryl with at least one unsubstituted position can be prepared by decarbonylation of compounds of formula Ib or Ic wherein $R^1$ represents a 5- or 6-membered heteroaryl which is substituted by a formyl group by treatment with a suitable acid such as toluene-4-sulfonic acid and in the presence of a suitable solvent such as MeOH under microwave conditions at temperatures around 120° C. (Scheme D, step a).

Compounds of structure If wherein $R^1$ represents a 5- or 6-membered heteroaryl with at least one methyl substituent can be prepared by Wolff-Kishner type reduction of compounds of formula Ib or Ic wherein $R^1$ represents a 5- or 6-membered heteroaryl which is substituted by one formyl group. The treatment with 4-toluene-sulfonyl hydrazide in the presence of toluene-4-sulfonic acid monohydrate with a suitable solvent such as a mixture of DMF and tetramethylene sulfone at temperatures around 100° C. affords the hydrazone intermediate which is consecutively reduced by treatment with sodium cyanoborohydride at temperatures around 100° C. (Scheme D, step a).

Compounds of structure Ij wherein $R^4$ represents hydroxy can be prepared by treatment of suitable compounds of formula Ib and Ic wherein $R^4$ represents methoxy with a suitable Lewis acid such as boron tribromide in the presence of a suitable solvent such as DCM at temperatures between −10° C. and RT (Scheme D, step a).

Compounds of structure Im wherein $R^1$ represents a hydroxymethyl substituted phenyl or 5- or 6-membered heteroaryl can be prepared by treatment of compounds of formula Ib and Ic wherein $R^1$ represents a formyl substituted phenyl or 5- or 6-membered heteroaryl by treatment with a suitable reducing reagent such as $NaBH_4$ in the presence of a suitable solvent such as MeOH or THF at temperatures between 0° C. and RT (Scheme D, step a).

Compounds of structure In wherein $R^1$ represents a 1-hydroxy-$(C_2-C_3)$-alkyl substituted phenyl or 5- or 6-membered heteroaryl can be prepared by treatment of compounds of formula Ib and Ic wherein $R^1$ represents a formyl substituted phenyl or 5- or 6-membered heteroaryl by treatment with a suitable Grignard reagent in the presence of a suitable solvent such as THF at temperatures between 0° C. and RT (Scheme D, step a).

Compounds of structure Iu wherein $R^1$ represents a $R^{14a}R^{14b}N-X^{14}-$ substituted phenyl, 5- or 6-membered heterocycle wherein $X^{14}$ represents a methylene and $R^1$ and $R^{14}$ independently represent hydrogen, $(C_{1-4})$alkyl, hydroxy-$(C_{2-4})$alkyl, $(C_{1-3})$alkoxy-$(C_{2-4})$alkyl; or $R^{14a}$ and $R^{14b}$ together with the nitrogen to which they are attached to form a 4- to 6-membered saturated ring optionally containing one additional ring heteroatom selected from oxygen and nitrogen; and wherein said ring is optionally mono-substituted with $(C_{1-4})$alkyl can be prepared by reductive amination of compounds of formula Ib or Ic wherein $R^1$ represents a formyl substituted phenyl or 5- or 6-membered heteroaryl using standard conditions such as treatment with $NaBH(OAc)_3$ in the optional presence of AcOH and a suitable solvent such as DCM or THF at temperatures around RT (Scheme D, step a).

Compounds of structure Ie wherein $R^1$ represents a chlorine substituted 5- or 6-membered heteroaryl can be prepared by chlorination of compounds of formula Id wherein $R^1$ represents a 5- or 6-membered heteroaryl with one unsubstituted position by treatment with a chlorinating reagent such as NCS in the presence of a suitable solvent such as THF at temperatures around RT (Scheme D, step b).

Compounds of structure Ik wherein X and Z represents CH and $R^4$ represents $-O-R^{41}$ wherein $R^{41}$ represents $(C_{1-4})$alkyl, $(C_{2-4})$alkyl which is substituted with one or two hydroxyl, $R^{41a}R^{41b}N-(C_{2-3})$alkylene-, wherein $R^{41a}$ and $R^{41b}$ independently represent hydrogen or $(C_{1-4})$alkyl; or $(C_4a)$heterocyclyl-$X^{41}-$, wherein $X^{41}$ represents a direct bond or $(C_{1-3})$alkylene, and wherein the $(C_{4-7})$heterocyclyl independently contains one or two ring heteroatoms independently selected from nitrogen and oxygen; wherein said $(C_{4-7})$heterocyclyl independently is unsubstituted, or mono-, or di-substituted, wherein the substituents are independently selected from $(C_{1-4})$alkyl or $(C_{1-4})$alkoxy-carbonyl attached to a ring nitrogen atom having a free valency can be prepared by alkylation of compounds of formula Ij wherein X and Z represents CH and $R^4$ represents hydroxyl by treatment with an appropriate halide such as $R^{41}-W$ wherein W represents chlorine or bromine in the presence of a suitable base such as $K_2CO_3$ and carrying out the rxn in a suitable solvent such as DMSO at temperatures between 50 and 105° C. (Scheme D, step b).

Compounds of structure Io wherein $R^1$ represents a 1-oxo-$(C_2-C_5)$-alkyl substituted phenyl or 5- or 6-membered heteroaryl can be prepared by oxidation of compounds of formula In wherein $R^1$ represents a (C1-$C_4$)-alkyl-hydroxymethyl substituted phenyl or 5- or 6-membered heteroaryl by treatment with an oxidizing reagent such as DMP in the presence of a suitable solvent such as DCM at temperatures around RT (Scheme D, step b).

Compounds of structure Ie can be prepared by Suzuki cross coupling of chlorides of structure Ie wherein $R^1$ represents a chlorine substituted 5- or 6-membered heteroaryl with a (C1-$C_4$)-alkyl boronic acid or boroxine in the presence of a suitable palladium catalyst such as PEPPSI-IPr, in the presence of a suitable base such as $K_2CO_3$ and heating in a suitable solvent such as dioxane at temperatures between 115° C. (Scheme D, step c).

Compounds of structure Ip wherein $R^1$ represents a 1-hydroxy-1-methyl-ethyl substituted phenyl or 5- or 6-membered heteroaryl can be prepared by treatment of compounds of formula Io wherein $R^1$ represents an acetyl substituted phenyl or 5- or 6-membered heteroaryl by treatment with a suitable Grignard reagent in the presence of a suitable solvent such as THF at temperatures between 0° C. and RT (Scheme D, step c).

Compounds of structure Ix wherein X and Z represents CH and $R^4$ represents a diol containing substituent (respectively a substituent containing a nitrogen atom having a free valency) can be prepared by acidic deprotection of compounds of structure Ik wherein $R^4$ represents a substituent which contains a ketal protected diol (respectively a substituent containing a Boc protected nitrogen) in the presence of a suitable acid such as aqueous HCl (respectively TFA) and a suitable solvent such as THF (respectively DCM) at temperatures between 0° C. and RT (Scheme D, step c).

Alkylation of the free hydroxyl group in compounds of structure Im wherein $R^1$ represents a hydroxymethyl substituted phenyl or 5- or 6-membered heteroaryl or in compounds of structure In wherein $R^1$ represents a 1-hydroxy-$(C_2-C_3)$-alkyl substituted phenyl or 5- or 6-membered heteroaryl with a suitable $(C_1-C_4)$-alkyl halide, in the presence of a suitable base such as NaH and in solvents such as THF, DMF or a mixture of both at temperatures between 0° C. and 50° C. may afford compounds of structure Iz (Scheme D, step d).

Compounds of structure Iae wherein $R^1$ represents a $R^{14a}R^{14b}N-CH(Me)-$, $R^{14a}R^{14b}N-CH(Et)-$, or $R^{14a}R^{14b}N-C(Me)_2$-substituted phenyl or 5- or 6-membered heteroaryl wherein $R^{14a}$ and $R^{14b}$ independently represent hydrogen, $(C_{1-4})$alkyl, hydroxy-$(C_{2-4})$alkyl, $(C_{1-3})$alkoxy-$(C_{2-4})$alkyl; or $R^{14a}$ and $R^{14b}$ together with the nitrogen to which they are attached to form a 4- to 6-membered saturated ring optionally containing one additional ring heteroatom selected from oxygen and nitrogen; and wherein said ring is optionally mono-substituted with $(C_{1-4})$alkyl (especially methyl), hydroxy, $(C_{1-4})$alkoxy (especially methoxy), or dimethylamino can be prepared following a two-step procedure: (i) chlorination by treatment of compounds of formula In wherein $R^1$ represents a 1-hydroxy-$(C_2-C_3)$-alkyl substituted phenyl or 5- or 6-membered heteroaryl with a chlorinating reagent such as $SOCl_2$ in the presence of a suitable solvent such as DCM at temperatures around RT and (ii) consecutive nucleophilic substitution with amines of formula $R^{14a}R^{14b}NH$ wherein $R^{14a}$ and $R^{14b}$ independently represent hydrogen, $(C_{1-4})$alkyl, hydroxy-$(C_{2-4})$alkyl, $(C_{1-3})$alkoxy-$(C_{2-4})$alkyl; or $R^{14a}$ and $R^{14b}$ together with the nitrogen to which they are attached to form a 4- to 6-membered saturated ring optionally containing one additional ring heteroatom selected from oxygen and nitrogen; and wherein said ring is optionally mono-substituted with $(C_{1-4})$alkyl (especially methyl), hydroxy, $(C_{1-4})$alkoxy (especially methoxy), or dimethylamino in the presence of a base such as TEA and a suitable solvent such as DCM at temperatures between 0° C. and RT (Scheme D, step e).

Compounds of structure D-1 can be prepared by chlorination of compounds of structure Ij wherein $R^4$ represents hydroxyl, Y represents $CR^5$ wherein $R^5$ represents hydrogen or $(C_1-C_3)$alkyl and one of X and Z or both represents N and the possible other one represents $CR^5$ wherein $R^5$ represents hydrogen or $(C_1-C_3)$alkyl, using a neat chlorinating reagent such as $POCl_3$ and heating at temperatures around 85° C. (Scheme D, step f).

Compounds of structure Iv wherein $R^5$ represents hydrogen or $(C_1-C_3)$alkyl, one of X and Z or both represents N and the possible other one represents $CR^5$ wherein $R^5$ represents hydrogen or $(C_1-C_3)$alkyl and $R^4$ represents $-NR^{42a}R^{42b}$ wherein $R^{42a}$ and $R^{42b}$ independently represent hydrogen, $(C_{1-4})$alkyl, $(C_{1-3})$alkoxy-$(C_{2-3})$alkyl, hydroxy-$(C_{2-3})$alkyl, or $R^{42a}$ and $R^{42b}$ together with the nitrogen to which they are attached form a 4- to 7-membered saturated ring optionally containing one further ring heteroatom selected from oxygen and nitrogen, wherein said ring is unsubstituted or mono-substituted with $(C_{1-3})$alkyl (especially methyl), or $(C_{1-3})$alkoxy (especially methoxy) can be prepared by aromatic nucleophilic substitution of neat amines of structure $HNR^{42a}R^{42b}$ wherein $R^{42a}$ and $R^{42b}$ are defined above on compounds of structure D-1 at temperatures between 100 and 140° C. Alternatively, Buchwald-Hartwig cross coupling conditions can be used by treatment with a suitable palladium catalyst such as RuPhos precatalyst and a suitable ligand such as RuPhos, in the presence of a suitable base such as $Cs_2CO3$ and heating in a suitable solvent such as t-BuOH at temperatures around 110° C. (Scheme D, step g).

Compounds of structure Iv wherein $R^5$ represents hydrogen or $(C_1-C_3)$alkyl, one of X and Z or both represents N and the possible other one represents $CR^5$ wherein $R^5$ represents hydrogen or $(C_1-C_3)$alkyl and $R^4$ represents $-O-R^{41}$ wherein $R^{41}$ represents $(C_{1-4})$alkyl (especially methyl); $(C_{2-4})$alkyl which is substituted with one or two hydroxy (especially 2-hydroxyethyl, 2,3-dihydroxypropyl); $R^{41a}R^{41b}N-(C_{2-3})$alkylene-, wherein $R^{41a}$ and $R^{41b}$ independently represent hydrogen or $(C_{1-4})$alkyl (especially such group is 2-dimethylamino-ethyl); or $(C_{4-7})$heterocyclyl-$X^{41}-$, wherein $X^{41}$ represents a direct bond or $(C_{1-3})$alkylene, and wherein the $(C_{4-7})$heterocyclyl independently contains one or two ring heteroatoms independently selected from nitrogen and oxygen; wherein said $(C_{4-7})$heterocyclyl independently is unsubstituted, or mono-, or di-substituted, wherein the substituents are independently selected from $(C_{1-4})$alkyl (especially methyl); and/or $(C_{1-4})$alkoxy-carbonyl attached to a ring nitrogen atom having a free valency can be prepared by aromatic nucleophilic substitution of alcohol of structure $HOR^{41}$ wherein $R^{41}$ is defined above on compounds of structure D-1 in the presence of a suitable base such as KOH and heating in a suitable solvent such as DMSO at temperatures around 50 (Scheme D, step g).

Compounds of structure Ix wherein $R^5$ represents hydrogen or $(C_1-C_3)$alkyl, one of X and Z or both represents N and the possible other one represents $CR^5$ wherein $R^5$ represents hydrogen or $(C_1-C_3)$alkyl and $R^4$ represents a diol containing substituent (respectively a substituent containing a nitrogen atom having a free valency) can be prepared by acidic deprotection of compounds of structure Iv wherein $R^4$ represents a substituent which contains a ketal protected diol (respectively a substituent containing a Boc protected nitrogen) in the presence of a suitable acid such as aqueous HCl (respectively TFA) and a suitable solvent such as THF (respectively DCM) at temperatures between 0° C. and RT (Scheme D, step h).

Compounds of structure D-2 can be prepared by Wittig type rxn between compounds of formula Ic wherein $R^1$ represents a formyl substituted phenyl and (methoxymethyl) triphenylphosphonium chloride by treatment with a strong base such as n-butyllithium in the presence of a suitable solvent such as THF at temperatures around -78° C. (Scheme D, step i).

Compounds of structure Iw can be prepared by acidic hydrolysis of enol ether of structure D-2 in the presence of a suitable acid such as aqueous HCl and heating in a suitable solvent such as THF at temperatures around 70° C. (Scheme D, step j).

Compounds of structure Iy wherein $R^1$ represents a $R^{14a}R^{14b}N-X^{14}-$ substituted phenyl, wherein $X^{14}$ represents a ethylene; and wherein $R^{14a}$ and $R^{14b}$ independently represent hydrogen, $(C_{1-4})$alkyl, hydroxy-$(C_{2-4})$alkyl, $(C_{1-3})$alkoxy-$(C_{2-4})$alkyl; or $R^{14a}$ and $R^{14b}$ together with the nitrogen to which they are attached to form a 4- to 6-membered saturated ring optionally containing one additional ring heteroatom selected from oxygen and nitrogen; and wherein said ring is optionally mono-substituted with $(C_{1-4})$alkyl (especially methyl), hydroxy, $(C_{1-4})$alkoxy (especially methoxy), or dimethylamino can be prepared by reductive amination of compounds of structure Iw with amines of structure $R^{14a}R^{14b}NH$ wherein $R^{14a}$ and $R^{14b}$ are defined above using standard conditions such as treatment with $NaBH(OAc)_3$ in the presence of AcOH and a suitable solvent such as DCM or THF at temperatures around RT (Scheme D, step k).

Scheme D

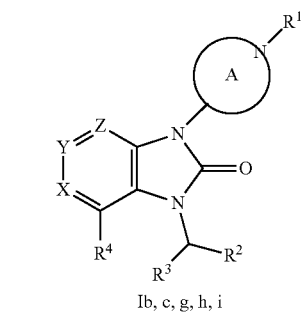

Ib, c, g, h, i

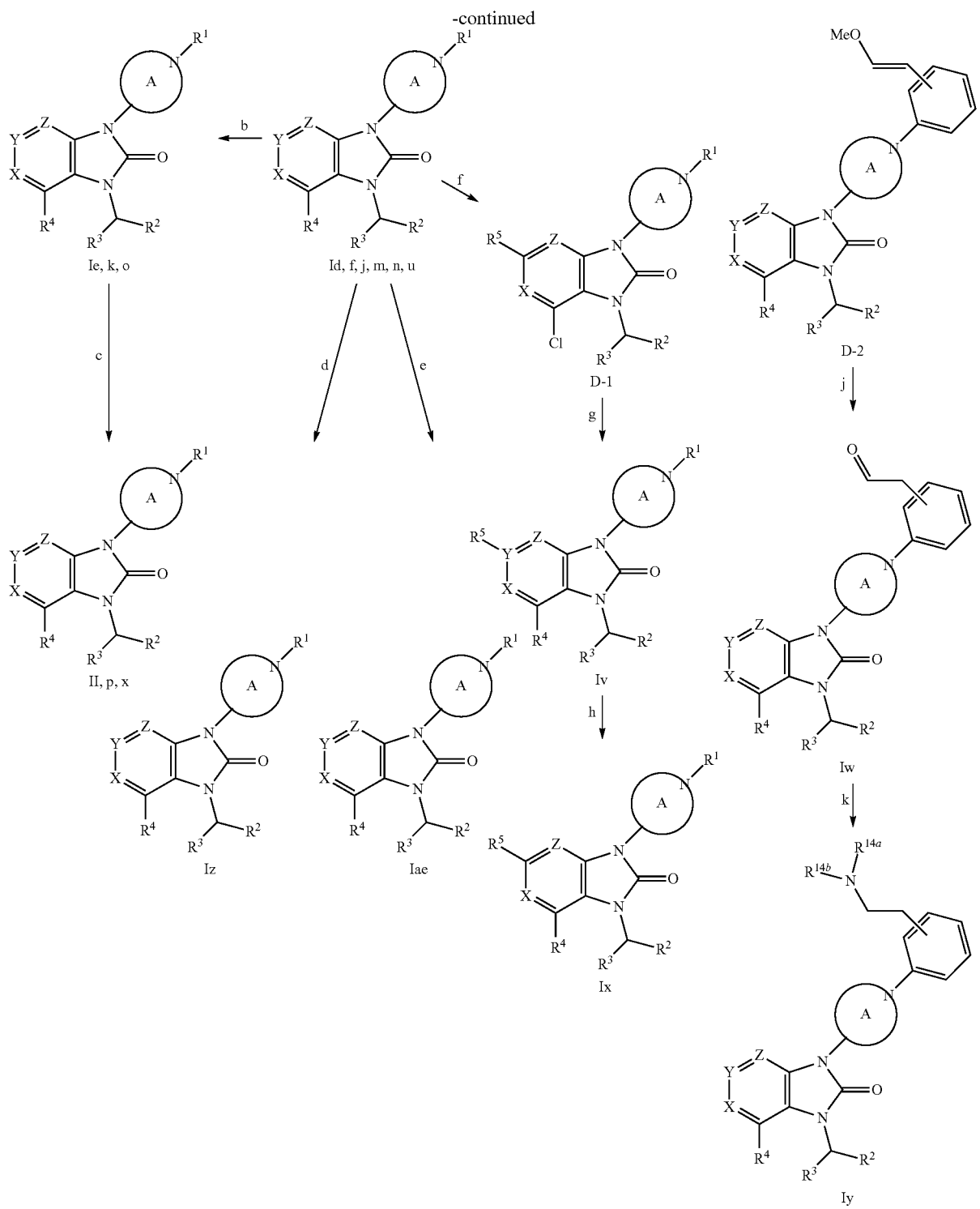

Compounds of structure Ir to It and Iaf can be prepared according to the synthetic route given in scheme E below.

The chlorine or bromine atom on either $R^1$ or $R^2$ which represent a phenyl or 5- or 6-membered heteroaryl or when X, Y or Z represents C—Cl or C—Br in compounds of structure Iq can be replaced by one hydrogen atom (respectively by one deuterium atom) by catalytic hydrogenation (respectively deuteration) using a suitable catalyst such as Pd/C in the presence of a suitable solvent such as EtOAc, MeOH or a mixture of both and under a hydrogen (respectively a deuterium) atmosphere at temperatures around RT. That transformation provides compounds of structure Ir. Catalytic transfer hydrogenation conditions using for instance ammonium formate can be an alternative procedure (Scheme E, step a).

Compounds of structure Iq wherein $R^4$ represents methoxycarbonyl can be transformed to compounds of formula E-1 by hydrolysis with a suitable base such as LiOH, NaOH or KOH in the presence of water and a suitable organic solvent such as THF, MeOH or EtOH or a mixture of them at temperatures between RT and 50° C. (Scheme E, step b).

Compounds of structure Is can be prepared by amide coupling of carboxylic acids of structure E-1 with amines of structure $R^{43a}R^{43b}NH$ wherein $R^{43a}$ and $R^{43b}$ independently represents hydrogen, $(C_{1-4})$alkyl, $(C_{1-3})$alkoxy-$(C_{2-3})$alkyl, or hydroxy-$(C_{2-3})$alkyl using standard amide coupling reagent such as EDC.HCl/HOBt, HATU or PyBOP in the presence of a suitable base such as DIPEA or $Et_3N$ and in a suitable solvent such as DCM or DMF at temperatures around RT (Scheme E, step c).

Compounds of structure It can be prepared by reduction of compounds of structure Iq wherein $R^4$ represents methoxycarbonyl by treatment with a suitable reducing reagent such as $CaBH_4$ (formed in situ from $NaBH_4$ and $CaCl_2$) in the presence of a suitable solvent such as EtOH at temperatures between 0° C. and RT (Scheme E, step d).

Compounds of structure Iq wherein $R^2$ represents an acetoxy substituted phenyl or 5- or 6-membered heteroaryl can be transformed to compounds of formula E-2 wherein $R^2$ represents an hydroxy substituted phenyl or 5- or 6-membered heteroaryl by hydrolysis with a suitable base such as LiOH, NaOH or KOH in the presence of water and a suitable organic solvent such as THF, MeOH or EtOH or a mixture of them at temperatures around RT (Scheme E, step e).

Compounds of structure Iaf wherein $R^2$ represents a $(C_{1-4})$alkoxy or $(C_{3-6})$cycloalkyl-$X^{21}$— substituted phenyl, wherein $X^{21}$ represents a —O—, or —$(C_{1-3})$alkylene-O—, and wherein the $(C_{3-6})$cycloalkyl independently contains one optional ring oxygen can be prepared by O-alkylation of compounds of structure E-2 wherein $R^2$ represents an hydroxy substituted phenyl with halogenide of formula $R^{2a}$—X wherein X represents chlorine or bromine and $R^{2a}$ represents $(C_{1-4})$alkyl, $(C_{3-6})$cycloalkyl or $(C_{3-6})$cycloalkyl-$(C_{1-3})$alkylene-, in the presence of a suitable base such as NaH or $K_2CO_3$ and in solvents such as THF, DMF or a mixture of both at temperatures between 0° C. and 100° C. (Scheme E, step f).

Scheme E

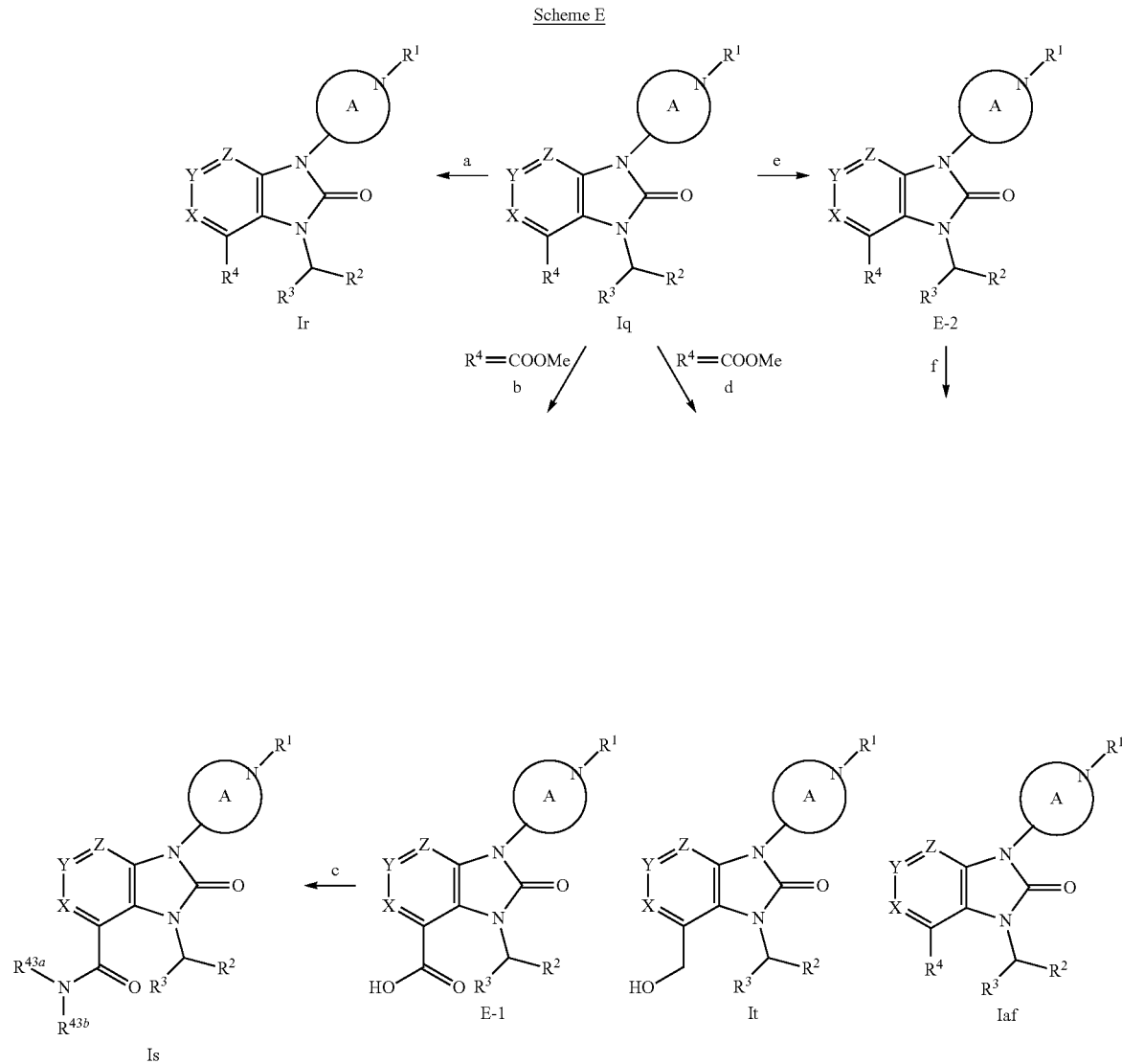

Compounds of structure Iaa, Iab, Iac, Iad, Iah, Iai and Iaj can be prepared according to the synthetic route given in scheme F below.

Compounds of structure Iah wherein $R^1$ represents a hydroxy substituted phenyl or 5- or 6-membered heteroaryl can be prepared by hydrolysis of the acetyl protecting group (respectively by cleavage of the benzyl protecting group) on compounds of formula Ic wherein $R^1$ represents a suitable acetoxy (respectively benzyloxy) substituted phenyl or 5- or 6-membered heteroaryl with a suitable base such as LiOH, NaOH or KOH in the presence of water and a suitable organic solvent such as THF, MeOH or EtOH or a mixture of them (respectively by catalytic hydrogenation using a suitable catalyst such as palladium hydroxide on carbon under a hydrogen atmosphere in the presence of a suitable solvent such as EtOAc) at temperatures around RT (Scheme F, step a).

Alkylation of the free hydroxyl group in compounds of structure Iah wherein $R^1$ represents a hydroxy substituted phenyl or 5- or 6-membered heteroaryl with a suitable halide of structure $R^{15}$—X wherein X represents bromine or chlorine and $R^{15}$ represents (C1-C$_4$)-alkyl, hydroxy-(C$_{2-3}$)alkyl, (C$_{1-4}$)alkoxy-(C$_{2-3}$)alkyl, (C$_{3-6}$)cycloalkyl, or (C$_{3-6}$)cycloalkyl-(C$_{1-3}$)alkyl in the presence of a suitable base such as NaH or K$_2$CO$_3$ and in solvents such as THF, DMF or a mixture of both at temperatures between 0° C. and 80° C. may afford compounds of structure Iai wherein $R^1$ represents a (C$_{1-4}$)alkoxy, hydroxy-(C$_{2-3}$)alkoxy, or (C$_{3-6}$)cycloalkyl-$X^{12}$— substituted phenyl or 5- or 6-membered heteroaryl, wherein $X^{12}$ represents a —O—, or —(C$_{1-3}$)alkylene-O—, and wherein the (C$_{3-6}$)cycloalkyl independently contains one optional ring oxygen (Scheme F, step b). Alternatively, alkylation of the free hydroxyl group in compounds of structure Iah wherein $R^1$ represents a hydroxy substituted phenyl or 5- or 6-membered heteroaryl can be achieved using Mitsunobu conditions by treatment with a suitable alcohol of structure $R^{15}$—OH wherein $R^{15}$ represents (C1-C$_4$)-alkyl, hydroxy-(C$_{2-3}$)alkyl, (C$_{1-4}$)alkoxy-(C$_{2-3}$)alkyl, (C$_{3-6}$)cycloalkyl, or (C$_{3-6}$)cycloalkyl-(C$_{1-3}$)alkyl and for instance a (cyanomethylene)trialkyl phosphorane reagent in the presence of a suitable solvent such as toluene at temperatures around 110° C. (Scheme F, step b). A possible protective group on the substituent $R^{15}$ can be consecutively cleaved by standard deprotection conditions to provide compounds of structure Iaj. Treatment for instance by TBAF in THF at temperatures around RT can lead to deprotection of TBDMS protected alcohol.

Compounds of structure Iaa wherein $R^1$ represents an amino substituted phenyl can be prepared by reduction of compounds of formula Ic wherein $R^1$ represents a nitro substituted phenyl by catalytic hydrogenation for instance using a suitable catalyst such as Pd/C under a hydrogen atmosphere in the presence of a suitable solvent such as EtOAc at temperatures around RT (Scheme F, step c).

Compounds of structure Iab wherein $R^1$ represents a bromine substituted phenyl can be prepared by a Sandmeyer type rxn of compounds of formula Iaa wherein $R^1$ represents an amino substituted phenyl using standard conditions such as treatment with NaNO$_2$ in aq. HBr at temperatures around −20° C. and consecutive treatment with CuBr at temperatures around 60° C. (Scheme F, step d).

Compounds of structure Iac wherein $R^1$ represents a $R^{14a}R^{14b}N$—$X^{14}$— substituted phenyl wherein $X^{14}$ represents 1,3-prop-1-ynylene; and wherein $R^{14a}$ and $R^{14b}$ independently represent (C$_{1-4}$)alkyl, (C$_{1-3}$)alkoxy-(C$_{2-4}$)alkyl; or $R^{14a}$ and $R^{14b}$ together with the nitrogen to which they are attached to form a 4- to 6-membered saturated ring optionally containing one additional ring heteroatom selected from oxygen and nitrogen; and wherein said ring is optionally mono-substituted with (C$_{1-4}$)alkyl (especially methyl), (C$_{1-4}$)alkoxy (especially methoxy), or dimethylamino can be prepared by Sonogashira type cross-coupling of bromides of formula Iab wherein $R^1$ represents a bromine substituted phenyl with $R^{14a}R^{14b}N$—CH$_2$—C—CH wherein $R^{14a}$ and $R^{14b}$ are defined above, in the presence of a suitable palladium catalyst such as bis(tri-tert-butylphosphine)paladium (0), in the presence of a suitable copper catalyst such as copper iodide, in the presence of a suitable base such as DBU and heating in a suitable solvent such as THF at temperatures around 70° C. (Scheme F, step e).

Compounds of structure Iad wherein $R^1$ represents a $R^{14a}R^{14b}N$—$X^4$— substituted phenyl wherein $X^{14}$ represents 1,3-propylene; and wherein $R^{14a}$ and $R^{14b}$ independently represent (C$_{1-4}$)alkyl, (C$_{1-3}$)alkoxy-(C$_{2-4}$)alkyl; or $R^{14a}$ and $R^{14b}$ together with the nitrogen to which they are attached to form a 4- to 6-membered saturated ring optionally containing one additional ring heteroatom selected from oxygen and nitrogen; and wherein said ring is optionally mono-substituted with (C$_{1-4}$)alkyl (especially methyl), (C$_{1-4}$)alkoxy (especially methoxy), or dimethylamino can be prepared by reduction of the acethylenic group in compounds of formula Iac wherein $R^1$ represents a $R^{14a}R^{14b}N$—$X^{14}$-substituted phenyl wherein $X^{14}$ represents 1,3-prop-1-ynylene; and wherein $R^{14a}$ and $R^{14b}$ are defined above using standard conditions such as catalytic hydrogenation with a suitable catalyst such as Pd/C and in the presence of a suitable solvent such as EtOAc and under a hydrogen atmosphere (Scheme F, step f).

Scheme F

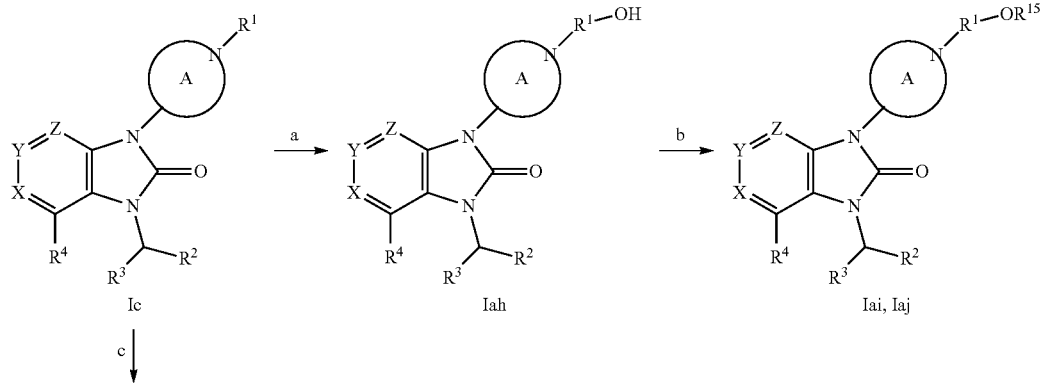

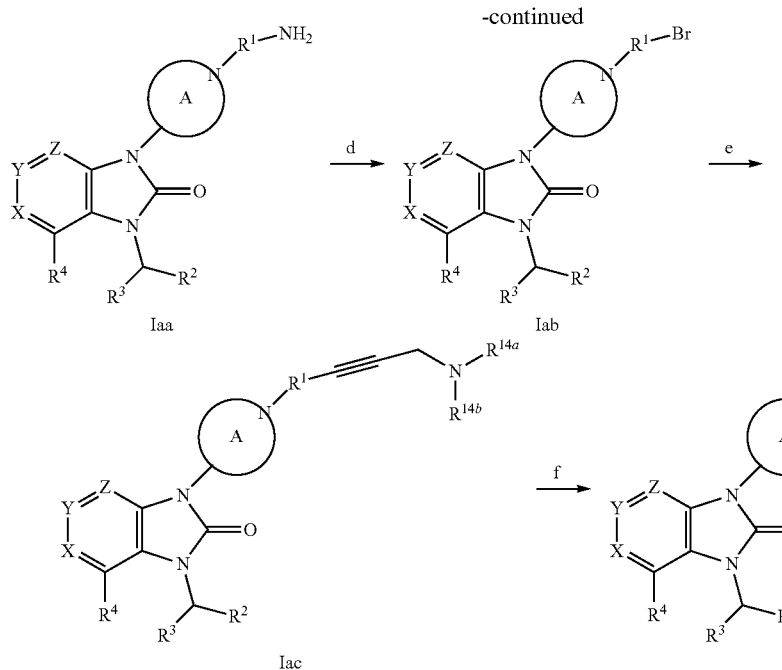

Iaa          Iab

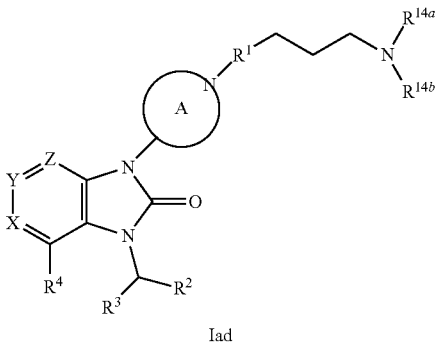

Iac          Iad

If not commercially available, amines of structure BB-4 can be prepared according to the synthetic route given in scheme G below.

Compounds of structure G-2 wherein $R^1$ represents an unsubstituted, mono-, di- or tri-substituted phenyl or 5- or 6-membered heteroaryl can be prepared by Buchwald-Hartwig cross coupling of halides of structure $R^1$—X wherein X represents iodine, bromine or chloride and $R^1$ represents an unsubstituted, mono-, di- or tri-substituted phenyl or 5- or 6-membered heteroaryl with an amine of structure G-1 in the presence of a suitable palladium catalyst such as $Pd_2(dba)_3$ and a ligand such as BINAP, in the presence of a suitable base such as sodium tert-butoxide and heating in a suitable solvent such as toluene at temperatures between 100° C. and 110° C. (Scheme G, step a).

Alternatively, compounds of structure G-2 wherein $R^1$ represents an unsubstituted, mono-, di- or tri-substituted phenyl or 5- or 6-membered heteroaryl can be prepared by aromatic nucleophilic substitution of amines of structure G-1 on activated halides of structure $R^1$—X wherein X represents fluorine or chlorine and $R^1$ represents a suitable mono-, di- or tri-substituted phenyl or 5- or 6-membered heteroaryl in the presence of a suitable base such as $K_2CO_3$ and heating in a suitable solvent such as DMSO at temperatures between 60° C. and 110° C. (Scheme G, step a).

Cleavage of the ketal protecting group in compounds of structure G-2 by acidic hydrolysis in the presence of a suitable acid such as aq. HCl and heating in a suitable solvent such as THF at temperatures around 70° C. may afford ketones of structure G-3 (Scheme G, step b).

Transformation of ketones of structure G-3 to amines of structure BB-4 can be achieved by reductive amination with for instance aq. ammonia under catalytic hydrogenation conditions using a suitable catalyst such as Pd/C in the presence of a suitable solvent such as dioxane under a hydrogen atmosphere at temperatures around RT (Scheme G, step c).

Compounds of structure G-5 wherein $R^1$ represents an unsubstituted, mono-, di- or tri-substituted phenyl or 5- or 6-membered heteroaryl can be prepared by aromatic nucleophilic substitution of amines of structure G-4 on activated halides of structure $R^1$—X wherein X represents fluorine or chlorine and $R^1$ represents a suitable mono-, di- or tri-substituted phenyl or 5- or 6-membered heteroaryl in the presence of a suitable base such as $K_2CO_3$ and heating in a suitable solvent such as DMSO at temperatures between 60° C. and 110° C. (Scheme G, step d).

Compounds of structure G-5 wherein $R^1$ represents a mono-, di- or tri-substituted phenyl which is substituted by one methyl group can be prepared following a four-step procedure: (i) aromatic nucleophilic substitution of amines of structure G-4 on halides of structure $R^1$—X wherein X represents fluorine or chlorine and $R^1$ represents a suitable mono-, di- or tri-substituted phenyl which is substituted by one formyl group in the presence of a suitable base such as $K_2CO_3$ and heating in a suitable solvent such as DMSO at temperatures between 60° C. and 110° C. and (ii) consecutive reduction of the benzaldehyde derivative by treatment with a suitable reducing reagent such as $NaBH_4$ in the presence of a suitable solvent such as MeOH at temperatures between 0° C. and RT and (iii) consecutive acetylation of the resulting benzyl alcohol by treatment with acetyl chloride in the presence of a suitable base such as TEA and in a suitable solvent such as DCM at temperatures between 0° C. and RT and (iv) final catalytic hydrogenation of the resulting benzyl ester with a suitable catalyst such as Pd/C in the presence of a suitable solvent such as EtOAc, MeOH or mixture thereof and under a hydrogen atmosphere at temperatures around RT (Scheme G, step d).

Cleavage of the Boc protecting group in compounds of structure G-5 can be performed using a suitable acid such as HCl or TFA in the presence of a suitable solvent such as dioxane, MeOH or DCM at temperatures around RT to afford amines of structure BB-4 (Scheme G, step e).

Scheme G

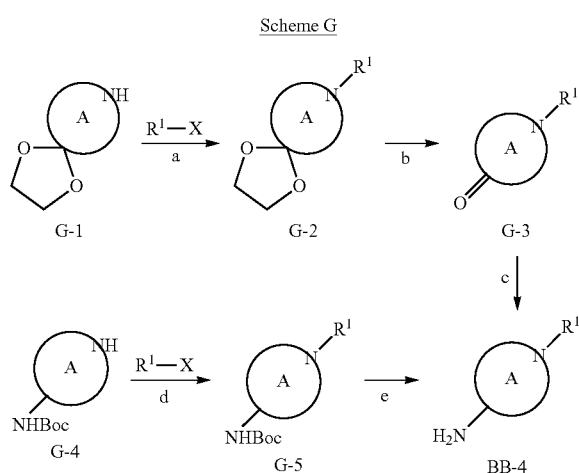

EXPERIMENTAL PART

Chemistry

All temperatures are stated in ° C. Commercially available starting materials were used as received without further purification. If not explicitly indicated as having a specific absolute configuration, example compounds or intermediates that are chiral are in general prepared as a racemic mixture of two enantiomers, even if the corresponding example compound's name or precursor's name is not preceded with the mention rac. Relative configuration is indicated for example as (R*,R*) meaning that the two respective absolute configurations are either (R,R) or (S,S); likewise, (R*,S*) indicates a relative configuration of either (R,S) or (S,R).

Characterization of Compounds

Compounds described in the invention are characterized by LC-MS data (retention time $t_R$ is given in min) and/or NMR using the conditions described below.

Analytical LC-MS:

Dionex Ultimate 3000 system with Dionex HPG-3200RS binary pump, Thermo MSQ Plus MS detector and Dionex DAD-3000RS PDA detector.

Eluents (acidic conditions): A: $H_2O$+0.04% TFA; B: MeCN; gradient: 5% B→95% B; runtime: 1.5 min; flow: 4.5 mL/min; detection: UV/Vis+MS Column Agilent Zorbax SB-aq, 4.6×50 mm, 3.5 μm NMR Spectroscopy:

Bruker Avance HD spectrometer equipped with a 500 MHz Ultrashield™ Magnet and a 5 mm DCH cryoprobe or Bruker Avance II spectrometer equipped with a 400 MHz Ultrashield™ Magnet and a BBO 5 mm probehead. Chemical shifts (δ) are reported in parts per million (ppm) relative to proton resonances resulting from incomplete deuteration of the NMR solvent, e.g. for dimethylsulfoxide δ(H) 2.49 ppm, for chloroform δ(H) 7.24 ppm. The abbreviations s, d, t, q and m refer to singlet, doublet, triplet, quartet, multiplet, respectively and br to broad. Coupling constants J are reported in Hz.

Purification of Compounds

The compounds were purified by either column chromatography on silica-gel and/or prep. LC-MS using the conditions described below.

Column Chromatography

Column chromatography (CC) was performed using prepacked cartridges (SNAP Ultra™, SNAP KP-SIL™, SNAP KP-NH™, Isolute™ Silica II or Isolute™ $NH_2$) from Biotage.

Preparative LC-MS:

Gilson 333/334 Prep-Scale HPLC pump equipped with Gilson LH215 autosampler, Dionex SRD-3200 degasser, Dionex ISO-3100A make-up pump, Dionex DAD-3000 DAD detector and Thermo MSQ Plus Single Quadrupole MS detector. Flow: 75 mL/min. Detection: UV/Vis and/or MS.

Additional informations for the purification are summerized in the table below using following explanations:

XBridge: column Waters XBridge C18, 10 μm, 30×75 mm

Acidic: eluant: A=$H_2O$ with 0.5% HCOOH, B=MeCN

Basic: eluant: A=$H_2O$ with 0.125% $NH_4OH$, B=MeCN

Very lipophilic gradient: 50% B→95% B over 4 min then 95% B over 2 min

Lipophilic gradient: 30% B→95% B over 4 min then 95% B over 2 min

Normal gradient: 20% B→95% B over 4 min then 95% B over 2 min

Polar gradient: 10% B→95% B over 4 min then 95% B over 2 min

Very polar gradient: 5% B→50% B over 3 min then 50% B→95% B over 1 min and finally 95% B over 2 min

| | XBridge | |
|---|---|---|
| | acidic | basic |
| Very lipophilic gradient | Method 1 | Method 5 |
| Lipophilic gradient | Method 2 | Method 6 |
| Normal gradient | Method 3 | |
| Polar gradient | Method 4 | |

Abbreviations (As Used Hereinbefore or Hereinafter)

Ac acetyl
AcOH acetic acid
AIBN azobisisobutyronitrile
anh. anhydrous
aq. aqueous
BINAP racemic 2,2'-bis(diphenylphosphino)-1,1'-binaphthyl
Boc tert.-butyloxycarbonyl
BrettPhos 2-(dicyclohexylphosphino)-3,6-dimethoxy-2',4',6'-triisopropyl-1,1'-biphenyl
BrettPhos precatalyst chloro[2-(dicyclohexylphosphino)-3,6-dimethoxy-2'-4'-6'-triisopropyl-1,1'-biphenyl][2-(2-aminoethyl)phenyl]palladium(II)
CC column chromatography
CDI carbonyl diimidazole
CPhos 2-dicyclohexylphosphino-2',6'-bis(N,N-dimethylamino)biphenyl
DBU 1,8-diazabicyclo[5.4.0]undec-7-ene
DCM dichloromethane
dioxane 1,4-dioxane
DIPEA diisopropyl-ethylamine, Hunig's base, ethyl-diisopropylamine
DMA dimethylacetamide
DMF dimethylformamide
DMP Dess Martin periodinane
DMSO dimethylsulfoxide eq equivalent(s)
EtOAc ethyl acetate
EtOH ethanol
Et$_2$O diethylether
g gram(s)
h hour(s)
HATU 2-(7-aza-1H-benzotriazole-1-yl)-1,1,3,3-tetramethyluronium hexafluorophosphate
Hept heptane
HPLC high performance liquid chromatography
LC-MS liquid chromatography-mass spectrometry
MeCN acetonitrile
MeI methyl iodide
MeOH methanol
mg milligram(s)
mL milliliter(s)
min minute(s)
mmol millimole(s)
MS mass spectroscopy
NaBH(OAc)$_3$ sodium triacetoxyborohydride
NaOMe sodium methoxide
NBS N-bromosuccinimide
n-BuOH n-butanol
NCS N-chlorosuccinimide
NMR nuclear magnetic resonance spectroscopy
OAc acetate
org. organic
ON overnight
PBS phosphate buffer saline
PEPPSI-IPr [1,3-bis(2,6-Diisopropylphenyl)imidazol-2-ylidene](3-chloropyridyl)palladium(II) dichloride
Pd$_2$(dba)$_3$ tris(dibenzylideneacetone)dipalladium(0)
prep. preparative
rac racemic
RT room temperature
RuPhos 2-dicyclohexylphosphino-2',6'-diisopropoxybiphenyl
RuPhos precatalyst chloro(2-dicyclohexylphosphino-2',6'-diisopropoxy-1,1'-biphenyl)[2-(2'-amino-1,1'-biphenyl)]palladium(II)
rxn reaction
sat. saturated
SEM [2-(trimethylsilyl)ethoxy]methyl
soln. solution
TBAF tetrabutylammonium fluoride
TBDMS tert-butyldimethylsilyl
t-BuOH tert-butanol
TEA triethylamine
TFA trifluoroacetic acid
THF tetrahydrofuran
t$_R$ retention time

Synthesis of Building Blocks BB-2

Synthesis of 4-chloro-2-methoxy-3-nitropyridine (BB-2-1)

To a suspension of 4-chloro-3-nitro-2-pyridone (1.0 g, 5.7 mmol) and silver carbonate (1.9 g, 6.9 mmol) in hexane (17 mL) was added MeI (0.72 mL, 11.5 mmol). The rxn mixture was heated to 80° C. for 1h and concentrated in vacuo. The crude was purified by CC using Hept/EtOAc to give the title compound as white solid.

LC-MS: t$_R$=0.82 min $^1$H NMR (400 MHz, DMSO-d6) δ:8.41 (d, J=5.6 Hz, 1H), 7.50 (d, J=5.6 Hz, 1H), 4.02 (s, 3H)

Synthesis of 4-chloro-1-methyl-3-nitro-1H-pyridin-2-one (BB-2-2)

To a suspension of 4-chloro-3-nitro-2-pyridone (1.0 g, 5.7 mmol) and K$_2$CO$_3$ (1.6 g, 11.5 mmol) in DMA (5 mL) was added MeI (0.72 mL, 11.5 mmol). The rxn mixture was heated to 45° C. and stirred for 1h. It was quenched with H$_2$O, acidified to pH 5 with a 25% aq. soln. of HCl and extracted with EtOAc (3×). The combined org. phases were washed with brine, dried over MgSO$_4$ and concentrated in vacuo.

LC-MS: t$_R$=0.60 min; [M+H]$^+$: 189.15

$^1$H NMR (400 MHz, DMSO-d6) δ:8.10 (d, J=7.4 Hz, 1H), 6.70 (d, J=7.4 Hz, 1H), 3.55 (s, 3H)

Synthesis of 4-chloro-6-methoxy-5-nitro-pyrimidine (BB-2-3)

A suspension of 4,6-dichloro-5-nitropyrimidine (2.0 g, 10.2 mmol) in anh. MeOH (37 mL) was cooled to 0° C. and NaOMe (579 mg, 10.2 mmol) was portionwise added over 10 min. The rxn mixture was stirred for 30 min and filtered. The filtrate was concentrated in vacuo and the crude was purified by CC using Hept/EtOAc.

LC-MS: t$_R$=0.75 min $^1$H NMR (400 MHz, DMSO-d6) δ:8.93 (s, 1H), 4.14 (s, 3H)

Synthesis of Building Blocks BB-3

Synthesis of 3-bromomethyl-2-trifluoromethyl-pyridine (BB-3-1) and 2-bromomethyl-3-trifluoromethyl-pyrazine (BB-3-5)

A suspension of methyl-heteroarene (1 eq) in chlorobenzene (4 mL/mmol) was heated to 50° C. and NBS (1.3 eq) was dropwise added at 50° C. The flask was purged with argon and AIBN (0.1 eq) was added in one portion. The rxn mixture was heated to 80° C. and stirred for 5h (see Table 1). After cooling to RT, the mixture was diluted with Et$_2$O and washed with a 1M aq. soln. of HCl (3×). The combined org. phases were washed with brine, dried over MgSO$_4$ and concentrated in vacuo. The crude was purified by CC using Hept/EtOAc.

TABLE 1

| BB-3 | Name | Methyl-heteroarene | t$_R$ [min] | $^1$H NMR (400 MHz, DMSO-d6) δ: |
|---|---|---|---|---|
| BB-3-1 | 3-Bromomethyl-2-trifluoromethyl-pyridine | 3-Methyl-2-(trifluoromethyl) pyridine | 0.80 | 8.72 (d, J = 4.6 Hz, 1 H), 8.23 (d, J = 7.8 Hz, 1 H), 7.79 (dd, |

TABLE 1-continued

| BB-3 | Name | Methyl-heteroarene | $t_R$ [min] | $^1$H NMR (400 MHz, DMSO-d6) δ: |
|---|---|---|---|---|
| BB-3-5 | 2-Bromomethyl-3-trifluoromethyl-pyrazine | 2-Methyl-3-(trifluoromethyl) pyrazine | 0.76 | $J_1$ = 4.6 Hz, $J_2$ = 7.9 Hz, 1 H), 4.84 (d, J = 0.7 Hz, 2 H) 9.03 (d, J = 2.2 Hz, 1 H), 8.84 (d, J = 2.3 Hz, 1 H), 4.84 (d, J = 0.9 Hz, 2 H) |

Synthesis of 3-chloromethyl-4-trifluoromethyl-pyridine (BB-3-2)

To a soln. of 4-trifluoromethyl-pyridin-3-yl-methanol (419 mg, 2.3 mmol) in DCM (7 mL) was added $SOCl_2$ (0.84 mL, 11.6 mmol). The rxn mixture was stirred for 1h at RT, quenched with a 10% aq. soln. of $Na_2CO_3$ and extracted with DCM (3×). The combined org. phases were washed with brine, dried over $MgSO_4$ and concentrated in vacuo. The crude was purified by CC using Hept/EtOAc.

LC-MS: $t_R$=0.79 min, [M+MeCN+H]$^+$: 237.05
$^1$H NMR (400 MHz, DMSO-d6) δ: 9.00 (s, 1H), 8.86 (dd, $J_1$=0.5 Hz, $J_2$=5.1 Hz, 1H), 7.81 (d, J=5.1 Hz, 1H), 4.95 (s, 2H)

Synthesis of 4-bromomethyl-3-trifluoromethyl-pyridine (BB-3-3) and 2-bromomethyl-3-trifluoromethyl-pyridine (BB-3-4)

The appropriate methylpyridine (1 eq) was dissolved in a 1M soln. of bromine in acetic acid (1 mL/mmol) and the solution was stirred ON at RT and for 6h at 80° C. (see Table 2). The mixture was basified with a 1M aq. soln. of NaOH and extracted with EtOAc (3×). The combined org. phases were washed with brine, dried over $MgSO_4$ and concentrated in vacuo. The crude dibromo product was dissolved in THF (4 mL/mmol) and DIPEA (1.05 eq) and diethyl phosphite (1.05 eq) were sequentially added at 0° C. The mixture was stirred for 10 min at 0° C. and ON at RT. It was quenched with water and extracted with EtOAc (3×). The combined org. phases were washed with a sat. aq. soln. of $NH_4Cl$ and brine, dried over $MgSO_4$ and concentrated in vacuo. The crude was purified by CC using Hept/EtOAc.

TABLE 2

| BB-3 | Name | Methyl-pyridine | $t_R$ [min] | $^1$H NMR (400 MHz, DMSO-d6) δ: |
|---|---|---|---|---|
| BB-3-3 | 4-Bromomethyl-3-trifluoromethyl-pyridine | 4-Methyl-3-(trifluoromethyl)pyridine | 0.80 | 8.96 (s, 1 H), 8.91 (d, J = 5.1 Hz, 1 H), 7.78 (d, J = 5.1 Hz, 1 H), 4.77 (s, 2 H) |
| BB-3-4 | 2-Bromomethyl-3-trifluoromethyl-pyridine | 2-Methyl-3-(trifluoromethyl)pyridine | 0.79 | 8.88 (d, J = 4.7 Hz, 1 H), 8.24 (d, J = 8.0 Hz, 1 H), 7.63 (m, 1 H), 4.76 (s, 2 H) |

Synthesis of (4-methoxy-pyrimidin-5-yl)-methanol (BB-3-6) and (4-trifluoromethyl-pyrimidin-5-yl)-methanol (BB-3-8)

To a suspension of carboxylic acid (1 eq) in anh. THF (5 mL/mmol) was added at −10° C. 4-methylmorpholine (1.8 eq) and ethyl chloroformate (1.5 eq). The mixture was stirred for 30 min at −10° C. and NaBH$_4$ (3 eq) was added in one portion. It was warmed to 0° C. and MeOH (3 mL/mmol) was added dropwise (see Table 3). The rxn mixture was stirred for 1h at 0° C. and for 1h at RT. It was quenched with water, acidified with a 1M aq. soln. of HCl until pH 4 and extracted with n-BuOH (3×). The combined org. phases were dried and concentrated in vacuo. The crude was purified by CC using Hept/EtOAc/MeOH.

TABLE 3

| BB-3 | Name | Carboxylic acid | $t_R$ [min] | MS-data m/z [M + H]$^+$ |
|---|---|---|---|---|
| BB-3-6 | (4-Methoxy-pyrimidin-5-yl)-methanol | 4-Methoxypyrimidine-5-carboxylic acid | 0.29 | 141.19 |
| BB-3-8 | (4-Trifluoromethyl-pyrimidin-5-yl)-methanol | 4-(Trifluoromethyl)pyrimidine-5-carboxylic acid | 0.47 | 220.08 [M + MeCN + H+] |

Synthesis of 5-(chloromethyl)-4-methoxypyrimidine (BB-3-7) and 5-(chloromethyl)-4-(trifluoromethyl) Pyrimidine (BB-3-9)

To a soln. of alcohol (1 eq) in DCM (5 mL/mmol) was added SOCl$_2$ (1.5 to 2.5 eq) at 0° C. The rxn mixture was stirred for 2h at RT (see Table 4) and partitioned between EtOAc and a sat. aq. soln. of NaHCO$_3$. The org. phase was washed with a sat. aq. soln. of NaHCO$_3$ (1×) and brine (1×), dried over MgSO$_4$ and concentrated in vacuo.

TABLE 4

| BB-3 | Name | Alcohol | $t_R$ [min] | MS-data m/z [M + H]$^+$ | $^1$H NMR (400 MHz, DMSO-d6) δ: |
|---|---|---|---|---|---|
| BB-3-7 | 5-(Chloromethyl)-4-methoxypyrimidine | (4-Methoxy-pyrimidin-5-yl)-methanol | 0.61 | 159.25 | |
| BB-3-9 | 5-(Chloromethyl)-4-(trifluoromethyl)pyrimidine | (4-Trifluoromethyl-pyrimidin-5-yl)-methanol | 0.72 | | 9.46 (s, 1 H), 9.33 (s, 1 H), 4.99 (d, J = 0.9 Hz, 2 H) |

Synthesis of 6-chloro-3-chloromethyl-4-methoxy-pyridazine (BB-3-10)

Step A:
6-Chloro-4-methoxy-pyridazine-3-carboxylic acid methyl ester

To a soln. of methyl 4,6-dichloropyridazine-3-carboxylate (550 mg, 2.66 mmol) in anh. THF (13 mL) was added dropwise at 0° C. a 25% soln. of NaOMe in MeOH (0.638 mL, 2.79 mmol). The rxn mixture was stirred ON at RT and poured onto a 1M aq. soln. of HCl. The soln. was neutralized with a sat. aq. soln. of NaHCO$_3$ and extracted with EtOAc (3×). The combined org. phases were washed with brine, dried over MgSO$_4$ and concentrated in vacuo. The crude was purified by CC using Hept/EtOAc.

LC-MS: $t_R$=0.54 min. [M+H]$^+$: 203.14

Step B:
(6-Chloro-4-methoxy-pyridazin-3-yl)-methanol

To a soln. of 6-chloro-4-methoxy-pyridazine-3-carboxylic acid methyl ester (120 mg, 0.592 mmol) in anh. EtOH (4.7 mL) was added CaCl$_2$ (20 mg, 0.178 mmol) and the rxn mixture was cooled to −10° C. NaBH$_4$ (56 mg, 1.48 mmol) was added portionwise and the mixture was stirred for 1.5 h at −10° C. and for 30 min at RT. It was quenched at 0° C. with water and EtOH was evaporated off. The residue was partitioned between EtOAc and water and the aq. phase was further extracted with EtOAc (2×). The combined org. phases were washed with brine (1×), dried over MgSO$_4$ and concentrated in vacuo.

LC-MS: $t_R$=0.40 min, [M+H]$^+$: 175.20

Step C: 6-Chloro-3-chloromethyl-4-methoxy-pyridazine (BB-3-10)

To a soln. of (6-Chloro-4-methoxy-pyridazin-3-yl)-methanol (73 mg, 0.393 mmol) in DCM (1.97 mL) was added $SOCl_2$ (0.043 mL, 0.59 mmol) at 0° C. The rxn mixture was stirred for 2h at RT and partitioned between EtOAc and a sat. aq. soln. of $NaHCO_3$. The org. phase was washed with a sat. aq. soln. of $NaHCO_3$ (1×) and brine (1×), dried over $MgSO_4$ and concentrated in vacuo.

LC-MS: $t_R$=0.63 min, $[M+H]^+$: 193.13

Synthesis of (6-chloro-4-isopropoxy-pyridazin-3-yl)-methanol (BB-3-11)

Step A: 6-Chloro-4-isopropoxy-pyridazine-3-carboxylic acid isopropyl ester

To a soln. of 4,6-dichloropyridazine-3-carboxylic acid methyl ester (500 mg, 2.42 mmol) in anh. THF (12 mL) was added dropwise at 0° C. a 2M soln. of lithium isopropoxide in THF (1.27 mL, 2.54 mmol). The rxn mixture was stirred for 30 min at 0° C. and poured into a 1M aq. soln. of HCl. The aq. soln. was neutralized with a sat. aq. soln. of $NaHCO_3$ and extracted with EtOAc (3×). The combined org. phases were washed with brine, dried over $MgSO_4$ and concentrated in vacuo. The crude was purified by CC using Hept/EtOAc.

LC-MS: $t_R$=0.82 min, $[M+H]^+$: 259.12

Step B: (6-Chloro-4-isopropoxy-pyridazin-3-yl)-methanol (BB-3-11)

To a soln. of 6-chloro-4-isopropoxy-pyridazine-3-carboxylic acid isopropyl ester (80 mg, 0.309 mmol) in anh. EtOH (4.6 mL) was added $CaCl_2$) (10 mg, 0.093 mmol) and the rxn mixture was cooled to −10° C. $NaBH_4$ (29 mg, 0.773 mmol) was added portionwise and the mixture was stirred for 30 min at −10° C. and for 1h min at RT. It was quenched at 0° C. with water and EtOH was evaporated off. The residue was partitioned between EtOAc and water and the aq. phase was further extracted with EtOAc (2×). The combined org. phases were washed with brine (1×), dried over $MgSO_4$ and concentrated in vacuo.

LC-MS: $t_R$=0.55 min, $[M+H]^+$: 203.14

Synthesis of (BB-3-12), (BB-3-13), (BB-3-14), (BB-3-15), (BB-3-16), (BB-3-17)

Step A: Esterification

To a soln. of carboxylic acid (1 eq) in anh. MeOH (4 mL/mmol) was added AcCl (3 eq) and the rxn mixture was stirred for 2.5 h at 80° C. (see Table 5). MeOH was evaporated off and the residue was partitioned between a sat. aq. soln. of $NaHCO_3$ and EtOAc. The org. phase was washed with a 10% aq. soln. of $Na_2CO_3$ (1×) and with brine (1×), dried over $MgSO_4$ and concentrated in vacuo.

TABLE 5

| BB-3A | Name | Carboxylic acid reactant | $t_R$ [min] | MS-data m/z $[M + H]^+$ |
|---|---|---|---|---|
| BB-3-12A | 4-Methylpyridazine-3-carboxylic acid methyl ester | 4-methylpyridazine-3-carboxylic acid | 0.47 | 153.43 |
| BB-3-13A | 3-Isopropoxy-pyrazine-2-carboxylic acid methyl ester | 3-Isopropoxy-pyrazine-2-carboxylic acid | 0.70 | 197.17 |
| BB-3-15A | 3-Isopropoxy-pyridine-2-carboxylic acid methyl ester | 3-Isopropoxy-pyridine-2-carboxylic acid | 0.64 | 196.21 |

Step a (Negishi): Synthesis of 3-Isopropyl-Pyrazine-2-Carboxylic Acid Ethyl Ester (BB-3-17A)

An oven dried flask was charged with 3-chloropyrazine-2-carboxylic acid ethyl ester (500 mg, 2.63 mmol), PEPPSI-IPr (18 mg, 0.026 mmol) and CPhos (12 mg, 0.026 mmol). The flask was evacuated and refilled with argon (3×) and toluene (5 mL) was added. The rxn mixture was cooled to 0° C. and a 0.5M soln. of 2-propyl zinc bromide in THF (6.83 mL, 3.41 mmol) was added dropwise. The rxn mixture was stirred for 72h at RT and partitioned between half sat. brine and DCM. The org. phase was dried over $MgSO_4$ and concentrated in vacuo. The crude was purified by CC using Hept/EtOAc.

LC-MS: $t_R$=0.74 min, $[M+H]^+$: 195.18

Step A (O-alkylation): synthesis of 2,4-difluoro-6-isopropoxybenzoic acid methyl ester (BB-3-19A)

To a soln. of methyl 2,4-difluoro-6-hydroxybenzoic acid methyl ester (200 mg, 1.01 mmol) and 2-propanol (0.116 mL, 1.51 mmol) in toluene (1.5 mL) was added a 1M soln. of (tributylphosphoranylidene)acetonitrile in toluene (2.02 mL, 2.02 mmol) under argon. The rxn mixture was heated to 110° C. and stirred for 2h. It was quenched with water and extracted with DCM (3×). The combined org. phases were washed with brine, dried over $MgSO_4$ and concentrated in vacuo. The crude was purified by CC using Hept/EtOAc.

LC-MS: $t_R$=0.89 min, $[M+H]^+$: 231.10

Step B: Methyl/ethyl ester reduction using $CaCl_2/NaBH_4$ (method A)

To a soln. of methyl ester (BB-3A) (1 eq) in anh. EtOH (15 mL/mmol) was added $CaCl_2$ (0.3 eq) and the rxn mixture was cooled to −10° C. NaBH₄ (2.5 eq) was added portionwise and the mixture was stirred for 30 min at −10° C. and for a given time at a given temperature (see Table 6). It was quenched at 0° C. with water and EtOH was evaporated off. The residue was partitioned between EtOAc and water and the aq. phase was further extracted with EtOAc (2×). The combined org. phases were washed with brine (1×), dried over MgSO₄ and concentrated in vacuo.

Step B: Methyl/Ethyl Ester Reduction Using LiAlH₄ (Method B)

To a of methyl or ethyl ester (1eq) in anh. THF (4.5 to 7 mL/mmol) was added dropwise at 0° C. a 2.4 M soln. of LiAlH₄ in THF (1 eq). The n mixture was stirred for 1.5 h at 0° C.(see Table 6), quenched with a sat. aq. soln. of NH₄Cl and extracted with EtOAc (3×). The combined org. phases were dried over MgSO₄ and concentrated in vacuo. When necessary the crude was purified by CC using EtOAc.

TABLE 6

| BB-3 | Name | Methyl/ethyl ester reactant | Method T [° C.] time [h] | $t_R$ [min] | MS-data m/z [M + H]⁺ | ¹H NMR (400 MHz, DMSO-d6) δ: |
|---|---|---|---|---|---|---|
| BB-3-12 | (4-Methyl-pyridazin-3-yl)-methanol | BB-3-12A | A RT 0.5 | 0.18 | 125.44 | |
| BB-3-13 | (3-Isopropoxy-pyrazin-2-yl)-methanol | BB-3-13A | A RT 0.5 | 0.58 | 169.11 | |
| BB-3-14 | (4-Isopropylpyridin-3-yl)methanol | 4-Isopropyl pyridine-3-carboxylic acid ethyl ester | A RT 48 | 0.34 | 152.45 | |
| BB-3-15 | (3-Isopropoxy-pyridin-2-yl)-methanol | BB-3-15A | A RT 24 | 0.40 | 168.47 | |
| BB-3-16 | (4-Isopropyl-pyrimidin-5-yl)-methanol | 4-Isopropyl pyrimidine-5-carboxylic acid ethyl ester | A 70 1 | 0.46 | 153.47 | |
| BB-3-17 | (3-Isopropyl-pyrazin-2-yl)-methanol | BB-3-17A | A 0 2.5 | 0.48 | 153.45 | |
| BB-3-18 | Mixture of (5-(trifluoromethyl)thiazol-4-yl)methanol and (2-(trifluoromethyl)thiazol-4-yl)methanol | Mixture of 5-(trifluoromethyl) thiazole-4-carboxylic acid ethyl ester and 2-(trifluoromethyl) thiazole-4-carboxylic acid ethyl ester | B 0 1.5 | 0.52 | 184.05 | |
| BB-3-19 | (2,4-Difluoro-6-isopropoxy-phenyl)-methanol | BB-3-19A | B 0 1.5 | 0.78 | no ionisation | 6.41-6.47 (m, 2 H), 4.70 (d, J = 1.5 Hz, 2 H), 4.58 (m, 1 H), 1.40-1.45 (m, 6 H) |

Synthesis of Building Blocks BB-4 (Via G-5)

Step A: Aromatic Nucleophilic Substitution

To a solution of the appropriate amine (1eq) and the appropriate fluoroarene (1.1 eq) in DMSO (0.9 mL/mmol) was added $K_2CO_3$ (2 eq) and the mixture was heated to 105° C. and stirred for 18h (see Table 7). It was quenched with water and extracted with DCM. The org. phase was washed with water (5×) and brine (1×), dried over $MgSO_4$ and concentrated in vacuo. The crude was purified by CC using DCM/MeOH.

TABLE 7

| BB-4A | Name | Reactant amine | Reactant fluoroarene | $t_R$ [min] | MS-data m/z $[M + H]^+$ |
|---|---|---|---|---|---|
| BB-4-1A | [(R)-1-(2-Fluoro-6-formyl-phenyl)-pyrrolidin-3-yl]-carbamic acid tert-butyl ester | (R)-(+)-3-(Boc-amino)pyrrolidine | 2,3-Difluoro benzaldehyde | 0.90 | 309.10 |
| BB-4-2A | [1-(2-Fluoro-6-formyl-phenyl)-piperidin-4-yl]-carbamic acid tert-butyl ester | 4-(N-Boc-amino) piperidine | 2,3-Difluoro benzaldehyde | 0.93 | 323.20 |
| BB-4-3A | [(R)-1-(2-Cyano-6-fluoro-phenyl)-pyrrolidin-3-yl]-carbamic acid tert-butyl ester | (R)-(+)-3-(Boc-amino)pyrrolidine | 2,3-Difluoro benzonitrile | 0.91 | 306.03 |

Step B: Reduction

A suspension of intermediate BB-4A (1 eq) in anh. MeOH (2 mL/mmol) was cooled to 0° C. and $NaBH_4$ (1.3- to 1.5 eq) was added portionwise at 0° C. (see Table 8). Then mixture was stirred for 1h at 0° C. to reach completion. It was carefully quenched by dropwise addition of water at 0° C. and extracted with EtOAc. The org. phase was washed with water and brine, dried over $MgSO_4$ and concentrated in vacuo.

TABLE 8

| BB-4B | Name | Reactant BB-4A | $t_R$ [min] | MS-data m/z $[M + H]^+$ |
|---|---|---|---|---|
| BB-4-1B | [(R)-1-(2-Fluoro-6-hydroxymethyl-phenyl)-pyrrolidin-3-yl]-carbamic acid tert-butyl ester | BB-4-1A | 0.77 | 311.11 |
| BB-4-2B | [1-(2-Fluoro-6-hydroxymethyl-phenyl)-piperidin-4-yl]-carbamic acid tert-butyl ester | BB-4-2A | 0.82 | 325.24 |

Step C: Acetylation

A solution of intermediate BB-4B (1 eq) and TEA (1.5 eq) in DCM (0.5 mL/mmol) was cooled to 0° C. and AcCl (1.5 eq) was added dropwise at 0° C. (see Table 9). The rxn mixture was stirred for 1 h at 0° C. to reach completion. It was diluted with DCM and washed with a 10% solution of citric acid (2×), with a sat. solution of $NaHCO_3$ (2×) and with brine (1×). The org. phase was dried over $MgSO_4$ and concentrated in vacuo. The crude was purified by CC using Hept/EtOAc.

TABLE 9

| BB-4C | Name | Reactant BB-4B | $t_R$ [min] | MS-data m/z $[M + H]^+$ |
|---|---|---|---|---|
| BB-4-1C | Acetic acid 2-((R)-3-tert-butoxycarbonylamino-pyrrolidin-1-yl)-3-fluoro-benzyl ester | BB-4-1B | 0.94 | 353.13 |

TABLE 9-continued

| BB-4C | Name | Reactant BB-4B | $t_R$ [min] | MS-data m/z $[M + H]^+$ |
|---|---|---|---|---|
| BB-4-2C | Acetic acid 2-(4-tert-butoxycarbonylamino-piperidin-1-yl)-3-fluoro-benzyl ester | BB-4-2B | 0.97 | 367.25 |

Step D: Hydrogenation

Intermediate BB-40C (1 eq) was dissolved in a mixture of MeOH (6 mL/mmol) and EtOAc (2 mL/mmol) and the flask was evacuated three times and refilled with nitrogen. Wet Pd/C (0.08 eq) was added and the flask was evacuated and refilled three times with hydrogen. The suspension was stirred under a hydrogen atmosphere for 3h (see Table 10) and filtered over a pad of Celite. The cake was washed with EtOAc and MeOH and the filtrate was concentrated in vacuo. The crude was purified by CC using Hept/EtOAc.

TABLE 10

| BB-4D (G-5) | Name | Reactant BB-4C | $t_R$ [min] | MS-data m/z $[M + H]^+$ |
|---|---|---|---|---|
| BB-4-1D | [(R)-1-(2-Fluoro-6-methyl-phenyl)-pyrrolidin-3-yl]-carbamic acid tert-butyl ester | BB-4-1C | 0.91 | 295.14 |
| BB-4-2D | [1-(2-Fluoro-6-methyl-phenyl)-piperidin-4-yl]-carbamic acid tert-butyl ester | BB-4-2C | 1.00 | 309.16 |

Final Step: Boc Cleavage

To a solution of intermediate BB-4D or BB-4A (1 eq) in DCM (4 mL/mmol) was added dropwise TFA (1 mL/mmol) and the rxn mixture was stirred for 1h to 18h at RT (see Table 11). It was basified with a 1M solution of NaOH until pH 12-13 and extracted with DCM (3×). The combined org. phases were dried over MgSO$_4$ and concentrated in vacuo.

TABLE 11

| BB-4 | Name | Reactant BB-4D (G-5) or BB-4A | $t_R$ [min] | MS-data m/z $[M + H]^+$ |
|---|---|---|---|---|
| BB-4-1 | (R)-1-(2-Fluoro-6-methyl-phenyl)-pyrrolidin-3-ylamine | BB-4-1D | 0.57 | 195.29 |
| BB-4-2 | 1-(2-Fluoro-6-methyl-phenyl)-piperidin-4-ylamine | BB-4-2D | 0.60 | 209.28 |
| BB-4-3 | 2-((R)-3-Amino-pyrrolidin-1-yl)-3-fluoro-benzonitrile | BB-4-3A | 0.49 | 205.89 |

Synthesis of Building Blocks BB-4 (Via G-2 and G-3)

Step A: Buchwald Hartwig

To a mixture of the appropriate amine G-1 (1 eq), the appropriate halide (1.2 eq) and sodium tert-butoxide (2 eq) in toluene (3 mL/mmol) under N$_2$, was added BINAP (0.2 eq) and Pd$_2$(dba)$_3$ (0.1 eq) (see Table 12). The rxn mixture was flushed with N$_2$, heated to 100° C. in a sealed vial and stirred for 24h. It was partitioned between water and EtOAc and the org. phase was washed with brine, dried over MgSO$_4$ and concentrated in vacuo. The crude was purified by CC using Hept/EtOAc.

TABLE 12

| G-2 | Name | Reactant amine (G-1) | Reactant halide | $t_R$ [min] | MS-data m/z $[M + H]^+$ |
|---|---|---|---|---|---|
| G-2-1 | 8-(2,6-Dimethyl-phenyl)-1,4-dioxa-8-aza-spiro[4.5]decane | 1,4-Dioxa-8-azaspiro[4.5]decane | 2-Bromo-1,3-dimethylbenzene | 0.92 | 248.24 |

Step B: Ketal Cleavage

To a soln. of ketal intermediate G-2 (1 eq) in anh. THF (3 mL/mmol) was added a 1M aq. sol. of HCl (2 mL/mmol) at RT (see Table 13). The rxn mixture was heated to 70° C. and stirred for 24h. It was quenched with a sat. aq. soln. of NaHCO$_3$ and extracted with EtOAc (3×). The combined org. phases were washed with brine, dried over MgSO$_4$ and concentrated in vacuo. The crude was purified by CC using Hept/EtOAc.

TABLE 13

| G-3 | Name | Reactant G-2 | $t_R$ [min] | MS-data m/z [M + H]$^+$ |
|---|---|---|---|---|
| G-3-1 | 1-(2,6-Dimethyl-phenyl)-piperidin-4-one | G-2-1 | 0.88 | 204.22 |

Final Step: Reductive Amination

To a soln. of ketone intermediate G-3 (1 eq) in dioxane (9.1 mL/mmol) was added a 25% aq. soln. of NH$_4$OH (38 eq) and H$_2$O (0.35 mL/mmol). The flask was evacuated three times and refilled with nitrogen. Wet Pd/C (0.06 eq) was added and the flask was evacuated and refilled three times with hydrogen. The suspension was stirred under a hydrogen atmosphere for 24h (see Table 14) and filtered over a pad of Celite. The cake was washed with dioxane and MeOH and the filtrate was concentrated in vacuo. The crude was purified by CC using DCM/MeOH.

TABLE 14

| BB-4 | Name | Reactant G-3 | $t_R$ [min] | MS-data m/z [M + H]$^+$ |
|---|---|---|---|---|
| BB-4-4 | 1-(2,6-Dimethyl-phenyl)-piperidin-4-ylamine | G-3-1 | 0.63 | 205.33 |

Synthesis of Building Block BB-8

Synthesis of Carbonic Acid 3-Methyl-Oxetan-3-Yl Ester Pentafluorophenyl Ester (BB-8-1), Carbonic Acid Oxetan-3-Yl Ester Pentafluorophenyl Ester (BB-8-2) and Carbonic Acid Pentafluorophenyl Ester 3-Trifluoromethyl-Oxetan-3-Yl Ester (BB-8-3)

A soln. of the appropriate alcohol (1 eq) and bis(pentafluorophenyl)carbonate (1.2 eq) in MeCN (0.55 mL/mmol) was cooled to 0° C. and Et$_3$N (3.2 eq) was added dropwise. The rxn mixture was stirred ON allowing the temperature to reach RT (see Table 15). The mixture was concentrated in vacuo and the residue was purified by CC using DCM/MeOH.

TABLE 15

| BB-8 | Name | Reactant alcohol | $t_R$ [min] | $^1$H NMR (400 MHz, DMSO-d6) δ: |
|---|---|---|---|---|
| BB-8-1 | Carbonic acid 3-methyl-oxetan-3-yl ester pentafluorophenyl ester | 3-Methyl oxetan-3-ol | 0.90 | 4.77 (d, J = 7.7 Hz, 2 H), 4.54 (d, J = 8.2 Hz, 2 H), 1.76 (s, 3 H) |
| BB-8-2 | Carbonic acid oxetan-3-yl ester pentafluorophenyl ester | 3-Hydroxy oxetane | 0.86 | 5.65 (m, 1 H), 4.87 (m, 2 H), 4.65 (ddd, J$_1$ = 0.9 Hz, J$_2$ = 4.7 Hz, J$_3$ = 8.1 Hz, 2 H) |

The carbonic acid pentafluorophenyl ester 3-trifluoromethyl-oxetan-3-yl ester (BB-8-3) was prepared according to Med. Chem. Commun., 2013, 4, 95.

Synthesis of 4-(2-bromo-3-fluoro-phenyl)-morpholine (BB-8-4)

To a soln. of 2-fluoro-6-morpholinoaniline (100 mg, 0.51 mmol) in anh. MeCN was added tert-butyl nitrite (0.121 mL, 1.02 mmol) and copper (II) bromide (137 mg, 0.612 mmol). The rxn mixture was stirred for 30 min at RT and partitioned between water and EtOAc. The aq. phase was washed with EtOAc (2×) and the combined org. phases were washed with brine (1×), dried over MgSO$_4$ and concentrated in vacuo. The crude was purified by CC using Hept/EtOAc and additionally by prep. LC-MS using method 2.

LC-MS: $t_R$=0.97 min, [M+H]$^+$: 260.05

Synthesis of 5-isopropyl-3H-[1,3,4]oxadiazol-2-one (BB-8-5)

CDI (1228 mg, 7.34 mmol) was added to a soln. of isobutyric acid hydrazide (500 mg, 4.9 mmol) in anh. dioxane (21 mL) and the rxn mixture was heated at 85° C. and stirred ON. Dioxane was evaporated off and the residue was partitioned between water and EtOAc. The org. phase was washed with brine (1×), dried over MgSO$_4$ and concentrated in vacuo. The crude was purified by CC using Hept/EtOAc.

LC-MS: $t_R$=0.49 min, [M+MeCN+H]$^+$: 170.27

$^1$H NMR (400 MHz, DMSO-d6) δ:12.05 (m, 1H), 2.86 (m, 1H), 1.19 (d, J=6.9 Hz, 6H)

Synthesis of 3-chloro-4-methoxy-2-methyl-pyridine (BB-8-6)

To a soln. of 3,4-dichloro-2-methylpyridine (228 mg, 1.3 mmol) in MeOH (6.7 mL) was added a 25% soln. of NaOMe in MeOH (3.5 mL, 15.3 mmol) and the soln. was heated to 65° C. for 18h. It was partitioned between DCM and water and the org. phase was washed with brine (1×), dried over MgSO$_4$ and concentrated in vacuo to give the title compound as white solid.

LC-MS: $t_R$=0.38 min, [M+H]$^+$: 158.43

$^1$H NMR (500 MHz, DMSO) δ: 8.28 (d, J=5.6 Hz, 1H), 7.07 (d, J=5.7 Hz, 1H), 3.92 (s, 3H), 2.51 (s, 3H)

Synthesis of (3-bromo-5-methoxy-pyridin-4-yl)-carbamic acid methyl ester (BB-10-1)

Step A (bromination): 3-bromo-5-methoxypyridin-4-amine

To a soln. of 4-amino-3-methoxypyridine (905 mg, 7 mmol) in MeCN (20 mL) was added N-bromosuccinimide (1384 mg, 7.7 mmol) and the soln. was stirred for 1h at RT. It was quenched with a sat. aq. soln. of $Na_2S_2O_3$ and extracted with EtOAc. The org. phase was washed with a sat. aq. soln. of $NaHCO_3$ (5×) and brine (1×), dried over $MgSO_4$ and concentrated in vacuo to give the title compound as brown oil.

LC-MS: $t_R$=0.38 min, $[M+H]^+$: 203.17

$^1$H NMR (500 MHz, DMSO) δ: 7.98 (s, 1H), 7.89 (s, 1H), 5.87 (s, 2H), 3.86 (s, 4H)

Step B (carbamate formation): (3-bromo-5-methoxy-pyridin-4-yl)-carbamic acid methyl ester (BB-10-1)

To a soln. of 3-bromo-5-methoxy-pyridin-4-ylamine (1140 mg, 5.61 mmol) and 2,6-lutidine (1.33 mL, 11.20 mmol) in DCM (40 mL) was added dropwise a soln. of methyl chloroformate (0.482 mL, 6.18 mmol) in DCM (5 mL) at 0° C. The rxn mixture was allowed to warm to RT and stirred for 18h. Additional amount of 2,6-lutidine (2.67 mL, 22.5 mmol) and methylchloroformate (0.876 mL, 11.2 mmol) was added at 0° C. and the rxn mixture stirred for 1h at RT. It was quenched with a sat. aq. soln. of $NaHCO_3$ and extracted with DCM (2×). The combined org. phases were dried over $MgSO_4$ and concentrated in vacuo. The crude was purified by CC using Hept/EtOAc.

LC-MS: $t_R$=0.62 min, $[M+H]^+$: 261.14

$^1$H NMR (400 MHz, DMSO) δ: 9.23 (s, 1H), 8.40 (s, 1H), 8.39 (s, 1H), 3.91 (s, 3H), 3.63 (s, 3H)

Synthesis of Intermediates of Formula A-1

To a soln. of 1-fluoro/chloro-2-nitro-(hetero)arene (BB-2, 1 eq) and Boc-protected diamine (BB-1, 1 to 1.2 eq) in DMSO (1.5 mL/mmol) was added DIPEA (2 eq) and the soln. was heated at a given temperature for a given time (see Table 16). The rxn mixture was partitioned between EtOAc and water. The org. phase was washed with water (4×) and with brine, dried over $MgSO_4$ and concentrated in vacuo. The crude was purified by CC using Hept/EtOAc and/or DCM/MeOH.

TABLE 16

| A-1 | Name | Reactant BB-2 | Reactant BB-1 | T [° C.] time [h] | $t_R$ [min] | MS-data m/z $[M+H]^+$ |
|---|---|---|---|---|---|---|
| A-1-1 | 4-(3-Methoxy-2-nitro-phenylamino)-piperidine-1-carboxylic acid tert-butyl ester | 3-Fluoro-2-nitroanisole | 1-N-Boc-4-aminopiperidine | 100 24 | 0.96 | 352.16 |
| A-1-2 | (R)-3-(3-Methoxy-2-nitro-phenylamino)-pyrrolidine-1-carboxylic acid tert-butyl ester | 3-Fluoro-2-nitroanisole | (R)-(+)-1-Boc-3-aminopyrrolidine | 100 24 | 0.92 | 338.74 |
| A-1-3 | (R)-3-(2-Methoxy-3-nitro-pyridin-4-ylamino)-pyrrolidine-1-carboxylic acid tert-butyl ester | BB-2-1 | (R)-(+)-1-Boc-3-aminopyrrolidine | 80 24 | 0.88 | 339.11 |
| A-1-4 | (R)-3-(4-Methoxy-3-nitro-pyridin-2-ylamino)-pyrrolidine-1-carboxylic acid tert-butyl ester | 2-Chloro-4-methoxy-3-nitro-pyridine | (R)-(+)-1-Boc-3-aminopyrrolidine | 85 24 | 0.87 | 339.13 |
| A-1-5 | 4-(3-Methoxy-2-nitro-phenylamino)-2-methyl-piperidine-1-carboxylic acid tert-butyl ester | 3-Fluoro-2-nitroanisole | 1-N-Boc-4-amino-2-methyl-piperidine | 100 24 | 0.98 | 366.22 |
| A-1-6 | 4-(3-Methoxy-2-nitro-phenylamino)-3-methyl-piperidine-1-carboxylic acid tert-butyl ester | 3-Fluoro-2-nitroanisole | 1-N-Boc-4-amino-3-methyl-piperidine | 100 24 | 0.98 | 366.39 |
| A-1-7 | 4-(3-Methoxy-2-nitro-phenylamino)-piperidine-1,3-dicarboxylic acid 1-tert-butyl ester 3-ethyl ester | 3-Fluoro-2-nitroanisole | 1-N-Boc-4-aminopiperidine-3-carboxylic acid ethyl ester | 90 24 | 0.97 | 424.14 |
| A-1-8 | 4-(3-Methyl-2-nitro-phenylamino)-piperidine-1-carboxylic acid tert-butyl ester | 3-Fluoro-2-nitrotoluene | 1-N-Boc-4-aminopiperidine | 100 18 | 1.14 | 336.32 |

Synthesis of Intermediates of Formula A-2

To a soln. of intermediate A-1 (1eq) in EtOAc (3 to 3.3 mL/mmol) was added 10% Pd/C moistened with ~50% water (0.01 to 0.05 eq) and the rxn mixture was hydrogenated under atmospheric pressure for a given time (see Table 17). It was filtered over a pad of celite and the filtrate was concentrated in vacuo. The crude was purified by CC using Hept/EtOAc or DCM/MeOH.

TABLE 17

| A-2 | Name | Reactant A-1 | time [h] | $t_R$ [min] | MS-data m/z $[M + H]^+$ |
|---|---|---|---|---|---|
| A-2-1 | 4-(2-Amino-3-methoxy-phenylamino)-piperidine-1-carboxylic acid tert-butyl ester | A-1-1 | 24 | 0.68 | 322.00 |
| A-2-2 | (R)-3-(2-Amino-3-methoxy-phenylamino)-pyrrolidine-1-carboxylic acid tert-butyl ester | A-1-2 | 10 | 0.67 | 308.13 |
| A-2-3 | (R)-3-(3-Amino-2-methoxy-pyridin-4-ylamino)-pyrrolidine-1-carboxylic acid tert-butyl ester | A-1-3 | 4.5 | 0.59 | 309.11 |
| A-2-4 | (R)-3-(3-Amino-4-methoxy-pyridin-2-ylamino)-pyrrolidine-1-carboxylic acid tert-butyl ester | A-1-4 | 3 | 0.58 | 309.18 |
| A-2-5 | 4-(2-Amino-3-methoxy-phenylamino)-2-methyl-piperidine-1-carboxylic acid tert-butyl ester | A-1-5 | 3.5 | 0.71 | 336.32 |
| A-2-6 | 4-(2-Amino-3-methoxy-phenylamino)-3-methyl-piperidine-1-carboxylic acid tert-butyl ester | A-1-6 | 1 | 0.72/0.73 | 336.23 |
| A-2-7 | 4-(2-Amino-3-methoxy-phenylamino)-piperidine-1,3-dicarboxylic acid 1-tert-butyl ester 3-ethyl ester | A-1-7 | 1 | 0.76 | 394.09 |
| A-2-8 | 4-(2-Amino-3-methyl-phenylamino)-piperidine-1-carboxylic acid tert-butyl ester | A-1-8 | 18 | 0.76 | 306.26 |

Synthesis of Intermediates of Formula A-3

To a soln. of intermediate A-2 (1 eq) in MeCN (3.7 mL/mmol) was added CDI (1.2 eq) and the rxn mixture was stirred at a given temperature for a given time (see Table 18). The solvent was evaporated off and the residue was partitioned between EtOAc or DCM and water. The org. phase was washed with brine, dried over $MgSO_4$ and concentrated in vacuo. The crude was purified by CC using Hept/EtOAc or DCM/MeOH.

TABLE 18

| A-3 | Name | Reactant A-2 | T [° C.] time [h] | $t_R$ [min] | MS-data m/z $[M + H]^+$ |
|---|---|---|---|---|---|
| A-3-1 | 4-(4-Methoxy-2-oxo-2,3-dihydro-benzoimidazol-1-yl)-piperidine-1-carboxylic acid tert-butyl ester | A-2-1 | RT 2 | 0.82 | 348.14 |
| A-3-2 | (R)-3-(4-Methoxy-2-oxo-2,3-dihydro-benzoimidazol-1-yl)-pyrrolidine-1-carboxylic acid tert-butyl ester | A-2-2 | RT 0.2 | 0.80 | 334.15 |
| A-3-3 | (R)-3-(4-Methoxy-2-oxo-2,3-dihydro-imidazo[4,5-c]pyridine-1-yl)-pyrrolidine-1-carboxylic acid tert-butyl ester | A-2-3 | RT 2 | 0.72 | 335.12 |
| A-3-4 | (R)-3-(7-Methoxy-2-oxo-1,2-dihydro-imidazo[4,5-b]pyridine-3-yl)-pyrrolidine-1-carboxylic acid tert-butyl ester | A-2-4 | 45° C. 0.2 | 0.74 | 335.34 |
| A-3-5 | 4-(4-Methoxy-2-oxo-2,3-dihydro-benzoimidazol-1-yl)-2-methyl-piperidine-1-carboxylic acid tert-butyl ester | A-2-5 | RT 0.25 | 0.86 | 362.21 |
| A-3-6 | 4-(4-Methoxy-2-oxo-2,3-dihydro-benzoimidazol-1-yl)-3-methyl-piperidine-1-carboxylic acid tert-butyl ester | A-2-6 | RT 0.75 | 0.85 | 362.21 |
| A-3-7 | 4-(4-Methoxy-2-oxo-2,3-dihydro-benzoimidazol-1-yl)-piperidine-1,3-dicarboxylic acid 1-tert-butyl ester3-ethyl ester | A-2-7 | RT 0.75 | 0.84 | 420.13 |
| A-3-8 | 4-(4-Methyl-2-oxo-2,3-dihydro-benzoimidazol-1-yl)-piperidine-1-carboxylic acid tert-butyl ester | A-2-8 | RT 21 | 0.97 | 332.31 |

Synthesis of Compounds of Formula Ia (from Compounds of Formula A-3)

Method A (K$_2$CO$_3$/DMF)

To a soln. of intermediate A-3 (1eq) in anh. DMF (3.5 to 6 mL/mmol) was added K$_2$CO$_3$(3eq) at RT then reactant BB-3 (1.1 to 2eq) at 0° C. The rxn mixture was allowed to reach RT and stirred at a given temperature for given time (see Table 19). It was quenched with water and extracted with EtOAc (3×). The combined org. phases were washed with brine, dried over MgSO$_4$ and concentrated in vacuo. The crude was purified by CC using Hept/EtOAc or DCM/MeOH or by trituration in a mixture of Hept/EtOAc 1/1 and filtration.

Method B (NaH/TH)

To a soln. of intermediate A-3(1eq) in anh. THF (3 mL/mmol) was added NaH (2eq, as a 60% dispersion in mineral oil) at RT followed by BB-3 (1.2 eq). When necessary in term of solubility, anh. DMF (0.1 to 2 mL/mmol) could be added. The rxn mixture was stirred at a given temperature for a given time (see Table 19), quenched with a sat. soln. of NaHCO$_3$ and extracted with EtOAc (3×). The combined org. phases were washed with brine, dried over MgSO$_4$ and concentrated in vacuo. The crude was purified by CC using Hept/EtOAc or DCM/MeOH

TABLE 19

| Ia | Name | Reactant A-3 | Reactant BB-3 | Method T [° C.] time [h] | $t_R$ [min] | MS-data m/z [M + H]$^+$ |
|---|---|---|---|---|---|---|
| Ia-1 | 4-[4-Methoxy-2-oxo-3-(2-trifluoromethyl-benzyl)-2,3-dihydro-benzoimidazol-1-yl]-piperidine-1-carboxylic acid tert-butyl ester (Example 1) | A-3-1 | 2-(Trifluoromethyl) benzyl bromide | A RT 24 | 1.04 | 505.98 |
| Ia-2 | (R)-3-[4-Methoxy-2-oxo-3-(2-trifluoromethyl-benzyl)-2,3-dihydro-benzoimidazol-1-yl]-pyrrolidine-1-carboxylic acid tert-butyl ester (Example 6) | A-3-2 | 2-(Trifluoromethyl) benzyl bromide | A RT 24 | 1.02 | 492.10 |
| Ia-3 | (R)-3-[4-Methoxy-2-oxo-3-(2-trifluoromethoxy-benzyl)-2,3-dihydro-benzoimidazol-1-yl]-pyrrolidine-1-carboxylic acid tert-butyl ester (Example 20) | A-3-2 | 2-(Trifluoromethoxy) benzyl bromide | B 50° C. 24 | 1.03 | 507.95 |
| Ia-4 | (R)-3-[4-Methoxy-2-oxo-3-(2-trifluoromethyl-benzyl)-2,3-dihydro-imidazo[4,5-c]pyridin-1-yl]-pyrrolidine-1-carboxylic acid tert-butyl ester (Example 39) | A-3-3 | 2-(Trifluoromethyl) benzyl bromide | A RT 1.5 | 1.01 | 493.15 |
| Ia-5 | (R)-3-[7-Methoxy-2-oxo-1-(2-trifluoromethyl-benzyl)-1,2-dihydro-imidazo[4,5-b]pyridine-3-yl]-pyrrolidine-1-carboxylic acid tert-butyl ester (Example 43) | A-3-4 | 2-(Trifluoromethyl) benzyl bromide | B 50° C. 5 | 1.00 | 493.13 |
| Ia-6 | 4-[4-Methoxy-2-oxo-3-(2-trifluoromethyl-pyridin-3-ylmethyl)-2,3-dihydro-benzoimidazol-1-yl]-piperidine-1-carboxylic acid tert-butyl ester | A-3-1 | BB-3-1 | A RT 24 | 0.99 | 507.13 |
| Ia-7 | 4-[4-Methoxy-2-oxo-3-(4-trifluoromethyl-pyridin-3-ylmethyl)-2,3-dihydro-benzoimidazol-1-yl]-piperidine-1-carboxylic acid tert-butyl ester (Example 53) | A-3-1 | BB-3-2 | A RT 3 | 1.01 | 507.13 |
| Ia-8 | (R)-3-[4-Methoxy-3-(2-methoxy-benzyl)-2-oxo-2,3-dihydro-benzoimidazol-1-yl]-pyrrolidine-1-carboxylic acid tert-butyl ester (Example 65) | A-3-2 | 2-Methoxybenzyl chloride | B RT 18 then 50° C. 4 | 0.98 | 454.19 |
| Ia-9 | 4-[4-Methoxy-2-oxo-3-(3-trifluoromethyl-pyridin-4-ylmethyl)-2,3-dihydro-benzoimidazol-1-yl]-piperidine-1-carboxylic acid tert-butyl ester | A-3-1 | BB-3-3 | A RT 24 | 1.02 | 507.14 |

TABLE 19-continued

| Ia | Name | Reactant A-3 | Reactant BB-3 | Method T [° C.] time [h] | $t_R$ [min] | MS-data m/z $[M + H]^+$ |
|---|---|---|---|---|---|---|
| Ia-10 | 4-[4-Methoxy-2-oxo-3-(3-trifluoromethyl-pyridin-2-ylmethyl)-2,3-dihydro-benzoimidazol-1-yl]-piperidine-1-carboxylic acid tert-butyl ester (Example 64) | A-3-1 | BB-3-4 | A RT 24 | 0.99 | 507.12 |
| Ia-11 | (R)-3-[4-Methoxy-3-(2-methoxy-benzyl)-2-oxo-2,3-dihydro-imidazo[4,5-c]pyridin-1-yl]-pyrrolidine-1-carboxylic acid tert-butyl ester | A-3-3 | 2-Methoxybenzyl chloride | A RT 24 | 0.95 | 455.21 |
| Ia-12 | 4-[4-Methoxy-2-oxo-3-(2-trifluoromethyl-benzyl)-2,3-dihydro-benzoimidazol-1-yl]-2-methyl-piperidine-1-carboxylic acid tert-butyl ester (Example 144) | A-3-5 | 2-(Trifluoromethyl) benzyl bromide | B RT 24 | 1.06 | 520.24 |
| Ia-13 | 4-[4-Methoxy-2-oxo-3-(2-trifluoromethyl-benzyl)-2,3-dihydro-benzoimidazol-1-yl]-3-methyl-piperidine-1-carboxylic acid tert-butyl ester (Example 146) | A-3-6 | 2-(Trifluoromethyl) benzyl bromide | A RT 1 then 50° C. 18 | 1.06 | 520.13 |
| Ia-14 | 4-[4-Methoxy-2-oxo-3-(2-trifluoromethyl-benzyl)-2,3-dihydro-benzoimidazol-1-yl]-piperidine-1,3-dicarboxylic acid 1-tert-butyl ester 3-ethyl ester (Example 164) | A-3-7 | 2-(Trifluoromethyl) benzyl bromide | A RT 8.5 | 1.04 | 578.05 |
| Ia-24 | 4-[4-Methyl-2-oxo-3-(2-trifluoromethyl-benzyl)-2,3-dihydro-benzoimidazol-1-yl]-piperidine-1-carboxylic acid tert-butyl ester | A-3-8 | 2-(Trifluoromethyl) benzyl bromide | A RT 18 | 1.21 | 490.29 |

Synthesis of Intermediates of Formula B-1

A mixture of BB1-6 (1eq) and BB1-5 (8.3 eq) in DIPEA (2 eq) was heated to 180° C. and stirred for a given temperature (see Table 20). It was partitioned between DCM and water and the org. phase was washed with brine, dried over $MgSO_4$ and concentrated in vacuo. The crude was purified by CC using Hept/EtOAc.

TABLE 20

| B-1 | Name | Reactant BB-6 | Reactant BB-5 | time [h] | $t_R$ [min] | MS-data m/z $[M + H]^+$ |
|---|---|---|---|---|---|---|
| B-1-1 | (2-Methoxy-6-nitro-phenyl)-(2-trifluoromethyl-benzyl)-amine | 2-Chloro-3-nitroanisole | 2-(Trifluoromethyl) benzylamine | 3.5 | 0.99 | 327.04 |

Synthesis of Intermediates of Formula B-2

To a suspension of intermediate B-1 (1eq) and zinc dust (10eq) in MeOH (10 mL/mmol) was added ammonium formate (10 eq) at 0° C.. The rxn mixture was stirred at a given temperature for a given time (see Table 21), filtered over a pad of celite and the filtrate was concentrated in vacuo. The crude was purified by CC using DCM/MeOH.

TABLE 21

| B-2 | Name | Reactant B-1 | T [° C.] time [h] | $t_R$ [min] | MS-data m/z $[M + H]^+$ |
|---|---|---|---|---|---|
| B-2-1 | 3-Methoxy-N2-(2-trifluoromethyl-benzyl)-benzene-1,2-diamine | B-1-1 | 0 0.5 | 0.74 | 297.07 |

Synthesis of Intermediates of Formula B-3

Intermediates B-3 were prepared using a similar protocol as for the synthesis of intermediates A-3 replacing intermediates A-2 by intermediates B-2 (see Table 22).

TABLE 22

| B-3 | Name | Reactant B-2 | T [° C.] time [h] | $t_R$ [min] | MS-data m/z $[M + H]^+$ |
|---|---|---|---|---|---|
| B-3-1 | 7-Methoxy-1-(2-trifluoromethyl-benzyl)-1,3-dihydro-benzoimidazol-2-one | B-2-1 | RT 2 | 0.87 | 323.06 |

Synthesis of Compounds of Formula Ia (from Compounds of Formula B-3)

To a soln. of intermediate B-3 (1 eq) and BB-7 (1.5 eq) in toluene (6.8 mL/mmol) was added a 1M soln. of (tributylphosphoranylidene)acetonitrile in toluene (2 eq) under argon. The rxn mixture was heated to 110° C. and stirred for a given time (see Table 23). It was quenched with water and extracted with EtOAc (3×). The combined org. phases were washed with brine, dried over $MgSO_4$ and concentrated in vacuo. The crude was purified by CC using Hept/EtOAc and/or DCM/MeOH. When necessary, an additional purification by prep. LC-MS Method 1 can be performed.

TABLE 23

| Ia | Name | Reactant B-3 | Reactant BB-7 | time [h] | $t_R$ [min] | MS-data m/z $[M + H]^+$ |
|---|---|---|---|---|---|---|
| Ia-15 | 4-[4-Methoxy-2-oxo-3-(2-trifluoromethyl-benzyl)-2,3-dihydro-benzoimidazol-1-yl]-azepane-1-carboxylic acid tert-butyl ester (Example 179) | B-3-1 | 4-Hydroxy azepane-1-carboxylic acid tert-butyl ester | 2 | 1.04 | 520.12 |
| Ia-16 | 5-[4-Methoxy-2-oxo-3-(2-trifluoromethyl-benzyl)-2,3-dihydro-benzoimidazol-1-yl]-2-aza-bicyclo[2.2.1]heptane-2-carboxylic acid tert-butyl ester (Example 188) | B-3-1 | 5-hydroxy-2-azabicyclo[2.2.1]heptane-2-carboxylic acid tert-butyl ester | 8 | 1.04 | 518.10 |
| Ia-17 | 6-[4-Methoxy-2-oxo-3-(2-trifluoromethyl-benzyl)-2,3-dihydro-benzoimidazol-1-yl]-3-aza-bicyclo[3.1.1]heptane-3-carboxylic acid tert-butyl ester (Example 191) | B-3-1 | 6-hydroxy-3-azabicyclo[3.1.1]heptane-3-carboxylic acid tert-butyl ester | 18 | 1.04 | 518.11 |

TABLE 23-continued

| Ia | Name | Reactant B-3 | Reactant BB-7 | time [h] | $t_R$ [min] | MS-data m/z [M + H]$^+$ |
|---|---|---|---|---|---|---|
| Ia-18 | (3R*,4S*)-3-[4-Methoxy-2-oxo-3-(2-trifluoromethyl-benzyl)-2,3-dihydro-benzoimidazol-1-yl]-4-methyl-pyrrolidine-1-carboxylic acid tert-butyl ester (Example 196) | B-3-1 | cis-1-Boc-4-methylpyrrolidin-3-ol | 18 | 1.03 | 506.13 |
| Ia-19 | (3R*,4R*)-3-[4-Methoxy-2-oxo-3-(2-trifluoromethyl-benzyl)-2,3-dihydro-benzoimidazol-1-yl]-4-methyl-pyrrolidine-1-carboxylic acid tert-butyl ester (Example 199) | B-3-1 | trans-1-Boc-4-methylpyrrolidin-3-ol | 18 | 1.03 | 506.12 |
| Ia-20 | 3-Fluoro-4-[4-methoxy-2-oxo-3-(2-trifluoromethyl-benzyl)-2,3-dihydro-benzoimidazol-1-yl]-piperidine-1-carboxylic acid tert-butyl ester (Example 210) | B-3-1 | 3-Fluoro-4-hydroxypiperidine-1-carboxylic acid tert-butyl ester | 18 | 1.03 | 524.04 |
| Ia-21 | 3-[4-Methoxy-2-oxo-3-(2-trifluoromethyl-benzyl)-2,3-dihydro-benzoimidazol-1-yl]-piperidine-1-carboxylic acid tert-butyl ester (Example 214) | B-3-1 | 1-Boc-3-hydroxypiperidine | 18 | 1.05 | 506.08 |
| Ia-22 | 3-[4-Methoxy-2-oxo-3-(2-trifluoromethyl-benzyl)-2,3-dihydro-benzoimidazol-1-yl]-azetidine-1-carboxylic acid tert-butyl ester (Example 213) | B-3-1 | 1-Boc-3-hydroxyazetidine | 16 | 1.01 | 478.03 |
| Ia-23 | 4-[4-Methoxy-2-oxo-3-(2-trifluoromethyl-benzyl)-2,3-dihydro-benzoimidazol-1-yl]-3,3-dimethyl-piperidine-1-carboxylic acid tert-butyl ester (Example 228) | B-3-1 | 1-Boc-4-hydroxy-3,3-dimethylpiperidine | 18 | 1.07 | 534.22 |

Synthesis of Intermediates of Formula C-1

To a soln. of intermediate Ia (1 eq) in DCM (2 to 10 mL/mmol) was added TEA (1.5 to 5 mL/mmol) and the rxn mixture was stirred at RT for a given time (see Table 24). It was quenched with a 1M soln. of NaOH until pH reached 12 to 13 and extracted with DCM (3×). The combined org. phases were washed with brine, dried over MgSO$_4$ and concentrated in vacuo. The crude was purified by CC using DCM/MeOH.

TABLE 24

| C-1 | Name | Reactant Ia | time [h] | $t_R$ [min] | MS-data m/z [M + H]$^+$ |
|---|---|---|---|---|---|
| C-1-1 | 4-Methoxy-1-piperidin-4-yl-3-(2-trifluoromethyl-benzyl)-1,3-dihydro-benzoimidazol-2-one | Ia-1 | 2.5 | 0.72 | 406.13 |
| C-1-2 | 4-Methoxy-1-(R)-pyrrolidin-3-yl-3-(2-trifluoromethyl-benzyl)-1,3-dihydro-benzoimidazol-2-one | Ia-2 | 0.5 | 0.73 | 392.17 |
| C-1-3 | 4-Methoxy-1-(R)-pyrrolidin-3-yl-3-(2-trifluoromethoxy-benzyl)-1,3-dihydro-benzoimidazol-2-one | Ia-3 | 2 | 0.73 | 407.93 |
| C-1-4 | 4-Methoxy-1-(R)-pyrrolidin-3-yl-3-(2-trifluoromethyl-benzyl)-1,3-dihydro-imidazo[4,5-c]pyridine-2-one | Ia-4 | 1 | 0.67 | 393.09 |
| C-1-5 | 7-Methoxy-3-(R)-pyrrolidin-3-yl-1-(2-trifluoromethyl-benzyl)-1,3-dihydro-imidazo[4,5-b]pyridine-2-one | Ia-5 | 1.5 | 0.68 | 393.23 |
| C-1-6 | 4-Methoxy-1-piperidin-4-yl-3-(2-trifluoromethyl-pyridin-3-ylmethyl)-1,3-dihydro-benzoimidazol-2-one | Ia-6 | 1.5 | 0.65 | 407.20 |
| C-1-7 | 4-Methoxy-1-piperidin-4-yl-3-(4-trifluoromethyl-pyridin-3-ylmethyl)-1,3-dihydro-benzoimidazol-2-one | Ia-7 | 0.7 | 0.65 | 407.19 |
| C-1-8 | 4-Methoxy-3-(2-methoxy-benzyl)-1-(R)-pyrrolidin-3-yl-1,3-dihydro-benzoimidazol-2-one | Ia-8 | 2.5 | 0.66 | 354.10 |
| C-1-9 | 4-Methoxy-1-piperidin-4-yl-3-(3-trifluoromethyl-pyridin-4-ylmethyl)-1,3-dihydro-benzoimidazol-2-one | Ia-9 | 0.5 | 0.66 | 407.19 |
| C-1-10 | 4-Methoxy-1-piperidin-4-yl-3-(3-trifluoromethyl-pyridin-2-ylmethyl)-1,3-dihydro-benzoimidazol-2-one | Ia-10 | 2 | 0.66 | 407.17 |
| C-1-11 | 4-Methoxy-3-(2-methoxy-benzyl)-1-(R)-pyrrolidin-3-yl-1,3-dihydro-imidazo[4,5-c]pyridine-2-one | Ia-11 | 2 | 0.62 | 355.14 |
| C-1-12 | 4-Methoxy-1-(2-methyl-piperidin-4-yl)-3-(2-trifluoromethyl-benzyl)-1,3-dihydro-benzoimidazol-2-one | Ia-12 | 18 | 0.73 | 420.15 |
| C-1-13 | 4-Methoxy-1-(3-methyl-piperidin-4-yl)-3-(2-trifluoromethyl-benzyl)-1,3-dihydro-benzoimidazol-2-one | Ia-13 | 1.5 | 0.73 | 420.14 |

TABLE 24-continued

| C-1 | Name | Reactant Ia | time [h] | $t_R$ [min] | MS-data m/z $[M + H]^+$ |
|---|---|---|---|---|---|
| C-1-14 | 1-Azepan-4-yl-4-methoxy-3-(2-trifluoromethyl-benzyl)-1,3-dihydro-benzoimidazol-2-one | Ia-15 | 0.5 | 0.74 | 420.11 |
| C-1-15 | 2-Aza-bicyclo[2.2.1]hept-5-yl-4-methoxy-3-(2-trifluoromethyl-benzyl)-1,3-dihydro-benzoimidazol-2-one | Ia-16 | 1 | 0.76 | 418.09 |
| C-1-16 | 1-(3-Aza-bicyclo[3.1.1]hept-6-yl)-4-methoxy-3-(2-trifluoromethyl-benzyl)-1,3-dihydro-benzoimidazol-2-one | Ia-17 | 0.5 | 0.75 | 418.10 |
| C-1-17 | trans-4-Methoxy-1-(4-methyl-pyrrolidin-3-yl)-3-(2-trifluoromethyl-benzyl)-1,3-dihydro-benzoimidazol-2-one | Ia-18 | 1 | 0.74 | 406.18 |
| C-1-18 | cis-4-Methoxy-1-(4-methyl-pyrrolidin-3-yl)-3-(2-trifluoromethyl-benzyl)-1,3-dihydro-benzoimidazol-2-one | Ia-19 | 1 | 0.74 | 406.11 |
| C-1-19 | 1-(3-Fluoro-piperidin-4-yl)-4-methoxy-3-(2-trifluoromethyl-benzyl)-1,3-dihydro-benzoimidazol-2-one | Ia-20 | 0.5 | 0.73/0.74 | 424.07 |
| C-1-20 | 4-Methoxy-1-piperidin-3-yl-3-(2-trifluoromethyl-benzyl)-1,3-dihydro-benzoimidazol-2-one | Ia-21 | 2 | 0.73 | 406.15 |
| C-1-21 | 1-Azetidin-3-yl-4-methoxy-3-(2-trifluoromethyl-benzyl)-1,3-dihydro-benzoimidazol-2-one | Ia-22 | 0.75 | 0.70 | 378.11 |
| C-1-22 | 1-(3,3-Dimethyl-piperidin-4-yl)-4-methoxy-3-(2-trifluoromethyl-benzyl)-1,3-dihydro-benzoimidazol-2-one | Ia-23 | 0.5 | 0.75 | 434.05 |
| C-1-23 | 4-Methyl-1-piperidin-4-yl-3-(2-trifluoromethyl-benzyl)-1,3-dihydro-benzoimidazol-2-one | Ia-24 | 1 | 0.82 | 390.25 |

Synthesis of Compounds of Formula Ib

Method A (Buchwald-Hartwig)

To a mixture of C-1 (1 eq), BB-8 (1.3 eq) and sodium tert-butoxide (2 eq) in toluene (3 to 10 mL/mmol) under $N_2$, was added BINAP (0.2 eq) and $Pd_2(dba)_3$ (0.1 eq). The rxn mixture was flushed with $N_2$, heated at a given temperature and stirred for a given time (see Table 25). It was partitioned between water and EtOAc and the org. phase was washed with brine, dried over $MgSO_4$ and concentrated in vacuo. The crude was purified by CC using Hept/EtOAc. When necessary an additional purification by prep. LC-MS was performed.

Method B (Reductive Amination)

To a soln. of C-1 (1 eq) in THF (10 mL/mmol) was added BB-8 (3 eq) and the rxn mixture was stirred for 1h. AcOH (1.1 eq) and $NaBH(OAc)_3$ (3 eq) were added and the rxn mixture was stirred at RT for a given time (see Table 25). It was quenched with a 1M aq. soln. of NaOH and extracted with DCM (3×). The combined org. phases were washed with brine, dried over $MgSO_4$ and concentrated in vacuo. The crude was purified by CC using Hept/EtOAc.

TABLE 25

| Ib | Name | Reactant C-1 | Reactant BB-8 | Method T [° C.] time [h] | $t_R$ [min] | MS-data m/z $[M + H]^+$ |
|---|---|---|---|---|---|---|
| Ib-1 | 1-[1-(2,6-Dimethyl-phenyl)-piperidin-4-yl]-4-methoxy-3-(2-trifluoromethyl-benzyl)-1,3-dihydro-benzoimidazol-2-one (Example 2) | C-1-1 | 2-Bromo-1,3-dimethylbenzene | A 100 18 | 1.15 | 510.12 |
| Ib-2 | 4-Methoxy-1-(1-phenyl-piperidin-4-yl)-3-(2-trifluoromethyl-benzyl)-1,3-dihydro-benzoimidazol-2-one (Example 4) | C-1-1 | Bromobenzene | A 100 18 | 0.91 | 481.94 |
| Ib-3 | 1-[1-(2,4-Dichloro-benzyl)-piperidin-4-yl]-4-methoxy-3-(2-trifluoromethyl-benzyl)-1,3-dihydro-benzoimidazol-2-one (Example 5) | C-1-1 | 2,4-Dichloro benzaldehyde | B RT 4 | 0.85 | 563.96 |
| Ib-4 | 1-[(R)-1-(2,6-Difluoro-phenyl)-pyrrolidin-3-yl]-4-methoxy-3-(2-trifluoromethyl-benzyl)-1,3-dihydro-benzoimidazol-2-one (Example 7) | C-1-2 | 2,6-Difluoro bromobenzene | A 100 18 | 1.09 | 504.07 |
| Ib-5 | 1-[(R)-1-(2,6-Dimethyl-phenyl)-pyrrolidin-3-yl]-4-methoxy-3-(2-trifluoromethyl-benzyl)-1,3-dihydro-benzoimidazol-2-one (Example 8) | C-1-2 | 2-Bromo-1,3-dimethylbenzene | A 100 18 | 1.00 | 496.12 |

TABLE 25-continued

| Ib | Name | Reactant C-1 | Reactant BB-8 | Method T [° C.] time [h] | $t_R$ [min] | MS-data m/z [M + H]$^+$ |
|---|---|---|---|---|---|---|
| Ib-6 | 1-[1-(2,6-Difluoro-phenyl)-piperidin-4-yl]-4-methoxy-3-(2-trifluoromethyl-benzyl)-1,3-dihydro-benzoimidazol-2-one (Example 9) | C-1-1 | 2,6-Difluoro bromobenzene | A 100 18 | 1.11 | 518.10 |
| Ib-7 | 1-[1-(2,6-Dimethoxy-phenyl)-piperidin-4-yl]-4-methoxy-3-(2-trifluoromethyl-benzyl)-1,3-dihydro-benzoimidazol-2-one (Example 10) | C-1-1 | 2-Bromo-1,3-dimethoxybenzene | A 100 18 | 0.87 | 542.08 |
| Ib-8 | 1-[1-(2-Fluoro-6-methoxy-phenyl)-piperidin-4-yl]-4-methoxy-3-(2-trifluoromethyl-benzyl)-1,3-dihydro-benzoimidazol-2-one (Example 11) | C-1-1 | 2-Bromo-3-fluoroanisole | A 100 18 | 1.04 | 529.98 |
| Ib-9 | 4-Methoxy-1-[1-(2-methoxy-6-methyl-phenyl)-piperidin-4-yl]-3-(2-trifluoromethyl-benzyl)-1,3-dihydro-benzoimidazol-2-one (Example 12) | C-1-1 | 2-Bromo-1-methoxy-3-methylbenzene | A 100 24 | 1.03 | 526.09 |
| Ib-10 | 1-[1-(2-Fluoro-6-methyl-phenyl)-piperidin-4-yl]-4-methoxy-3-(2-trifluoromethyl-benzyl)-1,3-dihydro-benzoimidazol-2-one (Example 13) | C-1-1 | 2-Bromo-3-fluorotoluene | A 100 18 | 1.14 | 514.04 |
| Ib-11 | 1-[(R)-1-(2-Fluoro-6-methyl-phenyl)-pyrrolidin-3-yl]-4-methoxy-3-(2-trifluoromethyl-benzyl)-1,3-dihydro-benzoimidazol-2-one (Example 15) | C-1-2 | 2-Bromo-3-fluorotoluene | A 100 18 | 1.09 | 500.25 |
| Ib-12 | 4-Methoxy-1-[(R)-1-(2-methoxy-phenyl)-pyrrolidin-3-yl]-3-(2-trifluoromethyl-benzyl)-1,3-dihydro-benzoimidazol-2-one (Example 16) | C-1-2 | 2-Bromoanisole | A 100 18 | 0.90 | 497.99 |
| Ib-13 | 1-[(R)-1-(2,6-Dimethoxy-phenyl)-pyrrolidin-3-yl]-4-methoxy-3-(2-trifluoromethyl-benzyl)-1,3-dihydro-benzoimidazol-2-one (Example 17) | C-1-2 | 2-Bromo-1,3-dimethoxybenzene | A 100 18 | 0.87 | 527.94 |
| Ib-14 | 4-Methoxy-1-[(R)-1-(2-methoxy-6-methyl-phenyl)-pyrrolidin-3-yl]-3-(2-trifluoromethyl-benzyl)-1,3-dihydro-benzoimidazol-2-one (Example 18) | C-1-2 | 2-Bromo-1-methoxy-3-methylbenzene | A 100 18 | 0.90 | 511.98 |
| Ib-15 | 1-[(R)-1-(2-Fluoro-6-methoxy-phenyl)-pyrrolidin-3-yl]-4-methoxy-3-(2-trifluoromethyl-benzyl)-1,3-dihydro-benzoimidazol-2-one (Example 19) | C-1-2 | 2-Bromo-3-fluoroanisole | A 100 18 | 0.98 | 515.95 |
| Ib-16 | 1-[(R)-1-(2,6-Dimethyl-phenyl)-pyrrolidin-3-yl]-4-methoxy-3-(2-trifluoromethoxy-benzyl)-1,3-dihydro-benzoimidazol-2-one (Example 22) | C-1-3 | 2-Bromo-1,3-dimethylbenzene | A 100 18 | 0.99 | 511.95 |
| Ib-17 | 1-[(R)-1-(2,6-Difluoro-phenyl)-pyrrolidin-3-yl]-4-methoxy-3-(2-trifluoromethoxy-benzyl)-1,3-dihydro-benzoimidazol-2-one (Example 23) | C-1-3 | 2,6-Difluoro bromobenzene | A 100 18 | 1.09 | 519.90 |
| Ib-18 | 4-Methoxy-1-[(R)-1-(2-methoxy-4-methyl-pyridin-3-yl)-pyrrolidin-3-yl]-3-(2-trifluoromethyl-benzyl)-1,3-dihydro-benzoimidazol-2-one (Example 33) | C-1-2 | 3-Bromo-2-methoxy-4-methylpyridine | A 100 18 | 1.00 | 513.12 |
| Ib-19 | 1-[(R)-1-(3,5-Difluoro-pyridin-4-yl)-pyrrolidin-3-yl]-4-methoxy-3-(2-trifluoromethyl-benzyl)-1,3-dihydro-benzoimidazol-2-one (Example 34) | C-1-2 | 4-Bromo-3,5-difluoropyridine | A 100 18 | 0.83 | 505.08 |

TABLE 25-continued

| Ib | Name | Reactant C-1 | Reactant BB-8 | Method T [° C.] time [h] | $t_R$ [min] | MS-data m/z [M + H]$^+$ |
|---|---|---|---|---|---|---|
| Ib-20 | 1-[(R)-1-(3,5-Dimethyl-pyridin-4-yl)-pyrrolidin-3-yl]-4-methoxy-3-(2-trifluoromethyl-benzyl)-1,3-dihydro-benzoimidazol-2-one (Example 36) | C-1-2 | 4-Bromo-3,5-dimethylpyridine hydrochloride | A 100 18 | 0.81 | 497.13 |
| Ib-21 | 1-[(R)-1-(2-Fluoro-4-methyl-pyridin-3-yl)-pyrrolidin-3-yl]-4-methoxy-3-(2-trifluoromethyl-benzyl)-1,3-dihydro-benzoimidazol-2-one (Example 37) | C-1-2 | 3-Bromo-2-fluoro-4-methylpyridine | A 100 18 | 1.07 | 501.11 |
| Ib-22 | 1-[(R)-1-(3,5-Dimethoxy-pyridin-4-yl)-pyrrolidin-3-yl]-4-methoxy-3-(2-trifluoromethyl-benzyl)-1,3-dihydro-benzoimidazol-2-one (Example 38) | C-1-2 | 4-Bromo-3,5-dimethoxypyridine | A 100 18 | 0.82 | 529.11 |
| Ib-23 | 1-[(R)-1-(2,6-Dimethyl-phenyl)-pyrrolidin-3-yl]-4-methoxy-3-(2-trifluoromethyl-benzyl)-1,3-dihydro-imidazo[4,5-c]pyridin-2-one (Example 41) | C-1-4 | 2-Bromo-1,3-dimethylbenzene | A 100 18 | 1.03 | 497.12 |
| Ib-24 | 1-[(R)-1-(2,6-Difluoro-phenyl)-pyrrolidin-3-yl]-4-methoxy-3-(2-trifluoromethyl-benzyl)-1,3-dihydro-imidazo[4,5-c]pyridin-2-one (Example 42) | C-1-4 | 2,6-Difluoro bromobenzene | A 100 18 | 1.08 | 505.06 |
| Ib-25 | 3-[(R)-1-(2,6-Dimethyl-phenyl)-pyrrolidin-3-yl]-7-methoxy-1-(2-trifluoromethyl-benzyl)-1,3-dihydro-imidazo[4,5-b]pyridin-2-one (Example 45) | C-1-5 | 2-Bromo-1,3-dimethylbenzene | A 100 18 | 0.86 | 497.14 |
| Ib-26 | 3-[(R)-1-(2,6-Difluoro-phenyl)-pyrrolidin-3-yl]-7-methoxy-1-(2-trifluoromethyl-benzyl)-1,3-dihydro-imidazo[4,5-b]pyridin-2-one (Example 46) | C-1-5 | 2,6-Difluoro bromobenzene | A 100 18 | 1.04 | 505.11 |
| Ib-27 | 4-Methoxy-1-[(R)-1-(2-methoxy-4-methyl-pyridin-3-yl)-pyrrolidin-3-yl]-3-(2-trifluoromethyl-benzyl)-1,3-dihydro-imidazo[4,5-c]pyridin-2-one (Example 47) | C-1-4 | 3-Bromo-2-methoxy-4-methylpyridine | A 100 18 | 1.05 | 514.13 |
| Ib-28 | 1-[(R)-1-(2-Fluoro-4-methyl-pyridin-3-yl)-pyrrolidin-3-yl]-4-methoxy-3-(2-trifluoromethyl-benzyl)-1,3-dihydro-imidazo[4,5-c]pyridin-2-one (Example 48) | C-1-4 | 3-Bromo-2-fluoro-4-methylpyridine | A 100 18 | 1.05 | 502.11 |
| Ib-29 | 1-[(R)-1-(2-Fluoro-6-methoxy-phenyl)-pyrrolidin-3-yl]-4-methoxy-3-(2-trifluoromethyl-benzyl)-1,3-dihydro-imidazo[4,5-c]pyridin-2-one (Example 49) | C-1-4 | 2-Bromo-3-fluoroanisole | A 100 18 | 1.03 | 517.13 |
| Ib-30 | 1-[(R)-1-(2-Fluoro-6-methyl-phenyl)-pyrrolidin-3-yl]-4-methoxy-3-(2-trifluoromethyl-benzyl)-1,3-dihydro-imidazo[4,5-c]pyridin-2-one (Example 50) | C-1-4 | 2-Bromo-3-fluorotoluene | A 100 18 | 1.10 | 501.12 |
| Ib-31 | 4-Methoxy-1-[(R)-1-(2-methoxy-6-methyl-phenyl)-pyrrolidin-3-yl]-3-(2-trifluoromethyl-benzyl)-1,3-dihydro-imidazo[4,5-c]pyridin-2-one (Example 51) | C-1-4 | 2-Bromo-1-methoxy-3-methylbenzene | A 100 18 | 0.88 | 513.05 |
| Ib-32 | 1-[1-(2,6-Dimethyl-phenyl)-piperidin-4-yl]-4-methoxy-3-(2-trifluoromethyl-pyridin-3-ylmethyl)-1,3-dihydro-benzoimidazol-2-one (Example 54) | C-1-6 | 2-Bromo-1,3-dimethylbenzene | A 100 18 | 1.11 | 511.15 |
| Ib-33 | 1-[1-(2,6-Difluoro-phenyl)-piperidin-4-yl]-4-methoxy-3-(2-trifluoromethyl-pyridin-3-ylmethyl)-1,3-dihydro-benzoimidazol-2-one (Example 55) | C-1-6 | 2,6-Difluoro bromobenzene | A 100 18 | 1.07 | 519.11 |

TABLE 25-continued

| Ib | Name | Reactant C-1 | Reactant BB-8 | Method T [° C.] time [h] | $t_R$ [min] | MS-data m/z [M + H]+ |
|---|---|---|---|---|---|---|
| Ib-34 | 1-[1-(2,6-Dimethyl-phenyl)-piperidin-4-yl]-4-methoxy-3-(4-trifluoromethyl-pyridin-3-ylmethyl)-1,3-dihydro-benzoimidazol-2-one (Example 58) | C-1-7 | 2-Bromo-1,3-dimethylbenzene | A 100 18 | 1.14 | 511.19 |
| Ib-35 | 1-[1-(2,6-Difluoro-phenyl)-piperidin-4-yl]-4-methoxy-3-(4-trifluoromethyl-pyridin-3-ylmethyl)-1,3-dihydro-benzoimidazol-2-one (Example 59) | C-1-7 | 2,6-Difluoro bromobenzene | A 100 24 | 1.09 | 519.15 |
| Ib-36 | 1-[(R)-1-(2,4-Dimethyl-pyridin-3-yl)-pyrrolidin-3-yl]-4-methoxy-3-(2-trifluoromethyl-benzyl)-1,3-dihydro-benzoimidazol-2-one (Example 66) | C-1-2 | 3-Bromo-2,4-dimethylpyridine | A 105 18 | 0.81 | 497.12 |
| Ib-37 | 1-[(R)-1-(2,6-Dimethyl-phenyl)-pyrrolidin-3-yl]-4-methoxy-3-(2-methoxy-benzyl)-1,3-dihydro-benzoimidazol-2-one (Example 67) | C-1-8 | 2-Bromo-1,3-dimethylbenzene | A 105 18 | 0.94 | 458.17 |
| Ib-38 | 1-[(R)-1-(2,6-Difluoro-phenyl)-pyrrolidin-3-yl]-4-methoxy-3-(2-methoxy-benzyl)-1,3-dihydro-benzoimidazol-2-one (Example 68) | C-1-8 | 2,6-Difluoro bromobenzene | A 105 18 | 1.05 | 466.49 |
| Ib-39 | 1-[1-(2,6-Dimethyl-phenyl)-piperidin-4-yl]-4-methoxy-3-(3-trifluoromethyl-pyridin-4-ylmethyl)-1,3-dihydro-benzoimidazol-2-one (Example 73) | C-1-9 | 2-Bromo-1,3-dimethylbenzene | A 100 18 | 1.16 | 511.17 |
| Ib-40 | 1-[1-(2,6-Difluoro-phenyl)-piperidin-4-yl]-4-methoxy-3-(3-trifluoromethyl-pyridin-4-ylmethyl)-1,3-dihydro-benzoimidazol-2-one (Example 74) | C-1-9 | 2,6-Difluoro bromobenzene | A 100 18 | 1.11 | 519.11 |
| Ib-41 | 1-[1-(2,6-Dimethyl-phenyl)-piperidin-4-yl]-4-methoxy-3-(3-trifluoromethyl-pyridin-2-ylmethyl)-1,3-dihydro-benzoimidazol-2-one (Example 75) | C-1-10 | 2-Bromo-1,3-dimethylbenzene | A 100 18 | 1.10 | 511.20 |
| Ib-42 | 1-[1-(2,6-Difluoro-phenyl)-piperidin-4-yl]-4-methoxy-3-(3-trifluoromethyl-pyridin-2-ylmethyl)-1,3-dihydro-benzoimidazol-2-one (Example 76) | C-1-10 | 2,6-Difluoro bromobenzene | A 100 18 | 1.06 | 519.11 |
| Ib-43 | 1-[(R)-1-(2,6-Dimethyl-phenyl)-pyrrolidin-3-yl]-4-methoxy-3-(2-methoxy-benzyl)-1,3-dihydro-imidazo[4,5-c]pyridin-2-one (Example 77) | C-1-11 | 2-Bromo-1,3-dimethylbenzene | A 100 18 | 0.98 | 459.16 |
| Ib-44 | 1-[(R)-1-(2-Fluoro-6-methyl-phenyl)-pyrrolidin-3-yl]-4-methoxy-3-(2-methoxy-benzyl)-1,3-dihydro-imidazo[4,5-c]pyridin-2-one (Example 78) | C-1-11 | 2-Bromo-3-fluorotoluene | A 100 18 | 1.05 | 463.12 |
| Ib-45 | 1-[(R)-1-(2-Fluoro-6-methyl-phenyl)-pyrrolidin-3-yl]-4-methoxy-3-(2-methoxy-benzyl)-1,3-dihydro-benzoimidazol-2-one (Example 110) | C-1-8 | 2-Bromo-3-fluorotoluene | A 100 18 | 1.04 | 462.24 |
| Ib-46 | 1-[1-(2-Fluoro-6-methyl-phenyl)-3-methyl-piperidin-4-yl]-4-methoxy-3-(2-trifluoromethyl-benzyl)-1,3-dihydro-benzoimidazol-2-one (Example 147) | C-1-13 | 2-Bromo-3-fluorotoluene | A 105 18 | 1.14 | 528.16 |

TABLE 25-continued

| Ib | Name | Reactant C-1 | Reactant BB-8 | Method T [° C.] time [h] | $t_R$ [min] | MS-data m/z [M + H]+ |
|---|---|---|---|---|---|---|
| Ib-47 | 1-[(R)-1-(2-Fluoro-phenyl)-pyrrolidin-3-yl]-4-methoxy-3-(2-trifluoromethyl-benzyl)-1,3-dihydro-benzoimidazol-2-one (Example 160) | C-1-2 | 1-Bromo-2-fluorobenzene | A 105 18 | 1.07 | 486.07 |
| Ib-48 | 1-[(R)-1-(2-Fluoro-6-morpholin-4-yl-phenyl)-pyrrolidin-3-yl]-4-methoxy-3-(2-trifluoromethyl-benzyl)-1,3-dihydro-benzoimidazol-2-one (Example 161) | C-1-2 | BB-8-4 | A 105 18 | 0.92 | 571.03 |
| Ib-49 | 1-[1-(2-Fluoro-6-methyl-phenyl)-azepan-4-yl]-4-methoxy-3-(2-trifluoromethyl-benzyl)-1,3-dihydro-benzoimidazol-2-one (Example 184) | C-1-14 | 2-Bromo-3-fluorotoluene | A 110 18 | 1.13 | 528.09 |
| Ib-50 | 1-[1-(2,6-Dimethyl-phenyl)-azepan-4-yl]-4-methoxy-3-(2-trifluoromethyl-benzyl)-1,3-dihydro-benzoimidazol-2-one (Example 185) | C-1-14 | 2-Bromo-1,3-dimethylbenzene | A 110 18 | 1.14 | 524.13 |
| Ib-51 | 1-[2-(2-Fluoro-6-methyl-phenyl)-2-aza-bicyclo[2.2.1]hept-5-yl]-4-methoxy-3-(2-trifluoromethyl-benzyl)-1,3-dihydro-benzoimidazol-2-one (Example 190) | C-1-15 | 2-Bromo-3-fluorotoluene | A 110 18 | 0.99 | 526.06 |
| Ib-52 | 1-[3-(2-Fluoro-6-methyl-phenyl)-3-aza-bicyclo[3.1.1]hept-6-yl]-4-methoxy-3-(2-trifluoromethyl-benzyl)-1,3-dihydro-benzoimidazol-2-one (Example 197) | C-1-16 | 2-Bromo-3-fluorotoluene | A 110 2.5 | 1.12 | 526.14 |
| Ib-53 | 1-[(3R*,4S*)-1-(2-Fluoro-6-methyl-phenyl)-4-methyl-pyrrolidin-3-yl]-4-methoxy-3-(2-trifluoromethyl-benzyl)-1,3-dihydro-benzoimidazol-2-one (Example 198) | C-1-17 | 2-Bromo-3-fluorotoluene | A 110 2 | 1.12 | 514.12 |
| Ib-54 | 1-[(3R*,4R*)-1-(2-Fluoro-6-methyl-phenyl)-4-methyl-pyrrolidin-3-yl]-4-methoxy-3-(2-trifluoromethyl-benzyl)-1,3-dihydro-benzoimidazol-2-one (Example 200) | C-1-18 | 2-Bromo-3-fluorotoluene | A 110 18 | 1.05 | 514.10 |
| Ib-55 | 4-Methoxy-1-[(R)-1-(2-trifluoromethoxy-phenyl)-pyrrolidin-3-yl]-3-(2-trifluoromethyl-benzyl)-1,3-dihydro-benzoimidazol-2-one (Example 201) | C-1-2 | 2-(Trifluoro-methoxy)bromo-benzene | A 110 20 | 1.10 | 552.02 |
| Ib-56 | 4-Methoxy-1-{(R)-1-[2-(2-methoxy-ethoxy)-phenyl]-pyrrolidin-3-yl}-3-(2-trifluoromethyl-benzyl)-1,3-dihydro-benzoimidazol-2-one (Example 204) | C-1-2 | 1-Bromo-2-(2-methoxy-ethoxy)benzene | A 110 20 | 0.91 | 542.05 |
| Ib-57 | 1-[3-Fluoro-1-(2-fluoro-6-methyl-phenyl)-piperidin-4-yl]-4-methoxy-3-(2-trifluoromethyl-benzyl)-1,3-dihydro-benzoimidazol-2-one (Example 211) | C-1-19 | 2-Bromo-3-fluorotoluene | A 110 2 | 1.09/1.11 | 532.02 |
| Ib-58 | 1-[1-(2-Fluoro-6-methyl-phenyl)-piperidin-3-yl]-4-methoxy-3-(2-trifluoromethyl-benzyl)-1,3-dihydro-benzoimidazol-2-one (Example 212) | C-1-20 | 2-Bromo-3-fluorotoluene | A 110 18 | 1.11 | 514.05 |
| Ib-59 | 1-[1-(2-Fluoro-6-methyl-phenyl)-azetidin-3-yl]-4-methoxy-3-(2-trifluoromethyl-benzyl)-1,3-dihydro-benzoimidazol-2-one (Example 215) | C-1-21 | 2-Bromo-3-fluorotoluene | A 110 2 | 1.07 | 486.04 |

TABLE 25-continued

| Ib | Name | Reactant C-1 | Reactant BB-8 | Method T [° C.] time [h] | $t_R$ [min] | MS-data m/z [M + H]$^+$ |
|---|---|---|---|---|---|---|
| Ib-60 | 1-[1-(2,6-Dimethyl-phenyl)-piperidin-3-yl]-4-methoxy-3-(2-trifluoromethyl-benzyl)-1,3-dihydro-benzoimidazol-2-one (Example 217) | C-1-20 | 2-Bromo-1,3-dimethylbenzene | A 110 20 | 1.11 | 510.09 |
| Ib-61 | 1-[1-(2-Fluoro-6-methyl-phenyl)-3,3-dimethyl-piperidin-4-yl]-4-methoxy-3-(2-trifluoromethyl-benzyl)-1,3-dihydro-benzoimidazol-2-one (Example 227) | C-1-22 | 2-Bromo-3-fluorotoluene | A 110 18 | 1.16 | 542.18 |
| Ib-62 | 1-[1-(2-Benzyloxy-phenyl)-piperidin-4-yl]-4-methoxy-3-(2-trifluoromethyl-benzyl)-1,3-dihydro-benzoimidazol-2-one (Example 231) | C-1-1 | 2-Benzyloxy bromobenzene | A 100 5 | 0.96 | 588.15 |
| Ib-63 | 4-Methoxy-1-(3'-methyl-3,4,5,6-tetrahydro-2H-[1,2']bipyridinyl-4-yl)-3-(2-trifluoromethyl-benzyl)-1,3-dihydro-benzoimidazol-2-one (Example 232) | C-1-1 | 2-Bromo-3-methylpyridine | A 110 18 | 0.81 | 497.06 |
| Ib-64 | 4-Methoxy-1-(3'-methoxy-3,4,5,6-tetrahydro-2H-[1,2']bipyridinyl-4-yl)-3-(2-trifluoromethyl-benzyl)-1,3-dihydro-benzoimidazol-2-one (Example 233) | C-1-1 | 2-Bromo-3-methoxypyridine | A 110 18 | 0.82 | 513.06 |
| Ib-65 | 4-Methoxy-1-(2'-methoxy-4'-methyl-3,4,5,6-tetrahydro-2H-[1,3']bipyridinyl-4-yl)-3-(2-trifluoromethyl-benzyl)-1,3-dihydro-benzoimidazol-2-one (Example 234) | C-1-1 | 3-Bromo-2-methoxy-4-methylpyridine | A 110 18 | 1.10 | 527.10 |
| Ib-66 | 1-(2'-Fluoro-4'-methyl-3,4,5,6-tetrahydro-2H-[1,3']bipyridinyl-4-yl)-4-methoxy-3-(2-trifluoromethyl-benzyl)-1,3-dihydro-benzoimidazol-2-one (Example 235) | C-1-1 | 3-Bromo-2-fluoro-4-methylpyridine | A 110 18 | 1.08 | 515.09 |
| Ib-67 | 1-(3'-Fluoro-3,4,5,6-tetrahydro-2H-[1,2']bipyridinyl-4-yl)-4-methoxy-3-(2-trifluoromethyl-benzyl)-1,3-dihydro-benzoimidazol-2-one (Example 236) | C-1-1 | 2-Bromo-3-fluoropyridine | A 110 18 | 1.00 | 501.12 |
| Ib-68 | 1-(2',4'-Dimethyl-3,4,5,6-tetrahydro-2H-[1,3']bipyridinyl-4-yl)-4-methoxy-3-(2-trifluoromethyl-benzyl)-1,3-dihydro-benzoimidazol-2-one (Example 237) | C-1-1 | 3-Bromo-2,4-dimethylpyridine | A 110 18 | 0.81 | 511.18 |
| Ib-69 | 1-(4'-Fluoro-2'-methyl-3,4,5,6-tetrahydro-2H-[1,3']bipyridinyl-4-yl)-4-methoxy-3-(2-trifluoromethyl-benzyl)-1,3-dihydro-benzoimidazol-2-one (Example 244) | C-1-1 | 3-Bromo-4-fluoro-2-methylpyridine | A 110 6 | 0.84 | 515.16 |
| Ib-70 | 1-[1-(2-Fluoro-6-methyl-phenyl)-piperidin-4-yl]-4-methyl-3-(2-trifluoromethyl-benzyl)-1,3-dihydro-benzoimidazol-2-one (Example 245) | C-1-23 | 2-Bromo-3-fluorotoluene | A 100 2 | 1.32 | 498.17 |
| Ib-71 | 4-[4-Methoxy-2-oxo-3-(2-trifluoromethyl-benzyl)-2,3-dihydro-benzoimidazol-1-yl]-4'-methyl-3,4,5,6-tetrahydro-2H-[1,3']bipyridinyl-2'-carbonitrile (Example 246) | C-1-1 | 3-Bromo-4-methyl-picolinonitrile | A 110 18 | 1.06 | 522.18 |
| Ib-72 | 4-Methoxy-1-(4'-methoxy-2'-methyl-3,4,5,6-tetrahydro-2H-[1,3']bipyridinyl-4-yl)-3-(2-trifluoromethyl-benzyl)-1,3-dihydro-benzoimidazol-2-one (Example 247) | C-1-1 | BB-8-6 | A 110 18 | 0.83 | 527.18 |

TABLE 25-continued

| Ib | Name | Reactant C-1 | Reactant BB-8 | Method T [° C.] time [h] | $t_R$ [min] | MS-data m/z [M + H]$^+$ |
|---|---|---|---|---|---|---|
| Ib-73 | 1-(2',4'-Dimethoxy-3,4,5,6-tetrahydro-2H-[1,3']bipyridinyl-4-yl)-4-methoxy-3-(2-trifluoromethyl-benzyl)-1,3-dihydro-benzoimidazol-2-one (Example 248) | C-1-1 | 3-Bromo-2,4-dimethoxypyridine | A 110 18 | 0.87 | 543.06 |
| Ib-74 | 4-Methoxy-1-[1-(4-methoxy-6-methyl-pyrimidin-5-yl)-piperidin-4-yl]-3-(2-trifluoromethyl-benzyl)-1,3-dihydro-benzoimidazol-2-one (Example 249) | C-1-1 | 5-Bromo-4-methoxy-6-methylpyrimidine | A 110 18 | 0.93 | 528.12 |
| Ib-75 | 1-[1-(4,6-Dimethoxy-pyrimidin-5-yl)-piperidin-4-yl]-4-methoxy-3-(2-trifluoromethyl-benzyl)-1,3-dihydro-benzoimidazol-2-one (Example 250) | C-1-1 | 5-Bromo-4,6-dimethoxypyrimidine | A 110 4 | 1.04 | 544.05 |

Synthesis of Compounds of Formula Ic

Method A (standard SN$_{Ar}$/CsF)

To a soln. of C-1 (1 eq) and BB-8 (to 1.1 eq) in DMSO (3 mL/mmol) was added CsF (2 eq). The rxn mixture was heated at a given temperature for a given time (see Table 26) and was partitioned between EtOAc and water. The org. phase was washed with water (3×) and with brine, dried over MgSO$_4$ and concentrated in vacuo. The crude was purified by CC using Hept/EtOAc.

Method B (PyBOP Activated SN$_{Ar}$)

C-1 (1 eq), BB-8 (1.5 eq) and DIPEA (3 eq) were dissolved in anh. DMF (5 mL/mmol) and the mixture was stirred for 5 min at RT. PyBOP (1.8 eq) was added portionwise and the rxn mixture was further stirred at RT for a given time (see Table 26). It was partitioned between EtOAc and a 5% aq. soln. of KHSO$_4$ and the org. phase was washed with a sat. aq. soln. of NaHCO$_3$ (2×) and brine, dried over MgSO$_4$ and concentrated in vacuo. The crude was purified by CC using Hept/EtOAc.

Method C (Standard SN$_{Ar}$/K$_2$CO$_3$)

The procedure is similar to method A replacing CsF by K$_2$CO$_3$ (2 eq).

Method D (PyBOP Activated SN$_{Ar}$+Cyclodehydration)

The procedure is similar to method B but the resulting open form product is additionally submitted to a cyclodehydration as follows:

The open form product (1 eq) was dissolved in anh. THF and Burgess' reagent (2.5 eq) was added portionwise at RT (see Table 26). The rxn mixture was stirred at 150° C. for 30 min under microwave condition and partitioned between EtOAc and H$_2$O. The org. phase was washed with brine, dried over MgSO$_4$ and concentrated in vacuo. The crude was purified by CC using Hept/EtOAc.

TABLE 26

| Ic | Name | Reactant C-1 | Reactant BB-8 | Method T [° C.] time [h] | $t_R$ [min] | MS-data m/z [M + H]$^+$ |
|---|---|---|---|---|---|---|
| Ic-1 | 3-Cyclopropyl-5-{4-[4-methoxy-2-oxo-3-(2-trifluoromethyl-benzyl)-2,3-dihydro-benzoimidazol-1-yl]-piperidin-1-yl}-1-methyl-1H-pyrazole-4-carbaldehyde (Example 14) | C-1-1 | 5-Chloro-3-cyclopropyl-1-methyl-1H-pyrazole-4-carbaldehyde | A 100 96 | 1.04 | 554.09 |
| Ic-2 | 1-[(R)-1-(5-Isopropyl-[1,3,4]oxadiazol-2-yl)-pyrrolidin-3-yl]-4-methoxy-3-(2-trifluoromethyl-benzyl)-1,3-dihydro-benzoimidazol-2-one (Example 69) | C-1-2 | BB-8-5 | B RT 18 | 0.98 | 502.14 |
| Ic-3 | 5-{(R)-3-[4-Methoxy-2-oxo-3-(2-trifluoromethyl-benzyl)-2,3-dihydro-benzoimidazol-1-yl]-pyrrolidin-1-yl}-1,3-dimethyl-1H-pyrazole-4-carbaldehyde (Example 71) | C-1-2 | 5-chloro-1,3-dimethyl-1H-pyrazole-4-carbaldehyde | A 100 18 | 0.99 | 514.16 |

TABLE 26-continued

| Ic | Name | Reactant C-1 | Reactant BB-8 | Method T [° C.] time [h] | $t_R$ [min] | MS-data m/z [M + H]$^+$ |
|---|---|---|---|---|---|---|
| Ic-4 | 3-Fluoro-2-{(R)-3-[4-methoxy-2-oxo-3-(2-trifluoromethyl-benzyl)-2,3-dihydro-benzoimidazol-1-yl]-pyrrolidin-1-yl}-benzonitrile (Example 82) | C-1-2 | 2,3-Difluoro benzonitrile | C 80 18 | 1.06 | 511.13 |
| Ic-5 | 3-Fluoro-2-{(R)-3-[4-methoxy-2-oxo-3-(2-trifluoromethyl-benzyl)-2,3-dihydro-benzoimidazol-1-yl]-pyrrolidin-1-yl}-benzaldehyde (Example 83) | C-1-2 | 2,3-Difluoro benzaldehyde | C 100 18 | 1.06 | 514.16 |
| Ic-6 | 4-Methoxy-3-(2-trifluoromethyl-benzyl)-1-[(R)-1-(5-trifluoromethyl-[1,3,4]oxadiazol-2-yl)-pyrrolidin-3-yl]-1,3-dihydro-benzoimidazol-2-one (Example 84) | C-1-2 | 5-(Trifluoromethyl)-1,3,4-oxadiazol-2-ol | D RT 24 | 1.00 | 528.10 |
| Ic-7 | 5-{(R)-3-[4-Methoxy-2-oxo-3-(2-trifluoromethyl-benzyl)-2,3-dihydro-benzoimidazol-1-yl]-pyrrolidin-1-yl}-1,3-dimethyl-1H-pyrazole-4-carbonitrile (Example 87) | C-1-2 | 5-chloro-1,3-dimethyl-1H-pyrazole-4-carbonitrile | A 80 24 | 1.00 | 511.34 |
| Ic-8 | 3-Fluoro-2-{(R)-3-[4-methoxy-3-(2-methoxy-benzyl)-2-oxo-2,3-dihydro-benzoimidazol-1-yl]-pyrrolidin-1-yl}-benzonitrile (Example 109) | C-1-8 | 2,3-Difluoro benzonitrile | C 105 3 | 1.02 | 473.21 |
| Ic-9 | 3-Fluoro-2-{4-[4-methoxy-2-oxo-3-(2-trifluoromethyl-benzyl)-2,3-dihydro-benzoimidazol-1-yl]-2-methyl-piperidin-1-yl}-benzaldehyde (Example 145) | C-1-13 | 2,3-Difluoro benzaldehyde | C 105 72 | 1.10 | 542.13 |
| Ic-10 | 1-[(R)-1-(2-Fluoro-6-nitro-phenyl)-pyrrolidin-3-yl]-4-methoxy-3-(2-trifluoromethyl-benzyl)-1,3-dihydro-benzoimidazol-2-one (Example 154) | C-1-2 | 2,3-Difluoro nitrobenzene | C 100 18 | 1.07 | 530.98 |
| Ic-11 | 1-[(R)-1-(4,5-Dichloro-pyridazin-3-yl)-pyrrolidin-3-yl]-4-methoxy-3-(2-trifluoromethyl-benzyl)-1,3-dihydro-benzoimidazol-2-one (Example 157) | C-1-2 | 3,4,5-Trichloro pyridazine | C RT 48 then 60 24 | 1.04 | 537.92 |
| Ic-12 | 1-[(R)-1-(3,5-Dichloro-pyridazin-4-yl)-pyrrolidin-3-yl]-4-methoxy-3-(2-trifluoromethyl-benzyl)-1,3-dihydro-benzoimidazol-2-one (Example 158) | C-1-2 | 3,4,5-Trichloro pyridazine | C RT 48 then 60 24 | 1.03 | 538.00 |

Synthesis of Compounds of Formula Id

To a soln. of Ic (1 eq) in MeOH (8 mL/mmol) was added toluene-4-sulfonic acid monohydrate (0.2 eq) and the rxn mixture was heated at 120° C. under microwave condition for a given time (see Table 27). It was concentrated in vacuo and partitioned between EtOAc and a sat. aq. soln. of NaHCO$_3$. The org. phase was washed with brine, dried over MgSO$_4$ and concentrated in vacuo. The crude was purified by CC using Hept/EtOAc.

TABLE 27

| Id | Name | Reactant Ic | T [° C.] time [h] | $t_R$ [min] | MS-data m/z [M + H]$^+$ |
|---|---|---|---|---|---|
| Id-1 | 1-[1-(5-Cyclopropyl-2-methyl-2H-pyrazol-3-yl)-piperidin-4-yl]-4-methoxy-3-(2-trifluoromethyl-benzyl)-1,3-dihydro-benzoimidazol-2-one (Example 21) | Ic-1 | 120 0.25 | 0.94 | 525.97 |
| Id-2 | 1-[(R)-1-(2,5-Dimethyl-2H-pyrazol-3-yl)-pyrrolidin-3-yl]-4-methoxy-3-(2-trifluoromethyl-benzyl)-1,3-dihydro-benzoimidazol-2-one (Example 79) | Ic-3 | 120 0.35 | 0.84 | 486.33 |

Synthesis of Compounds of Formula Ie

To a soln. of Id (1 eq) in THF (4.5 mL/mmol) was added NCS (1.4 eq) and the rxn mixture was stirred at RT for a given time (see Table 28). It was partitioned between EtOAc and water and the org. phase was washed with brine, dried over MgSO$_4$ and concentrated in vacuo. The crude was purified by CC using Hept/EtOAc.

TABLE 28

| Ie | Name | Reactant Id | time [h] | $t_R$ [min] | MS-data m/z [M + H]$^+$ |
|---|---|---|---|---|---|
| Ie-1 | 1-[1-(4-Chloro-5-cyclopropyl-2-methyl-2H-pyrazol-3-yl)-piperidin-4-yl]-4-methoxy-3-(2-trifluoromethyl-benzyl)-1,3-dihydro-benzoimidazol-2-one (Example 24) | Id-1 | 1 | 1.11 | 560.11 |
| Ie-2 | 1-[(R)-1-(4-Chloro-2,5-dimethyl-2H-pyrazol-3-yl)-pyrrolidin-3-yl]-4-methoxy-3-(2-trifluoromethyl-benzyl)-1,3-dihydro-benzoimidazol-2-one (Example 80) | Id-2 | 0.25 | 1.07 | 520.12 |

Synthesis of Compounds of Formula If

To a stirred soln. of Ic (1eq) in a mixture of DMF (0.5 mL) was added toluene-4-sulfonic acid monohydrate (0.13 eq) and 4-toluenesulfonyhydrazide (1.3eq) followed by sulfolane (0.5 mL) (see Table 29). The mixture was stirred at 100° C. for 1h and cooled to RT. Sodium cyanoborohydride (4eq) was added portionwise and the mixture was stirred at 100° C. for 24h. It was quenched with a sat. aq. soln. of NaHCO$_3$ and extracted 3× with EtOAc. The combined org. phases were washed with brine, dried over MgSO$_4$ and concentrated in vacuo. The crude was purified by prep. LC-MS using method 3.

TABLE 29

| If | Name | Reactant Ic | $t_R$ [min] | MS-data m/z [M + H]$^+$ |
|---|---|---|---|---|
| If-1 | 1-[1-(5-Cydopropyl-2,4-dimethyl-2H-pyrazol-3-yl)-piperidin-4-yl]-4-methoxy-3-(2-trifluoromethyl-benzyl)-1,3-dihydro-benzoimidazol-2-one (Example 25) | Ic-1 | 0.95 | 540.15 |

Synthesis of Compounds of Formula Iq

To a soln. of C-1 (1 eq) and TEA (3eq) in a given solvent (5 mL/mmol) (see) was added at 0° C. alkyl choroformate or pentafluorophenylcarbonate-8 (1.2eq). The rxn mixture was allowed to warm to RT and stirred at a given temperature for a given time (see Table 30). It was partitioned between DCM and a sat. aq. soln. of NaHCO$_3$. The org. phase was washed with brine, dried over MgSO$_4$ and concentrated in vacuo. The crude was purified by CC using DCM/MeOH or Hept/EtOAc. If necessary a second purification by prep. L-MS using method 2, 3 or 6 can be performed.

TABLE 30

| Ig | Name | Reactant C-1 | Reactant BB-8 | Solvent T [° C.] time [h] | $t_R$ [min] | MS-data m/z [M + H]$^+$ |
|---|---|---|---|---|---|---|
| Ig-1 | (R)-3-[4-Methoxy-2-oxo-3-(2-trifluoromethyl-benzyl)-2,3-dihydro-benzoimidazol-1-yl]-pyrrolidine-1-carboxylic acid methyl ester (Example 26) | C-1-2 | Methyl chloroformate | DCM RT 2 | 0.95 | 450.04 |
| Ig-2 | 4-[4-Methoxy-2-oxo-3-(2-trifluoromethyl-benzyl)-2,3-dihydro-benzoimidazol-1-yl]-piperidine-1-carboxylic acid methyl ester (Example 29) | C-1-1 | Methyl chloroformate | DCM RT 1 | 0.97 | 464.05 |

TABLE 30-continued

| Ig | Name | Reactant C-1 | Reactant BB-8 | Solvent T [° C.] time [h] | $t_R$ [min] | MS-data m/z [M + H]$^+$ |
|---|---|---|---|---|---|---|
| Ig-3 | (R)-3-[4-Methoxy-2-oxo-3-(2-trifluoromethyl-benzyl)-2,3-dihydro-benzoimidazol-1-yl]-pyrrolidine-1-carboxylic acid ethyl ester (Example 60) | C-1-2 | Ethyl chloroformate | DCM RT 18 | 0.97 | 464.06 |
| Ig-4 | (R)-3-[4-Methoxy-2-oxo-3-(2-trifluoromethyl-benzyl)-2,3-dihydro-benzoimidazol-1-yl]-pyrrolidine-1-carboxylic acid isopropyl ester (Example 61) | C-1-2 | Isopropylchloroformate | DCM RT 18 | 1.00 | 478.09 |
| Ig-5 | (R)-3-[4-Methoxy-2-oxo-3-(2-trifluoromethyl-benzyl)-2,3-dihydro-benzoimidazol-1-yl]-pyrrolidine-1-carboxylic acid butyl ester (Example 62) | C-1-2 | n-Butyl chloroformate | DCM RT 18 | 1.03 | 492.11 |
| Ig-6 | (R)-3-[4-Methoxy-2-oxo-3-(2-trifluoromethyl-benzyl)-2,3-dihydro-benzoimidazol-1-yl]-pyrrolidine-1-carboxylic acid phenyl ester (Example 63) | C-1-2 | Phenyl chloroformate | DCM RT 18 | 1.01 | 512.10 |
| Ig-7 | (R)-3-[4-Methoxy-2-oxo-3-(2-trifluoromethyl-benzyl)-2,3-dihydro-benzoimidazol-1-yl]-pyrrolidine-1-carboxylic acid 3-methyl-oxetan-3-yl ester (Example 70) | C-1-2 | BB-8-1 | DMF 110° C. 0.25 | 0.95 | 506.13 |
| Ig-8 | (R)-3-[4-Methoxy-2-oxo-3-(2-trifluoromethyl-benzyl)-2,3-dihydro-benzoimidazol-1-yl]-pyrrolidine-1-carboxylic acid oxetan-3-yl ester (Example 72) | C-1-2 | BB-8-2 | DMF 110° C. 0.25 | 0.93 | 492.09 |
| Ig-9 | (R)-3-[4-Methoxy-2-oxo-3-(2-trifluoromethyl-benzyl)-2,3-dihydro-benzoimidazol-1-yl]-pyrrolidine-1-carboxylic acid 3-trifluoromethyl-oxetan-3-yl ester (Example 86) | C-1-2 | BB-8-3 | DMF 110° C. 0.5 | 1.00 | 560.13 |

Synthesis of Compounds of Formula Ih

To a soln. of C-1(1 eq) and TEA (3eq) in DCM (5 mL/mmol) was added at 0° C. acid chloride BB1-8 (1 to 1.2 eq). The rxn mixture was stirred at RT for a given time (see Table 31) and partitioned between DCM and a sat. aq. soln. of NaHCO$_3$. The org. phase was washed with brine, dried over MgSO$_4$ and concentrated in vacuo. The crude was purified by CC using Hept/EtOAc.

TABLE 31

| Ih | Name | Reactant C-1 | Reactant BB-8 | time [h] | $t_R$ [min] | MS-data m/z [M + H]$^+$ |
|---|---|---|---|---|---|---|
| Ih-1 | 1-((R)-1-Benzoyl-pyrrolidin-3-yl)-4-methoxy-3-(2-trifluoromethyl-benzyl)-1,3-dihydro-benzoimidazol-2-one (Example 27) | C-1-2 | Benzoyl chloride | 1.5 | 0.97 | 496.00 |
| Ih-2 | 1-[1-(2,2-Dimethyl-propionyl)-piperidin-4-yl]-4-methoxy-3-(2-trifluoromethyl-benzyl)-1,3-dihydro-benzoimidazol-2-one (Example 28) | C-1-1 | Pivaloyl chloride | 1 | 1.00 | 490.12 |
| Ih-3 | 1-(1-Benzoyl-piperidin-4-yl)-4-methoxy-3-(2-trifluoromethyl-benzyl)-1,3-dihydro-benzoimidazol-2-one (Example 30) | C-1-1 | Benzoyl chloride | 1 | 0.98 | 510.10 |
| Ih-4 | 1-(1-Cyclopropanecarbonyl-piperidin-4-yl)-4-methoxy-3-(2-trifluoromethyl-benzyl)-1,3-dihydro-benzoimidazol-2-one (Example 222) | C-1-1 | Cyclopropane carbonyl chloride | 1.5 | 0.95 | 474.07 |

Synthesis of Compounds of Formula Ii

Method a (Sodium Triacetoxyborohydride)

To a soln. of C-1 (1eq) in a mixture of DCM (25 mL/mmol) and MeOH (50 mL/mmol) were added AcOH (1.2 eq) and aldehyde BB-8 (1.3 eq) followed by NaBH(OAc)$_3$ (1.4 eq) portionwise. The rxn mixture was stirred at RT for a given time (see Table 32). It was quenched with a sat. aq. soln. of NaHCO$_3$ and extracted with DCM (3×). The combined org. phases were dried over MgSO$_4$ and concentrated in vacuo. The crude was purified by CC using DCM/MeOH.

Method B (Indium(III) Chloride/Triethylsilane)

To a soln. of C-1 (1eq) in MeOH (5 mL/mmol) was added BB1-8 (1.1 eq) and the rxn mixture was stirred for 15 min. Triethylsilane (2eq) and indium(III) chloride (0.3 eq) were added and the rxn mixture was stirred at RT for a given time (see Table 32). It was quenched with a sat. aq. soln. of K$_2$CO$_3$ and extracted with DCM (3×). The combined org. phases were washed with brine, dried over MgSO$_4$ and concentrated in vacuo. The crude was purified by prep. LC-MS using method 6.

Method C (Alkylation)

To a soln. of C-1 (1eq) in MeCN (5 mL/mmol) was added K$_2$CO$_3$ (4 eq) and BB-8 (5 eq) and the rxn mixture was stirred at 65° C. for a given time (see Table 32). It was partitioned between EtOAc and water and the org. phase was washed with brine, dried over MgSO$_4$ and concentrated in vacuo. The crude was purified by CC using DCM/MeOH.

TABLE 32

| Ii | Name | Reactant C-1 | Reactant BB-8 | Method time [h] | $t_R$ [min] | MS-data m/z [M + H]$^+$ |
|---|---|---|---|---|---|---|
| Ii-1 | 4-Methoxy-1-((R)-1-methyl-pyrrolidin-3-yl)-3-(2-trifluoromethyl-benzyl)-1,3-dihydro-benzoimidazol-2-one (Example 31) | C-1-2 | Formaldehyde (37% in H$_2$O) | A 18 | 0.75 | 406.15 |
| Ii-2 | 1-((R)-1-Isopropyl-pyrrolidin-3-yl)-4-methoxy-3-(2-trifluoromethyl-benzyl)-1,3-dihydro-benzoimidazol-2-one (Example 32) | C-1-2 | Acetone | B 18 | 0.76 | 434.13 |
| Ii-3 | 1-(1-Isopropyl-piperidin-4-yl)-4-methoxy-3-(2-trifluoromethyl-benzyl)-1,3-dihydro-benzoimidazol-2-one (Example 35) | C-1-1 | 2-Iodopropane | C 2 | 0.76 | 448.13 |

Synthesis of Compounds of Formula Ij

Method a (Methyl Ether Cleavage with BBr$_3$)

To soln. of Ib (1eq) in DCM (4 mL/mmol) was added dropwise at 0° C. a 1M soln. of BBr$_3$ in DCM (3eq). The rxn mixture was allowed to warm to RT and stirred for a given time (see Table 33). The mixture was quenched with chilled H$_2$O and extracted with DCM (3×). The combined org. phases were dried over MgSO$_4$ and concentrated in vacuo. The crude was purified by CC using Hept/EtOAc.

Method B (Methoxypyridine Cleavage with BBr$_3$)

To a soln. of Ib (1 eq) in DCM (20 to 35 mL/mmol) was added dropwise at −10° C. a 1M soln. of BBr$_3$ in DCM (2 eq). The rxn mixture was stirred at −10° C. for 30 min, allowed to warm to RT and stirred for a given time (see Table 33). The mixture was quenched with chilled H$_2$, basified with a sat. aq. soln. of NaHCO$_3$ and extracted with EtOAc (3×). The combined org. phases were washed with brine, dried over MgSO$_4$ and concentrated in vacuo. The crude was purified by CC using Hept/EtOAc or DCM/MeOH.

TABLE 33

| Ij | Name | Reactant | Method time [h] | $t_R$ [min] | MS-data m/z [M + H]$^+$ |
|---|---|---|---|---|---|
| Ij-1 | 1-[(R)-1-(2-Fluoro-6-methyl-phenyl)-pyrrolidin-3-yl]-4-hydroxy-3-(2-trifluoromethyl-benzyl)-1,3-dihydro-benzoimidazol-2-one (Example 40) | Ib-11 | A 18 | 0.99 | 486.11 |
| Ij-2 | 1-[(R)-1-(2,6-Dimethyl-phenyl)-pyrrolidin-3-yl]-4-hydroxy-3-(2-trifluoromethyl-benzyl)-1,3-dihydro-benzoimidazol-2-one (Example 44) | Ib-5 | A 3 | 0.91 | 482.15 |

TABLE 33-continued

| Ij | Name | Reactant | Method time [h] | $t_R$ [min] | MS-data m/z $[M + H]^+$ |
|---|---|---|---|---|---|
| Ij-3 | 1-[(R)-1-(2-Fluoro-6-methoxy-phenyl)-pyrrolidin-3-yl]-4-hydroxy-3-(2-trifluoromethyl-benzyl)-1,3-dihydro-2H-imidazo[4,5-c]pyridin-2-one (tautomeric form: 1-[(R)-1-(2-Fluoro-6-methoxy-phenyl)-pyrrolidin-3-yl]-3-(2-trifluoromethyl-benzyl)-3,5-dihydro-1H-imidazo[4,5-c]pyridine-2,4-dione) (Example 56) | Ib-29 | B 18 | 0.85 | 503.10 |
| Ij-4 | 1-[(R)-1-(2-Fluoro-6-methyl-phenyl)-pyrrolidin-3-yl]-4-hydroxy-3-(2-trifluoromethyl-benzyl)-1,3-dihydro-2H-imidazo[4,5-c]pyridin-2-one (tautomeric form 1-[(R)-1-(2-Fluoro-6-methyl-phenyl)-pyrrolidin-3-yl]-3-(2-trifluoromethyl-benzyl)-3,5-dihydro-1H-imidazo[4,5-c]pyridine-2,4-dione) (Example 57) | Ib-30 | B 42 | 0.94 | 487.22 |
| Ij-5 | 1-[(R)-1-(2-Fluoro-6-methyl-phenyl)-pyrrolidin-3-yl]-4-hydroxy-3-(2-methoxy-benzyl)-1,3-dihydro-imidazo[4,5-c]pyridin-2-one (tautomeric form 1-[(R)-1-(2-Fluoro-6-methyl-phenyl)-pyrrolidin-3-yl]-3-(2-methoxy-benzyl)-3,5-dihydro-1H-imidazo[4,5-c]pyridine-2,4-dione (Example 81) | Ib-44 | B 24 | 0.88 | 449.14 |
| Ij-6 | 1-[(R)-1-(2,6-Dimethyl-phenyl)-pyrrolidin-3-yl]-4-hydroxy-3-(2-trifluoromethyl-benzyl)-1,3-dihydro-2H-imidazo[4,5-c]pyridin-2-one (tautomeric form 1-[(R)-1-(2,6-Dimethyl-phenyl)-pyrrolidin-3-yl]-3-(2-trifluoromethyl-benzyl)-3,5-dihydro-1H-imidazo[4,5-c]pyridine-2,4-dione) (Example 93) | Ib-23 | B 36 | 0.85 | 483.15 |
| Ij-7 | 4-Hydroxy-1-[(R)-1-(2-methoxy-6-methyl-phenyl)-pyrrolidin-3-yl]-3-(2-trifluoromethyl-benzyl)-1,3-dihydro-2H-imidazo[4,5-c]pyridin-2-one (tautomeric form 1-[(R)-1-(2-Methoxy-6-methyl-phenyl)-pyrrolidin-3-yl]-3-(2-trifluoromethyl-benzyl)-3,5-dihydro-1H-imidazo[4,5-c]pyridine-2,4-dione) (Example 94) | Ib-31 | B 36 | 0.75 | 499.15 |

35

Synthesis of Compounds of Formula Ik

To a stirred soln. of Ij (1 eq) in DMSO (10 mL/mmol) was added $K_2C_3$ (2 eq) followed by the corresponding halide (1.1 eq). The rxn mixture was stirred at a given temperature for a given time (see Table 34). It was partitioned between EtOAc and $H_2O$. The org. phase was washed with water (3×) and brine, dried over $MgSO_4$ and concentrated in vacuo. The crude was purified by CC using Hept/EtOAc or by prep. LC-MS using method 3.

TABLE 34

| Ik | Name | Reactant Ij | Reactant halide | T [° C.] time [h] | $t_R$ [min] | MS-data m/z $[M + H]^+$ |
|---|---|---|---|---|---|---|
| Ik-1 | 1-[(R)-1-(2,6-Dimethyl-phenyl)-pyrrolidin-3-yl]-4-(2-hydroxy-ethoxy)-3-(2-trifluoromethyl-benzyl)-1,3-dihydro-benzoimidazol-2-one (Example 52) | Ij-2 | 2-Bromoethanol | 50 72 | 0.92 | 526.15 |
| Ik-2 | 1-[(R)-1-(2-Fluoro-6-methyl-phenyl)-pyrrolidin-3-yl]-4-(oxetan-3-yloxy)-3-(2-trifluoromethyl-benzyl)-1,3-dihydro-benzoimidazol-2-one (Example 149) | Ij-1 | 3-Bromoxetane | 105 2 then 60 72 | 1.06 | 542.10 |
| Ik-3 | 1-[(R)-1-(2-Fluoro-6-methyl-phenyl)-pyrrolidin-3-yl]-4-(2-hydroxy-ethoxy)-3-(2-trifluoromethyl-benzyl)-1,3-dihydro-benzoimidazol-2-one (Example 150) | Ij-1 | 2-Bromoethanol | 100 1.5 then 80 18 | 1.00 | 529.99 |
| Ik-4 | 4-(2,2-Dimethyl-[1,3]dioxolan-4-ylmethoxy)-1-[(R)-1-(2-fluoro-6-methyl-phenyl)-pyrrolidin-3-yl]-3-(2-trifluoromethyl-benzyl)-1,3-dihydro-benzoimidazol-2-one (Example 151) | Ij-1 | 4-(Bromomethyl)-2,2-dimethyl-1,3-dioxolane | 100 1.5 then 80 18 | 1.10 | 600.05 |

Synthesis of compounds of formula Il

To a mixture of Ie (1 eq), boron species (3 eq) and K$_2$C3(5 eq) in dioxane (4 mL/mmol) under N$_2$, was added PEPPSI-Pr (0.1 eq). The rxn mixture was flushed with N$_2$, heated at a given temperature and stirred for a given time (see Table 35). It was partitioned between water and EtOAc and the org. phase was washed with brine, dried over MgSO$_4$ and concentrated in vacuo. The crude was purified by CC using Hept/EtOAc. When necessary an additional purification by prep. LC-MS was performed.

TABLE 35

| Ie | Name | Reactant Ie | Boron species | T [° C.] time [h] | $t_R$ [min] | MS-data m/z [M + H]$^+$ |
|---|---|---|---|---|---|---|
| Ie | 4-Methoxy-3-(2-trifluoromethyl-benzyl)-1-[(R)-1-(2,4,5-trimethyl-2H-pyrazol-3-yl)-pyrrolidin-3-yl]-1,3-dihydro-benzoimidazol-2-one (Example 85) | Ie-2 | Trimethyl boroxine | 115 5.5 | 0.90 | 500.98 |

Synthesis of Compounds of Formula Im

To a stirred soln. of Ic (1 eq) in MeOH (4 mL/mmol) was added portionwise at 0° C. NaBH$_4$ (2 eq). The rxn mixture was stirred at RT for a given time (see Table 36) and quenched with H$_2$O. It was extracted with DCM (3×) and the combined org. phases were washed with brine, dried over MgSO$_4$ and concentrated in vacuo. The crude was purified by CC using Hept/EtOAc.

TABLE 36

| Im | Name | Reactant Ic | time [h] | $t_R$ [min] | MS-data m/z [M + H]$^+$ |
|---|---|---|---|---|---|
| Im-1 | 1-[(R)-1-(2-Fluoro-6-hydroxymethyl-phenyl)-pyrrolidin-3-yl]-4-methoxy-3-(2-trifluoromethyl-benzyl)-1,3-dihydro-benzoimidazol-2-one (Example 88) | Ic-5 | 1 | 0.99 | 516.15 |

Synthesis of Compounds of Formula in

To a stirred soln. of Ic (1 eq) in THF (20 mL/mmol) under argon was added dropwise at 0° C. a 3M soln. of MeMgBr in Et$_2$O (2 eq). The rxn mixture was stirred for a given time (see Table 37) allowing temperature to reach RT. The mixture was cooled to 0° C., quenched with a sat. aq. soln. of NH$_4$C and extracted with EtOAc (3×). The combined org. phases were washed with brine, dried over MgSO$_4$ and concentrated in vacuo. The crude was purified by CC using Hept/EtOAc.

TABLE 37

| In | Name | Reactant Ic | time [h] | $t_R$ [min] | MS-data m/z [M + H]$^+$ |
|---|---|---|---|---|---|
| In-1 | 1-{(R)-1-[2-Fluoro-6-(1-hydroxy-ethyl)-phenyl]-pyrrolidin-3-yl}-4-methoxy-3-(2-trifluoromethyl-benzyl)-1,3-dihydro-benzoimidazol-2-one (Example 89) | Ic-5 | 0.25 | 1.00 | 530.05 |

Synthesis of Compounds of Formula Io

To a stirred soln. of In (1eq) in DCM (3 mL/mmol) was added a 15% soln. of DMP in DCM (1.5 eq). The rxn mixture was stirred at RT for a given time (see Table 38). The mixture was quenched with a sat. aq. soln. of NaHCO$_3$ and extracted with DCM (3×). The combined org. phases were washed with brine, dried over MgSO$_4$ and concentrated in vacuo. The crude was purified by CC using Hept/EtOAc.

TABLE 38

| Io | Name | Reactant Ic | time [h] | $t_R$ [min] | MS-data m/z [M + H]$^+$ |
|---|---|---|---|---|---|
| Io-1 | 1-[(R)-1-(2-Acetyl-6-fluoro-phenyl)-pyrrolidin-3-yl]-4-methoxy-3-(2-trifluoromethyl-benzyl)-1,3-dihydro-benzoimidazol-2-one (Example 90) | In-1 | 4.5 | 1.04 | 528.15 |

Synthesis of Compounds of Formula Ip

The procedure was similar to the one synthesizing compounds of formula In except that reactant Ic were replaced by reactant Io (see Table 39).

TABLE 39

| Ip | Name | Reactant In | time [h] | $t_R$ [min] | MS-data m/z [M + H]$^+$ |
|---|---|---|---|---|---|
| Ip-1 | 1-{(R)-1-[2-Fluoro-6-(1-hydroxy-1-methyl-ethyl)-phenyl]-pyrrolidin-3-yl}-4-methoxy-3-(2-trifluoromethyl-benzyl)-1,3-dihydro-benzoimidazol-2-one (Example 91) | Io-1 | 0.4 | 0.96 | 544.17 |

Synthesis of Intermediates of Formula C-3

Intermediates C-3 were prepared using a similar protocol as for the synthesis of intermediates A-1 replacing amine building blocks BB-1 by amine building blocks BB-4 (see Table 40).

TABLE 40

| C-3 | Name | Reactant BB-2 | Reactant BB-4 | T [° C.] time [h] | $t_R$ [min] | MS-data m/z [M + H]$^+$ |
|---|---|---|---|---|---|---|
| C-3-1 | [(R)-1-(2-Fluoro-6-methyl-phenyl)-pyrrolidin-3-yl]-(3-methoxy-2-nitro-phenyl)-amine | 3-Fluoro-2-nitroanisole | BB-4-1 | 105 24 | 1.03 | 346.08 |
| C-3-2 | 3-[(R)-1-(2-Cyano-6-fluoro-phenyl)-pyrrolidin-3-ylamino]-2-nitro-benzoic acid methyl ester | Methyl 3-Fluoro-2-nitrobenzoate | BB-4-3 | 85 24 | 0.96 | 385.16 |
| C-3-3 | 3-Fluoro-2-[(R)-3-(6-methoxy-5-nitro-pyrimidin-4-ylamino)-pyrrolidin-1-yl]-benzonitrile | BB-2-3 | BB-4-3 | 105 3 | 0.95 | 359.13 |
| C-3-4 | [1-(2-Fluoro-6-methyl-phenyl)-piperidin-4-yl]-(3-methoxy-2-nitro-phenyl)-amine | 3-Fluoro-2-nitroanisole | BB-4-2 | 105 24 | 1.07 | 360.22 |
| C-3-5 | [(R)-1-(2-Fluoro-6-methyl-phenyl)-pyrrolidin-3-yl]-(4-methoxy-6-methyl-3-nitro-pyridin-2-yl)-amine | 2-Chloro-4-methoxy-6-methyl-3-nitropyridine | BB-4-1 | 50 48 | 1.01 | 361.05 |
| C-3-6 | (6-Bromo-3-methoxy-2-nitro-phenyl)-[1-(2,6-dimethyl-phenyl)-piperidin-4-yl]-amine | 4-Bromo-3-fluoro-2-nitroanisole | BB-4-4 | 100 18 | 1.11 | 433.93 |

Synthesis of Intermediates of Formula C-4

Intermediates C-4 were prepared using a similar protocol (method A) as for the synthesis of intermediates A-2 replacing intermediates A-1 by intermediates C-3 (see Table 41).
Alternatively, intermediates C-4 were prepared using the protocol described below (method B).

Method B (Ammonium Formate/Zn Dust)

To a suspension of intermediate C-3(1 eq) in MeOH (18.7 mL/mmol) was added Zn dust (10 eq) and the rxn mixture was cooled to 0° C. Ammonium formate (10 eq) was added and the rxn mixture was stirred at RT for a given time (see Table 41). It was filtered over a pad of celite and the filtrate was concentrated in vacuo. The residue was diluted with EtOAc and washed with a sat. aq. soln. of $NaHCO_3$. The org. phase was washed with brine, dried over $MgSO_4$ and concentrated in vacuo. The crude was purified by CC using Hept/EtOAc.

TABLE 41

| C-4 | Name | Reactant C-3 | Method time [h] | $t_R$ [min] | MS-data m/z $[M + H]^+$ |
|---|---|---|---|---|---|
| C-4-1 | N1-[(R)-1-(2-Fluoro-6-methyl-phenyl)-pyrrolidin-3-yl]-3-methoxy-benzene-1,2-diamine | C-3-1 | A 24 | 0.75 | 316.13 |
| C-4-2 | 2-Amino-3-[(R)-1-(2-cyano-6-fluoro-phenyl)-pyrrolidin-3-ylamino]-benzoic acid methyl ester | C-3-2 | A 2.5 | 0.97 | 355.14 |
| C-4-3 | 2-[(R)-3-(5-Amino-6-methoxy-pyrimidin-4-ylamino)-pyrrolidin-1-yl]-3-fluoro-benzonitrile | C-3-3 | A 1 | 0.75 | 329.11 |
| C-4-4 | N1-[1-(2-Fluoro-6-methyl-phenyl)-piperidin-4-yl]-3-methoxy-benzene-1,2-diamine | C-3-4 | A 3 | 0.78 | 330.11 |
| C-4-5 | N2-[(R)-1-(2-Fluoro-6-methyl-phenyl)-pyrrolidin-3-yl]-4-methoxy-6-methyl-pyridine-2,3-diamine | C-3-5 | A 2 | 0.74 A | 331.08 |
| C-4-6 | 3-Bromo-N2-[1-(2,6-dimethyl-phenyl)-piperidin-4-yl]-6-methoxy-benzene-1,2-diamine | C-3-6 | B 0.3 | 1.03 | 404.15 |

Synthesis of Intermediates of Formula C-6 (from Intermediates of Formula C-4)

Intermediates C-6 were prepared using a similar protocol as for the synthesis of intermediates A-3 replacing intermediates A-2 by intermediates C-4 (see Table 42).

TABLE 42

| C-6 | Name | Reactant C-4 | T [° C.] time [h] | $t_R$ [min] | MS-data m/z $[M + H]^+$ |
|---|---|---|---|---|---|
| C-6-1 | 1-[(R)-1-(2-Fluoro-6-methyl-phenyl)-pyrrolidin-3-yl]-4-methoxy-1,3-dihydro-benzoimidazol-2-one | C-4-1 | RT 1 | 0.88 | 342.15 |
| C-6-2 | 1-[(R)-1-(2-Cyano-6-fluoro-phenyl)-pyrrolidin-3-yl]-2-oxo-2,3-dihydro-1H-benzoimidazole-4-carboxylic acid methyl ester | C-4-2 | 55 3 | 0.91 | 381.11 |
| C-6-3 | 3-Fluoro-2-[(R)-3-(6-methoxy-8-oxo-7,8-dihydro-purin-9-yl)-pyrrolidin-1-yl]-benzonitrile | C-4-3 | RT 24 | 0.82 | 355.13 |
| C-6-4 | 1-[1-(2-Fluoro-6-methyl-phenyl)-piperidin-4-yl]-4-methoxy-1,3-dihydro-benzoimidazol-2-one | C-4-4 | RT 4.5 | 0.96 | 356.06 |
| C-6-5 | 3-[(R)-1-(2-Fluoro-6-methyl-phenyl)-pyrrolidin-3-yl]-7-methoxy-5-methyl-1,3-dihydro-imidazo[4,5-b]pyridine-2-one | C-4-5 | RT 2.5 | 0.73 | 357.05 |
| C-6-6 | 7-Bromo-1-[1-(2,6-dimethyl-phenyl)-piperidin-4-yl]-4-methoxy-1,3-dihydro-benzoimidazol-2-one | C-4-6 | up to 80 48 | 1.04 | 430.06 |

Synthesis of Intermediates of Formula C-5

Intermediates C-5 were prepared using a similar protocol as for the synthesis of intermediates C-1 replacing intermediates Ia by intermediates A-3 (see Table 43).

TABLE 43

| C-5 | Name | Reactant A-3 | time [h] | $t_R$ [min] | MS-data m/z $[M + H]^+$ |
|---|---|---|---|---|---|
| C-5-1 | 4-Methoxy-1-piperidin-4-yl-1,3-dihydro-benzoimidazol-2-one | A-3-1 | 0.25 | 0.47 | 248.20 |
| C-5-2 | 4-Methoxy-1-(R)-pyrrolidin-3-yl-1,3-dihydro-benzoimidazol-2-one | A-3-2 | 1 | 0.46 | 234.15 |

Synthesis of Intermediate of Formula C-6 (from C-5)

To a soln. of C-5 (1 eq) in DMSO (1.5 mL/mmol) was added $K_2CO_3$ (2 eq) and BB-8 (1.2 eq). The rxn mixture was heated at a given temperature for a given time (see Table 44) and was partitioned between DCM and water. The org. phase was washed with water (3×) and with brine, dried over $MgSO_4$ and concentrated in vacuo. The crude was purified by CC using EtOAc/MeOH.

TABLE 44

| C-6 | Name | Reactant C-5 | Reactant BB-8 | T [° C.] time [h] | $t_R$ [min] | MS-data m/z $[M + H]^+$ |
|---|---|---|---|---|---|---|
| C-6-7 | 3-Fluoro-2-[4-(4-methoxy-2-oxo-2,3-dihydro-benzoimidazol-1-yl)-piperidin-1-yl]-benzonitrile | C-5-1 | 2,3-Difluorobenzonitrile | 100 3 | 0.90 | 367.12 |
| C-6-8 | 3-Fluoro-2-[(R)-3-(4-methoxy-2-oxo-2,3-dihydro-benzoimidazol-1-yl)-pyrrolidin-1-yl]-benzonitrile | C-5-2 | 2,3-Difluorobenzonitrile | 100 18 | 0.87 | 353.17 |

Synthesis of Compounds of Formula Iq

Compounds of formula Iq were prepared using similar protocols (method A or B) as for the synthesis of intermediates or examples Ia replacing intermediates A-3 by intermediates C-6 (see Table 45). Alternatively, intermediates or examples Iq were prepared using the protocol described below (method C).

Method C (Mitsunobu)

To a soln. of intermediate C-6 (1eq) and BB-3(to 1.5eq) in toluene (3.4 to 6.8 mL/mmol) was added a 1M soln. of (tributylphosphoranylidene)acetonitrile in toluene (2 eq) under argon. The rxn mixture was heated to 110° C. and stirred for a given time (see Table 45). It was quenched with water and extracted with EtOAc (3×). The combined org. phases were washed with brine, dried over $MgSO_4$ and concentrated in vacuo. The crude was purified by CC using Hept/EtOAc and/or DCM/MeOH. When necessary, an additional purification by prep. LC-MS using method 1 or 2 can be performed.

TABLE 45

| Iq | Name | Reactant C-6 | Reactant BB-3 | Method T [° C.] time [h] | $t_R$ [min] | MS-data m/z $[M + H]^+$ |
|---|---|---|---|---|---|---|
| Iq-1 | 3-(6-Chloro-4-methoxy-pyridazin-3-ylmethyl)-1-[(R)-1-(2-fluoro-6-methyl-phenyl)-pyrrolidin-3-yl]-4-methoxy-1,3-dihydro-benzoimidazol-2-one (Example 92) | C-6-1 | BB-3-10 | A RT to 45° C. 40 | 0.96 | 498.14 |
| Iq-2 | 1-[(R)-1-(2-Cyano-6-fluoro-phenyl)-pyrrolidin-3-yl]-2-oxo-3-(2-trifluoromethyl-benzyl)-2,3-dihydro-1H-benzoimidazole-4-carboxylic acid methyl ester (Example 98) | C-6-2 | 2-(Trifluoromethyl) benzyl bromide | A RT 24 | 1.05 | 539.24 |

TABLE 45-continued

| Iq | Name | Reactant C-6 | Reactant BB-3 | Method T [° C.] time [h] | $t_R$ [min] | MS-data m/z [M + H]$^+$ |
|---|---|---|---|---|---|---|
| Iq-3 | 3-Fluoro-2-{(R)-3-[6-methoxy-8-oxo-7-(2-trifluoromethyl-benzyl)-7,8-dihydro-purin-9-yl]-pyrrolidin-1-yl}-benzonitrile (Example 104) | C-6-3 | 2-(Trifluoromethyl) benzyl bromide | A RT 3 | 1.05 | 513.19 |
| Iq-4 | 3-Fluoro-2-{(R)-3-[6-methoxy-7-(2-methoxy-benzyl)-8-oxo-7,8-dihydro-purin-9-yl]-pyrrolidin-1-yl}-benzonitrile (Example 105) | C-6-3 | 2-Methoxybenzyl chloride | A RT 4 | 1.01 | 475.11 |
| Iq-5 | 1-[1-(2-Fluoro-6-methyl-phenyl)-piperidin-4-yl]-3-(2-isopropoxy-benzyl)-4-methoxy-1,3-dihydro-benzoimidazol-2-one (Example 166) | C-6-4 | 1-(Chloromethyl)-2-(propan-2-yloxy)benzene | A RT to 60° C. 24 | 1.13 | 504.11 |
| Iq-6 | 3-[(R)-1-(2-Fluoro-6-methyl-phenyl)-pyrrolidin-3-yl]-7-methoxy-5-methyl-1-(2-trifluoromethyl-benzyl)-1,3-dihydro-imidazo[4,5-b]pyridin-2-one (Example 171) | C-6-5 | 2-(Trifluoromethyl) benzyl bromide | A RT 1.5 | 1.03 | 515.03 |
| Iq-7 | 3-Fluoro-2-{4-[4-methoxy-2-oxo-3-(3-trifluoromethyl-pyrazin-2-ylmethyl)-2,3-dihydro-benzoimidazol-1-yl]-piperidin-1-yl}-benzonitrile (Example 96) | C-6-7 | BB-3-5 | A RT 24 | 1.03 | 527.11 |
| Iq-8 | 3-Fluoro-2-{4-[4-methoxy-3-(3-methoxy-pyrazin-2-ylmethyl)-2-oxo-2,3-dihydro-benzoimidazol-1-yl]-piperidin-1-yl}-benzonitrile (Example 97) | C-6-7 | 2-(Bromomethyl)-3-methoxypyrazine | A RT 24 | 0.99 | 489.11 |
| Iq-9 | 3-Fluoro-2-{(R)-3-[4-methoxy-2-oxo-3-(3-trifluoromethyl-pyrazin-2-ylmethyl)-2,3-dihydro-benzoimidazol-1-yl]-pyrrolidin-1-yl}-benzonitrile (Example 111) | C-6-8 | BB-3-5 | A RT 24 | 1.01 | 513.01 |
| Iq-10 | 3-Fluoro-2-{(R)-3-[4-methoxy-3-(3-methoxy-pyrazin-2-ylmethyl)-2-oxo-2,3-dihydro-benzoimidazol-1-yl]-pyrrolidin-1-yl}-benzonitrile (Example 112) | C-6-8 | 2-(Bromomethyl)-3-methoxy pyrazine hydrochloride | A RT 24 | 0.97 | 475.22 |
| Iq-11 | 3-Fluoro-2-{4-[4-methoxy-3-(4-methoxy-pyrimidin-5-ylmethyl)-2-oxo-2,3-dihydro-benzoimidazol-1-yl]-piperidin-1-yl}-benzonitrile (Example 113) | C-6-7 | BB-3-7 | A RT 24 | 0.99 | 489.19 |
| Iq-12 | 3-Fluoro-2-{(R)-3-[4-methoxy-3-(4-methoxy-pyrimidin-5-ylmethyl)-2-oxo-2,3-dihydro-benzoimidazol-1-yl]-pyrrolidin-1-yl}-benzonitrile (Example 114) | C-6-8 | BB-3-7 | A RT 24 | 0.95 | 475.12 |
| Iq-13 | 3-Fluoro-2-{4-[4-methoxy-2-oxo-3-(4-trifluoromethyl-pyrimidin-5-ylmethyl)-2,3-dihydro-benzoimidazol-1-yl]-piperidin-1-yl}-benzonitrile (Example 117) | C-6-7 | BB-3-9 | A RT 24 | 1.05 | 527.11 |
| Iq-14 | 3-Fluoro-2-{(R)-3-[4-methoxy-2-oxo-3-(4-trifluoromethyl-pyrimidin-5-ylmethyl)-2,3-dihydro-benzoimidazol-1-yl]-pyrrolidin-1-yl}-benzonitrile (Example 153) | C-6-8 | BB-3-9 | A RT 48 | 1.01 | 512.96 |

TABLE 45-continued

| Iq | Name | Reactant C-6 | Reactant BB-3 | Method T [° C.] time [h] | $t_R$ [min] | MS-data m/z $[M + H]^+$ |
|---|---|---|---|---|---|---|
| Iq-15 | 1-[(R)-1-(2-Fluoro-6-methyl-phenyl)-pyrrolidin-3-yl]-3-(2-isopropoxy-benzyl)-4-methoxy-1,3-dihydro-benzoimidazol-2-one (Example 165) | C-6-1 | 1-(Chloromethyl)-2-(propan-2-yloxy)benzene | A RT 24 then 60 2 | 1.08 | 490.11 |
| Iq-16 | 1-[(R)-1-(2-Fluoro-6-methyl-phenyl)-pyrrolidin-3-yl]-4-methoxy-3-(3-trifluoromethyl-pyrazin-2-ylmethyl)-1,3-dihydro-benzoimidazol-2-one (Example 167) | C-6-1 | BB-3-5 | A 60 24 | 1.03 | 502.04 |
| Iq-17 | 1-[1-(2-Fluoro-6-methyl-phenyl)-piperidin-4-yl]-4-methoxy-3-(3-trifluoromethyl-pyrazin-2-ylmethyl)-1,3-dihydro-benzoimidazol-2-one (Example 168) | C-6-4 | BB-3-5 | A 60 24 | 1.08 | 516.01 |
| Iq-18 | 1-[(R)-1-(2-Fluoro-6-methyl-phenyl)-pyrrolidin-3-yl]-4-methoxy-3-(3-methoxy-pyrazin-2-ylmethyl)-1,3-dihydro-benzoimidazol-2-one (Example 169) | C-6-1 | 2-(Bromomethyl)-3-methoxypyrazine hydrochloride | A 60 24 then 100 18 | 0.98 | 464.11 |
| Iq-19 | 1-[1-(2-Fluoro-6-methyl-phenyl)-piperidin-4-yl]-4-methoxy-3-(3-methoxy-pyrazin-2-ylmethyl)-1,3-dihydro-benzoimidazol-2-one (Example 170) | C-6-4 | 2-(Bromomethyl)-3-methoxypyrazine hydrochloride | A 60 24 then 100 18 | 1.04 | 478.24 |
| Iq-20 | 3-(6-Chloro-4-isopropoxy-pyridazin-3-ylmethyl)-1-[(R)-1-(2-fluoro-6-methyl-phenyl)-pyrrolidin-3-yl]-4-methoxy-1,3-dihydro-benzoimidazol-2-one (Example 172) | C-6-1 | BB-3-11 | C 110 3 | 1.02 | 526.12 |
| Iq-21 | 1-[(R)-1-(2-Fluoro-6-methyl-phenyl)-pyrrolidin-3-yl]-4-methoxy-3-(4-methyl-pyridazin-3-ylmethyl)-1,3-dihydro-benzoimidazol-2-one (Example 174) | C-6-1 | BB-3-12 | C 110 1.5 | 0.88 | 448.14 |
| Iq-22 | 1-[(R)-1-(2-Fluoro-6-methyl-phenyl)-pyrrolidin-3-yl]-4-methoxy-3-(4-methoxy-pyrimidin-5-ylmethyl)-1,3-dihydro-benzoimidazol-2-one (Example 175) | C-6-1 | BB-3-6 | C 110 1.5 | 0.99 | 464.15 |
| Iq-23 | 1-[(R)-1-(2-Fluoro-6-methyl-phenyl)-pyrrolidin-3-yl]-4-methoxy-3-(4-trifluoromethyl-pyrimidin-5-ylmethyl)-1,3-dihydro-benzoimidazol-2-one (Example 176) | C-6-1 | BB-3-8 | C 110 4 | 1.04 | 502.06 |
| Iq-24 | 1-[(R)-1-(2-Fluoro-6-methyl-phenyl)-pyrrolidin-3-yl]-3-(3-isopropoxy-pyrazin-2-ylmethyl)-4-methoxy-1,3-dihydro-benzoimidazol-2-one (Example 177) | C-6-1 | BB-3-13 | C 110 2 | 1.05 | 492.17 |
| Iq-25 | 1-[1-(2-Fluoro-6-methyl-phenyl)-piperidin-4-yl]-3-(3-isopropoxy-pyrazin-2-ylmethyl)-4-methoxy-1,3-dihydro-benzoimidazol-2-one (Example 178) | C-6-4 | BB-3-13 | C 2 | 1.10 | 506.19 |
| Iq-26 | 1-[(R)-1-(2-Fluoro-6-methyl-phenyl)-pyrrolidin-3-yl]-3-(4-isopropyl-pyridin-3-ylmethyl)-4-methoxy-1,3-dihydro-benzoimidazol-2-one (Example 180) | C-6-1 | BB-3-14 | C 110 1.5 | 0.85 | 475.17 |

TABLE 45-continued

| Iq | Name | Reactant C-6 | Reactant BB-3 | Method T [° C.] time [h] | $t_R$ [min] | MS-data m/z [M + H]$^+$ |
|---|---|---|---|---|---|---|
| Iq-27 | 1-[1-(2-Fluoro-6-methyl-phenyl)-piperidin-4-yl]-3-(4-isopropyl-pyridin-3-ylmethyl)-4-methoxy-1,3-dihydro-benzoimidazol-2-one (Example 181) | C-6-4 | BB-3-14 | C 110 1.5 | 0.89 | 489.20 |
| Iq-28 | 1-[(R)-1-(2-Fluoro-6-methyl-phenyl)-pyrrolidin-3-yl]-3-(3-isopropoxy-pyridin-2-ylmethyl)-4-methoxy-1,3-dihydro-benzoimidazol-2-one (Example 182) | C-6-1 | BB-3-15 | C 110 1.5 | 0.90 | 491.16 |
| Iq-29 | 1-[1-(2-Fluoro-6-methyl-phenyl)-piperidin-4-yl]-3-(3-isopropoxy-pyridin-2-ylmethyl)-4-methoxy-1,3-dihydro-benzoimidazol-2-one (Example 183) | C-6-4 | BB-3-15 | C 110 1.5 | 0.94 | 505.13 |
| Iq-30 | 1-[(R)-1-(2-Fluoro-6-methyl-phenyl)-pyrrolidin-3-yl]-3-(4-isopropyl-pyrimidin-5-ylmethyl)-4-methoxy-1,3-dihydro-benzoimidazol-2-one (Example 186) | C-6-1 | BB-3-16 | C 110 3 | 1.06 | 476.09 |
| Iq-31 | 1-[1-(2-Fluoro-6-methyl-phenyl)-piperidin-4-yl]-3-(3-isopropyl-pyrazin-2-ylmethyl)-4-methoxy-1,3-dihydro-benzoimidazol-2-one (Example 187) | C-6-4 | BB-3-17 | C 110 1.5 | 1.07 | 490.16 |
| Iq-32 | 1-[(R)-1-(2-Fluoro-6-methyl-phenyl)-pyrrolidin-3-yl]-3-(3-isopropyl-pyrazin-2-ylmethyl)-4-methoxy-1,3-dihydro-benzoimidazol-2-one (Example 189) | C-6-1 | BB-3-17 | C 110 1.5 | 1.01 | 476.10 |
| Iq-33 | 1-[1-(2-Fluoro-6-methyl-phenyl)-piperidin-4-yl]-3-(4-isopropyl-pyrimidin-5-ylmethyl)-4-methoxy-1,3-dihydro-benzoimidazol-2-one (Example 192) | C-6-4 | BB-3-16 | C 110 24 | 1.13 | 490.17 |
| Iq-34 | 1-[(R)-1-(2-Fluoro-6-methyl-phenyl)-pyrrolidin-3-yl]-4-methoxy-3-(2-trifluoromethyl-pyridin-3-ylmethyl)-1,3-dihydro-benzoimidazol-2-one (Example 195) | C-6-1 | (2-(Trifluoromethyl) pyridin-3-yl) methanol | C 110 2 | 1.05 | 501.12 |
| Iq-35 | 1-[(R)-1-(2-Fluoro-6-methyl-phenyl)-pyrrolidin-3-yl]-4-methoxy-3-(3-trifluoromethyl-pyridin-2-ylmethyl)-1,3-dihydro-benzoimidazol-2-one (Example 202) | C-6-1 | (3-(Trifluoromethyl) pyridin-2-yl) methanol | C 110 18 | 1.03 | 501.05 |
| Iq-36 | 1-[(R)-1-(2-Fluoro-6-methyl-phenyl)-pyrrolidin-3-yl]-4-methoxy-3-(4-trifluoromethyl-pyridin-3-ylmethyl)-1,3-dihydro-benzoimidazol-2-one (Example 203) | C-6-1 | (4-(Trifluoromethyl) pyridin-3-yl) methanol | C 110 2 | 1.08 | 501.09 |
| Iq-37 | 3-(2-Cyclopropoxy-benzyl)-1-[(R)-1-(2-fluoro-6-methyl-phenyl)-pyrrolidin-3-yl]-4-methoxy-1,3-dihydro-benzoimidazol-2-one (Example 208) | C-6-1 | 1-(Bromomethyl)-2-cyclopropyloxy benzene | A RT 6 | 1.06 | 488.12 |
| Iq-38 | 3-(2-Cyclopropoxy-benzyl)-1-[1-(2-fluoro-6-methyl-phenyl)-piperidin-4-yl]-4-methoxy-1,3-dihydro-benzoimidazol-2-one (Example 209) | C-6-4 | 1-(Bromomethyl)-2-cyclopropyloxy benzene | A RT 18 then 60 3.5 | 1.13 | 502.15 |

TABLE 45-continued

| Iq | Name | Reactant C-6 | Reactant BB-3 | Method T [° C.] time [h] | $t_R$ [min] | MS-data m/z $[M + H]^+$ |
|---|---|---|---|---|---|---|
| Iq-39 | 1-[1-(2-Fluoro-6-methyl-phenyl)-piperidin-4-yl]-4-methoxy-3-(3-trifluoromethyl-pyridin-2-ylmethyl)-1,3-dihydro-benzoimidazol-2-one (Example 216) | C-6-4 | [3-(trifluoromethyl) pyridin-2-yl] methanol | C 110 24 | 1.09 | 515.10 |
| Iq-40 | 1-[(R)-1-(2-Fluoro-6-methyl-phenyl)-pyrrolidin-3-yl]-4-methoxy-3-(2-trifluoromethyl-thiazol-4-ylmethyl)-1,3-dihydro-benzoimidazol-2-one (Example 218) | C-6-1 | BB-3-18 | C 110 18 | 1.04 | 507.00 |
| Iq-41 | 1-[1-(2-Fluoro-6-methyl-phenyl)-pyrrolidin-3-yl]-4-methoxy-3-[(S)-1-(2-trifluoromethyl-phenyl)-ethyl]-1,3-dihydro-benzoimidazol-2-one (Example 219) | C-6-1 | 1-(2-(trifluoromethyl) phenyl)ethan-1-ol | C 110 2.5 | 1.07 | 514.02 |
| Iq-42 | 3-(2,4-Difluoro-6-isopropoxy-benzyl)-1-[(R)-1-(2-fluoro-6-methyl-phenyl)-pyrrolidin-3-yl]-4-methoxy-1,3-dihydro-benzoimidazol-2-one (Example 220) | C-6-1 | BB-3-19 | C 110 2.5 | 1.09 | 526.04 |
| Iq-43 | 1-[(R)-1-(2-Fluoro-6-methyl-phenyl)-pyrrolidin-3-yl]-4-methoxy-3-(2-methyl-4-trifluoromethyl-thiazol-5-ylmethyl)-1,3-dihydro-benzoimidazol-2-one (Example 221) | C-6-1 | [2-methyl-4-(trifluoromethyl)-1,3-thiazol-5-yl]methanol | C 110 4 | 1.06 | 521.01 |
| Iq-44 | 3-(2-Cyclopropyl-benzyl)-1-[1-(2-fluoro-6-methyl-phenyl)-piperidin-4-yl]-4-methoxy-1,3-dihydro-benzoimidazol-2-one (Example 223) | C-6-4 | (2-Cyclopropylphenyl) methanol | C 110 2 | 1.14 | 486.13 |
| Iq-45 | 2-{3-[1-(2-fluoro-6-methyl-phenyl)-piperidin-4-yl]-7-methoxy-2-oxo-2,3-dihydro-benzoimidazol-1-ylmethyl}-phenyl acetate | C-6-4 | 2-(Chloromethyl)phenyl acetate | A 70 10 | 1.08 | 504.16 |
| Iq-46 | 4-Bromo-3-[1-(2,6-dimethyl-phenyl)-piperidin-4-yl]-7-methoxy-1-(2-trifluoromethyl-benzyl)-1,3-dihydro-benzoimidazol-2-one | C-6-6 | 2-(Trifluoromethyl) benzyl bromide | A RT 2 | 1.20 | 588.03 |

Synthesis of Compounds of Formula Ir

Method A

To a soln. of intermediate Iq (1 eq) in EtOH (5 to 12 mL/mmol) was added ammonium formate (2 eq) and 10% Pd/C moistened with ~50% water (0.05 eq) and the rxn mixture was heated to 65° C. for a given time (see Table 46). It was filtered over a pad of celite and the filtrate was concentrated in vacuo. The crude was purified by CC using EtOAc/MeOH or DCM/MeOH.

Method B

To a soln. of intermediate Iq (1 eq) in a mixture of EtOAc (65 mL/mmol) and MeOH (89 mL/mmol) was added 10% Pd/C moistened with ~50% water (0.1 eq) and the rxn mixture was hydrogenated under an atmospheric pressure of deuterium for a given time (see Table 46). It was filtered over a pad of celite and the filtrate was concentrated in vacuo. The crude was purified by CC using Hept/EtOAc.

TABLE 46

| Ir | Name | Reactant Iq | Method time [h] | $t_R$ [min] | MS-data m/z $[M + H]^+$ |
|---|---|---|---|---|---|
| Ir-1 | 1-[(R)-1-(2-Fluoro-6-methyl-phenyl)-pyrrolidin-3-yl]-4-methoxy-3-(4-methoxy-pyridazin-3-ylmethyl)-1,3-dihydro-benzoimidazol-2-one (Example 95) | Iq-1 | A 24 | 0.81 | 464.18 |
| Ir-2 | 1-[(R)-1-(2-Fluoro-6-methyl-phenyl)-pyrrolidin-3-yl]-3-(4-isopropoxy-pyridazin-3-ylmethyl)-4-methoxy-1,3-dihydro-benzoimidazol-2-one (Example 173) | Iq-20 | A 1 | 0.87 | 492.16 |
| Ir-3 | 1-(1-(2,6-dimethylphenyl)piperidin-4-yl)-4-methoxy-3-(2-(trifluoromethyl)benzyl)-1,3-dihydro-benzoimidazol-2-one-7-d (Example 3) | Iq-46 | B 4.5 | 1.14 | 511.18 |

Synthesis of Acid Intermediates of Formula E-1

To a soln. of intermediates Iq (1 eq) in a 1/1/1 mixture of TH/MeOH/water (9 mL/mmol) was added lithium hydroxide hydrate (4 eq). The rxn mixture was heated to 50° C. and stirred for a given time (see Table 47). It was diluted with water and extracted with $Et_2$ (3×). The aq. phase was acidified until pH 2-3 with a 1 M soln. of HCl and extracted with DCM (3×). The combined org. phases were dried over $MgSO_4$ and concentrated in vacuo.

TABLE 47

| E-1 | Name | Reactant Iq | time [h] | $t_R$ [min] | MS-data m/z $[M + H]^+$ |
|---|---|---|---|---|---|
| E-1-1 | 1-[(R)-1-(2-cyano-6-fluoro-phenyl)-pyrrolidin-3-yl]-2-oxo-3-(2-trifluoromethyl-benzyl)-2,3-dihydro-1H-benzoimidazole-4-carboxylic acid | Iq-2 | 2 | 0.97 | 525.10 |

Synthesis of Compounds of Formula Is

To a soln. of acids of formula E-1 (1 eq) in DMF (4 mL/mmol) was added DIPEA (3 eq) and HATU (1 eq). The rxn mixture was stirred for 5 min at RT and the appropriate amine (1.2 eq) pure or as soln. was added. The rxn mixture was further stirred ON at RT (see Table 48) and diluted with DCM. The org. phase was washed with water and brine, dried over $MgSO_4$ and concentrated in vacuo. The crude was purified by CC using Hept/EtOAc.

TABLE 48

| Is | Name | Reactant E-1 | Amine | $t_R$ [min] | MS-data m/z $[M + H]^+$ |
|---|---|---|---|---|---|
| Is-1 | 1-[(R)-1-(2-Cyano-6-fluoro-phenyl)-pyrrolidin-3-yl]-2-oxo-3-(2-trifluoromethyl-benzyl)-2,3-dihydro-1H-benzoimidazole-4-carboxylic acid methylamide (Example 99) | E-1-1 | 2M soln. of methylamine in THF | 0.94 | 538.21 |
| Is-2 | 1-[(R)-1-(2-Cyano-6-fluoro-phenyl)-pyrrolidin-3-yl]-2-oxo-3-(2-trifluoromethyl-benzyl)-2,3-dihydro-1H-benzoimidazole-4-carboxylic acid amide (Example 100) | E-1-1 | 0.5M soln. of ammonia in dioxane | 0.91 | 524.16 |
| Is-3 | 1-[(R)-1-(2-Cyano-6-fluoro-phenyl)-pyrrolidin-3-yl]-2-oxo-3-(2-trifluoromethyl-benzyl)-2,3-dihydro-1H-benzoimidazole-4-carboxylic acid dimethylamide (Example 101) | E-1-1 | 2M soln. of dimethylamine in THF | 0.98 | 552.21 |
| Is-4 | 1-[(R)-1-(2-Cyano-6-fluoro-phenyl)-pyrrolidin-3-yl]-2-oxo-3-(2-trifluoromethyl-benzyl)-2,3-dihydro-1H-benzoimidazole-4-carboxylic acid (2-hydroxy-ethyl)-amide (Example 193) | E-1-1 | Ethanolamine | 0.88 | 568.04 |
| Is-5 | 1-[(R)-1-(2-Cyano-6-fluoro-phenyl)-pyrrolidin-3-yl]-2-oxo-3-(2-trifluoromethyl-benzyl)-2,3-dihydro-1H-benzoimidazole-4-carboxylic acid (2-methoxy-ethyl)-amide (Example 194) | E-1-1 | 2-Methoxy ethylamine | 0.95 | 582.1 |

Synthesis of Compounds of Formula It

To a soln. of compounds of formula Iq (1 eq) and $CaCl_2$ (0.3 eq) in EtOH (15 mL/mmol) was added at 0° C. a suspension of $NaBH_4$ (2.5 eq) in EtOH (8 mL/mmol). The rxn mixture was allowed to warm to RT and stirred at that temperature for a given time (see Table 49). It was quenched with water and extracted with DCM (3×). The combined org. phases were dried over $MgSO_4$ and concentrated in vacuo. The crude was purified by CC using Hept/EtOAc.

TABLE 49

| It | Name | Reactant Iq | time [h] | $t_R$ [min] | MS-data m/z $[M + H]^+$ |
|---|---|---|---|---|---|
| It-1 | 3-Fluoro-2-{(R)-3-[4-hydroxymethyl-2-oxo-3-(2-trifluoromethyl-benzyl)-2,3-dihydro-benzoimidazol-1-yl]-pyrrolidin-1-yl}-benzonitrile (Example 102) | Iq-2 | 24 | 0.97 | 511.24 |

Synthesis of Compounds of Formula Iu

Method A (Reductive Amination I)

To a stirred soln. of Ic (1eq) in a mixture of DCM (25 mL/mmol), MeOH (50 mL/mmol) and AcOH (1.2 eq) was added the appropriate amine (1.3 eq) followed by NaBH(OAc)$_3$ (1.4 eq). The rxn mixture was stirred at RT for a given time (see Table 50) and the volatiles were evaporated in vacuo. The residue was partitioned between DCM and a sat. aq. soln. of $NaHCO_3$. The org. phase was dried over $MgSO_4$ and concentrated in vacuo. The crude was purified by prep. LC-MS using method 4 and 5.

Method B (Reductive Amination II)

To a stirred soln. of aldehyde Ic (1eq) and the appropriate amine (1.1eq) in THF (4 mL/mmol) was added NaBH(OAc)$_3$ (1.5eq). The rxn mixture was stirred at RT for a given time (see Table 50) and partitioned between DCM and a 1M aq. soln. of NaOH. The org. phase was dried over $MgSO_4$ and concentrated in vacuo. The crude was purified by prep. LC-MS using method 2.

TABLE 50

| Iu | Name | Reactant Ic | Reactant amine | Method time [h] | $t_R$ [min] | MS-data m/z $[M + H]^+$ |
|---|---|---|---|---|---|---|
| Iu-1 | 1-[(R)-1-(2-Fluoro-6-methylaminomethyl-phenyl)-pyrrolidin-3-yl]-4-methoxy-3-(2-trifluoromethyl-benzyl)-1,3-dihydro-benzoimidazol-2-one (Example 103) | Ic-5 | 2M soln. of methylamine in THF | A 1 | 0.86 | 529.27 |
| Iu-2 | 1-[(R)-1-(2-Dimethylaminomethyl-6-fluoro-phenyl)-pyrrolidin-3-yl]-4-methoxy-3-(2-trifluoromethyl-benzyl)-1,3-dihydro-benzoimidazol-2-one (Example 106) | Ic-5 | 2M soln. of dimethylamine in THF | A 24 | 0.90 | 543.30 |
| Iu-3 | 1-[(R)-1-(2-Fluoro-6-{[(2-hydroxy-ethyl)-methyl-amino]-methyl}-phenyl)-pyrrolidin-3-yl]-4-methoxy-3-(2-trifluoromethyl-benzyl)-1,3-dihydro-benzoimidazol-2-one (Example 107) | Ic-5 | 2-(Methylamino)ethanol | A 24 | 0.86 | 573.28 |
| Iu-4 | 1-[(R)-1-(2-Azetidin-1-ylmethyl-6-fluoro-phenyl)-pyrrolidin-3-yl]-4-methoxy-3-(2-trifluoromethyl-benzyl)-1,3-dihydro-benzoimidazol-2-one (Example 108) | Ic-5 | Azetidine | A 18 | 0.91 | 555.25 |
| Iu-5 | 1-[(R)-1-(2-Fluoro-6-morpholin-4-ylmethyl-phenyl)-pyrrolidin-3-yl]-4-methoxy-3-(2-trifluoromethyl-benzyl)-1,3-dihydro-benzoimidazol-2-one (Example 115) | Ic-5 | Morpholine | A 24 | 0.90 | 585.14 |
| Iu-6 | 1-[(R)-1-(2-Fluoro-6-pyrrolidin-1-ylmethyl-phenyl)-pyrrolidin-3-yl]-4-methoxy-3-(2-trifluoromethyl-benzyl)-1,3-dihydro-benzoimidazol-2-one (Example 116) | Ic-5 | Pyrrolidine | A 2 | 0.93 | 569.16 |
| Iu-7 | 1-{(R)-1-[2-Fluoro-6-(4-methyl-piperazin-1-ylmethyl)-phenyl]-pyrrolidin-3-yl}-4-methoxy-3-(2-trifluoromethyl-benzyl)-1,3-dihydro-benzoimidazol-2-one (Example 132) | Ic-5 | 1-Methyl piperazine | B 1.5 | 0.76 | 598.30 |
| Iu-8 | 1-[(R)-1-(2-Fluoro-6-piperidin-1-ylmethyl-phenyl)-pyrrolidin-3-yl]-4-methoxy-3-(2-trifluoromethyl-benzyl)-1,3-dihydro-benzoimidazol-2-one (Example 133) | Ic-5 | Piperidine | B 18 | 0.94 | 583.26 |
| Iu-9 | 1-{(R)-1-[2-Fluoro-6-(4-hydroxy-piperidin-1-ylmethyl)-phenyl]-pyrrolidin-3-yl}-4-methoxy-3-(2-trifluoromethyl-benzyl)-1,3-dihydro-benzoimidazol-2-one (Example 134) | Ic-5 | 4-Hydroxy piperidine | B 18 | 0.87 | 599.27 |
| Iu-10 | 1-[(R)-1-(2-Fluoro-6-piperazin-1-ylmethyl-phenyl)-pyrrolidin-3-yl]-4-methoxy-3-(2-trifluoromethyl-benzyl)-1,3-dihydro-benzoimidazol-2-one (Example 135) | Ic-5 | Piperazine | B 18 | 0.73 | 584.24 |
| Iu-11 | 1-{(R)-1-[2-(4-Dimethylamino-piperidin-1-ylmethyl)-6-fluoro-phenyl]-pyrrolidin-3-yl}-4-methoxy-3-(2-trifluoromethyl-benzyl)-1,3-dihydro-benzoimidazol-2-one (Example 136) | Ic-5 | 4-Dimethyl amino piperidine | B 18 | 0.73 | 626.30 |
| Iu-12 | 1-{(R)-1-[2-Fluoro-6-(4-methoxy-piperidin-1-ylmethyl)-phenyl]-pyrrolidin-3-yl}-4-methoxy-3-(2-trifluoromethyl-benzyl)-1,3-dihydro-benzoimidazol-2-one (Example 137) | Ic-5 | 4-Methoxy piperidine | B 3.5 | 0.92 | 613.08 |
| Iu-13 | 1-{(R)-1-[2-Fluoro-6-(3-methoxy-pyrrolidin-1-ylmethyl)-phenyl]-pyrrolidin-3-yl}-4-methoxy-3-(2-trifluoromethyl-benzyl)-1,3-dihydro-benzoimidazol-2-one (Example 138) | Ic-5 | 3-Methoxy pyrrolidine | B 3.5 | 0.92 | 599.07 |
| Iu-14 | 1-[(R)-1-(2-Fluoro-6-{[(2-methoxy-ethyl)-methyl-amino]-methyl}-phenyl)-pyrrolidin-3-yl]-4-methoxy-3-(2-trifluoromethyl-benzyl)-1,3-dihydro-benzoimidazol-2-one (Example 139) | Ic-5 | N-(2-Methoxy ethyl) methylamine | B 3.5 | 0.91 | 587.10 |

TABLE 50-continued

| Iu | Name | Reactant Ic | Reactant amine | Method time [h] | $t_R$ [min] | MS-data m/z [M + H]+ |
|---|---|---|---|---|---|---|
| Iu-15 | 1-[(R)-1-(2-{[Ethyl-(2-hydroxy-ethyl)-amino]-methyl}-6-fluoro-phenyl)-pyrrolidin-3-yl]-4-methoxy-3-(2-trifluoromethyl-benzyl)-1,3-dihydro-benzoimidazol-2-one (Example 140) | Ic-5 | 2-(Ethylamino)ethanol | B 3.5 | 0.87 | 587.40 |
| Iu-16 | 1-[(R)-1-(2-{[Bis-(2-hydroxy-ethyl)-amino]-methyl}-6-fluoro-phenyl)-pyrrolidin-3-yl]-4-methoxy-3-(2-trifluoromethyl-benzyl)-1,3-dihydro-benzoimidazol-2-one (Example 141) | Ic-5 | Diethanol amine | B 72 | 0.83 | 603.14 |
| Iu-17 | 1-((R)-1-{2-Fluoro-6-[(2-methoxy-1-methyl-ethylamino)-methyl]-phenyl}-pyrrolidin-3-yl)-4-methoxy-3-(2-trifluoromethyl-benzyl)-1,3-dihydro-benzoimidazol-2-one (Example 142) | Ic-5 | 2-Amino-1-methoxy propane | B 3.5 | 0.90 | 587.27 |
| Iu-18 | 1-{(R)-1-[2-Fluoro-6-(3-methoxy-azetidin-1-ylmethyl)-phenyl]-pyrrolidin-3-yl}-4-methoxy-3-(2-trifluoromethyl-benzyl)-1,3-dihydro-benzoimidazol-2-one (Example 143) | Ic-5 | 3-Methoxy azetidine | B 3.5 | 0.92 | 585.20 |

Synthesis of Intermediates of Formula D-1

A suspension of Ij (1eq) in POCl$_3$ (2 mL/mmol) was heated to 85° C. and stirred ON (see Table 51). The rxn mixture was carefully quenched with a ice cold 2M aq. soln. of NaOH and extracted with EtOAc (3x). The combined org. phases were washed with brine, dried over MgSO$_4$ and concentrated in vacuo. The crude was purified by CC using Hept/EtOAc.

TABLE 51

| D-1 | Name | Reactant Ij | $t_R$ [min] | MS-data m/z [M + H]+ |
|---|---|---|---|---|
| D-1-1 | 4-Chloro-1-[(R)-1-(2,6-dimethyl-phenyl)-pyrrolidin-3-yl]-3-(2-trifluoromethyl-benzyl)-1,3-dihydro-imidazo[4,5-c]pyridin-2-one | Ij-6 | 1.06 | 501.09 |
| D-1-2 | 4-Chloro-1-[(R)-1-(2-fluoro-6-methyl-phenyl)-pyrrolidin-3-yl]-3-(2-trifluoromethyl-benzyl)-1,3-dihydro-imidazo[4,5-c]pyridin-2-one | Ij-4 | 1.09 | 505.03 |

Synthesis of Compounds of Formula Iv

Method A (Amine as Solvent)

A soln. of D-1 (1 eq) in the appropriate amine (mL/mmol) was heated to a given temperature and stirred for a given time (see Table 52). The rxn mixture was diluted with EtOAc and washed with a sat. aq. soln. of NaHCO$_3$ (2x) and with brine. The org. phase was dried over MgSO$_4$ and concentrated in vacuo. The crude was purified by CC using Hept/EtOAc.

Method B (Alcohol/KOH/DMSO)

To stirred soln. of D-1 (1eq) in DMSO (8 mL/mmol) was added the appropriate alcohol (5 to 10eq) and KOH (2.5 eq). The rxn mixture was heated to a given temperature for a given time (see Table 52). It was diluted with EtOAc and washed with H$_2$O (3x) and brine. The org. phase was dried over MgSO$_4$ and concentrated in vacuo. The crude was purified by CC using Hept/EtOAc or DCM/MeOH.

Method C (Buchwald)

An oven dried flask was charged with intermediate D-1 (1 eq), the appropriate amine (1.2 eq), Cs$_2$CO$_3$ (2.5 eq) RuPhos precatalyst (0.1 eq) and RuPhos (0.1 eq). The flask was evacuated and refilled with argon (3x) and t-BuOH (17 mL/mmol) was added. The rxn mixture was degassed under vacuum, refilled with argon (3x) and heated to a given temperature and stirred for a given time (see Table 52). It was partitioned between water and EtOAc and the org. phase was washed with brine, dried over MgSO$_4$ and concentrated in vacuo. The crude was purified by prep. LC-MS using method 2 and 5.

TABLE 52

| Iv | Name | Reactant D-1 | Reactant amine/ alcohol | Method T [° C.] time [h] | $t_R$ [min] | MS-data m/z [M + H]$^+$ |
|---|---|---|---|---|---|---|
| Iv-1 | 1-[(R)-1-(2,6-Dimethyl-phenyl)-pyrrolidin-3-yl]-4-(2-hydroxy-ethylamino)-3-(2-trifluoromethyl-benzyl)-1,3-dihydro-imidazo[4,5-c]pyridin-2-one (Example 118) | D-1-1 | Ethanol amine | A 100 72 then 130 72 | 0.81 | 526.28 |
| Iv-2 | 1-[(R)-1-(2,6-Dimethyl-phenyl)-pyrrolidin-3-yl]-4-(2-hydroxy-ethoxy)-3-(2-trifluoromethyl-benzyl)-1,3-dihydro-imidazo[4,5-c]pyridin-2-one (Example 119) | D-1-1 | Ethylene glycol | B 50 2.5 | 0.97 | 527.17 |
| Iv-3 | 4-(2-Dimethylamino-ethoxy)-1-[(R)-1-(2-fluoro-6-methyl-phenyl)-pyrrolidin-3-yl]-3-(2-trifluoromethyl-benzyl)-1,3-dihydro-imidazo[4,5-c]pyridin-2-one (Example 120) | D-1-2 | Dimethyl amino ethanol | B 50 1.5 | 0.85 | 558.14 |
| Iv-4 | 1-[(R)-1-(2-Fluoro-6-methyl-phenyl)-pyrrolidin-3-yl]-4-(2-morpholin-4-yl-ethoxy)-3-(2-trifluoromethyl-benzyl)-1,3-dihydro-imidazo[4,5-c]pyridin-2-one (Example 121) | D-1-2 | 4-(2-Hydroxy ethyl) morpholine | B 50 1.5 | 0.85 | 600.11 |
| Iv-5 | 4-[1-[(R)-1-(2-Fluoro-6-methyl-phenyl)-pyrrolidin-3-yl]-2-oxo-3-(2-trifluoromethyl-benzyl)-2,3-dihydro-1H-imidazo[4,5-c]pyridin-4-yloxy]-piperidine-1-carboxylic acid tert-butyl ester (Example 122) | D-1-2 | tert-Butyl 4-hydroxy-1-piperidine carboxylate | B 50 2 | 1.15 | 670.17 |
| Iv-6 | 1-[(R)-1-(2-Fluoro-6-methyl-phenyl)-pyrrolidin-3-yl]-4-[(2-hydroxy-ethyl)-methyl-amino]-3-(2-trifluoromethyl-benzyl)-1,3-dihydro-imidazo[4,5-c]pyridin-2-one (Example 123) | D-1-2 | 2-(Methylamino)ethanol | A 120 48 then 130 120 | 0.86 | 544.22 |
| Iv-7 | 4-(2,2-Dimethyl-[1,3]dioxolan-4-ylmethoxy)-1-[(R)-1-(2-fluoro-6-methyl-phenyl)-pyrrolidin-3-yl]-3-(2-trifluoromethyl-benzyl)-1,3-dihydro-imidazo[4,5-c]pyridin-2-one (Example 125) | D-1-2 | 2,2-Dimethyl-4-hydroxy methyl-1,3-dioxolane | B 50 4 | 1.10 | 601.34 |
| Iv-8 | 1-[(R)-1-(2-Fluoro-6-methyl-phenyl)-pyrrolidin-3-yl]-4-(oxetan-3-yloxy)-3-(2-trifluoromethyl-benzyl)-1,3-dihydro-imidazo[4,5-c]pyridin-2-one (Example 127) | D-1-2 | 3-Hydroxy oxetane | B 80 72 then 50 120 | 1.08 | 543.20 |
| Iv-9 | 1-[(R)-1-(2-Fluoro-6-methyl-phenyl)-pyrrolidin-3-yl]-4-morpholin-4-yl-3-(2-trifluoromethyl-benzyl)-1,3-dihydro-imidazo[4,5-c]pyridin-2-one (Example 129) | D-1-2 | Morpholine | A 100 770 | 0.97 | 556.25 |
| Iv-10 | 1-[(R)-1-(2-Fluoro-6-methyl-phenyl)-pyrrolidin-3-yl]-4-(1-methyl-pyrrolidin-3-yloxy)-3-(2-trifluoromethyl-benzyl)-1,3-dihydro-imidazo[4,5-c]pyridin-2-one (Example 130) | D-1-2 | 1-Methyl-3-pyrrolidinol | B 50 2 | 0.85 | 570.13 |
| Iv-11 | 1-[(R)-1-(2-Fluoro-6-methyl-phenyl)-pyrrolidin-3-yl]-4-(3-methoxy-azetidin-1-yl)-3-(2-trifluoromethyl-benzyl)-1,3-dihydro-imidazo[4,5-c]pyridin-2-one (Example 205) | D-1-2 | 3-Methoxy azetidine hydrochloride | C 110 2 | 0.91 | 556.13 |
| Iv-12 | 1-[(R)-1-(2-Fluoro-6-methyl-phenyl)-pyrrolidin-3-yl]-4-(4-methyl-piperazin-1-yl)-3-(2-trifluoromethyl-benzyl)-1,3-dihydro-imidazo[4,5-c]pyridin-2-one (Example 206) | D-1-2 | 1-Methyl piperazine | A 120 48 then 140 120 | 0.82 | 569.14 |
| Iv-13 | 1-[(R)-1-(2-Fluoro-6-methyl-phenyl)-pyrrolidin-3-yl]-4-(2-methoxy-ethylamino)-3-(2-trifluoromethyl-benzyl)-1,3-dihydro-imidazo[4,5-c]pyridin-2-one (Example 207) | D-1-2 | 2-Methoxy ethyl amine | A 140 144 | 0.87 | 544.15 |

Synthesis of Intermediates of Formula 0-2

A suspension of (methoxymethyl)triphenylphosphonium chloride (1.2 eq) in anh. THF (12.5 mL/mmol) was cooled to −78° C. A 1.6 M soln. of n-butyllithium in hexanes (1.2 eq) was dropwise added at −78° C. and the mixture was stirred for 30 min at −78° C. A solution of aldehyde Ic (1eq) in anh. THF (6.25 mL/mmol) was dropwise added at −7800 and the rxn mixture was stirred for a given time (see Table 53) at RT. It was quenched with a sat. aq. soln. of $NH_4Cl$ and extracted with DCM (3×). The combined org. phases were washed with brine, dried over $MgSO_4$ and concentrated in vacuo. The crude was purified by CC using DCM/MeOH and/or by prep. LC-MS using method 1.

TABLE 53

| D-2 | Name | Reactant Ic | time [h] | $t_R$ [min] | MS-data m/z $[M + H]^+$ |
|---|---|---|---|---|---|
| D-2-1 | 1-{(R)-1-[2-Fluoro-6-((E)-2-methoxy-vinyl)-phenyl]-pyrrolidin-3-yl}-4-methoxy-3-(2-trifluoromethyl-benzyl)-1,3-dihydro-benzoimidazol-2-one | Ic-5 | 18 | 1.08-1.09 | 542.27 |

Synthesis of Compounds of Formula Iw

To a soln. of enol ether D-2 (1 eq) in anh. THF (8.7 mL/mmol) was added a 5M aq. soln. of HCl (1.8 mL/mmol) and the rxn mixture was heated to 70° C. and stirred for a given time (see Table 54). The mixture was diluted with $Et_2O$ and washed with $H_2O$ and a sat. aq. soln. of $NaHCO_3$. The org. phase was dried over $MgSO_4$ and concentrated in vacuo. The crude was purified by CC using DCM/MeOH.

TABLE 54

| Iw | Name | Reactant D-2 | time [h] | $t_R$ [min] | MS-data m/z $[M + H]^+$ |
|---|---|---|---|---|---|
| Iw-1 | (3-Fluoro-2-{(R)-3-[4-methoxy-2-oxo-3-(2-trifluoromethyl-benzyl)-2,3-dihydro-benzoimidazol-1-yl]-pyrrolidin-1-yl}-phenyl)-acetaldehyde (Example 126) | D-2-1 | 0.6 | 0.89 | 528.13 |

Synthesis of Compounds of Formula Ix

Method A (Boc Cleavage)

To a solution of intermediate Iv (1 eq) in DCM (4 mL/mmol) was added dropwise TFA (1 mL/mmol) and the rxn mixture was stirred at RT for a given time (see Table 55). It was basified with a 1M solution of NaOH until pH 12-13 and extracted with DCM (3×). The combined org. phases were dried over $MgSO_4$ and concentrated in vacuo. The crude was purified by prep. LC-MS using method 4.

Method B (Ketal Cleavage)

To a soln. of ketal Iv or Ik (1 eq) in anh. THF (9 mL/mmol) was added a 25% aq. soln. of HCl (3 mL/mmol) at 0° C. and the rxn mixture was stirred for a given time (see Table 55) at RT. The rxn mixture was quenched with a sat. aq. soln. of $NaHCO_3$ and extracted with EtOAc (3×). The combined org. phases were washed with brine, dried over $MgSO_4$ and concentrated in vacuo. The crude was purified by CC using Hept/EtOAc.

TABLE 55

| Ix | Name | Reactant Iv or Ik | Method | time [h] | $t_R$ [min] | MS-data m/z $[M + H]^+$ |
|---|---|---|---|---|---|---|
| Ix-1 | 1-[(R)-1-(2-Fluoro-6-methyl-phenyl)-pyrrolidin-3-yl]-4-(piperidin-4-yloxy)-3-(2-trifluoromethyl-benzyl)-1,3-dihydro-imidazo[4,5-c]pyridin-2-one (Example 124) | Iv-5 | A | 1.5 | 0.83 | 570.27 |
| Ix-2 | 4-(2,3-Dihydroxy-propoxy)-1-[(R)-1-(2-fluoro-6-methyl-phenyl)-pyrrolidin-3-yl]-3-(2-trifluoromethyl-benzyl)-1,3-dihydro-imidazo[4,5-c]pyridin-2-one (Example 128) | Iv-7 | B | 1 | 0.94 | 561.21 |

TABLE 55-continued

| Ix | Name | Reactant Iv or Ik | Method time [h] | $t_R$ [min] | MS-data m/z [M + H]$^+$ |
|---|---|---|---|---|---|
| Ix-3 | 4-(2,3-Dihydroxy-propoxy)-1-[(R)-1-(2-fluoro-6-methyl-phenyl)-pyrrolidin-3-yl]-3-(2-trifluoromethyl-benzyl)-1,3-dihydro-benzoimidazol-2-one (Example 152) | Ik-4 | B 18 | 0.94 | 560.10 |

Synthesis of Compounds of Formula Iy

To a stirred soln. of Iw (1 eq) in DCM (4 mL/mmol) was added AcOH (1.5 eq) and the appropriate amine (1.1 eq) followed by NaBH(OAc)$_3$ (1.5 eq). The n mixture was stirred at RT for a given time (see Table 56) and partitioned between DCM and a sat. aq. soln. of NaHCO$_3$. The org. phase was dried over MgSO$_4$ and concentrated in vacuo. The crude was purified by CC using EtOAc/MeOH.

TABLE 56

| Iy | Name | Reactant Iw | Reactant amine | time [h] | $t_R$ [min] | MS-data m/z [M + H]$^+$ |
|---|---|---|---|---|---|---|
| Iy-1 | 1-{(R)-1-[2-Fluoro-6-(2-morpholin-4-yl-ethyl)-phenyl]-pyrrolidin-3-yl}-4-methoxy-3-(2-trifluoromethyl-benzyl)-1,3-dihydro-benzoimidazol-2-one (Example 131) | Iw-1 | morpholine | 2 | 0.89 | 599.32 |

Synthesis of Compounds of Formula Iz

To a stirred suspension of alcohol In (1eq) in THF (15 mL/mmol) was added at 0° C. NaH (5 eq). The mixture was stirred for 10 min and the corresponding halide (1.5 eq) was added. The rxn mixture was allowed to reach RT and stirred at a given temperature for a given time (see Table 57). It was quenched with water and extracted with DCM (3×). The combined org. phases were dried over MgSO$_4$ and concentrated in vacuo. The crude was purified by CC using Hept/EtOAc or DCM/MeOH.

TABLE 57

| Iz | Name | Reactant In | Reactant halide | T [° C.] time [h] | $t_R$ [min] | MS-data m/z [M + H]$^+$ |
|---|---|---|---|---|---|---|
| Iz-1 | 1-{(R)-1-[2-Fluoro-6-(1-methoxy-ethyl)-phenyl]-pyrrolidin-3-yl}-4-methoxy-3-(2-trifluoromethyl-benzyl)-1,3-dihydro-benzoimidazol-2-one (Example 148) | In-1 | Methyl iodide | RT 4 | 1.09 | 543.92 |

Synthesis of Compounds of Formula Iaa

To a soln. of intermediate Ic (1 eq) in EtOAc (3 mL/mmol) was added 10% Pd/C moistened with ~50% water (0.01 eq) and the rxn mixture was hydrogenated under atmospheric pressure for a given time (see Table 58). It was filtered over a pad of celite and the filtrate was concentrated in vacuo. The crude was purified by CC using Hept/EtOAc.

TABLE 58

| Iaa | Name | Reactant Ic | time [h] | $t_R$ [min] | MS-data m/z $[M + H]^+$ |
|---|---|---|---|---|---|
| Iaa-1 | 1-[(R)-1-(2-Amino-6-fluoro-phenyl)-pyrrolidin-3-yl]-4-methoxy-3-(2-trifluoromethyl-benzyl)-1,3-dihydro-benzoimidazol-2-one (Example 155) | Ic-10 | 1 | 1.01 | 501.03 |

Synthesis of Compounds of Formula Iab

A stirred soln. of aniline Iaa (1 eq) in a 48% aq. soln. of HBr (2.7 mL/mmol) was cooled to −20° C. and a soln. of NaNO$_2$ (1 eq) in H$_2$O (0.4 mL/mmol) was dropwise added. The mixture was stirred for 30 min at 0° C. and a soln. of CuBr (0.55 eq) in a 48% aq. soln. of HBr (0.8 mL/mmol) was dropwise added. The rxn mixture was heated to 60° C. and stirred for a given time (see Table 59). The pH was adjusted to around 7 by the addition of a 2M aq. soln. of NaOH and the mixture was extracted with EtOAc (3×). The combined org. phases were washed with brine, dried over MgSO$_4$ and concentrated in vacuo. The crude was purified by prep. LC-MS using method 1.

TABLE 59

| Iab | Name | Reactant Iaa | time [h] | $t_R$ [min] | MS-data m/z $[M + H]^+$ |
|---|---|---|---|---|---|
| Iab-1 | 1-[(R)-1-(2-Bromo-6-fluoro-phenyl)-pyrrolidin-3-yl]-4-methoxy-3-(2-trifluoromethyl-benzyl)-1,3-dihydro-benzoimidazol-2-one (Example 156) | Iaa-1 | 1 | 1.11 | 563.96 |

Synthesis of Compounds of Formula Iac

To a degassed mixture of bromide Iaa (1 eq) and alkyne (1.6 eq) in anh. THF (24 mL/mmol) was added under argon CuI (0.06 eq), bis(tri-tert-butyl phosphine)palladium(0) (0.05 eq) and DBU (1.3 eq). The mixture was heated to 70° C. and stirred for 2h (see Table 60). The volatiles were evaporated off and the residue was purified by prep. L-MS using method 3.

TABLE 60

| Iac | Name | Reactant Iab | Reactant alkyne | $t_R$ [min] | MS-data m/z $[M + H]^+$ |
|---|---|---|---|---|---|
| Iac-1 | 1-{(R)-1-[2-Fluoro-6-(3-morpholin-4-yl-prop-1-ynyl)-phenyl]-pyrrolidin-3-yl}-4-methoxy-3-(2-trifluoromethyl-benzyl)-1,3-dihydro-benzoimidazol-2-one (Example 159) | Iab-1 | 4-(Prop-2-yn-1-yl) morpholine | 0.87 | 609.04 |

Synthesis of Compounds of Formula Iad

To a soln. of alkyne Iac (1eq) in EtOAc (3 mL/mmol) was added 10% Pd/C moistened with ~50% water (0.01 eq) and the rxn mixture was hydrogenated under atmospheric pressure for a given time (see Table 61). It was filtered over a pad of celite and the filtrate was concentrated in vacuo. The crude was purified by prep. LC-MS using method 5.

TABLE 61

| Iad | Name | Reactant Iac | time [h] | $t_R$ [min] | MS-data m/z $[M + H]^+$ |
|---|---|---|---|---|---|
| Iad-1 | 1-{(R)-1-[2-Fluoro-6-(3-morpholin-4-yl-propyl)-phenyl]-pyrrolidin-3-yl}-4-methoxy-3-(2-trifluoromethyl-benzyl)-1,3-dihydro-benzoimidazol-2-one (Example 162) | Iac-1 | 7 | 0.87 | 613.09 |

Synthesis of Compounds of Formula Iae

A soln. of alcohol In (1 eq) in DCM (3 mL/mmol) was cooled to 0° C. and thionyl chloride (1.1 eq) was dropwise added. The rxn mixture was stirred for 30 min at RT and the volatiles were evaporated off. The residue was taken in DCM (5 mL/mmol) and TEA (5 eq) followed by the appropriate amine (1.1 eq) were added at 0° C. The mixture was allowed to warm to RT and stirred for a given time (see Table 62). It was diluted with DCM and washed with a 1M aq. soln. of NaOH. The org. phase was dried over $MgSO_4$ and concentrated in vacuo. The crude was purified by prep. LC-MS using method 2 and 5.

TABLE 62

| Iae | Name | Reactant In | Reactant amine | time [h] | $t_R$ [min] | MS-data m/z $[M + H]^+$ |
|---|---|---|---|---|---|---|
| Iae-1 | 1-((R)-1-{2-Fluoro-6-[1-(3-methoxy-azetidin-1-yl)-ethyl]-phenyl}-pyrrolidin-3-yl)-4-methoxy-3-(2-trifluoromethyl-benzyl)-1,3-dihydro-benzoimidazol-2-one (Example 163) | In-1 | 3-Methoxy azetidine | 4 | 0.91/0.93 | 599.04 |

Synthesis of Intermediates of Formula E-2

To a soln. of carboxylic ester Iq (1 eq) in THF (7.2 mL/mmol) was added a 2M aq. soln. of NaOH (10 eq) and the rxn mixture was stirred at RT for a given time (see Table 63). It was acidified with a 1M aq. soln. of HCl until pH-4-5 and extracted with EtOAc (3×). The combined org. phases were washed with brine, dried over $MgSO_4$ and concentrated in vacuo. The crude was purified by CC using Hept/EtOAc.

TABLE 63

| E-2 | Name | Reactant Iq | time [h] | $t_R$ [min] | MS-data m/z $[M + H]^+$ |
|---|---|---|---|---|---|
| E-2-1 | 1-[1-(2-Fluoro-6-methyl-phenyl)-piperidin-4-yl]-3-(2-hydroxy-benzyl)-4-methoxy-1,3-dihydro-benzoimidazol-2-one | Iq-45 | 4 | 1.09 | 462.11 |

Synthesis of Compounds of Formula Iaf

Method A (NaH/THF)

To a stirred suspension of phenol E-2 (1eq) in THF (15 mL/mmol) was added at 0° C. NaH (5eq). The mixture was stirred for 10 min and the corresponding halide (1.5 eq) was added. The rxn mixture was stirred at a given temperature for a given time (see Table 64). It was quenched with water and extracted with EtOAc (3×). The combined org. phases were dried over $MgSO_4$ and concentrated in vacuo. The crude was purified by CC using Hept/EtOAc.

Method B ($K_2CO_3$/DMF)

To a stirred soln. of phenol E-2 (1 eq) in anh. DMF (8 mL/mmol) was added $K_2CO_3$(2 eq) and the corresponding halide (2eq). The rxn mixture was stirred for a given time and a given temperature (see Table 64). Additional amount of halide (3×2eq) were added to bring the rxn to completion. It was partitioned between EtOAc and $H_2O$ and the org. phase was washed with brine, dried over $MgSO_4$ and concentrated in vacuo. The crude was purified

TABLE 64

| Iaf | Name | Reactant E-2 | Reactant halide | Method T [° C.] time [h] | $t_R$ [min] | MS-data m/z [M + H]+ |
|---|---|---|---|---|---|---|
| Iaf-1 | 3-(2-Cyclopropylmethoxy-benzyl)-1-[1-(2-fluoro-6-methyl-phenyl)-piperidin-4-yl]-4-methoxy-1,3-dihydro-benzoimidazol-2-one (Example 224) | E-2-1 | (Bromo methyl) cyclopropane | A 60° C. 18 h | 1.14 | 516.20 |
| Iaf-2 | 1-[1-(2-Fluoro-6-methyl-phenyl)-piperidin-4-yl]-4-methoxy-3-[2-(oxetan-3-yloxy)-benzyl]-1,3-dihydro-benzoimidazol-2-one (Example 225) | E-2-1 | 3-Bromo oxetane | B up to 90° C. 120 | 1.08 | 518.17 |
| Iaf-3 | 3-(2-Cyclobutoxy-benzyl)-1-[1-(2-fluoro-6-methyl-phenyl)-piperidin-4-yl]-4-methoxy-1,3-dihydro-benzoimidazol-2-one (Example 226) | E-2-1 | Bromo cyclobutane | B up to 100° C. 120 | 1.15 | 516.18 |

Synthesis of Intermediates of Formula C-2

To a soln. of methyl carbamate BB-10 (1 eq) in MeCN (4.3 mL/mmol) was added $K_2CO_3$ (2.2 eq) and the corresponding halide (1.05 eq). The rxn mixture was heated to a given temperature and stirred for a given time (see Table 65). It was filtered and the filtrate was concentrated in vacuo. The crude was purified by CC using Hept/EtOAc.

TABLE 65

| C-2 | Name | Reactant BB-10 | Reactant halide | T [° C.] time [h] | $t_R$ [min] | MS-data m/z [M + H]+ |
|---|---|---|---|---|---|---|
| C-2-1 | (3-Bromo-5-methoxy-pyridin-4-yl)-(2-trifluoromethyl-benzyl)-carbamic acid methyl ester | BB-10-1 | 2-(Trifluoromethyl) benzyl bromide | 80 2 | 1.09 | 419.05 |

Synthesis of Compounds of Formula Iag

Sodium tert-butoxide (6 eq), BrettPhos precatalyst (0.3 eq) and BrettPhos (0.3 eq) were placed in a sealed cap vial and a soln. of intermediate-2 (3 eq) and amine BB-4 (1eq) in anh. dioxane were added. The rxn mixture was flushed with $N_2$, heated at a given temperature and stirred for a given time (see Table 66). It was quenched with water and extracted with DCM (3×). The combined org. phases were dried over $MgSO_4$ and concentrated in vacuo. The crude was purified by prep. LC-MS using method 1.

TABLE 66

| Iag | Name | Reactant C-2 | Reactant BB-4 | T [° C.] time [h] | $t_R$ [min] | MS-data m/z $[M + H]^+$ |
|---|---|---|---|---|---|---|
| Iag-1 | 3-[1-(2-Fluoro-6-methyl-phenyl)-piperidin-4-yl]-7-methoxy-1-(2-trifluoromethyl-benzyl)-1,3-dihydro-imidazo[4,5-c]pyridin-2-one (Example 229) | C-2-1 | BB-4-2 | 80 2 | 1.01 | 515.23 |

Synthesis of Compounds of Formula Iah

To a soln. of intermediate Ib (1 eq) in EtOH (20 mL/mmol) was added 20% palladium hydroxide on carbon (0.1 eq) and the rxn mixture was hydrogenated under atmospheric pressure for a given time (see Table 67). It was filtered over a pad of celite and the filtrate was concentrated in vacuo. The crude was purified by CC using Hept/EtOAc.

TABLE 67

| Iah | Name | Reactant Ib | time [h] | $t_R$ [min] | MS-data m/z $[M + H]^+$ |
|---|---|---|---|---|---|
| Iah-1 | 1-[1-(2-Hydroxy-phenyl)-piperidin-4-yl]-4-methoxy-3-(2-trifluoromethyl-benzyl)-1,3-dihydro-benzoimidazol-2-one (Example 230) | Ib-62 | 96 | 0.83 | 498.02 |

Synthesis of Compounds of Formula Iai

To a soln. of intermediate Iah (1 eq) and alcohol $R^{15}$—OH (1 to 1.5eq) in toluene (10 mL/mmol) was added a 1M soln. of (tributylphosphoranylidene)acetonitrile in toluene (2eq) under argon. The rxn mixture was heated to 110° C. and stirred for a given time (see Table 68). It was quenched with water and extracted with DCM (3×). The combined org. phases were washed with brine, dried over $MgSO_4$ and concentrated in vacuo. The crude was purified by CC using Hept/EtOAc or DCM/MeOH. When necessary, an additional purification by prep. LC-MS using method 5 can be performed.

TABLE 68

| Iai | Name | Reactant Iah | Alcohol $R^{15}$—OH | time [h] | $t_R$ [min] | MS-data m/z $[M + H]^+$ |
|---|---|---|---|---|---|---|
| Iai-1 | 1-(1-{2-[2-(tert-Butyl-dimethyl-silanyloxy)-ethoxy]-phenyl}-piperidin-4-yl)-4-methoxy-3-(2-trifluoromethyl-benzyl)-1,3-dihydro-benzoimidazol-2-one | Iah-1 | 2-(t-Butyl dimethylsiloxy) ethanol | 4.5 | 1.00 | 656.18 |

TABLE 68-continued

| Iai | Name | Reactant Iah | Alcohol R$^{15}$—OH | time [h] | $t_R$ [min] | MS-data m/z [M + H]$^+$ |
|---|---|---|---|---|---|---|
| Iai-2 | 4-Methoxy-1-{1-[2-(tetrahydro-pyran-4-yloxy)-phenyl]-piperidin-4-yl}-3-(2-trifluoromethyl-benzyl)-1,3-dihydro-benzoimidazol-2-one (Example 239) | Iah-1 | Tetrahydro-2H-pyran-4-ol | 4.5 | 0.89 | 582.17 |
| Iai-3 | 1-[1-(2-Cyclopropylmethoxy-phenyl)-piperidin-4-yl]-4-methoxy-3-(2-trifluoromethyl-benzyl)-1,3-dihydro-benzoimidazol-2-one (Example 240) | Iah-1 | Hydroxymethyl cyclopropane | 4.5 | 0.92 | 552.20 |
| Iai-4 | 1-[1-(2-Cyclobutoxy-phenyl)-piperidin-4-yl]-4-methoxy-3-(2-trifluoromethyl-benzyl)-1,3-dihydro-benzoimidazol-2-one (Example 241) | Iah-1 | Cyclobutanol | 4.5 | 0.91 | 552.11 |
| Iai-5 | 4-Methoxy-1-{1-[2-(oxetan-3-yloxy)-phenyl]-piperidin-4-yl}-3-(2-trifluoromethyl-benzyl)-1,3-dihydro-benzoimidazol-2-one (Example 242) | Iah-1 | Oxetan-3-ol | 18 | 0.88 | 554.18 |
| Iai-6 | 1-[1-(2-Butoxy-phenyl)-piperidin-4-yl]-4-methoxy-3-(2-trifluoromethyl-benzyl)-1,3-dihydro-benzoimidazol-2-one (Example 243) | Iah-1 | 1-Butanol | 18 | 0.94 | 554.22 |

Synthesis of Compounds of Formula Iaj

To a soln. of Iai (1 eq) in THF (20 mL/mmol) was added dropwise a 1M soln. of TBAF in THF (1.2 eq) and the rxn mixture was stirred at RT for a given time (see Table 69). It was partitioned between EtOAc and a sat. aq. soln. of NaHCO$_3$. The org. phase was dried over MgSO$_4$ and concentrated in vacuo. The crude was purified by prep. LC-MS using method 6.

TABLE 69

| Iaj | Name | Reactant Iai | time [h] | $t_R$ [min] | MS-data m/z [M + H]$^+$ |
|---|---|---|---|---|---|
| Iaj-1 | 1-{1-[2-(2-Hydroxy-ethoxy)-phenyl]-piperidin-4-yl}-4-methoxy-3-(2-trifluoromethyl-benzyl)-1,3-dihydro-benzoimidazol-2-one (Example 238) | Iai-1 | 18 | 0.82 | 542.18 |

II. Biological Assays
In Vitro Assay
hC5a DISCO IC$_{50}$ Assay

Adherent cells (CHO-K1 C5AR1 beta-arrestin cell line, DiscoverX, CA USA) are washed with PBS, detached by incubation with Dissociation Buffer (Gibco Cat #13151-014, 2 ml per 165 cm2 dish) for 3 minutes, then washed with 10 ml PBS (without Mg++ and Ca++) and counted. 7500 cells/384-well are seeded out in 384-well plates (Cell culture plate MTP384 white Polystyrene, Corning, Cat #3570) in 20 μl/well Cell plating medium (F12 HAMs/10% FCS/1% P/S) and incubated at 37° C./5% CO2/24h.

5 μl Antagonist at 6-fold end concentration or DMSO control is added to assay medium and subsequently 5 μl 1-10 nM C5a agonist at 6 fold end concentration. Cells are centrifuged for 1 min at 1000 rpm and incubated for 1.5 hour in at 37° C. Plates are equilibrated at room temperature for several minutes before adding 12 μl/well Detection Reagent (PathHunter Detection Kit, DiscoverX, Cat #93-0001). Plates are centrifuged for 1 min at 1000 rpm and incubated for 45 minutes at RT before being measured on a Fluostar Optima, BMG Labtech. IC$_{50}$ values are calculated from a serial dilution range of antagonist using inhouse software and given in nmol/l.

The calculated IC$_{50}$ values may fluctuate depending on the daily cellular assay performance. Fluctuations of this kind are known to those skilled in the art. Average IC$_{50}$ values from several measurements are given as geometric mean values.

Antagonistic activities of exemplified compounds are displayed in Table 70 below.

TABLE 70 list of examples and their antagonistic activities

| Example Number | Compound No | C5aR IC$_{50}$ (nM) |
|---|---|---|
| 1 | Ia-1 | 621 |
| 2 | Ib-1 | 18 |
| 3 | Ir-3 | 23 |
| 4 | Ib-2 | 131 |
| 5 | Ib-3 | 284 |
| 6 | Ia-2 | 66 |
| 7 | Ib-4 | 11 |
| 8 | Ib-5 | 14 |
| 9 | Ib-6 | 32 |
| 10 | Ib-7 | 23 |

TABLE 70-continued list of examples and their antagonistic activities

| Example Number | Compound No | C5aR IC$_{50}$ (nM) |
|---|---|---|
| 11 | Ib-8 | 29 |
| 12 | Ib-9 | 10 |
| 13 | Ib-10 | 16 |
| 14 | Ic-1 | 216 |
| 15 | Ib-11 | 13 |
| 16 | Ib-12 | 19 |
| 17 | Ib-13 | 22 |
| 18 | Ib-14 | 13 |
| 19 | Ib-15 | 12 |
| 20 | Ia-3 | 36 |
| 21 | Id-1 | 3442 |
| 22 | Ib-16 | 30 |
| 23 | Ib-17 | 8 |
| 24 | Ie-1 | 330 |
| 25 | If-1 | 185 |
| 26 | Ig-1 | 459 |
| 27 | Ih-1 | 3344 |
| 28 | Ih-2 | 1326 |
| 29 | Ig-2 | 182 |
| 30 | Ih-3 | 1523 |
| 31 | Ii-1 | 3454 |
| 32 | Ii-2 | 642 |
| 33 | Ib-18 | 8 |
| 34 | Ib-19 | 27 |
| 35 | Ii-3 | 4510 |
| 36 | Ib-20 | 450 |
| 37 | Ib-21 | 7 |
| 38 | Ib-22 | 470 |
| 39 | Ia-4 | 2434 |
| 40 | Ij-1 | 6 |
| 41 | Ib-23 | 18 |
| 42 | Ib-24 | 75 |
| 43 | Ia-5 | 393 |
| 44 | Ij-2 | 13 |
| 45 | Ib-25 | 16 |
| 46 | Ib-26 | 39 |
| 47 | Ib-27 | 95 |
| 48 | Ib-28 | 165 |
| 49 | Ib-29 | 132 |
| 50 | Ib-30 | 42 |
| 51 | Ib-31 | 62 |
| 52 | Ik-1 | 30 |
| 53 | Ia-7 | 1845 |
| 54 | Ib-32 | 43 |
| 55 | Ib-33 | 178 |
| 56 | Ij-3 | 717 |
| 57 | Ij-4 | 89 |
| 58 | Ib-34 | 25 |
| 59 | Ib-35 | 49 |
| 60 | Ig-3 | 84 |
| 61 | Ig-4 | 65 |
| 62 | Ig-5 | 99 |
| 63 | Ig-6 | 729 |
| 64 | Ia-10 | 2916 |
| 65 | Ia-8 | 396 |
| 66 | Ib-36 | 60 |
| 67 | Ib-37 | 36 |
| 68 | Ib-38 | 84 |
| 69 | Ic-2 | 2819 |
| 70 | Ig-7 | 538 |
| 71 | Ic-3 | 133 |
| 72 | Ig-8 | 397 |
| 73 | Ib-39 | 272 |
| 74 | Ib-40 | 1330 |
| 75 | Ib-41 | 27 |
| 76 | Ib-42 | 38 |
| 77 | Ib-43 | 89 |
| 78 | Ib-44 | 121 |
| 79 | Id-2 | 911 |
| 80 | Ie-2 | 157 |
| 81 | Ij-5 | 2427 |
| 82 | Ic-4 | 28 |
| 83 | Ic-5 | 23 |
| 84 | Ic-6 | 2035 |
| 85 | Ie-1 | 712 |
| 86 | Ig-9 | 229 |
| 87 | Ic-7 | 629 |
| 88 | Im-1 | 39 |
| 89 | In-1 | 44 |
| 90 | Io-1 | 38 |
| 91 | Ip-1 | 70 |
| 92 | Iq-1 | 2024 |
| 93 | Ij-6 | 149 |
| 94 | Ij-7 | 313 |
| 95 | Ir-1 | 191 |
| 96 | Iq-7 | 231 |
| 97 | Iq-8 | 1351 |
| 98 | Iq-2 | 165 |
| 99 | Is-1 | 391 |
| 100 | Is-2 | 1428 |
| 101 | Is-3 | 1580 |
| 102 | It-1 | 759 |
| 103 | Iu-1 | 669 |
| 104 | Iq-3 | 863 |
| 105 | Iq-4 | 4483 |
| 106 | Iu-2 | 227 |
| 107 | Iu-3 | 1318 |
| 108 | Iu-4 | 360 |
| 109 | Ic-8 | 61 |
| 110 | Ib-45 | 6 |
| 111 | Iq-9 | 264 |
| 112 | Iq-10 | 511 |
| 113 | Iq-11 | 2240 |
| 114 | Iq-12 | 1543 |
| 115 | Iu-5 | 21 |
| 116 | Iu-6 | 165 |
| 117 | Iq-13 | 308 |
| 118 | Iv-1 | 201 |
| 119 | Iv-2 | 12 |
| 120 | Iv-3 | 659 |
| 121 | Iv-4 | 270 |
| 122 | Iv-5 | 509 |
| 123 | Iv-6 | 42 |
| 124 | Ix-1 | 5220 |
| 125 | Iv-7 | 124 |
| 126 | Iw-1 | 20 |
| 127 | Iv-8 | 17 |
| 128 | Ix-2 | 207 |
| 129 | Iv-9 | 53 |
| 130 | Iv-10 | 3908 |
| 131 | Iy-1 | 53 |
| 132 | Iu-7 | 314 |
| 133 | Iu-8 | 70 |
| 134 | Iu-9 | 2265 |
| 135 | Iu-10 | 5764 |
| 136 | Iu-11 | 1586 |
| 137 | Iu-12 | 133 |
| 138 | Iu-13 | 156 |
| 139 | Iu-14 | 227 |
| 140 | Iu-15 | 1034 |
| 141 | Iu-16 | 2128 |
| 142 | Iu-17 | 108 |
| 143 | Iu-18 | 108 |
| 144 | Ia-12 | 312 |
| 145 | Ic-9 | 16 |
| 146 | Ia-13 | 201 |
| 147 | Ib-46 | 20 |
| 148 | Iz-1 | 28 |
| 149 | Ik-2 | 14 |
| 150 | Ik-3 | 11 |
| 151 | Ik-4 | 31 |
| 152 | Ix-3 | 38 |
| 153 | Iq-14 | 215 |
| 154 | Ic-10 | 23 |
| 155 | Iaa-1 | 15 |
| 156 | Iab-1 | 21 |
| 157 | Ic-11 | 630 |
| 158 | Ic-12 | 683 |
| 159 | Iac-1 | 73 |
| 160 | Ib-47 | 35 |

TABLE 70-continued list of examples and their antagonistic activities

| Example Number | Compound No | C5aR IC$_{50}$ (nM) |
|---|---|---|
| 161 | Ib-48 | 69 |
| 162 | Iad-1 | 135 |
| 163 | Iae-1 | 591 |
| 164 | Ia-14 | 179 |
| 165 | Iq-15 | 6 |
| 166 | Iq-5 | 17 |
| 167 | Iq-16 | 6 |
| 168 | Iq-17 | 10 |
| 169 | Iq-18 | 17 |
| 170 | Iq-19 | 45 |
| 171 | Iq-6 | 64 |
| 172 | Iq-20 | 275 |
| 173 | Ir-2 | 107 |
| 174 | Iq-21 | 544 |
| 175 | Iq-22 | 221 |
| 176 | Iq-23 | 48 |
| 177 | Iq-24 | 24 |
| 178 | Iq-25 | 49 |
| 179 | Ia-15 | 122 |
| 180 | Iq-26 | 9 |
| 181 | Iq-27 | 22 |
| 182 | Iq-28 | 9 |
| 183 | Iq-29 | 14 |
| 184 | Ib-49 | 36 |
| 185 | Ib-50 | 36 |
| 186 | Iq-30 | 14 |
| 187 | Iq-31 | 26 |
| 188 | Ia-16 | 313 |
| 189 | Iq-32 | 13 |
| 190 | Ib-51 | 118 |
| 191 | Ia-17 | 114 |
| 192 | Iq-33 | 42 |
| 193 | Is-4 | 632 |
| 194 | Is-5 | 1485 |
| 195 | Iq-34 | 20 |
| 196 | Ia-18 | 139 |
| 197 | Ib-52 | 74 |
| 198 | Ib-53 | 15 |
| 199 | Ia-19 | 119 |
| 200 | Ib-54 | 19 |
| 201 | Ib-55 | 31 |
| 202 | Iq-35 | 2 |
| 203 | Iq-36 | 6 |
| 204 | Ib-56 | 30 |
| 205 | Iv-11 | 45 |
| 206 | Iv-12 | 2298 |
| 207 | Iv-13 | 508 |
| 208 | Iq-37 | 19 |
| 209 | Iq-38 | 34 |
| 210 | Ia-20 | 2294 |
| 211 | Ib-57 | 27 |
| 212 | Ib-58 | 2079 |
| 213 | Ia-22 | 469 |
| 214 | Ia-21 | 205 |
| 215 | Ib-59 | 27 |
| 216 | Iq-39 | 12 |
| 217 | Ib-60 | 158 |
| 218 | Iq-40 | 346 |
| 219 | Iq-41 | 34 |
| 220 | Iq-42 | 109 |
| 221 | Iq-43 | 175 |
| 222 | Ih-4 | 2651 |
| 223 | Iq-44 | 130 |
| 224 | Iaf-1 | 18 |
| 225 | Iaf-2 | 40 |
| 226 | Iaf-3 | 36 |
| 227 | Ib-61 | 30 |
| 228 | Ia-23 | 259 |
| 229 | Iag-1 | 268 |
| 230 | Iah-1 | 129 |
| 231 | Ib-62 | 66 |
| 232 | Ib-63 | 82 |
| 233 | Ib-64 | 195 |
| 234 | Ib-65 | 17 |
| 235 | Ib-66 | 28 |
| 236 | Ib-67 | 171 |
| 237 | Ib-68 | 90 |
| 238 | Iaj-1 | 133 |
| 239 | Iai-2 | 82 |
| 240 | Iai-3 | 46 |
| 241 | Iai-4 | 36 |
| 242 | Iai-5 | 74 |
| 243 | Iai-6 | 61 |
| 244 | Ib-69 | 227 |
| 245 | Ib-70 | 111 |
| 246 | Ib-71 | 39 |
| 247 | Ib-72 | 563 |
| 248 | Ib-73 | 182 |
| 249 | Ib-74 | 273 |
| 250 | Ib-75 | 853 |

The invention claimed is:
1. A compound of formula (I)

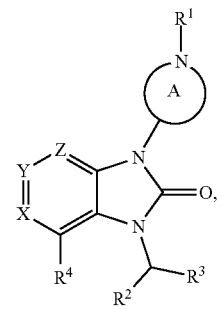

Formula (I)

or a pharmaceutically acceptable salt thereof,
wherein
ring A represents a saturated 4- to 7-membered monocyclic carbocyclic ring containing the ring nitrogen atom to which $R^1$ is attached, wherein said ring independently is unsubstituted, or mono-, or di-substituted wherein the substituents are independently selected from the group consisting of $(C_{1-3})$alkyl, fluoro, and $(C_{1-4})$alkoxy-carbonyl; or
ring A represents a saturated 7- or 8-membered bridged bi-cyclic carbocyclic ring containing the ring nitrogen atom to which $R^1$ is attached, wherein said ring is unsubstituted;
X and Z independently represent $CR^5$ or N; and Y represents $CR^5$; or, in case both X and Z represent CH, Y may in addition represent N; wherein each $R^5$ independently represents hydrogen, or $(C_{1-3})$alkyl;
$R^1$ represents
(C1-4)alkyl;
CO—$R^{11}$ wherein $R^{11}$ represents $(C_{1-4})$alkyl; $(C_{1-4})$alkoxy; phenyl, phenoxy; $(C_{3-6})$cycloalkyl; or $(C_{3-6})$cycloalkoxy optionally containing one ring oxygen and optionally mono-substituted with methyl or trifluoromethyl;
benzyl wherein the phenyl ring of said benzyl is optionally mono- or di-substituted with halogen; or
phenyl, or 5- or 6-membered heteroaryl; wherein said phenyl or 5- or 6-membered heteroaryl independently is unsubstituted, mono-, di- or tri-substituted, wherein the substituents are independently selected from the group consisting of
$(C_{1-4})$alkyl;
$(C_{1-4})$alkoxy;
$(C_{1-3})$fluoroalkyl;
$(C_{1-3})$fluoroalkoxy;
halogen;
cyano;
nitro;
hydroxy;
hydroxy-$(C_{1-3})$alkyl;
$(C_{1-4})$alkoxy-$(C_{1-3})$alkyl;
hydroxy-$(C_{2-3})$alkoxy;
$(C_{1-4})$alkoxy-$(C_{2-3})$alkoxy;
$(C_{3-6})$cycloalkyl-$X^{12}$—, wherein $X^{12}$ represents a direct bond, —O—, or —$(C_{1-3})$alkylene-O—, and wherein the $(C_{3-6})$cycloalkyl independently contains one optional ring oxygen;
$R^{13}$—CO—$X^{13}$—, wherein $X^{13}$ represents a direct bond or $(C_{1-3})$alkylene, and $R^{13}$ represents hydrogen or $(C_{1-4})$alkyl);
3-(morpholin-4-yl)-prop-1-ynyl;
$R^{14a}R^{14b}N$—$X^{14}$—, wherein $X^{14}$ represents a direct bond or $(C_{1-3})$alkylene; and wherein $R^{14a}$ and $R^{14b}$ independently represent hydrogen, $(C_{1-4})$alkyl, hydroxy-$(C_{2-4})$alkyl, $(C_{1-3})$alkoxy-$(C_{2-4})$alkyl; or $R^{14a}$ and $R^{14b}$ together with the nitrogen to which they are attached to form a 4- to 6-membered saturated ring optionally containing one additional ring heteroatom selected from oxygen and nitrogen; and wherein said ring is optionally mono-substituted with $(C_{1-4})$alkyl, hydroxy, $(C_{1-4})$alkoxy, or dimethylamino; and
benzyloxy, wherein the phenylring of benzyloxy is optionally mono- or di-substituted with halogen or methyl;
$R^2$ represents phenyl, or 5- or 6-membered heteroaryl; wherein said phenyl or 5- or 6-membered heteroaryl independently is mono-, di- or tri-substituted, wherein the substituents are independently selected from the group consisting of
$(C_{1-4})$alkyl;
$(C_{1-4})$alkoxy;
$(C_{1-3})$fluoroalkyl;
$(C_{1-3})$fluoroalkoxy;
halogen; and
$(C_{3-6})$cycloalkyl-$X^{21}$—, wherein $X^{21}$ represents a direct bond, —O—, or —$(C_{1-3})$alkylene-O—, and wherein the $(C_{3-6})$cycloalkyl independently contains one optional ring oxygen;
$R^3$ represents hydrogen, or $(C_{1-3})$alkyl; and
$R^4$ represents
$(C_{1-4})$alkyl;
hydroxy-$(C_{1-3})$alkyl;
—O—$R^{41}$, wherein $R^{41}$ represents
hydrogen;
$(C_{1-4})$alkyl;
$(C_{2-4})$alkyl which is substituted with one or two hydroxy;
$R^{41a}R^{41b}N$—$(C_{2-3})$alkylene-, wherein $R^{41a}$ and $R^{41b}$ independently represent hydrogen or $(C_{1-4})$alkyl; or
$(C_{4-7})$heterocyclyl-$X^{41}$—, wherein $X^{41}$ represents a direct bond or $(C_{1-3})$alkylene, and wherein the $(C_{4-7})$heterocyclyl independently contains one or two ring heteroatoms independently selected from the group consisting of nitrogen and oxygen;

wherein said $(C_{4-7})$heterocyclyl independently is unsubstituted, or mono-, or di-substituted, wherein the substituents are independently selected from the group consisting of:
$(C_{1-4})$alkyl; and/or
$(C_{1-4})$alkoxy-carbonyl attached to a ring nitrogen atom having a free valency;
—$NR^{42a}R^{42b}$ wherein $R^{42a}$ and $R^{42b}$ independently represent hydrogen, $(C_{1-4})$alkyl, $(C_{1-3})$alkoxy-$(C_{2-3})$alkyl, hydroxy-$(C_{2-3})$alkyl, or $R^{42a}$ and $R^{42b}$ together with the nitrogen to which they are attached form a 4- to 7-membered saturated ring optionally containing one further ring heteroatom selected from the group consisting of oxygen and nitrogen, wherein said ring is unsubstituted or mono-substituted with $(C_{1-3})$alkyl or $(C_{1-3})$alkoxy; or
—CO—$R^{43}$ wherein $R^{43}$ represents $(C_{1-4})$alkoxy, or —$NR^{43a}R^{43b}$ wherein $R^{43a}$ and $R^{43b}$ independently represent hydrogen, $(C_{1-4})$alkyl, $(C_{1-3})$alkoxy-$(C_{2-3})$alkyl or hydroxy-$(C_{2-3})$alkyl.

2. The compound according to claim 1, or a pharmaceutically acceptable salt thereof, wherein
ring A represents a saturated 4- to 7-membered mono-cyclic carbocyclic ring containing the ring nitrogen atom to which $R^1$ is attached, wherein said ring independently is unsubstituted, or mono-substituted with $(C_{1-3})$alkyl, fluoro, or $(C_{1-4})$alkoxy-carbonyl, or di-substituted wherein the substituents are two $(C_{1-3})$alkyl substituents, or two fluoro substituents; or
ring A represents a saturated 7- or 8-membered bridged bi-cyclic carbocyclic ring containing the ring nitrogen atom to which $R^1$ is attached, wherein said ring is unsubstituted.

3. The compound according to claim 1, or a pharmaceutically acceptable salt thereof; wherein ring A represents a saturated 4- to 7-membered mono-cyclic carbocyclic ring containing the ring nitrogen atom to which $R^1$ is attached, wherein said ring independently is unsubstituted, or mono-substituted with $(C_{1-3})$alkyl, fluoro, or $(C_{1-4})$alkoxy-carbonyl, or di-substituted wherein the substituents are two $(C_{1-3})$alkyl substituents, or two fluoro substituents.

4. The compound according to claim 1, or a pharmaceutically acceptable salt thereof; wherein
X represents $CR^5$; Z represents $CR^5$; and Y represents $CR^5$; wherein each $R^5$ independently represents hydrogen, or $(C_{1-3})$alkyl;
X represents CH; Z represents N; and Y represents $CR^5$; wherein each $R^5$ independently represents hydrogen, or $(C_{1-3})$alkyl;
X represents N; Z represents $CR^5$; and Y represents $CR^5$; wherein each $R^5$ independently represents hydrogen or $(C_{1-3})$alkyl;
X represents N; Z represents N; and Y represents $CR^5$; wherein $R^5$ represents hydrogen, or $(C_{1-3})$alkyl.

5. The compound according to claim 1, or a pharmaceutically acceptable salt thereof; wherein one of X and Z represents CH or N; the other represents CH; and Y represents $CR^5$, wherein $R^5$ represents hydrogen or $(C_{1-3})$alkyl.

6. The compound according to claim 1, or a pharmaceutically acceptable salt thereof; wherein $R^1$ represents
$(C_{1-4})$alkyl;
—CO—$R^{11}$ wherein $R^{11}$ represents $(C_{1-4})$alkyl; $(C_{1-4})$alkoxy; phenyl, phenoxy; or $(C_{3-6})$cycloalkoxy optionally containing one ring oxygen and optionally mono-substituted with methyl or trifluoromethyl;
benzyl wherein the phenyl ring of said benzyl is optionally mono- or di-substituted with halogen;

phenyl which is unsubstituted, mono-, di- or tri-substituted, wherein the substituents are independently selected from the group consisting of
$(C_{1-4})$alkyl;
$(C_{1-4})$alkoxy;
$(C_{1-3})$fluoroalkyl;
$(C_{1-3})$fluoroalkoxy;
halogen;
cyano;
nitro;
hydroxy;
hydroxy-$(C_{1-3})$alkyl;
$(C_{1-4})$alkoxy-$(C_{1-3})$alkyl;
hydroxy-$(C_{2-3})$alkoxy;
$(C_{1-4})$alkoxy-$(C_{2-3})$alkoxy;
$(C_{3-6})$cycloalkyl-$X^{12}$—, wherein $X^{12}$ represents a direct bond, —O—, or —$(C_{1-3})$alkylene-O—, and wherein the $(C_{3-6})$cycloalkyl independently contains one optional ring oxygen;
$R^{13}$—CO—$X^{13}$—, wherein $X^{13}$ represents a direct bond or $(C_{1-3})$alkylene, and $R^{13}$ represents hydrogen or $(C_{1-4})$alkyl;
3-(morpholin-4-yl)-prop-1-ynyl;
$R^{14a}R^{14b}N$—$X^{14}$—, wherein $X^{14}$ represents a direct bond or $(C_{1-3})$alkylene; and wherein $R^{14a}$ and $R^{14b}$ independently represent hydrogen, $(C_{1-4})$alkyl, hydroxy-$(C_{2-4})$alkyl, $(C_{1-3})$alkoxy-$(C_{2-4})$alkyl; or $R^{14a}$ and $R^{14b}$ together with the nitrogen to which they are attached to form a 4- to 6-membered saturated ring optionally containing one additional ring heteroatom selected from oxygen and nitrogen; and wherein said ring is optionally mono-substituted with $(C_{1-4})$alkyl, hydroxy, $(C_{1-4})$alkoxy, or dimethylamino; and
benzyloxy; or
5- or 6-membered heteroaryl; wherein said 5- or 6-membered heteroaryl independently is mono-, di- or tri-substituted, wherein the substituents are independently selected from the group consisting of
$(C_{1-4})$alkyl;
$(C_{1-4})$alkoxy;
$(C_{1-3})$fluoroalkyl;
$(C_{1-3})$fluoroalkoxy;
halogen;
cyano;
$(C_{3-6})$cycloalkyl-$X^{12}$—, wherein $X^{12}$ represents a direct bond, —O—, or —$(C_{1-3})$alkylene-O; and
$R^{13}$—CO—$X^{13}$—, wherein $X^{13}$ represents a direct bond or $(C_{1-3})$alkylene, and $R^{13}$ represents hydrogen or $(C_{1-4})$alkyl.

7. The compound according to claim 1, or a pharmaceutically acceptable salt thereof; wherein
$R^1$ represents
—CO—$R^{11}$ wherein $R^{11}$ represents $(C_{1-4})$alkyl; or $(C_{1-4})$alkoxy;
phenyl which is mono-, or di- or tri-substituted, wherein the substituents are independently selected from the group consisting of
$(C_{1-4})$alkyl;
$(C_{1-4})$alkoxy;
$(C_{1-3})$fluoroalkyl;
$(C_{1-3})$fluoroalkoxy;
halogen;
cyano;
nitro;
hydroxy-$(C_{1-3})$alkyl;
$(C_{1-4})$alkoxy-$(C_{1-3})$alkyl;
hydroxy-$(C_{2-3})$alkoxy;
$(C_{1-4})$alkoxy-$(C_{2-3})$alkoxy;
$(C_{3-6})$cycloalkyl-$X^{12}$—, wherein $X^{12}$ represents a direct bond, —O—, or —$(C_{1-3})$alkylene-O—; and
$R^{14a}R^{14b}N$—$X^{14}$—, wherein $X^{14}$ represents a direct bond or $(C_{1-3})$alkylene; and wherein $R^{14a}$ and $R^{14b}$ independently represent hydrogen, $(C_{1-4})$alkyl, hydroxy-$(C_{2-4})$alkyl, $(C_{1-3})$alkoxy-$(C_{2-4})$alkyl; or $R^{14a}$ and $R^{14b}$ together with the nitrogen to which they are attached to form a 4- to 6-membered saturated ring optionally containing one additional ring heteroatom selected from oxygen and nitrogen; and wherein said ring is optionally mono-substituted with $(C_{1-4})$alkyl, hydroxy, $(C_{1-4})$alkoxy, or dimethylamino; or
5- or 6-membered heteroaryl; wherein said 5- or 6-membered heteroaryl independently is mono-, di- or tri-substituted, wherein the substituents are independently selected from the group consisting of
$(C_{1-4})$alkyl;
$(C_{1-4})$alkoxy;
$(C_{1-3})$fluoroalkyl;
halogen;
cyano; and
$(C_{3-6})$cycloalkyl-$X^{12}$—, wherein $X^{12}$ represents a direct bond.

8. The compound according to claim 1, or a pharmaceutically acceptable salt thereof; wherein $R^2$ represents phenyl, or 6-membered heteroaryl; wherein said phenyl or 6-membered heteroaryl independently is mono-, or di-substituted, wherein the substituents are independently selected from the group consisting of
$(C_{1-4})$alkyl;
$(C_{1-4})$alkoxy;
$(C_{1-3})$fluoroalkyl;
$(C_{1-3})$fluoroalkoxy;
halogen; and
$(C_{3-6})$cycloalkyl-$X^{21}$—, wherein $X^{21}$ represents a direct bond, —O—, or —$(C_{1-3})$alkylene-O—, and wherein the $(C_{3-6})$cycloalkyl independently contains one optional ring oxygen.

9. The compound according to claim 1, or a pharmaceutically acceptable salt thereof; wherein $R^2$ represents phenyl, or 6-membered heteroaryl; wherein said phenyl or 6-membered heteroaryl is mono-substituted in ortho position with regard to the point of attachment of the rest of the molecule, wherein the substituent is independently selected from the group consisting of
$(C_{1-4})$alkyl;
$(C_{1-4})$alkoxy;
$(C_{1-3})$fluoroalkyl;
$(C_{1-3})$fluoroalkoxy; and
$(C_{3-6})$cycloalkyl-$X^{21}$—, wherein $X^{21}$ represents a direct bond, —O—, or —$(C_{1-3})$alkylene-O—, and wherein the $(C_{3-6})$cycloalkyl independently contains one optional ring oxygen.

10. The compound according to claim 1, or a pharmaceutically acceptable salt thereof; wherein
$R^4$ represents
$(C_{1-4})$alkyl;
hydroxy-$(C_{1-3})$alkyl;
—O—$R^{41}$, wherein $R^{41}$ represents
hydrogen;
$(C_{1-4})$alkyl;
$(C_{2-4})$alkyl which is substituted with one or two hydroxy;

$R^{41a}R^{41b}N$—$(C_{2-3})$alkylene-, wherein $R^{41a}$ and $R^{41b}$ independently represent hydrogen or $(C_{1-4})$alkyl; or $(C_{4-7})$heterocyclyl-$X^{41}$—, wherein $X^{41}$ represents a direct bond or $(C_{1-3})$alkylene, and wherein the $(C_{4-7})$heterocyclyl independently contains one or two ring heteroatoms independently selected from the group consisting of nitrogen and oxygen; wherein the oxygen atom of such group $(C_{4-7})$heterocyclyl-$X^{41}$—O— is separated by at least two (ring and/or chain) carbon atoms from such ring heteroatom; wherein said $(C_{4-7})$heterocyclyl independently is unsubstituted, or mono-, or di-substituted, wherein the substituents are independently selected from the group consisting of:
$(C_{1-4})$alkyl; and/or
$(C_{1-4})$alkoxy-carbonyl attached to a ring nitrogen atom having a free valency;

—$NR^{42a}R^{42b}$ wherein $R^{42a}$ represents hydrogen or $(C_{1-4})$alkyl, and $R^{42b}$ independently represents hydrogen, $(C_{1-4})$alkyl, $(C_{1-3})$alkoxy-$(C_{2-3})$alkyl, hydroxy-$(C_{2-3})$alkyl, or $R^{42a}$ and $R^{42b}$ together with the nitrogen to which they are attached form a 4- to 7-membered saturated ring optionally containing one further ring heteroatom selected from the group consisting of oxygen and nitrogen, wherein said ring is unsubstituted or mono-substituted with $(C_{1-3})$alkyl, or $(C_{1-3})$alkoxy; or —CO—$R^{43}$ wherein $R^{43}$ represents $(C_{1-4})$alkoxy; or —$NR^{43a}R^{43b}$ wherein $R^{43a}$ represents hydrogen or $(C_{1-4})$alkyl, and $R^{43b}$ independently represents hydrogen, $(C_{1-4})$alkyl, $(C_{1-3})$alkoxy-$(C_{2-3})$alkyl, or hydroxy-$(C_{2-3})$alkyl.

11. The compound according to claim 1, or a pharmaceutically acceptable salt thereof; wherein
$R^4$ represents
$(C_{1-4})$alkyl;
hydroxy-$(C_{1-3})$alkyl;
—O—$R^{41}$, wherein $R^{41}$ represents
hydrogen;
$(C_{1-4})$alkyl;
$(C_{2-4})$alkyl which is substituted with one or two hydroxy;
$R^{41a}R^{41b}N$—$(C_{2-3})$alkylene-, wherein $R^{41a}$ and $R^{41b}$ independently represent hydrogen or $(C_{1-4})$alkyl; or $(C_{4-7})$heterocyclyl-$X^{41}$—, wherein $X^{41}$ represents a direct bond or —$CH_2$—, and wherein the $(C_{4-7})$heterocyclyl independently contains one or two ring heteroatoms independently selected from the group consisting of nitrogen and oxygen; wherein the oxygen atom of such group $(C_{4-7})$heterocyclyl-$X^{41}$—O— is separated by at least two (ring and/or chain) carbon atoms from such ring heteroatom; wherein said $(C_{4-7})$heterocyclyl independently is unsubstituted, or mono-substituted with $(C_{1-4})$alkyl at a ring nitrogen atom having a free valency, or di-substituted with methyl;

—$NR^{42a}R^{42b}$ wherein $R^{42a}$ represents hydrogen or $(C_{1-4})$alkyl, and $R^{42b}$ independently represents $(C_{1-4})$alkyl, $(C_{1-3})$alkoxy-$(C_{2-3})$alkyl, hydroxy-$(C_{2-3})$alkyl; or $R^{42}a$ and $R^{42b}$ together with the nitrogen to which they are attached form a 4- to 7-membered saturated ring optionally containing one further ring heteroatom selected from the group consisting of oxygen and nitrogen, wherein said ring is unsubstituted, or mono-substituted with $(C_{1-3})$alkyl attached to a ring nitrogen atom having a free valency, or $(C_{1-3})$alkoxy attached to a ring carbon; or —CO—$R^{43}$ wherein $R^{43}$ represents $(C_{1-4})$alkoxy; or —$NR^{43a}R^{43b}$ wherein $R^{43a}$ represents hydrogen or $(C_{1-4})$alkyl, and $R^{43b}$ independently represents hydrogen, $(C_{1-4})$alkyl, $(C_{1-3})$alkoxy-$(C_{2-3})$alkyl, or hydroxy-$(C_{2-3})$alkyl.

12. The compound according to claim 4, or a pharmaceutically acceptable salt thereof, wherein X represents $CR^5$; Z represents $CR^5$; and Y represents $CR^5$; wherein each $R^5$ independently represents hydrogen, or $(C_{1-3})$alkyl; wherein at maximum one $R^5$ is different from hydrogen.

13. The compound according to claim 4, or a pharmaceutically acceptable salt thereof, wherein X represents N; Z represents $CR^5$; and Y represents $CR^5$; wherein each $R^5$ independently represents hydrogen or $(C_{1-3})$alkyl; wherein at maximum one $R^5$ is different from hydrogen.

14. A compound according to claim 1 which is
4-[4-methoxy-2-oxo-3-(2-trifluoromethyl-benzyl)-2,3-dihydro-benzoimidazol-1-yl]-piperidine-1-carboxylic acid tert-butyl ester;
1-[1-(2,6-dimethyl-phenyl)-piperidin-4-yl]-4-methoxy-3-(2-trifluoromethyl-benzyl)-1,3-dihydro-benzoimidazol-2-one;
1-(1-(2,6-dimethylphenyl)piperidin-4-yl)-4-methoxy-3-(2-(trifluoromethyl)benzyl)-1,3-dihydro-benzoimidazol-2-one-7-d;
4-methoxy-1-(1-phenyl-piperidin-4-yl)-3-(2-trifluoromethyl-benzyl)-1,3-dihydro-benzoimidazol-2-one;
1-[1-(2, 4-dichloro-benzyl)-piperidin-4-yl]-4-methoxy-3-(2-trifluoromethyl-benzyl)-1,3-dihydro-benzoimidazol-2-one;
(R)-3-[4-methoxy-2-oxo-3-(2-trifluoromethyl-benzyl)-2,3-dihydro-benzoimidazol-1-yl]-pyrrolidine-1-carboxylic acid tert-butyl ester;
1-[(R)-1-(2,6-difluoro-phenyl)-pyrrolidin-3-yl]-4-methoxy-3-(2-trifluoromethyl-benzyl)-1,3-dihydro-benzoimidazol-2-one;
1-[(R)-1-(2,6-dimethyl-phenyl)-pyrrolidin-3-yl]-4-methoxy-3-(2-trifluoromethyl-benzyl)-1,3-dihydro-benzoimidazol-2-one;
1-[1-(2,6-difluoro-phenyl)-piperidin-4-yl]-4-methoxy-3-(2-trifluoromethyl-benzyl)-1,3-dihydro-benzoimidazol-2-one;
1-[1-(2,6-dimethoxy-phenyl)-piperidin-4-yl]-4-methoxy-3-(2-trifluoromethyl-benzyl)-1,3-dihydro-benzoimidazol-2-one;
1-[1-(2-fluoro-6-methoxy-phenyl)-piperidin-4-yl]-4-methoxy-3-(2-trifluoromethyl-benzyl)-1,3-dihydro-benzoimidazol-2-one;
4-methoxy-1-[1-(2-methoxy-6-methyl-phenyl)-piperidin-4-yl]-3-(2-trifluoromethyl-benzyl)-1,3-dihydro-benzoimidazol-2-one;
1-[1-(2-fluoro-6-methyl-phenyl)-piperidin-4-yl]-4-methoxy-3-(2-trifluoromethyl-benzyl)-1,3-dihydro-benzoimidazol-2-one;
3-cyclopropyl-5-{4-[4-methoxy-2-oxo-3-(2-trifluoromethyl-benzyl)-2,3-dihydro-benzoimidazol-1-yl]-piperidin-1-yl}-1-methyl-1h-pyrazole-4-carb aldehyde;
1-[(R)-1-(2-fluoro-6-methyl-phenyl)-pyrrolidin-3-yl]-4-methoxy-3-(2-trifluoromethyl-benzyl)-1,3-dihydro-benzoimidazol-2-one;
4-methoxy-1-[(R)-1-(2-methoxy-phenyl)-pyrrolidin-3-yl]-3-(2-trifluoromethyl-benzyl)-1,3-dihydro-benzoimidazol-2-one;

1-[(R)-1-(2,6-dimethoxy-phenyl)-pyrrolidin-3-yl]-4-methoxy-3-(2-trifluoromethyl-benzyl)-1,3-dihydro-benzoimidazol-2-one;
4-methoxy-1-[(R)-1-(2-methoxy-6-methyl-phenyl)-pyrrolidin-3-yl]-3-(2-trifluoromethyl-benzyl)-1,3-dihydro-benzoimidazol-2-one;
1-[(R)-1-(2-fluoro-6-methoxy-phenyl)-pyrrolidin-3-yl]-4-methoxy-3-(2-trifluoromethyl-benzyl)-1,3-dihydro-benzoimidazol-2-one;
(R)-3-[4-methoxy-2-oxo-3-(2-trifluoromethoxy-benzyl)-2,3-dihydro-benzoimidazol-1-yl]-pyrrolidine-1-carboxylic acid tert-butyl ester;
1-[1-(5-cyclopropyl-2-methyl-2h-pyrazol-3-yl)-piperidin-4-yl]-4-methoxy-3-(2-trifluoromethyl-benzyl)-1,3-dihydro-benzoimidazol-2-one;
1-[(R)-1-(2,6-dimethyl-phenyl)-pyrrolidin-3-yl]-4-methoxy-3-(2-trifluoromethoxy-benzyl)-1,3-dihydro-benzoimidazol-2-one;
1-[(R)-1-(2,6-difluoro-phenyl)-pyrrolidin-3-yl]-4-methoxy-3-(2-trifluoromethoxy-benzyl)-1,3-dihydro-benzoimidazol-2-one;
1-[1-(4-chloro-5-cyclopropyl-2h-pyrazol-3-yl)-piperidin-4-yl]-4-methoxy-3-(2-trifluoromethyl-benzyl)-1,3-dihydro-benzoimidazol-2-one;
1-[1-(5-cyclopropyl-2,4-dimethyl-2h-pyrazol-3-yl)-piperidin-4-yl]-4-methoxy-3-(2-trifluoromethyl-benzyl)-1,3-dihydro-benzoimidazol-2-one;
(R)-3-[4-methoxy-2-oxo-3-(2-trifluoromethyl-benzyl)-2,3-dihydro-benzoimidazol-1-yl]-pyrrolidine-1-carboxylic acid methyl ester;
1-((R)-1-benzoyl-pyrrolidin-3-yl)-4-methoxy-3-(2-trifluoromethyl-benzyl)-1,3-dihydro-benzoimidazol-2-one;
1-[1-(2,2-dimethyl-propionyl)-piperidin-4-yl]-4-methoxy-3-(2-trifluoromethyl-benzyl)-1,3-dihydro-benzoimidazol-2-one;
4-[4-methoxy-2-oxo-3-(2-trifluoromethyl-benzyl)-2,3-dihydro-benzoimidazol-1-yl]-piperidine-1-carboxylic acid methyl ester;
1-(1-benzoyl-piperidin-4-yl)-4-methoxy-3-(2-trifluoromethyl-benzyl)-1,3-dihydro-benzoimidazol-2-one;
4-methoxy-1-(R)-1-methyl-pyrrolidin-3-yl)-3-(2-trifluoromethyl-benzyl)-1,3-dihydro-benzoimidazol-2-one;
1-((R)-1-isopropyl-pyrrolidin-3-yl)-4-methoxy-3-(2-trifluoromethyl-benzyl)-1,3-dihydro-benzoimidazol-2-one;
4-methoxy-1-[(R)-1-(2-methoxy-4-methyl-pyridin-3-yl)-pyrrolidin-3-yl]-3-(2-trifluoromethyl-benzyl)-1,3-dihydro-benzoimidazol-2-one;
1-[(R)-1-(3,5-difluoro-pyridin-4-yl)-pyrrolidin-3-yl]-4-methoxy-3-(2-trifluoromethyl-benzyl)-1,3-dihydro-benzoimidazol-2-one;
1-(1-isopropyl-piperidin-4-yl)-4-methoxy-3-(2-trifluoromethyl-benzyl)-1,3-dihydro-benzoimidazol-2-one;
1-[(R)-1-(3,5-dimethyl-pyridin-4-yl)-pyrrolidin-3-yl]-4-methoxy-3-(2-trifluoromethyl-benzyl)-1,3-dihydro-benzoimidazol-2-one;
1-[(R)-1-(2-fluoro-4-methyl-pyridin-3-yl)-pyrrolidin-3-yl]-4-methoxy-3-(2-trifluoromethyl-benzyl)-1,3-dihydro-benzoimidazol-2-one;
1-[(R)-1-(3,5-dimethoxy-pyridin-4-yl)-pyrrolidin-3-yl]-4-methoxy-3-(2-trifluoromethyl-benzyl)-1,3-dihydro-benzoimidazol-2-one;
(R)-3-[4-methoxy-2-oxo-3-(2-trifluoromethyl-benzyl)-2,3-dihydro-imidazo[4,5-c]pyridin-1-yl]-pyrrolidine-1-carboxylic acid tert-butyl ester;
1-[(R)-1-(2-fluoro-6-methyl-phenyl)-pyrrolidin-3-yl]-4-hydroxy-3-(2-trifluoromethyl-benzyl)-1,3-dihydro-benzoimidazol-2-one;
1-[(R)-1-(2,6-dimethyl-phenyl)-pyrrolidin-3-yl]-4-methoxy-3-(2-trifluoromethyl-benzyl)-1,3-dihydro-imidazo[4,5-c]pyridin-2-one;
1-[(R)-1-(2,6-difluoro-phenyl)-pyrrolidin-3-yl]-4-methoxy-3-(2-trifluoromethyl-benzyl)-1,3-dihydro-imidazo[4,5-c]pyridin-2-one;
(R)-3-[7-methoxy-2-oxo-1-(2-trifluoromethyl-benzyl)-1,2-dihydro-imidazo[4,5-b]pyridin-3-yl]-pyrrolidine-1-carboxylic acid tert-butyl ester;
1-[(R)-1-(2,6-dimethyl-phenyl)-pyrrolidin-3-yl]-4-hydroxy-3-(2-trifluoromethyl-benzyl)-1,3-dihydro-benzoimidazol-2-one;
3-[(R)-1-(2,6-dimethyl-phenyl)-pyrrolidin-3-yl]-7-methoxy-1-(2-trifluoromethyl-benzyl)-1,3-dihydro-imidazo[4,5-b]pyridin-2-one;
3-[(R)-1-(2,6-difluoro-phenyl)-pyrrolidin-3-yl]-7-methoxy-1-(2-trifluoromethyl-benzyl)-1,3-dihydro-imidazo[4,5-b]pyridin-2-one;
4-methoxy-1-[(R)-1-(2-methoxy-4-methyl-pyridin-3-yl)-pyrrolidin-3-yl]-3-(2-trifluoromethyl-benzyl)-1,3-dihydro-imidazo[4,5-c]pyridin-2-one;
1-[(R)-1-(2-fluoro-4-methyl-pyridin-3-yl)-pyrrolidin-3-yl]-4-methoxy-3-(2-trifluoromethyl-benzyl)-1,3-dihydro-imidazo[4,5-c]pyridin-2-one;
1-[(R)-1-(2-fluoro-6-methoxy-phenyl)-pyrrolidin-3-yl]-4-methoxy-3-(2-trifluoromethyl-benzyl)-1,3-dihydro-imidazo[4,5-c]pyridin-2-one;
1-[(R)-1-(2-fluoro-6-methyl-phenyl)-pyrrolidin-3-yl]-4-methoxy-3-(2-trifluoromethyl-benzyl)-1,3-dihydro-imidazo[4,5-c]pyridin-2-one;
4-methoxy-1-[(R)-1-(2-methoxy-6-methyl-phenyl)-pyrrolidin-3-yl]-3-(2-trifluoromethyl-benzyl)-1,3-dihydro-imidazo[4,5-c]pyridin-2-one;
1-[(R)-1-(2,6-dimethyl-phenyl)-pyrrolidin-3-yl]-4-(2-hydroxy-ethoxy)-3-(2-trifluoromethyl-benzyl)-1,3-dihydro-benzoimidazol-2-one;
4-[4-methoxy-2-oxo-3-(4-trifluoromethyl-pyridin-3-ylmethyl)-2,3-dihydro-benzoimidazol-1-yl]-piperidine-1-carboxylic acid tert-butyl ester;
1-[1-(2,6-dimethyl-phenyl)-piperidin-4-yl]-4-methoxy-3-(2-trifluoromethyl-pyridin-3-ylmethyl)-1,3-dihydro-benzoimidazol-2-one;
1-[1-(2,6-difluoro-phenyl)-piperidin-4-yl]-4-methoxy-3-(2-trifluoromethyl-pyridin-3-ylmethyl)-1,3-dihydro-benzoimidazol-2-one;
1-[(R)-1-(2-fluoro-6-methoxy-phenyl)-pyrrolidin-3-yl]-3-(2-trifluoromethyl-benzyl)-3,5-dihydro-1h-imidazo[4,5-c]pyridine-2,4-dione;
1-[(R)-1-(2-fluoro-6-methyl-phenyl)-pyrrolidin-3-yl]-3-(2-trifluoromethyl-benzyl)-3,5-dihydro-1h-imidazo[4,5-c]pyridine-2, 4-dione;
1-[1-(2,6-dimethyl-phenyl)-piperidin-4-yl]-4-methoxy-3-(4-trifluoromethyl-pyridin-3-ylmethyl)-1,3-dihydro-benzoimidazol-2-one;
1-[1-(2,6-difluoro-phenyl)-piperidin-4-yl]-4-methoxy-3-(4-trifluoromethyl-pyridin-3-ylmethyl)-1,3-dihydro-benzoimidazol-2-one;
(R)-3-[4-methoxy-2-oxo-3-(2-trifluoromethyl-benzyl)-2,3-dihydro-benzoimidazol-1-yl]-pyrrolidine-1-carboxylic acid ethyl ester;
(R)-3-[4-methoxy-2-oxo-3-(2-trifluoromethyl-benzyl)-2,3-dihydro-benzoimidazol-1-yl]-pyrrolidine-1-carboxylic acid isopropyl ester;

(R)-3-[4-methoxy-2-oxo-3-(2-trifluoromethyl-benzyl)-2,3-dihydro-benzoimidazol-1-yl]-pyrrolidine-1-carboxylic acid butyl ester;

(R)-3-[4-methoxy-2-oxo-3-(2-trifluoromethyl-benzyl)-2,3-dihydro-benzoimidazol-1-yl]-pyrrolidine-1-carboxylic acid phenyl ester;

4-[4-methoxy-2-oxo-3-(3-trifluoromethyl-pyridin-2-ylmethyl)-2,3-dihydro-benzoimidazol-1-yl]-piperidine-1-carboxylic acid tert-butyl ester;

(R)-3-[4-methoxy-3-(2-methoxy-benzyl)-2-oxo-2,3-dihydro-benzoimidazol-1-yl]-pyrrolidine-1-carboxylic acid tert-butyl ester;

1-[(R)-1-(2,4-dimethyl-pyridin-3-yl)-pyrrolidin-3-yl]-4-methoxy-3-(2-trifluoromethyl-benzyl)-1,3-dihydro-benzoimidazol-2-one;

1-[(R)-1-(2,6-dimethyl-phenyl)-pyrrolidin-3-yl]-4-methoxy-3-(2-methoxy-benzyl)-1,3-dihydro-benzoimidazol-2-one;

1-[(R)-1-(2,6-difluoro-phenyl)-pyrrolidin-3-yl]-4-methoxy-3-(2-methoxy-benzyl)-1,3-dihydro-benzoimidazol-2-one;

1-[(R)-1-(5-isopropyl-[1,3,4]oxadiazol-2-yl)-pyrrolidin-3-yl]-4-methoxy-3-(2-trifluoromethyl-benzyl)-1,3-dihydro-benzoimidazol-2-one;

(R)-3-[4-methoxy-2-oxo-3-(2-trifluoromethyl-benzyl)-2,3-dihydro-benzoimidazol-1-yl]-pyrrolidine-1-carboxylic acid 3-methyl-oxetan-3-yl ester;

5-{(R)-3-[4-methoxy-2-oxo-3-(2-trifluoromethyl-benzyl)-2,3-dihydro-benzoimidazol-1-yl]-pyrrolidin-1-yl}-1,3-dimethyl-1h-pyrazole-4-carb aldehyde;

(R)-3-[4-methoxy-2-oxo-3-(2-trifluoromethyl-benzyl)-2,3-dihydro-benzoimidazol-1-yl]-pyrrolidine-1-carboxylic acid oxetan-3-yl ester;

1-[1-(2,6-dimethyl-phenyl)-piperidin-4-yl]-4-methoxy-3-(3-trifluoromethyl-pyridin-4-ylmethyl)-1,3-dihydro-benzoimidazol-2-one;

1-[1-(2,6-difluoro-phenyl)-piperidin-4-yl]-4-methoxy-3-(3-trifluoromethyl-pyridin-4-ylmethyl)-1,3-dihydro-benzoimidazol-2-one;

1-[1-(2,6-dimethyl-phenyl)-piperidin-4-yl]-4-methoxy-3-(3-trifluoromethyl-pyridin-2-ylmethyl)-1,3-dihydro-benzoimidazol-2-one;

1-[1-(2,6-difluoro-phenyl)-piperidin-4-yl]-4-methoxy-3-(3-trifluoromethyl-pyridin-2-ylmethyl)-1,3-dihydro-benzoimidazol-2-one;

1-[(R)-1-(2,6-dimethyl-phenyl)-pyrrolidin-3-yl]-4-methoxy-3-(2-methoxy-benzyl)-1,3-dihydro-imidazo[4,5-c]pyridin-2-one;

1-[(R)-1-(2-fluoro-6-methyl-phenyl)-pyrrolidin-3-yl]-4-methoxy-3-(2-methoxy-benzyl)-1,3-dihydro-imidazo[4,5-c]pyridin-2-one;

1-[(R)-1-(2,5-dimethyl-2h-pyrazol-3-yl)-pyrrolidin-3-yl]-4-methoxy-3-(2-trifluoromethyl-benzyl)-1,3-dihydro-benzoimidazol-2-one;

1-[(R)-1-(4-chloro-2,5-dimethyl-2h-pyrazol-3-yl)-pyrrolidin-3-yl]-4-methoxy-3-(2-trifluoromethyl-benzyl)-1,3-dihydro-benzoimidazol-2-one;

1-[(R)-1-(2-fluoro-6-methyl-phenyl)-pyrrolidin-3-yl]-3-(2-methoxy-benzyl)-3,5-dihydro-1h-imidazo[4,5-c]pyridine-2,4-dione;

3-fluoro-2-{(R)-3-[4-methoxy-2-oxo-3-(2-trifluoromethyl-benzyl)-2,3-dihydro-benzoimidazol-1-yl]-pyrrolidin-1-yl}-benzonitrile;

3-fluoro-2-{(R)-3-[4-methoxy-2-oxo-3-(2-trifluoromethyl-benzyl)-2,3-dihydro-benzoimidazol-1-yl]-pyrrolidin-1-yl}-benzaldehyde;

4-methoxy-3-(2-trifluoromethyl-benzyl)-1-[(R)-1-(5-trifluoromethyl-[1,3,4]oxadiazol-2-yl)-pyrrolidin-3-yl]-1,3-dihydro-benzoimidazol-2-one;

4-methoxy-3-(2-trifluoromethyl-benzyl)-1-[(R)-1-(2,4,5-trimethyl-2h-pyrazol-3-yl)-pyrrolidin-3-yl]-1,3-dihydro-benzoimidazol-2-one;

(R)-3-[4-methoxy-2-oxo-3-(2-trifluoromethyl-benzyl)-2,3-dihydro-benzoimidazol-1-yl]-pyrrolidine-1-carboxylic acid 3-trifluoromethyl-oxetan-3-yl ester;

5-{(R)-3-[4-methoxy-2-oxo-3-(2-trifluoromethyl-benzyl)-2,3-dihydro-benzoimidazol-1-yl]-pyrrolidin-1-yl}-1,3-dimethyl-1h-pyrazole-4-carbonitrile;

1-[(R)-1-(2-fluoro-6-hydroxymethyl-phenyl)-pyrrolidin-3-yl]-4-methoxy-3-(2-trifluoromethyl-benzyl)-1,3-dihydro-benzoimidazol-2-one;

1-{(R)-1-[2-fluoro-6-(1-hydroxy-ethyl)-phenyl]-pyrrolidin-3-yl}-4-methoxy-3-(2-trifluoromethyl-benzyl)-1,3-dihydro-benzoimidazol-2-one;

1-[(R)-1-(2-acetyl-6-fluoro-phenyl)-pyrrolidin-3-yl]-4-methoxy-3-(2-trifluoromethyl-benzyl)-1,3-dihydro-benzoimidazol-2-one;

1-{(R)-1-[2-fluoro-6-(1-hydroxy-1-methyl-ethyl)-phenyl]-pyrrolidin-3-yl}-4-methoxy-3-(2-trifluoromethyl-benzyl)-1,3-dihydro-benzoimidazol-2-one;

3-(6-chloro-4-methoxy-pyridazin-3-ylmethyl)-1-[(R)-1-(2-fluoro-6-methyl-phenyl)-pyrrolidin-3-yl]-4-methoxy-1,3-dihydro-benzoimidazol-2-one;

1-[(R)-1-(2,6-dimethyl-phenyl)-pyrrolidin-3-yl]-3-(2-trifluoromethyl-benzyl)-3,5-dihydro-1h-imidazo [4,5-c]pyridine-2,4-dione;

1-[(R)-1-(2-methoxy-6-methyl-phenyl)-pyrrolidin-3-yl]-3-(2-trifluoromethyl-benzyl)-3,5-dihydro-1h-imidazo[4,5-c]pyridine-2,4-dione;

1-[(R)-1-(2-fluoro-6-methyl-phenyl)-pyrrolidin-3-yl]-4-methoxy-3-(4-methoxy-pyridazin-3-ylmethyl)-1,3-dihydro-benzoimidazol-2-one;

3-fluoro-2-{4-[4-methoxy-2-oxo-3-(3-trifluoromethyl-pyrazin-2-ylmethyl)-2,3-dihydro-benzoimidazol-1-yl]-piperidin-1-yl}-benzonitrile;

3-fluoro-2-{4-[4-methoxy-3-(3-methoxy-pyrazin-2-ylmethyl)-2-oxo-2,3-dihydro-benzoimidazol-1-yl]-piperidin-1-yl}-benzonitrile;

1-[(R)-1-(2-cyano-6-fluoro-phenyl)-pyrrolidin-3-yl]-2-oxo-3-(2-trifluoromethyl-benzyl)-2,3-dihydro-1h-benzoimidazole-4-carboxylic acid methyl ester;

1-[(R)-1-(2-cyano-6-fluoro-phenyl)-pyrrolidin-3-yl]-2-oxo-3-(2-trifluoromethyl-benzyl)-2,3-dihydro-1h-benzoimidazole-4-carboxylic acid methylamide;

1-[(R)-1-(2-cyano-6-fluoro-phenyl)-pyrrolidin-3-yl]-2-oxo-3-(2-trifluoromethyl-benzyl)-2,3-dihydro-1h-benzoimidazole-4-carboxylic acid amide;

1-[(R)-1-(2-cyano-6-fluoro-phenyl)-pyrrolidin-3-yl]-2-oxo-3-(2-trifluoromethyl-benzyl)-2,3-dihydro-1h-benzoimidazole-4-carboxylic acid dimethylamide;

3-fluoro-2-{(R)-3-[4-hydroxymethyl-2-oxo-3-(2-trifluoromethyl-benzyl)-2,3-dihydro-benzoimidazol-1-yl]-pyrrolidin-1-yl}-benzonitrile;

1-[(R)-1-(2-fluoro-6-methylaminomethyl-phenyl)-pyrrolidin-3-yl]-4-methoxy-3-(2-trifluoromethyl-benzyl)-1,3-dihydro-benzoimidazol-2-one;

3-fluoro-2-{(R)-3-[6-methoxy-8-oxo-7-(2-trifluoromethyl-benzyl)-7,8-dihydro-purin-9-yl]-pyrrolidin-1-yl}-benzonitrile;

3-fluoro-2-{(R)-3-[6-methoxy-7-(2-methoxy-benzyl)-8-oxo-7,8-dihydro-purin-9-yl]-pyrrolidin-1-yl}-benzonitrile;

1-[(R)-1-(2-dimethylaminomethyl-6-fluoro-phenyl)-pyrrolidin-3-yl]-4-methoxy-3-(2-trifluoromethyl-benzyl)-1,3-dihydro-benzoimidazol-2-one;

1-[(R)-1-(2-fluoro-6-{[(2-hydroxy-ethyl)-methyl-amino]-methyl}-phenyl)-pyrrolidin-3-yl]-4-methoxy-3-(2-trifluoromethyl-benzyl)-1,3-dihydro-benzoimidazol-2-one;

1-[(R)-1-(2-azetidin-1-ylmethyl-6-fluoro-phenyl)-pyrrolidin-3-yl]-4-methoxy-3-(2-trifluoromethyl-benzyl)-1,3-dihydro-benzoimidazol-2-one;

3-fluoro-2-{(R)-3-[4-methoxy-3-(2-methoxy-benzyl)-2-oxo-2,3-dihydro-benzoimidazol-1-yl]-pyrrolidin-1-yl}-benzonitrile;

1-[(R)-1-(2-fluoro-6-methyl-phenyl)-pyrrolidin-3-yl]-4-methoxy-3-(2-methoxy-benzyl)-1,3-dihydro-benzoimidazol-2-one;

3-fluoro-2-{(R)-3-[4-methoxy-2-oxo-3-(3-trifluoromethyl-pyrazin-2-ylmethyl)-2,3-dihydro-benzoimidazol-1-yl]-pyrrolidin-1-yl}-benzonitrile;

3-fluoro-2-{(R)-3-[4-methoxy-3-(3-methoxy-pyrazin-2-ylmethyl)-2-oxo-2,3-dihydro-benzoimidazol-1-yl]-pyrrolidin-1-yl}-benzonitrile;

3-fluoro-2-{4-[4-methoxy-3-(4-methoxy-pyrimidin-5-ylmethyl)-2-oxo-2,3-dihydro-benzoimidazol-1-yl]-piperidin-1-yl}-benzonitrile;

3-fluoro-2-{(R)-3-[4-methoxy-3-(4-methoxy-pyrimidin-5-ylmethyl)-2-oxo-2,3-dihydro-benzoimidazol-1-yl]-pyrrolidin-1-yl}-benzonitrile;

1-[(R)-1-(2-fluoro-6-morpholin-4-ylmethyl-phenyl)-pyrrolidin-3-yl]-4-methoxy-3-(2-trifluoromethyl-benzyl)-1,3-dihydro-benzoimidazol-2-one;

1-[(R)-1-(2-fluoro-6-pyrrolidin-1-ylmethyl-phenyl)-pyrrolidin-3-yl]-4-methoxy-3-(2-trifluoromethyl-benzyl)-1,3-dihydro-benzoimidazol-2-one;

3-fluoro-2-{4-[4-methoxy-2-oxo-3-(4-trifluoromethyl-pyrimidin-5-ylmethyl)-2,3-dihydro-benzoimidazol-1-yl]-piperidin-1-yl}-benzonitrile;

1-[(R)-1-(2,6-dimethyl-phenyl)-pyrrolidin-3-yl]-4-(2-hydroxy-ethylamino)-3-(2-trifluoromethyl-benzyl)-1,3-dihydro-imidazo [4,5-c]pyridin-2-one;

1-[(R)-1-(2,6-dimethyl-phenyl)-pyrrolidin-3-yl]-4-(2-hydroxy-ethoxy)-3-(2-trifluoromethyl-benzyl)-1,3-dihydro-imidazo [4,5-c]pyridin-2-one;

4-(2-dimethylamino-ethoxy)-1-[(R)-1-(2-fluoro-6-methyl-phenyl)-pyrrolidin-3-yl]-3-(2-trifluoromethyl-benzyl)-1,3-dihydro-imidazo [4,5-c]pyridin-2-one;

1-[(R)-1-(2-fluoro-6-methyl-phenyl)-pyrrolidin-3-yl]-4-(2-morpholin-4-yl-ethoxy)-3-(2-trifluoromethyl-benzyl)-1,3-dihydro-imidazo [4,5-c]pyridin-2-one;

4-[1-[(R)-1-(2-fluoro-6-methyl-phenyl)-pyrrolidin-3-yl]-2-oxo-3-(2-trifluoromethyl-benzyl)-2,3-dihydro-1h-imidazo[4,5-c]pyridin-4-yloxy]-piperidine-1-carboxylic acid tert-butyl ester;

1-[(R)-1-(2-fluoro-6-methyl-phenyl)-pyrrolidin-3-yl]-4-[(2-hydroxy-ethyl)-methyl-amino]-3-(2-trifluoromethyl-benzyl)-1,3-dihydro-imidazo[4,5-c]pyridin-2-one;

1-[(R)-1-(2-fluoro-6-methyl-phenyl)-pyrrolidin-3-yl]-4-(piperidin-4-yloxy)-3-(2-trifluoromethyl-benzyl)-1,3-dihydro-imidazo[4,5-c]pyridin-2-one;

4-(2,2-dimethyl-[1,3]dioxolan-4-ylmethoxy)-1-[(R)-1-(2-fluoro-6-methyl-phenyl)-pyrrolidin-3-yl]-3-(2-trifluoromethyl-benzyl)-1,3-dihydro-imidazo[4,5-c]pyridin-2-one;

(3-fluoro-2-{(R)-3-[4-methoxy-2-oxo-3-(2-trifluoromethyl-benzyl)-2,3-dihydro-benzoimidazol-1-yl]-pyrrolidin-1-yl}-phenyl)-acetaldehyde;

1-[(R)-1-(2-fluoro-6-methyl-phenyl)-pyrrolidin-3-yl]-4-(oxetan-3-yloxy)-3-(2-trifluoromethyl-benzyl)-1,3-dihydro-imidazo[4,5-c]pyridin-2-one;

4-(2,3-dihydroxy-propoxy)-1-[(R)-1-(2-fluoro-6-methyl-phenyl)-pyrrolidin-3-yl]-3-(2-trifluoromethyl-benzyl)-1,3-dihydro-imidazo[4,5-c]pyridin-2-one;

1-[(R)-1-(2-fluoro-6-methyl-phenyl)-pyrrolidin-3-yl]-4-morpholin-4-yl-3-(2-trifluoromethyl-benzyl)-1,3-dihydro-imidazo[4,5-c]pyridin-2-one;

1-[(R)-1-(2-fluoro-6-methyl-phenyl)-pyrrolidin-3-yl]-4-(1-methyl-pyrrolidin-3-yloxy)-3-(2-trifluoromethyl-benzyl)-1,3-dihydro-imidazo[4,5-c]pyridin-2-one;

1-{(R)-1-[2-fluoro-6-(2-morpholin-4-yl-ethyl)-phenyl]-pyrrolidin-3-yl}-4-methoxy-3-(2-trifluoromethyl-benzyl)-1,3-dihydro-benzoimidazol-2-one;

1-{(R)-1-[2-fluoro-6-(4-methyl-piperazin-1-ylmethyl)-phenyl]-pyrrolidin-3-yl}-4-methoxy-3-(2-trifluoromethyl-benzyl)-1,3-dihydro-benzoimidazol-2-one;

1-[(R)-1-(2-fluoro-6-piperidin-1-ylmethyl-phenyl)-pyrrolidin-3-yl]-4-methoxy-3-(2-trifluoromethyl-benzyl)-1,3-dihydro-benzoimidazol-2-one;

1-{(R)-1-[2-fluoro-6-(4-hydroxy-piperidin-1-ylmethyl)-phenyl]-pyrrolidin-3-yl}-4-methoxy-3-(2-trifluoromethyl-benzyl)-1,3-dihydro-benzoimidazol-2-one;

1-[(R)-1-(2-fluoro-6-piperazin-1-ylmethyl-phenyl)-pyrrolidin-3-yl]-4-methoxy-3-(2-trifluoromethyl-benzyl)-1,3-dihydro-benzoimidazol-2-one;

1-{(R)-1-[2-(4-dimethylamino-piperidin-1-ylmethyl)-6-fluoro-phenyl]-pyrrolidin-3-yl}-4-methoxy-3-(2-trifluoromethyl-benzyl)-1,3-dihydro-benzoimidazol-2-one;

1-{(R)-1-[2-fluoro-6-(4-methoxy-piperidin-1-ylmethyl)-phenyl]-pyrrolidin-3-yl}-4-methoxy-3-(2-trifluoromethyl-benzyl)-1,3-dihydro-benzoimidazol-2-one;

1-{(R)-1-[2-fluoro-6-(3-methoxy-pyrrolidin-1-ylmethyl)-phenyl]-pyrrolidin-3-yl}-4-methoxy-3-(2-trifluoromethyl-benzyl)-1,3-dihydro-benzoimidazol-2-one;

1-[(R)-1-(2-fluoro-6-{[(2-methoxy-ethyl)-methyl-amino]-methyl}-phenyl)-pyrrolidin-3-yl]-4-methoxy-3-(2-trifluoromethyl-benzyl)-1,3-dihydro-benzoimidazol-2-one;

1-[(R)-1-(2-{[ethyl-(2-hydroxy-ethyl)-amino]-methyl}-6-fluoro-phenyl)-pyrrolidin-3-yl]-4-methoxy-3-(2-trifluoromethyl-benzyl)-1,3-dihydro-benzoimidazol-2-one;

1-[(R)-1-(2-{[bis-(2-hydroxy-ethyl)-amino]-methyl}-6-fluoro-phenyl)-pyrrolidin-3-yl]-4-methoxy-3-(2-trifluoromethyl-benzyl)-1,3-dihydro-benzoimidazol-2-one;

1-((R)-1-{2-fluoro-6-[(2-methoxy-1-methyl-ethyl-amino)-methyl]-phenyl}-pyrrolidin-3-yl)-4-methoxy-3-(2-trifluoromethyl-benzyl)-1,3-dihydro-benzoimidazol-2-one;

1-{(R)-1-[2-fluoro-6-(3-methoxy-azetidin-1-ylmethyl)-phenyl]-pyrrolidin-3-yl}-4-methoxy-3-(2-trifluoromethyl-benzyl)-1,3-dihydro-benzoimidazol-2-one;

4-[4-methoxy-2-oxo-3-(2-trifluoromethyl-benzyl)-2,3-dihydro-benzoimidazol-1-yl]-2-methyl-piperidine-1-carboxylic acid tert-butyl ester;

3-fluoro-2-{4-[4-methoxy-2-oxo-3-(2-trifluoromethyl-benzyl)-2,3-dihydro-benzoimidazol-1-yl]-2-methyl-piperidin-1-yl}-benzaldehyde;

4-[4-methoxy-2-oxo-3-(2-trifluoromethyl-benzyl)-2,3-dihydro-benzoimidazol-1-yl]-3-methyl-piperidine-1-carboxylic acid tert-butyl ester;

1-[1-(2-fluoro-6-methyl-phenyl)-3-methyl-piperidin-4-yl]-4-methoxy-3-(2-trifluoromethyl-benzyl)-1,3-dihydro-benzoimidazol-2-one;

1-{(R)-1-[2-fluoro-6-(1-methoxy-ethyl)-phenyl]-pyrrolidin-3-yl}-4-methoxy-3-(2-trifluoromethyl-benzyl)-1,3-dihydro-benzoimidazol-2-one;

1-[(R)-1-(2-fluoro-6-methyl-phenyl)-pyrrolidin-3-yl]-4-(oxetan-3-yloxy)-3-(2-trifluoromethyl-benzyl)-1,3-dihydro-benzoimidazol-2-one;

1-[(R)-1-(2-fluoro-6-methyl-phenyl)-pyrrolidin-3-yl]-4-(2-hydroxy-ethoxy)-3-(2-trifluoromethyl-benzyl)-1,3-dihydro-benzoimidazol-2-one;

4-(2,2-dimethyl-[1,3]dioxolan-4-ylmethoxy)-1-[(R)-1-(2-fluoro-6-methyl-phenyl)-pyrrolidin-3-yl]-3-(2-trifluoromethyl-benzyl)-1,3-dihydro-benzoimidazol-2-one;

4-(2,3-dihydroxy-propoxy)-1-[(R)-1-(2-fluoro-6-methyl-phenyl)-pyrrolidin-3-yl]-3-(2-trifluoromethyl-benzyl)-1,3-dihydro-benzoimidazol-2-one;

3-fluoro-2-{(R)-3-[4-methoxy-2-oxo-3-(4-trifluoromethyl-pyrimidin-5-ylmethyl)-2,3-dihydro-benzoimidazol-1-yl]-pyrrolidin-1-yl}-benzonitrile;

1-[(R)-1-(2-fluoro-6-nitro-phenyl)-pyrrolidin-3-yl]-4-methoxy-3-(2-trifluoromethyl-benzyl)-1,3-dihydro-benzoimidazol-2-one;

1-[(R)-1-(2-amino-6-fluoro-phenyl)-pyrrolidin-3-yl]-4-methoxy-3-(2-trifluoromethyl-benzyl)-1,3-dihydro-benzoimidazol-2-one;

1-[(R)-1-(2-bromo-6-fluoro-phenyl)-pyrrolidin-3-yl]-4-methoxy-3-(2-trifluoromethyl-benzyl)-1,3-dihydro-benzoimidazol-2-one;

1-[(R)-1-(4,5-dichloro-pyridazin-3-yl)-pyrrolidin-3-yl]-4-methoxy-3-(2-trifluoromethyl-benzyl)-1,3-dihydro-benzoimidazol-2-one;

1-[(R)-1-(3,5-dichloro-pyridazin-4-yl)-pyrrolidin-3-yl]-4-methoxy-3-(2-trifluoromethyl-benzyl)-1,3-dihydro-benzoimidazol-2-one;

1-{(R)-1-[2-fluoro-6-(3-morpholin-4-yl-prop-1-ynyl)-phenyl]-pyrrolidin-3-yl}-4-methoxy-3-(2-trifluoromethyl-benzyl)-1,3-dihydro-benzoimidazol-2-one;

1-[(R)-1-(2-fluoro-phenyl)-pyrrolidin-3-yl]-4-methoxy-3-(2-trifluoromethyl-benzyl)-1,3-dihydro-benzoimidazol-2-one;

1-[(R)-1-(2-fluoro-6-morpholin-4-yl-phenyl)-pyrrolidin-3-yl]-4-methoxy-3-(2-trifluoromethyl-benzyl)-1,3-dihydro-benzoimidazol-2-one;

1-{(R)-1-[2-fluoro-6-(3-morpholin-4-yl-propyl)-phenyl]-pyrrolidin-3-yl}-4-methoxy-3-(2-trifluoromethyl-benzyl)-1,3-dihydro-benzoimidazol-2-one;

1-((R)-1-{2-fluoro-6-[1-(3-methoxy-azetidin-1-yl)-ethyl]-phenyl}-pyrrolidin-3-yl)-4-methoxy-3-(2-trifluoromethyl-benzyl)-1,3-dihydro-benzoimidazol-2-one;

4-[4-methoxy-2-oxo-3-(2-trifluoromethyl-benzyl)-2,3-dihydro-benzoimidazol-1-yl]-piperidine-1,3-dicarboxylic acid 1-tert-butyl ester 3-ethyl ester;

1-[(R)-1-(2-fluoro-6-methyl-phenyl)-pyrrolidin-3-yl]-3-(2-isopropoxy-benzyl)-4-methoxy-1,3-dihydro-benzoimidazol-2-one;

1-[1-(2-fluoro-6-methyl-phenyl)-piperidin-4-yl]-3-(2-isopropoxy-benzyl)-4-methoxy-1,3-dihydro-benzoimidazol-2-one;

1-[(R)-1-(2-fluoro-6-methyl-phenyl)-pyrrolidin-3-yl]-4-methoxy-3-(3-trifluoromethyl-pyrazin-2-ylmethyl)-1,3-dihydro-benzoimidazol-2-one;

1-[1-(2-fluoro-6-methyl-phenyl)-piperidin-4-yl]-4-methoxy-3-(3-trifluoromethyl-pyrazin-2-ylmethyl)-1,3-dihydro-benzoimidazol-2-one;

1-[(R)-1-(2-fluoro-6-methyl-phenyl)-pyrrolidin-3-yl]-4-methoxy-3-(3-methoxy-pyrazin-2-ylmethyl)-1,3-dihydro-benzoimidazol-2-one;

1-[1-(2-fluoro-6-methyl-phenyl)-piperidin-4-yl]-4-methoxy-3-(3-methoxy-pyrazin-2-ylmethyl)-1,3-dihydro-benzoimidazol-2-one;

3-[(R)-1-(2-fluoro-6-methyl-phenyl)-pyrrolidin-3-yl]-7-methoxy-5-methyl-1-(2-trifluoromethyl-benzyl)-1,3-dihydro-imidazo[4,5-b]pyridin-2-one;

3-(6-chloro-4-isopropoxy-pyridazin-3-ylmethyl)-1-[(R)-1-(2-fluoro-6-methyl-phenyl)-pyrrolidin-3-yl]-4-methoxy-1,3-dihydro-benzoimidazol-2-one;

1-[(R)-1-(2-fluoro-6-methyl-phenyl)-pyrrolidin-3-yl]-3-(4-isopropoxy-pyridazin-3-ylmethyl)-4-methoxy-1,3-dihydro-benzoimidazol-2-one;

1-[(R)-1-(2-fluoro-6-methyl-phenyl)-pyrrolidin-3-yl]-4-methoxy-3-(4-methyl-pyridazin-3-ylmethyl)-1,3-dihydro-benzoimidazol-2-one;

1-[(R)-1-(2-fluoro-6-methyl-phenyl)-pyrrolidin-3-yl]-4-methoxy-3-(4-methoxy-pyrimidin-5-ylmethyl)-1,3-dihydro-benzoimidazol-2-one;

1-[(R)-1-(2-fluoro-6-methyl-phenyl)-pyrrolidin-3-yl]-4-methoxy-3-(4-trifluoromethyl-pyrimidin-5-ylmethyl)-1,3-dihydro-benzoimidazol-2-one;

1-[(R)-1-(2-fluoro-6-methyl-phenyl)-pyrrolidin-3-yl]-3-(3-isopropoxy-pyrazin-2-ylmethyl)-4-methoxy-1,3-dihydro-benzoimidazol-2-one;

1-[1-(2-fluoro-6-methyl-phenyl)-piperidin-4-yl]-3-(3-isopropoxy-pyrazin-2-ylmethyl)-4-methoxy-1,3-dihydro-benzoimidazol-2-one;

4-[4-methoxy-2-oxo-3-(2-trifluoromethyl-benzyl)-2,3-dihydro-benzoimidazol-1-yl]-azepane-1-carboxylic acid tert-butyl ester;

1-[(R)-1-(2-fluoro-6-methyl-phenyl)-pyrrolidin-3-yl]-3-(4-isopropyl-pyridin-3-ylmethyl)-4-methoxy-1,3-dihydro-benzoimidazol-2-one;

1-[1-(2-fluoro-6-methyl-phenyl)-piperidin-4-yl]-3-(4-isopropyl-pyridin-3-ylmethyl)-4-methoxy-1,3-dihydro-benzoimidazol-2-one;

1-[(R)-1-(2-fluoro-6-methyl-phenyl)-pyrrolidin-3-yl]-3-(3-isopropoxy-pyridin-2-ylmethyl)-4-methoxy-1,3-dihydro-benzoimidazol-2-one;

1-[1-(2-fluoro-6-methyl-phenyl)-piperidin-4-yl]-3-(3-isopropoxy-pyridin-2-ylmethyl)-4-methoxy-1,3-dihydro-benzoimidazol-2-one;

1-[1-(2-fluoro-6-methyl-phenyl)-azepan-4-yl]-4-methoxy-3-(2-trifluoromethyl-benzyl)-1,3-dihydro-benzoimidazol-2-one;

1-[1-(2,6-dimethyl-phenyl)-azepan-4-yl]-4-methoxy-3-(2-trifluoromethyl-benzyl)-1,3-dihydro-benzoimidazol-2-one;

1-[(R)-1-(2-fluoro-6-methyl-phenyl)-pyrrolidin-3-yl]-3-(4-isopropyl-pyrimidin-5-ylmethyl)-4-methoxy-1,3-dihydro-benzoimidazol-2-one;

1-[1-(2-fluoro-6-methyl-phenyl)-piperidin-4-yl]-3-(3-isopropyl-pyrazin-2-ylmethyl)-4-methoxy-1,3-dihydro-benzoimidazol-2-one;

5-[4-methoxy-2-oxo-3-(2-trifluoromethyl-benzyl)-2,3-dihydro-benzoimidazol-1-yl]-2-aza-bicyclo[2.2.1]heptane-2-carboxylic acid tert-butyl ester;

1-[(R)-1-(2-fluoro-6-methyl-phenyl)-pyrrolidin-3-yl]-3-(3-isopropyl-pyrazin-2-ylmethyl)-4-methoxy-1,3-dihydro-benzoimidazol-2-one;

1-[2-(2-fluoro-6-methyl-phenyl)-2-aza-bicyclo[2.2.1]hept-5-yl]-4-methoxy-3-(2-trifluoromethyl-benzyl)-1,3-dihydro-benzoimidazol-2-one;

6-[4-methoxy-2-oxo-3-(2-trifluoromethyl-benzyl)-2,3-dihydro-benzoimidazol-1-yl]-3-aza-bicyclo[3.1.1]heptane-3-carboxylic acid tert-butyl ester;
1-[1-(2-fluoro-6-methyl-phenyl)-piperidin-4-yl]-3-(4-isopropyl-pyrimidin-5-ylmethyl)-4-methoxy-1,3-dihydro-benzoimidazol-2-one;
1-[(R)-1-(2-cyano-6-fluoro-phenyl)-pyrrolidin-3-yl]-2-oxo-3-(2-trifluoromethyl-benzyl)-2,3-dihydro-1h-benzoimidazole-4-carboxylic acid (2-hydroxy-ethyl)-amide;
1-[(R)-1-(2-cyano-6-fluoro-phenyl)-pyrrolidin-3-yl]-2-oxo-3-(2-trifluoromethyl-benzyl)-2,3-dihydro-1h-benzoimidazole-4-carboxylic acid (2-methoxy-ethyl)-amide;
1-[(R)-1-(2-fluoro-6-methyl-phenyl)-pyrrolidin-3-yl]-4-methoxy-3-(2-trifluoromethyl-pyridin-3-ylmethyl)-1,3-dihydro-benzoimidazol-2-one;
(3r*, 4s*)-3-[4-methoxy-2-oxo-3-(2-trifluoromethyl-benzyl)-2,3-dihydro-benzoimidazol-1-yl]-4-methyl-pyrrolidine-1-carboxylic acid tert-butyl ester;
1-[3-(2-fluoro-6-methyl-phenyl)-3-aza-bicyclo[3.1.1]hept-6-yl]-4-methoxy-3-(2-trifluoromethyl-benzyl)-1,3-dihydro-benzoimidazol-2-one;
1-[(3r*,4s*)-1-(2-fluoro-6-methyl-phenyl)-4-methyl-pyrrolidin-3-yl]-4-methoxy-3-(2-trifluoromethyl-benzyl)-1,3-dihydro-benzoimidazol-2-one;
(3r*,4r*)-3-[4-methoxy-2-oxo-3-(2-trifluoromethyl-benzyl)-2,3-dihydro-benzoimidazol-1-yl]-4-methyl-pyrrolidine-1-carboxylic acid tert-butyl ester;
1-[(3r*,4r*)-1-(2-fluoro-6-methyl-phenyl)-4-methyl-pyrrolidin-3-yl]-4-methoxy-3-(2-trifluoromethyl-benzyl)-1,3-dihydro-benzoimidazol-2-one;
4-methoxy-1-[(R)-1-(2-trifluoromethoxy-phenyl)-pyrrolidin-3-yl]-3-(2-trifluoromethyl-benzyl)-1,3-dihydro-benzoimidazol-2-one;
1-[(R)-1-(2-fluoro-6-methyl-phenyl)-pyrrolidin-3-yl]-4-methoxy-3-(3-trifluoromethyl-pyridin-2-ylmethyl)-1,3-dihydro-benzoimidazol-2-one;
1-[(R)-1-(2-fluoro-6-methyl-phenyl)-pyrrolidin-3-yl]-4-methoxy-3-(4-trifluoromethyl-pyridin-3-ylmethyl)-1,3-dihydro-benzoimidazol-2-one;
4-methoxy-1-{(R)-1-[2-(2-methoxy-ethoxy)-phenyl]-pyrrolidin-3-yl}-3-(2-trifluoromethyl-benzyl)-1,3-dihydro-benzoimidazol-2-one;
1-[(R)-1-(2-fluoro-6-methyl-phenyl)-pyrrolidin-3-yl]-4-(3-methoxy-azetidin-1-yl)-3-(2-trifluoromethyl-benzyl)-1,3-dihydro-imidazo[4,5-c]pyridin-2-one;
1-[(R)-1-(2-fluoro-6-methyl-phenyl)-pyrrolidin-3-yl]-4-(4-methyl-piperazin-1-yl)-3-(2-trifluoromethyl-benzyl)-1,3-dihydro-imidazo[4,5-c]pyridin-2-one;
1-[(R)-1-(2-fluoro-6-methyl-phenyl)-pyrrolidin-3-yl]-4-(2-methoxy-ethylamino)-3-(2-trifluoromethyl-benzyl)-1,3-dihydro-imidazo[4,5-c]pyridin-2-one;
3-(2-cyclopropoxy-benzyl)-1-[(R)-1-(2-fluoro-6-methyl-phenyl)-pyrrolidin-3-yl]-4-methoxy-1,3-dihydro-benzoimidazol-2-one;
3-(2-cyclopropoxy-benzyl)-1-[1-(2-fluoro-6-methyl-phenyl)-piperidin-4-yl]-4-methoxy-1,3-dihydro-benzoimidazol-2-one;
3-fluoro-4-[4-methoxy-2-oxo-3-(2-trifluoromethyl-benzyl)-2,3-dihydro-benzoimidazol-1-yl]-piperidine-1-carboxylic acid tert-butyl ester;
1-[3-fluoro-1-(2-fluoro-6-methyl-phenyl)-piperidin-4-yl]-4-methoxy-3-(2-trifluoromethyl-benzyl)-1,3-dihydro-benzoimidazol-2-one;
1-[1-(2-fluoro-6-methyl-phenyl)-piperidin-3-yl]-4-methoxy-3-(2-trifluoromethyl-benzyl)-1,3-dihydro-benzoimidazol-2-one;
3-[4-methoxy-2-oxo-3-(2-trifluoromethyl-benzyl)-2,3-dihydro-benzoimidazol-1-yl]-azetidine-1-carboxylic acid tert-butyl ester;
3-[4-methoxy-2-oxo-3-(2-trifluoromethyl-benzyl)-2,3-dihydro-benzoimidazol-1-yl]-piperidine-1-carboxylic acid tert-butyl ester;
1-[1-(2-fluoro-6-methyl-phenyl)-azetidin-3-yl]-4-methoxy-3-(2-trifluoromethyl-benzyl)-1,3-dihydro-benzoimidazol-2-one;
1-[1-(2-fluoro-6-methyl-phenyl)-piperidin-4-yl]-4-methoxy-3-(3-trifluoromethyl-pyridin-2-ylmethyl)-1,3-dihydro-benzoimidazol-2-one;
1-[1-(2,6-dimethyl-phenyl)-piperidin-3-yl]-4-methoxy-3-(2-trifluoromethyl-benzyl)-1,3-dihydro-benzoimidazol-2-one;
1-[(R)-1-(2-fluoro-6-methyl-phenyl)-pyrrolidin-3-yl]-4-methoxy-3-(2-trifluoromethyl-thiazol-4-ylmethyl)-1,3-dihydro-benzoimidazol-2-one;
1-[1-(2-fluoro-6-methyl-phenyl)-pyrrolidin-3-yl]-4-methoxy-3-[(s)(S)-1-(2-trifluoromethyl-phenyl)-ethyl]-1,3-dihydro-benzoimidazol-2-one;
3-(2,4-difluoro-6-isopropoxy-benzyl)-1-[(R)-1-(2-fluoro-6-methyl-phenyl)-pyrrolidin-3-yl]-4-methoxy-1,3-dihydro-benzoimidazol-2-one;
1-[(R)-1-(2-fluoro-6-methyl-phenyl)-pyrrolidin-3-yl]-4-methoxy-3-(2-methyl-4-trifluoromethyl-thiazol-5-ylmethyl)-1,3-dihydro-benzoimidazol-2-one;
1-(1-cyclopropanecarbonyl-piperidin-4-yl)-4-methoxy-3-(2-trifluoromethyl-benzyl)-1,3-dihydro-benzoimidazol-2-one;
3-(2-cyclopropyl-benzyl)-1-[1-(2-fluoro-6-methyl-phenyl)-piperidin-4-yl]-4-methoxy-1,3-dihydro-benzoimidazol-2-one;
3-(2-cyclopropylmethoxy-benzyl)-1-[1-(2-fluoro-6-methyl-phenyl)-piperidin-4-yl]-4-methoxy-1,3-dihydro-benzoimidazol-2-one;
1-[1-(2-fluoro-6-methyl-phenyl)-piperidin-4-yl]-4-methoxy-3-[2-(oxetan-3-yloxy)-benzyl]-1,3-dihydro-benzoimidazol-2-one;
3-(2-cyclobutoxy-benzyl)-1-[1-(2-fluoro-6-methyl-phenyl)-piperidin-4-yl]-4-methoxy-1,3-dihydro-benzoimidazol-2-one;
1-[1-(2-fluoro-6-methyl-phenyl)-3,3-dimethyl-piperidin-4-yl]-4-methoxy-3-(2-trifluoromethyl-benzyl)-1,3-dihydro-benzoimidazol-2-one;
4-[4-methoxy-2-oxo-3-(2-trifluoromethyl-benzyl)-2,3-dihydro-benzoimidazol-1-yl]-3,3-dimethyl-piperidine-1-carboxylic acid tert-butyl ester;
3-[1-(2-fluoro-6-methyl-phenyl)-piperidin-4-yl]-7-methoxy-1-(2-trifluoromethyl-benzyl)-1,3-dihydro-imidazo[4,5-c]pyridin-2-one;
1-[1-(2-hydroxy-phenyl)-piperidin-4-yl]-4-methoxy-3-(2-trifluoromethyl-benzyl)-1,3-dihydro-benzoimidazol-2-one;
1-[1-(2-benzyloxy-phenyl)-piperidin-4-yl]-4-methoxy-3-(2-trifluoromethyl-benzyl)-1,3-dihydro-benzoimidazol-2-one;
4-methoxy-1-(3'-methyl-3,4,5,6-tetrahydro-2h-[1,2']bipyridinyl-4-yl)-3-(2-trifluoromethyl-benzyl)-1,3-dihydro-benzoimidazol-2-one;
4-methoxy-1-(3'-methoxy-3,4,5,6-tetrahydro-2h-[1,2']bipyridinyl-4-yl)-3-(2-trifluoromethyl-benzyl)-1,3-dihydro-benzoimidazol-2-one;

4-methoxy-1-(2'-methoxy-4'-methyl-3,4,5,6-tetrahydro-2h-[1,3']bipyridinyl-4-yl)-3-(2-trifluoromethyl-benzyl)-1,3-dihydro-benzoimidazol-2-one;

1-(2'-fluoro-4'-methyl-3,4,5,6-tetrahydro-2h-[1,3']bipyridinyl-4-yl)-4-methoxy-3-(2-trifluoromethyl-benzyl)-1,3-dihydro-benzoimidazol-2-one;

1-(3'-fluoro-3,4,5,6-tetrahydro-2h-[1,2']bipyridinyl-4-yl)-4-methoxy-3-(2-trifluoromethyl-benzyl)-1,3-dihydro-benzoimidazol-2-one;

1-(2',4'-dimethyl-3,4,5,6-tetrahydro-2h-[1,3']bipyridinyl-4-yl)-4-methoxy-3-(2-trifluoromethyl-benzyl)-1,3-dihydro-benzoimidazol-2-one;

1-{1-[2-(2-hydroxy-ethoxy)-phenyl]-piperidin-4-yl}-4-methoxy-3-(2-trifluoromethyl-benzyl)-1,3-dihydro-benzoimidazol-2-one;

4-methoxy-1-{1-[2-(tetrahydro-pyran-4-yloxy)-phenyl]-piperidin-4-yl}-3-(2-trifluoromethyl-benzyl)-1,3-dihydro-benzoimidazol-2-one;

1-[1-(2-cyclopropylmethoxy-phenyl)-piperidin-4-yl]-4-methoxy-3-(2-trifluoromethyl-benzyl)-1,3-dihydro-benzoimidazol-2-one;

1-[1-(2-cyclobutoxy-phenyl)-piperidin-4-yl]-4-methoxy-3-(2-trifluoromethyl-benzyl)-1,3-dihydro-benzoimidazol-2-one;

4-methoxy-1-{1-[2-(oxetan-3-yloxy)-phenyl]-piperidin-4-yl}-3-(2-trifluoromethyl-benzyl)-1,3-dihydro-benzoimidazol-2-one;

1-[1-(2-butoxy-phenyl)-piperidin-4-yl]-4-methoxy-3-(2-trifluoromethyl-benzyl)-1,3-dihydro-benzoimidazol-2-one;

1-(4'-fluoro-2'-methyl-3,4,5,6-tetrahydro-2h-[1,3']bipyridinyl-4-yl)-4-methoxy-3-(2-trifluoromethyl-benzyl)-1,3-dihydro-benzoimidazol-2-one;

1-[1-(2-fluoro-6-methyl-phenyl)-piperidin-4-yl]-4-methyl-3-(2-trifluoromethyl-benzyl)-1,3-dihydro-benzoimidazol-2-one;

4-[4-methoxy-2-oxo-3-(2-trifluoromethyl-benzyl)-2,3-dihydro-benzoimidazol-1-yl]-4'-methyl-3,4,5,6-tetrahydro-2h-[1,3']bipyridinyl-2'-carbonitrile;

4-methoxy-1-(4'-methoxy-2'-methyl-3,4,5,6-tetrahydro-2h-[1,3']bipyridinyl-4-yl)-3-(2-trifluoromethyl-benzyl)-1,3-dihydro-benzoimidazol-2-one;

1-(2',4'-dimethoxy-3,4,5,6-tetrahydro-2h-[1,3']bipyridinyl-4-yl)-4-methoxy-3-(2-trifluoromethyl-benzyl)-1,3-dihydro-benzoimidazol-2-one;

4-methoxy-1-[1-(4-methoxy-6-methyl-pyrimidin-5-yl)-piperidin-4-yl]-3-(2-trifluoromethyl-benzyl)-1,3-dihydro-benzoimidazol-2-one; or 1-[1-(4,6-dimethoxy-pyrimidin-5-yl)-piperidin-4-yl]-4-methoxy-3-(2-trifluoromethyl-benzyl)-1,3-dihydro-benzoimidazol-2-one;

or a pharmaceutically acceptable salt thereof.

15. A pharmaceutical composition comprising at least one therapeutically inert excipient and a compound according to claim 1, or a pharmaceutically acceptable salt thereof.

16. A medicament comprising the compound according to claim 1, or a pharmaceutically acceptable salt thereof.

* * * * *